(12) United States Patent
Robinson et al.

(10) Patent No.: US 8,623,379 B2
(45) Date of Patent: Jan. 7, 2014

(54) COMPOSITIONS AND METHODS FOR GENERATING AN IMMUNE RESPONSE

(75) Inventors: Harriet L. Robinson, Atlanta, GA (US); James Smith, Decatur, GA (US); Jian Hua, Dunwoody, GA (US)

(73) Assignee: Emory University, Atlanta, GA (US)

( * ) Notice: Subject to any disclaimer, the term of this patent is extended or adjusted under 35 U.S.C. 154(b) by 311 days.

(21) Appl. No.: 10/336,566

(22) Filed: Jan. 3, 2003

(65) Prior Publication Data

US 2003/0175292 A1 Sep. 18, 2003

Related U.S. Application Data

(63) Continuation-in-part of application No. 10/093,953, filed on Mar. 8, 2002, now abandoned, and a continuation-in-part of application No. 09/798,675, filed on Mar. 2, 2001, now abandoned, said application No. 10/093,953 is a continuation-in-part of application No. PCT/US01/06795, filed on Mar. 2, 2001, application No. 10/336,566, which is a continuation-in-part of application No. PCT/US02/06713, filed on Mar. 1, 2002.

(60) Provisional application No. 60/325,004, filed on Sep. 26, 2001, provisional application No. 60/324,845, filed on Sep. 25, 2001, provisional application No. 60/186,364, filed on Mar. 2, 2000, provisional application No. 60/251,083, filed on Dec. 1, 2000, provisional application No. 60/274,434, filed on Mar. 8, 2001.

(51) Int. Cl.
| | |
|---|---|
| *C12Q 1/70* | (2006.01) |
| *C12N 15/63* | (2006.01) |
| *C12N 15/33* | (2006.01) |
| *C12N 15/48* | (2006.01) |
| *C12N 15/49* | (2006.01) |
| *A61K 39/21* | (2006.01) |

(52) U.S. Cl.
USPC .................. 424/199.1; 424/204.1; 424/208.1; 424/232.1; 435/320.1

(58) Field of Classification Search
USPC ............................................ 424/199.1, 184.1
See application file for complete search history.

(56) References Cited

U.S. PATENT DOCUMENTS

| | | | |
|---|---|---|---|
| 5,169,763 A | 12/1992 | Kieny et al. | |
| 5,185,146 A | 2/1993 | Altenburger | |
| 5,256,767 A | 10/1993 | Salk et al. | |
| 5,445,953 A | 8/1995 | Dorner et al. | |
| 5,494,807 A | 2/1996 | Paoletti et al. | |
| 5,589,466 A | 12/1996 | Felgner et al. | |
| 5,593,972 A | 1/1997 | Weiner et al. | |
| 5,614,404 A | 3/1997 | Mazzara et al. | |
| 5,676,950 A | 10/1997 | Small et al. | |
| 5,736,368 A | 4/1998 | Mazzara et al. | |
| 5,741,492 A | 4/1998 | Hurwitz et al. | |
| 5,747,324 A | 5/1998 | Mazzara et al. | |
| 5,747,338 A | 5/1998 | Giese et al. | |
| 5,756,103 A | 5/1998 | Paoletti et al. | |
| 5,766,599 A | 6/1998 | Paoletti et al. | |
| 5,795,577 A | 8/1998 | Kieny et al. | |
| 5,817,637 A | 10/1998 | Weiner et al. | |
| 5,846,946 A | 12/1998 | Huebner et al. | 514/44 |
| 5,849,304 A | 12/1998 | Moss et al. | |
| 5,853,725 A | 12/1998 | Salk et al. | |
| 5,858,775 A | 1/1999 | Johnson | 435/320.1 |
| 5,863,542 A | 1/1999 | Paoletti et al. | |
| 5,879,925 A | 3/1999 | Rovinski et al. | |
| 5,911,989 A | 6/1999 | Katinger et al. | 424/160.1 |
| 5,928,930 A | 7/1999 | Salk et al. | |
| 5,985,641 A | 11/1999 | Haynes et al. | |
| 6,051,410 A | 4/2000 | Mazzara et al. | |
| 6,077,662 A | 6/2000 | Compans et al. | 435/5 |
| 6,080,408 A | 6/2000 | Rovinski et al. | |
| 6,086,891 A | 7/2000 | Hurwitz et al. | |
| 6,099,847 A | 8/2000 | Tobin et al. | |
| 6,103,244 A | 8/2000 | Dorner et al. | |

(Continued)

FOREIGN PATENT DOCUMENTS

| | | |
|---|---|---|
| EP | 0 335 635 | 10/1989 |
| EP | 0 538 496 | 8/1991 |

(Continued)

OTHER PUBLICATIONS

Cheonis N. Status Report on HIV Vaccine Development [online]. San Francisco AIDS Foundation, Winter 2000 [retrieved on Mar. 27, 2006], Retrieved from the Internet: <http://www.thebody.com/sfaf/winter00/vaccine.html#>.*
Ho, M. AIDS Vaccines Trials Dangerous [online]. ISIS News, No. 11/12, Oct. 2001 [retrieved on Mar. 27, 2006]. Retrieved from the internet: <http://www.i-sis.org.uk/isisnews/i-sisnews11-19.php>.*
Tonini et al. Current approaches to developing a preventative HIV vaccine. Current Opinion in Investigational Drugs 2005, vol. 6, No. 2, p. 155-162.*
Kusumi et al. Human immunodeficiency virus type 1 envelope gene structure and diversity in vivo and after cocultivation in vitro. Journal of Virology, Feb. 1992, vol. 66, No. 2, p. 875-885.*
Meyerhans et al. Temporal fluctuations in HIV quasispeCies in vivo are not reflected by sequential HIV isolations. Cell 1989, vol. 58, p. 901-910.*
Derosiers. Prospects for an AIDS vaccine. Nature Medicine Mar. 2004, vol. 10, No. 3, p. 221-223.*

(Continued)

*Primary Examiner* — Louise Humphrey
(74) *Attorney, Agent, or Firm* — King & Spalding

(57) ABSTRACT

We have developed DNA and viral vectors that can be used, alone or in combination, as a vaccine against one HIV clade, subtype, or recombinant form of HIV or against multiple HIV clades, subtypes, or recombinant forms. Moreover, the vectors can encode a variety of antigens, which may be obtained from one clade or from two or more different clades, and the antigens selected and/or the manner in which the vectors are formulated (e.g., mixed) can be manipulated to generate a protective immune response against a variety of clades (e.g., the clades to which a patient is most likely to be exposed; with the proportions of the components of the vaccine tailored to the extent of the patient's risk to a particular clade or clades).

18 Claims, 69 Drawing Sheets

(56) References Cited

U.S. PATENT DOCUMENTS

| | | | |
|---|---|---|---|
| 6,121,021 | A | 9/2000 | Rovinski et al. |
| 6,140,114 | A | 10/2000 | Klatzmann et al. |
| 6,156,952 | A | 12/2000 | Bryant et al. ............... 800/11 |
| 6,171,596 | B1 | 1/2001 | Earl et al. |
| 6,204,250 | B1 | 3/2001 | Bot et al. |
| 6,214,804 | B1 | 4/2001 | Felgner et al. |
| 6,221,633 | B1 | 4/2001 | Ertl et al. |
| 6,265,183 | B1 | 7/2001 | Dorner et al. |
| 6,291,157 | B1 | 9/2001 | Rovinski et al. |
| 6,306,625 | B1 | 10/2001 | Jacobs et al. |
| 6,448,083 | B1 | 9/2002 | Larocca et al. ............ 435/456 |
| 6,544,527 | B1 | 4/2003 | Rovinski et al. .......... 424/208.1 |
| 6,554,527 | B1 | 4/2003 | O'Donnell et al. ........ 424/208.1 |
| 6,663,871 | B1 * | 12/2003 | McMichael et al. ....... 424/199.1 |
| 6,841,381 | B1 | 1/2005 | Robinson et al. ......... 435/320.1 |

FOREIGN PATENT DOCUMENTS

| | | |
|---|---|---|
| WO | WO 89/09620 | 10/1989 |
| WO | WO 89/12095 | 12/1989 |
| WO | WO 91/07425 | 5/1991 |
| WO | WO 97/27311 | 7/1997 |
| WO | WO 98/56919 | 12/1998 |
| WO | WO 99/63098 | 12/1999 |
| WO | WO 00/00216 | 1/2000 |
| WO | WO 01/02607 | 1/2001 |
| WO | WO 01/47955 | 7/2001 |
| WO | WO 01/52886 | 7/2001 |
| WO | WO 01/82962 | 11/2001 |
| WO | WO 01/92470 | 12/2001 |
| WO | WO02/072754 | 9/2002 |
| WO | WO 03/004657 | 1/2003 |
| WO | WO03/004657 | 1/2003 |
| WO | WO 03/072754 | 9/2003 |

OTHER PUBLICATIONS

Leslie et al. HIV evolution: CTL escape mutation and reversion after transmission. Nature Medicine Mar. 2004 vol. 10, No. 3, pp. 282-289.*

Altman et al. HIV escape: there and back again. Nature Medicine Mar. 2004 vol. 10, No. 3, p. 229-230.*

Friedrich et al. Reversion of CTL escape—variant immunodeficiency viruses in vivo. Nature Medicine Mar. 2004 vol. 10, No. 3, p. 275-281.*

Gallo. The end or the beginning of the drive to an HIV-preventive vaccine: a view from over 20 years. Lancet 2005, vol. 366, p. 1897-1898.*

Haigwood, Predictive Value of Primate Models for AIDS. AIDS Reviews 2004, vol. 6, p. 187-198.*

Puls et al. Therapeutic vaccination against HIV: current progress and future possibilities. Clinical Science 2006, vol. 110, p. 59-71.*

Von Laer et al. Gene therapy for HIV infection: what does it need to make it work? The Journal of Gene Medicine 2006, vol. 8, p. 658-667.*

Mizrahi et al. Mutagenesis of the Conserved Aspartic Acid4 43, Glutamic Acid 478, Asparagine 494, and Aspartic Acid 498 Residues in the Ribonuclease H Domain of p66/p51 Human Immunodeficiency Virus Type I Reverse Transcriptase. The Journal of Biological Chemistry, Jul. 1994, vol. 269, No. 30, pp. 19245-19249.*

Ayyavoo et al. Immunogenicity of a novel DNA vaccine cassette expressing multiple human immunodeficiency virus (HIV-1) accessory genes. AIDS 2000, vol. 14, pp. 1-9.*

Englund et al. Integration is Required for Productive Infection of Monocyte-Derived Macrophages by Human Immunodeficiency Virus Type 1. Journal of Virology, May 1995, vol. 69, No. 5, pp. 3216-3219.*

Caselli et al. DNA Immunization with HIV-1 tat Mutated in the trans Activation Domain Induces Humoral and Cellular Immune Responses Against Wild-Type Tat. The Journal of Immunology, 1999, vol. 162, pp. 5631-5638.*

Zhang et al. Nucleocapsid Protein Effects on the Specificity of Retrovirus RNA Encapsidation. Journal of Virology, Sep. 1995, vol. 69, No. 9, pp. 5716-5722.*

Le Grice et al. Active site mutagenesis of the AIDS virus protease and its alleviation by trans complementation. The EMBO Journal 1988, vol. 7, No. 8, pp. 2547-2553.*

Wakefield et al. In Vitro Enzymatic Activity of Human Immunodeficiency Virus Type 1 Reverse Transcriptase Mutants in the Highly Conserved YMDD Amino Acid Motif Correlates with the Infectious Potential of the Proviral Genome. Journal of Virology, Nov. 1992, vol. 66, No. 11, p. 6806-6812.*

Sonnen et al. Characterization of pGA1, a new plasmid from Corynebacterium glutamicum LP-6. Gene 1991, vol. 107, p. 69-74.*

Rodenburg et al. Near Full-Length Clones and Reference Sequences for Subtype C Isolates of HIV Type 1 from Three Different Continents. AIDS Research and Human Retroviruses, Jan. 2001, vol. 17, No. 2, pp. 161-168.*

Allen et al., "Induction of AIDS virus-specific CTL activity in fresh, unstimulated peripheral blood lymphocytes from rhesus macaques vaccinated with a DNA prime/modified vaccinia virus Ankara boost regimen," J. Immunol., 164: 4968-4978, 2000.

Amara et al., "Control of a Mucosal Challenge and Prevention of AIDS by a Multiprotein DNA/MVA Vaccine," Science, 292: 69-74, 2001.

Andre et al., "Increased immune response elicited by DNA vaccination with a synthetic gp120 sequence with optimized codon usage," J. Virol., 72: 1497-1503, 1998.

Antoine et al., "The Complete Genomic Sequence of the Modified Vaccinia Ankara Strain: Comparison with Other Orthopoxviruses", Virology, 244: 365-96, 1998.

Asakura et al., "Induction of HIV-1 specific mucosal immune responses by DNA vaccination," Scand. J. Immunol., 46: 326-330, 1997.

Bachmann and Zinkernagel, "Neutralizing antiviral B cell responses," in Ann. Rev. Immunol., 15: 235-270, 1997.

Barouch et al., "Reduction of Simian-human immunodeficiency virus 89.6P viremia in rhesus monkeys by recombinant modified vaccinia virus Ankara vaccination," J. Virol., 75: 5151-5158, 2001.

Barouch et al., "Control of Viremia and prevention of clinical AIDS in rhesis monkeys by cytokine-augmented DNA vaccination," Science, 290: 486-492, 2000.

Barouch et al., "Augmentation of immune responses to HIV-1 and simian immunodeficiency virus DNA caccines by IL-2/IG plasmid administration in rhesus monkeys", Proc. Natl. Acad. Sci. U.S.A., 97:4192-7, Apr. 11, 2000.

Barry et al., "Protection against mycoplasma infection using expression-library immunization," Nature, 377: 632-635, 1995.

Berger, "HIV Entry and Tropism: the chemokine receptor connection," AIDS, 11(Suppl. A): S3-16, 1997.

Benson et al., J. Virol., "Recombinant vaccine-induced protection against the highly pathogenic simian immunodeficiency virus SIV(mac251): dependence on route of challenge exposure," 72: 4170-4182, 1998.

Blanchard et al., "Modified vaccinia virus Ankara undergoes limited replication in human cells and lacks several immunomodulatory proteins: implications for use as a human vaccine," J. Gen. Virol., 79: 1159-1167, 1998.

Bohm et al., "DNA vector constructs that prime hepatitis B surface antigen-specific cytotoxic T lymphocyte and antibody responses in mice after intramuscular injection," J. Immuno. Methods, 193: 29-40, 1996.

Bohm et al., "Routes of plasmid DNA vaccination that prime murine humoral and cellular immune responses," Vaccine, 16: 949-54, 1998.

Bolivar et al., "Construction and Characterization of New Cloning Vehicles: (II. A Multipurpose Cloning System)," Gene, 2: 95-113, 1977.

Boyer et al., "Protection of chimpanzees from high-dose heterologous HIV-1 challenge by DNA vaccination," Nature Med., 3: 526-532, 1997.

Boyle et al., "Influence of cellular location of expressed antigen on the efficacy of DNA vaccination: cytotoxic T lymphocyte and anti-

(56) References Cited

OTHER PUBLICATIONS body responses are suboptimal when antigen is cytoplasmic after intramuscular DNA immunization," Int. Immunol., 9: 1897-1906, 1997.
Boyle et al., "Enhanced responses to a DNA vaccine encoding a fusion antigen that is directed to sites of immune induction," Nature, 392: 408-411, 1998.
Burton and Montefiori, "The antibody response in HIV-1 infection," AIDS, 11(Suppl a):S87-98, 1997.
Calarota et al., "Cellular cytotoxic response induced by DNA vaccination in HIV-1-infected patients," Lancet, 351: 1320-1325, 1998.
Cardoso et al., "Immunization with Plasmid DNA Encoding for the Measles Virus Hemagglutinin and Nucleoprotein Leads to Humoral and Cell-Mediated Immunity," Virology, 225: 293-299, 1998.
Carroll and Moss, "Host Range, and Cytopathogenicity of the Highly Attenuated MVA Strain of Vaccina Virus: Propagation and Generation of Recombinant Viruses in a Nonhuman Mammalian Cell Line", Virology, 238:198-211, 1997.
Chapman et al., "Effect of intron a from human cytomegalovirus (Towne) immediate-early gene on heterologous expression in mammalian cells," Nucl. Acids Res., 19: 3979-3986, 1991.
Chen et al., "Protective Immunity Induced by Oral Immunization with a Rotavirus DNA Vaccine Encapsulated in Microparticles," J. Virol., 72: 5757-5761, 1998.
Chun et al., "Early establishment of a pool of latently infected, resting CD4+ T cells during primary HIV-1 infection," Proc. Natl. Acad. USA, 95: 8869-8873, 1998.
Collman et al., "An Infection Molecular Clone of an Unusual Microphage-Tropic and Highly Cytopathic Strain of Human Immunodeficiency Virus Type 1," J. Virol., 66: 7517-7521, 1992.
Condon et al., "DNA-based immunization by in vivo transfection of dendritic cells," Nat Med., 2:1122-1128, 1996.
Corr et al., "Gene Vaccination with Naked Plasmid DNA: Mechanism of CTL Priming," J. Exp. Med., 184: 1555-1560, 1996.
Dempsey et al., C3d of Complement as a Molecular Adjuvant: Bridging Innate and Acquired Immunity, Science, 271: 348-350, 1996.
Durbin et al., "Comparison of the immunogenicity and efficacy of a replication-defective vaccinia virus expressing antigens of human parainfluenza virus type 3 (HPIV3) with those of a live attenuated HPIV3 vaccine candidate in rhesus monkeys passively immunized with PIV3 antibodies," J. Infect. Dis., 179: 1345-1351, 1999.
Durbin et al., "The immunogenicity and efficacy of intranasally or parenterally administered replication-deficient vaccinia-parainfluenza virus type 3 recombinants in rhesus monkeys", Vaccine, 16: 1324-30, 1998.
Egan et al., "Simian immunodeficiency virus (SIV) gag DNA-vaccinated rhesus monkeys develop secondary cytotoxic T-lymphocyte responses and control viral replication after pathogenic SIV infection," J Virol., 74:7485-7495, 2000.
Endo et al., "Short- and Long-term Clinical Outcomes in Rhesus Monkeys Inoculated with a Highly Pathogenic Chimeric Simian/Human Immunodeficiency Virus", J. Virol., 74:6935-45, 2000.
Esparza and Bhamarapravati, "Accelerating the development and future availability of JIV-1 vaccines: why, when, where, and how?", Lancet, 355: 2061-6, 2000.
Evans DT et al., "Virus-specific T-lymphocyte responses select for amino-acid variation in simian immunodeficiency virus Env and Nef," Nat. Med., 5: 1270-1276, 1999.
Feltquate et al., "Different T Helper Cell Types and Antibody Isotypes Generated by Saline and Gene Gun DNA Immunization," J. Immunol. 158: 2278-2284, 1997.
Finzi et al., "Latent infection of CD4 T cells provides a mechanism for lifelong persistence of HIV-1, even in patients on effective combination therapy", Nat. Med. 5: 1270-6, 1996.
Fomsgaard et al., "Improved Humoral and Cellular Immune Responses Against the gp120 V3 Loop of HIV-1 Following Genetic Immunization with a Chimeric DNA Vaccine Encoding the V3 Inserted into the Hepatitis B Surface Antigen," Scand. J. Immunol., 47: 289-295, 1998.

Fu et al., "Priming of Cytotoxic T Lymphocytes by DNA Vaccines: Requirement for Professional Antigen Presenting Cells and Evidence for Antigen Transfer from Myocytes," Mol. Med., 3: 362-371, 1997.
Furci et al., "Antigen-driven C-C Chemokine-mediated HIV-1 Suppression by CD4 T Cells from Exposed Uninfected Individuals Expressing the Wild-type CCR-5 Allele", J. Exp. Med., 186:455-60, 1997.
Fynan et al., "DNA vaccines: Protective immunizations by parenteral, mucosal, and gene-gun inoculations," Proc. Natl. Acad. Sci. USA, 90: 11478-11482, 1993.
Gorelick et al., "Nucleocapsid Protein Zinc-Finger Mutants of Simian Immunodeficiency Virus Strain Mne Produce Virions That are Replication Defective in Vitro and in Vivo", Virology, 259-70, 1999.
Goulder et al., "Anti-HIV cellular immunity: recent advances towards vaccine design", AIDS, 13: S121-36, 1999.
Hakim et al., "A Nine-Amino Acid Peptide from IL-1β Augments Antitumor Immune Responses Induced by Protein and DNA Vaccines," J. Immunol., 157: 5503-5511, 1996.
Hanke, "Effective Induction of Simian Immunodeficiency Virus-Specific Cytotoxic T Lymphocytes in Macaques by Using a Multiepitope Gene and DNA Prime-Modified Vaccinia Virus Ankara Boost Vaccination Regimen," J. Virol., 73: 7524-7532, 1999.
Hanke et al., "Enhancement of MHC class I-restricted peptide-specific T cell induction by a DNA prime/MVA boost vaccination regime," Vaccine, 16: 439-445, 1998a.
Hanke et al., "DNA multi-CTL epitope vaccines for HIV and *Plasmodium faciparum*: immunogenicity in mice," Vaccine, 16: 426-435, 1998b.
Hartikka et al., "An Improved Plasmid DNA Expression Vector for Direct Injection into Skeletal MusCle," Hum. Gen. Therapy, 7: 1205-1217, 1996.
Hirsch et al., "Prolonged Clinical Latency and Survival of Macaques Given a Whole Inactivated Simian Immunodeficiency Virus Vaccine", J. Infect. Dis., 170:51-9, 1994.
Hofmann-Lehmann et al., "Sensitive and robust one-tube real-time reverse Transcriptase-polymerase chain reaction to quantify SIV RNA load: comparison of one-versus two-enzyme systems," AIDS Res. Hum. Retroviruses, 16: 1247-1257, 2000.
Inchauspe et al., "Plasmid DNA Expressing a Secreted or a Nonsecreted Form of Hepatitis C Virus Nucleocapsid: Comparative Studies of Antibody and T-Helper Responses Following Genetic Immunization," DNA Cell Biol., 16: 185-195, 1997.
Iwasaki et al., "Enhanced CTL responses mediated by plasmid DNA immunogens encoding costimulatory molecules and cytokines," J. Immunol., 158: 4591-4601, 1997a.
Iwasaki et al., "The dominant role of bone-marrow derived cells in CTL induction following plasmid DNA immunization at different sites," J. Immunol., 159: 11-14, 1997b.
Jin et al., "Dramatic Rise in Plasma Viremia after CD8 T Cell Depletion in Simian Immunodeficiency Virus-infected Macaques", J. Exp. Med., 189: 991-8, 1999.
Jones et al., "Poly (DL-lactide-co-glycolide)-encapsulated plasmid DNA elicits systemic and mucosal antibody responses to encoded protein after oral administration," Vaccine, 15: 814-817, 1997.
Knapp et al., "A high frequency of Mamu-A*01 in the rhesus macaque detected by polymerase chain reaction with sequence-specific primers and direct sequencing," Tissue Antigens, 50: 657-661, 1997.
Korber et al., "Epidemiological and Immunological Implications of the Global Variability of HIV" *Retroviral Immunology*, B. Walker, D. Pantaleo, Eds (The Humana Press, Totowa, NH, in press).
Lechner et al., "Analysis of Successful Immune Responses in Persons Infected with Hepatitis C Virus", J. Exp. Med., 191:1499-1512, 2000.
Letvin et al., "Cytotoxic T lymphocytes specific for the simian immunodeficiency virus", lmmunol. Rev., 170: 127-34, 1999.
Letvin et at., "Potent, protective anti-HIV immune responses generated by bimodal HIV envelope DNA plus protein vaccination," Proc. Natl. Acad. Sci. USA, 94: 9378-9383, 1997.
Li et al., "Infection of Cynomolgus Monkeys with a Chimeric HIV-2/SIV$_{mac}$ Virus That Expresses the HIV-1 Envelope Glycoproteins," J. of AIDS, 5: 639-646, 1992.

(56) References Cited

OTHER PUBLICATIONS

Lifson et al., "The Extent of Early Viral Replication is a Critical Determinant of the Natural History of Simian Immunodeficiency Virus Infection", J. Virol., 71: 9508-14, 1997.

Livingston et al., "The Induction of Mucosal Immunity in the Female Genital Tract Using Gene-Gun Technology (Part 1: Antigen Expression)," Ann. New York Acad. Sci., 772: 265-267, 1995.

Lu et al., "SIV DNA vaccine trial in macaques: post-challenge necropsy in vaccine and control groups," Vaccine 15: 920-923, 1997.

Maecker et al., "DNA vaccination with cytokine fusion constructs biases the immune response to ovalbumin," Vaccine, 15: 1687-1696, 1997.

Maecker et al., "Cytotoxic T Cell Responses to DNA Vaccination: Dependence on Antigen Presentation via Class II MHC[1]," J. Immunol., 161: 6532-6536, 1998.

Mahnel et al., "[Experiences with immunization against orthopox viruses of humans and animals using vaccine strain MVA]," Berl. Munch Tierarztl Wochenschr, 107: 253-256, 1994. [English Translation of Abstract Attached].

Manthorpe et al., "Gene Therapy by Intramuscular Injection of Plasmid DNA: Studies on Firefly Luciferase Gene Expression in Mice," Hum. Gene Therapy, 4: 419-431, 1993.

Mayr et al., "[The smallpox vaccination strain MVA: marker, genetic structure,.experience gained with the parenteral vaccination and behavior in organisms with a debilitated defence mechanism (author's trans1)]," Zentralbl. Bakteriol., 167: 375-390, 1978. [English Translation of Abstract Attached].

McCluskie et al., "Direct Gene Transfer to the Respiratory Tract of Mice with Pure Plasmid and Lipid-Formulated DNA", Antisense Nucleic Acid Drug Dev., 8: 401-414, 1998.

Mellors et al., "Prognosis in HIV-1 Infection Predicted by the Quantity of Virus in Plasma" Science, 272:1167-70, 1996.

Montefiori et al., "Neutralizing antibodies in sera from macaques infected with chimeric simian-human immunodeficiency virus containing the envelope glycoproteins of either a laboratory-adapted variant or a primary isolate of human immunodeficiency virus type 1," J. Virol., 72: 3427-3431, 1998.

Montefiori et al., "Evaluation of antiviral drugs and neutralizing antibodies to human immunodeficiency virus by a rapid and sensitive microtiter infection assay," J. Clin. Microbiol., 26: 231-237, 1988.

Montgomery et al., "Heterologous and Homologous Protection Against Influenza a by DNA Vaccination: Optimization of DNA Vectors," DNA Cell Biol., 12: 777-783, 1993.

Moore et al., "HIV-1 neutralization: the consequences of viral adaptation to growth on transformed T cells," AIDS, 9(Suppl. A):S117-136, 1995.

Murali-Krishna et al., "Counting Antigen-Specific CD8 T Cells: A Reevaluation of Bystander Activation during Viral Infection," Immunity, 8:177-187, 1998.

Murali-Krishna et al., "Persistence of Memory CD8T Cells in MHC Class 1-Deficient Mice", Science, 286:1377-81, 1999.

Ourmanov et al., "Comparative efficacy of recombinant modified vaccinia virus Ankara expressing simian immunodeficiency virus (SIV) Gag-Pol and/or Env in macaques challenged with pathogenic SIV," J. Virol., 74: 2740-2751, 2000.

Ourmanov et al., "Recombinant modified vaccinia virus ankara expressing the surface gp120 of simian immunodeficiency virus (SIV) primes for a rapid neutralizing antibody response to SIV infection in macaques," J. Virol., 74: 2960-2965, 2000.

Pertmer and Robinson, "Studies on Antibody Responses Following Neonatal Immunization with Influenza Hemagglutinin DNA or Protein," Virology, 257:406-414, (1999).

Pertmer et al., "Influenza Virus Nucleoprotein-Specific Immunoglobin G Subclass and Cytokine Responses Elicited by DNA Vaccination Are Dependent on the Route of Vector DNA Delivery," J. Virol., 70: 6119-6125, 1996.

Pertmer et al., "Gene gun-based nucleic acid immunization: elicitation of humoral and cytotoxic T lymphocyte responses following epidermal delivery of nanogram quantities of DNA," Vaccine, 13: 1427-1430, 1995.

Poignard et al., "Neutralizing Antibodies Have Limited Effects on the Control of Established HIV-1 Infection in Vivo," Immunity, 10: 431-438, 1999.

Power et al., "A valid ELISPOT assay for enumeration of ex vivo, antigen-specific, IFNγ-producing T cells," J. Immunol. Methods, 227: 99-107, 1999.

Reimann et al., "A Chimeric Simian/Human Immunodeficiency Virus Expressing a Primary Patient Human Immunodeficiency Virus Type 1 Isolate env Causes an AIDS-Like Disease after in Vivo Passage in Rhesus Monkeys," J. Virol., 70: 6922-6928, 1996.

Robinson and Pertmer, "DNA Vaccines: Basic Studies and Res., 55: 1-74, 2000. Applications," in *Adv. Virus Res.*, 55: 1-74, 2000.

Robinson et al., "AIDS Vaccines: Heterologous Prime/Boost Strategies for raising . Protective T Cell Responses", AIDS Reviews, 2:105-110, 2000.

Robinson and Pertmer, Nucleic Acid Immunology, in *Current Protocols in Ummunology*, (R. Coico, Ed.), vol. 1, pp. 2.14.1-2.14.19.3 vols. John Wiley & Sons, Inc., New York.

Robinson et al., "The Scientific Future of DNA for Immunization," American Academy of Microbiology, May 13-Jun. 2, 1996, 1997.

Robinson et al., "Neutralizing antibody-independent containment of immunodeficiency virus challenges by DNA priming and recombinant pox virus booster immunizations," Nature Med., 5: 526, 1999.

Rodriguez et al., "DNA Immunization: Ubiquitination of a Viral Protein Enhances.Cytotoxic T-Lymphocyte Induction and Antiviral Protection but Abrogates Antibody Induction," J. Virol., 71: 8497-8503, 1997.

Ross et al., "C3d enhancement of antibodies to hemagglutinin accelerates protection against influenza virus challenge," Nat. Immunology, 1:127-131, 2000.

Ross et al., "Enhanced Avidity Maturation of Antibody to Human Immunodeficiency Virus Envelope: DNA Vaccination with gp120-C3d Fusion Proteins," AIDS Res. Human Retro., 17(a):829-835, 2001.

Rubbert et al., "Multifactorial nature of non cytolytic CD8+ T cell-mediated suppression of HIV replication: beta-chemokine dependent and independent effects," AIDS Res. Hum. Retroviruses 13: 63-9, 1997.

Sasaki et al., "Comparison of Intranasal and Intramuscular Immunization against Human Immunodeficiency Virus Type 1 with a DNA-Monophosphoryl Lipid A Adjuvant Vaccine," Infect. Immunol., 66: 823-826, 1998.

Sauter et al., "An Internalization Signal in the Simian Immunodeficiency Virus Transmembrane Protein Cytoplasmic Domain Modulates Expression of Envelope Glycoproteins on the Cell Surface", J. Cell Biol., 132: 795-811, 1996.

Schmitz et al., "Control of Viremia in Simian Immunodeficiency Virus Infection by CD8 Lymphocytes", Science, 283: 857-60, 1999.

Schneider et al., "Induction of CD8 cells using heterologous prime-boost immunisation strategies", Immunol. Rev., 170: 29-38, 1999.

Schneider et al., "Enhanced immunogenicity for CD8+ T cell induction and complete protective efficacy of malaria DNA vaccination by boosting with modified vaccinia virus Ankara," Nat. Med., 4: 397-402, 1998.

Scholtissek et al., "A cloning cartridge of $\lambda t_o$ terminator," Nucleic Acids Res., 15: 3185, 1987.

Sizemore et al., "Attenuated *shigella* as a DNA Delivery Vehicle for DNA-Mediated Immunization," Science, 270: 299-302, 1995.

Sizemore et al., "Attenuated bacteria as a DNA delivery vehicle for DNA-mediated immunization," Vaccine, 15: 804-807, 1997.

Staprans et al., "Simian Immunodeficiency Virus Disease Course is Predicted by the Extent of Virus replication during Primary Infection", J. Virol., 73:4829-39, 1999.

Staprans et al., "Quantitative Methods to Monitor Viral Load in Simian Infections," in *Viral Genome Methods*, K. Adolph, Ed., CRC Press, Boca Raton, FL, pp. 167-184, 1996).

Stittelaar et al., "Protective immunity in macaques vaccinated with a modified vaccinia virus Ankara-based measles virus vaccine in the presence of passively acquired antibodies," J. Virol., 74: 4236-4243, 2000.

Subbarao et al., "Genetic variability of HIV1," AIDS, 10(Suppl. A):S13-23, 1996.

(56) References Cited

OTHER PUBLICATIONS

Sutcliffe, "Complete nucleotide sequence of the *Escherichia coli* plasmid pBR322," Cold Spring Harbor Quant. Biol., 43:77-90, 1979.
Sutter et al., "Nonreplicating vaccinia vector efficiently expresses recombinant genes," Proc. Natl. Acad. Sci. USA, 89: 10847-10851, 1992.
Tang et al., "Genetic immunization is a simple method for eliciting an immune response," Nature, 356: 152-154, 1992.
Thomson et al., "Delivery of Multiple CD8 Cytotoxic T Cell Epitopes by DNA Vaccination," J. Immunol., 160: 1717-1723, 1998.
Tobery et al., "Targeting of HIV-1 Antigens for Rapid Intracellular Degradation Enhances Cytotoxic T Lymphocyte (CTL) Recognition and the Induction of De Novo CTL Responses in Vivo After Immunization," J. Exp. Med., 185: 909-920, 1997.
Tomaras et al., "CD8 T cell-mediated suppressive activity inhibits HIV-1 after virus entry with kinetics indicating effects on virus gene expression", Proc. Natl. Acad. Sci. U.S.A, 97:3503-8, 2000.
Torres et al., "DNA immunization: effect of secretion of DNA-expressed hemaggutinins on antibody responses," Vaccine, 18: 805-814, 2000.
Torres et al., "Differential Dependence on Target Site Tissue for Gene Gun and Intramuscular DNA Immunizations," J. Immunol., 158: 4529-4532, 1997.
Uchijima et al., "Optimization of Codon Usage of Plasmid DNA Vaccine is Required for the Effective MHC Class I-Restricted T Cell Responses Against an Intracellular Bacterium," J. Immunol., 161: 5594-5599, 1998.
Ulmer et al., "Heterologous Protection Against Influenza by Injection of DNA Encoding a Viral Protein," Science 259: 1745-1749, 1993.
Villinger et al., "Induction of Long-Term Protective Effects against Heterologous Challenge in SIVhu-Infected Macaques", Virology, 278:194-206, 2000.
Waldrop et al., "Determination of Antigen-specific Memory/Effector CD4 T Cell Frequencies by Flow Cytometry", J. Clin. Invest., 99:1739-50, 1997.
Watson et al., "Plasma Viremia in Macaques Infected with Simian Immunodeficiency Virus: Plasma Viral Load Early in Infection Predicts Survival", J. Virol., 71: 284-90, 1997.
Wild et al., "Polyvalent vaccination against hepatitis B surface and core antigen using a dicistronic expression plasmid," Vaccine, 16: 353-360, 1998.
Wolff et al. "Direct Gene Transfer into Mouse Muscle in Vivo," Science, 247: 1465-1468, 1990.
Wu et al., "Deoxyribonucleic Acid Vaccines Encoding Antigens With Rapid Proteasome-Dependent Degradation Are Highly Efficient Inducers of Cytolytic T Lymphocytes," J. Immunol., 159: 6037-6043, 1997.
Wyand et al., "Protection by live, attenuated simian immunodeficiency virus against heterologous challenge," J. Virol., 73: 8356-8363, 1999.
Wyatt et al., "Marker Rescue of the Host Range Restriction Defects of Modified Vaccinia Virus Ankara," Virology, 251:334-42, 1998.
Xiang et al., "Manipulation of the Immune Response to a Plasmid-Encoded Viral Antigen by Coinoculation with Plasmids Expressing Cytokines," Immunity, 2: 129-135, 1995.
Yamamoto et al., "Highly sensitive qualitative and quantitative detection of reverse transcriptase activity: optimization, validation, and comparative analysis with other detection systems," J. Virol. Methods, 61: 135-143, 1996.
Yang and Walker, "CD8+ cells in human immunodeficiency virus type I pathogenesis: cytolytic and noncytolytic inhibition of viral replication," Adv. Immunol., 66: 273-311, 1997.
Zajac et al., "Viral Immune Evasion Due to Presistence of Activated T Cells Without Effector Function", J. Exp. Med., 188:2205-13, 1998.
Amara et al., "Different patterns of immune responses but similar control of a simianhuman immunodeficiency virus 89.6P mucosal challenge by modified vaccinia virus Ankara (MVA) and DNA/MVA vaccines," J. Virol., 76:7625-31, 2002.

Jacobsen et al., "Characterization of Human Immunodeficiency Virus Type I Mutants with Decreased Sensitivity to Proteinase Inhibitor Ro 31/8959," Virology, 206:527-534, 1995.
Meyer et al., "Search for a putative scrapie genome in purified prion fractions reveals a paucity of nucleic acids," J. Gen. Virol., 72:1031-1038, 1991.
Smith et al., "Recombinant vaccinia viruses as new live vaccines," Biotechnol Genet Eng Rev., 2:383-407, 1984.
Amara et al., "Different Patterns of Immune Responses but Similar Control of a Simian-Human Immunodeficiency Virus 89.6P Mucosal Challenge by Modified Vaccinia Virus Ankara (MVA) and DNA/MVA Vaccines," *J. Virology* 76:7625-7631 (2002).
Jacobsen et al., "Characterization of Human Immunodeficiency Virus Type 1 Mutants with Decreased Sensitivity to Proteinase Inhibitor Ro 31-8959," *J. Virology* 206:527-534 (1995).
Meyer et al., "Mapping of deletions in the genome of the highly attenuated vaccinia virus MVA and their influence on virulence," *J. Gen. Virology* 72:1031-1038 (1991).
Smith et al., "Recombinant Vaccinia Viruses as New Live Vaccines," *Biotechnology & Genetic Engineering Reviews* 2:383-407 (1984).
Huang et al., "Human Immunodeficiency Virus Type 1-Specific Immunity . . ." J. of Virology 75:4947-4951, 2001.
Kong et al., "Immunogenicity of Mutliple Gene and Clade Human Immunodeficiency.." J. of Virology 77(23):12764-12772, 2003.
Megede et al., "Increased Expression and Immunogenicity of Sequence-Modified . . ." J. of Virology 74(6):2628-2635, 2000.
Persson et al., "Modifications of HIV-1 Retrovirus-Like Particles to Enhance . . ." Biologicals 26:255-265, 1998.
Smith et al., "Multiprotein HIV Type 1 Clade B DNA/MVA Vaccine: . . ." AIDS Research and Human Retroviruses 20(6):654-665, 2004.
Accession No. AF430344; (XP-002321209); Smith et al., Oct. 9, 2001.
Accession No. AF426288; (XP-002321210); Smith et al., Mar. 12, 2002.
Burton et al., "Why do we not have an HIV vaccine and how can we make one?" Nature Med. 4:495-498, 1998.
Feinberg et al., "AIDS vaccine models" Challenging challenge viruses Nature Med. 8(3):207-210, 2002.
Letvin, N.L. "Progress in the development of an HIV-1 vaccine" Science 280:1875-1880, 1998.
Belyakov et al., "Induction of a Mucosal Cytotoxic T-Lymphocyte Response by . . ." J. of Virology 72(1):8264-8272, 1998.
Davison et al., "Structure of Vaccinia Virus Early Promoters" J. Mol. Biol. 210:749-769, 1989.
Earl, P.L. et al., "Comparison of vaccine strategies using recombinant *env-gag-pol* MVA with or without an oligomeric env protein boost in the SHIV rhesus macaque model" *Virology* (2002) 294:270-281.
Girard, M. et al., "New prospects, for the development of a vaccine against human immunodeficiency virus type 1. An overview" *C.R. Acad. Sci. Paris, Sciences de la Vie/Life Sciences* (1999) 322:959-966.
Gomez, C.E. et alk, 2001 "Recombinant proteins produced by vaccinia virus vectors can be incorporated within the virion (IMV form) into different compartments" *Arch Virol.* 146(5):875-892.
Haffar et al., "The Carboxy Terminus of Human Immunodeficiency Virus Type I gp 160 . . ." J. of Virology 64(6):3100-3103, 1990.
Hanke et al., "Development of a DNA-MVA/HIVA vaccine for Kenya" Vaccine 20:1995-1998, 2002.
Hanke et al., "Effective induction of HIV-specific CTL by multi-epitope using gene gun . . ." Vaccine 17:589-596, 1999.
Hanke et al., "Immunogenicities of intravenous and intramuscular administrations of modified vaccinia . . ." J. of General Virology 79:83-90, 1998.
Hanke et al., "Lack of toxicity and persistence in the mouse associated with administration of candidate . . ." Vaccine 21:108-114, 2002.
Hanke et al., "Pre-clinical development of a multi-CTL epitope-based DNA prime MVA boost vaccine for ADS" Immunology Letters 66:177-181, 1999.
Hirsch, V.M. et al., 1995 "Limited virus replication following SIV challenge of macaques immunized with attenuated MVA vaccinia expressing SIV sm *env*and *gag-pol*" Vaccines 95:195-200.

(56) References Cited

OTHER PUBLICATIONS

Karacostas, V. et al., 1989 "Human immunodeficiency virus-like particles produced by a vaccinia virus expression vector" *PNAS USA* 86:8964-8967.
Masternak et al., "cis- and trans-Acting Elements Involved in Reactivation of Vaccinia Virus Early Transcription" J. of Virology 70(12):8737-8746, 1996.
Men, R. et al., "Immunization of rhesus monkeys with a recombinant of modified vaccinia virus Ankara expressing a truncated envelope glycoprotein of dengue type 2 virus induced resistance to dengue type 2 virus challenge" *Vaccine* (2000) 18:3113-3122.
Moss, B. et al., 2000 "Retroviruses of human AIDS and related animal diseases" in: Colloque des Cent Gardes, 12$^{th}$, Paris, France, Oct. 25-27, 1999, Meeting Date 1999, 105-107, Eds. M. Girard & B. Dodet, Editions Scientifiques et Medicales Elsevier, Paris, Fr. (Abstract).
Wee et al., "A DNA/MVA-based candidate human immunodeficiency virus for Kenya induces . . ." J. of General Virology 83:75-80, 2002.
Wyatt et al., "Development of a replication-deficient recombinant vaccinia virus vaccine effective against . . ." Vaccine 14(15):1451-1458, 1996.
Wyatt et al., "Priming and boosting immunity to respiratory syncytial virus by recombinant replication-defective . . ." Vaccine 18:392-397, 2000.
Andersson et al., "Cloning, Structure, and Expression of the Mitochondrial Cytochrome P-450 . . ." J. of Biol. Chem. vol. 264 (14)1222-8229, 1989.
Markmeyer et al., "The pAX plasmids: new gene-fusion vectors for sequencing, mutagenesis and expression of proteins in *E.coli*," *Gene* 93:129-134 (1990).
Mizuno et al., "Mutational analysis of two zinc-finger motifs in HIV type 1 nucleocapsid proteins: effects on proteolytic processing of Gag precursors and particle formation," *Aides Research and Human Retroviruses* 12(9):793-800 (1996).
Wang et al., "Mammalian cell/vaccinia virus expression vectors with increased stability of retroviral sequences in *E.coli*; production of feline immunodeficiency virus envelope protein," *Gene* 153:197-202 (1995).
U.S. Appl. No. 09/798,675, mail date Jul. 1, 2002, Restriction Requirement.
U.S. Appl. No. 09/798,675, mail date Feb. 27, 2003, Non-Final Office Action.
U.S. Appl. No. 09/798,675, mail date Dec. 5, 2003, Final Office Action.
U.S. Appl. No. 09/798,675, mail date Jun. 9, 2004, Non-Final Office Action.
U.S. Appl. No. 10/093,953, mail date Jul. 15, 2005, Non-Final Office Action.
U.S. Appl. No. 11/009,063, mail date Apr. 13, 2007, Non-Final Office Action.
U.S. Appl. No. 11/333,770, mail date Mar. 21, 2007, Restriction Requirement.
U.S. Appl. No. 10/646,628, mail Dec. 12, 2004, Restriction Requirement.
U.S. Appl. No. 10/646,628, mail date Sep. 20, 2005, Non-Final Office Action.
U.S. Appl. No. 10/646,628, mail date Sep. 13, 2006, Final Office Action.
U.S. Appl. No. 10/646,628, mail date Jul. 19, 2007, Non-Final Office Action.
U.S. Appl. No. 11/764,766, filed Jun. 18, 2007.
U.S. Appl. No. 12/033,300, filed Feb. 19, 2008.
U.S. Appl. No. 12/018,150, filed Jan. 22, 2008.
U.S. Appl. No. 11/574,285, filed Feb. 26, 2007.
Sipsas et al., "Identification of Type-specific Cytotoxic Y Lymphocyte Responses . . ." J. Clin. Invest. vol. 99(4):752-762, 1997.
Chen W-J et al., "cDNA cloning and expression of the peptide-binding beta subunit of rat p21<ras>farnesyltransferase, the counterpart of yeast DPR1/RAM1," Cell 66:327-334 (1991).
Gendler S J et al., "Molecular Cloning and Expression of Human Tumor-Associated Polymorphic Epithelial Mucin," Journal of Biological Chemistry 265:15286-15293 (1990).
Karlsson et al., "Characterization of Molecularly Cloned Simian-Human Immunodeficiency Viruses Causing Rapid CD4 Lymphocyte Depletion in Rhesus Monkeys", J. Virol., 71: 4218-25, 1997.
Kawabata et al., "The Fate of Plasmid DNA After Intravenous Injection in Mice: Involvement of Scavenger Receptors in Its Hepatic Uptake," Pharm. Res., 12: 825-830, 1995.
Kent et al., "Enhanced T-Cell Immunogenicity and Protective Efficacy of a Human Immunodeficiency Virus Type 1 Vaccine Regimen Consisting of Consecutive Priming with DNA and Recombinant Fowlpox Virus," J. Virol., 72: 10180-10188, 1998.
Kern et al., "Target Structures of the CD8(+)-T-cell response to human cytomegalovirus: the 72-kilodalton major immediate-early protein revisited," J. Virol., 73: 8179-8184, 1999.
Knapp et al., "A high frequency of Mamu-A*01 in the rhesus macaque detected by polymerase chain reaction with sequence-specific primers and direct sequencing," Tissue Antigens, 50:657-661, 1997.
Korber et al., "Epidemiological and Immunological Implications of the Global Variability of HIV" *Retroviral Immunology*, B. Walker, D. Pantaleo, Eds (The Humana Press, Totowa, NH, In press), pp. 1-32, 2001.
Kuroda et al., "Analysis of Gag-specific Cytotoxic T Lymphocytes in Simian Immunodeficiency Virus-infected Rhesus Monkeys by Cell Staining with a Tetrameric Major Histocompatibility Complex Class I-Peptide Complex," J. Exp. Med., 187: 1373-1381, 1998.
Lau et al., "Cytotoxic T-cell memory without antigen", Nature, 369: 648-52, 1994.
Lechner et al., "Analysis of Successful Immune Responses in Persons Infected with Hepatitis C Virus", J. Exp. Med., 191: 1499-1512, 2000.
Letvin et al., "Cytotoxic T lymphocytes specific for the simian immunodeficiency virus", Immunol. Rev., 170: 127-34, 1999.
Letvin et al., "Potent protective anti-HIV immune responses generated by bimodal HIV envelope DNA plus protein vaccination," Proc. Natl. Acad. Sci. USA, 94: 9378-9383, 1997.
Levy et al., "Controlling HIV pathogenesis: the role of the noncytotoxic anti-HIV response of CD8 T cells", Immunol. Today, 17: 217-24, 1996.
Lew et al., "Cancer Gene Therapy Using Plasmid DNA: Pharmacokinetic Study of DNA Following Injection in Mice," Hum. Gene Ther., 6: 553, 1995.
Lewis, et al., "Limited Protection from a Pathogenic Chimeric Simian-Human Immunodeficiency Virus Challenge following Immunization with Attenuated Simian Immunodeficiency Virus", J. Virol., 73: 1262-70, 1999.
Li et al., "Infection of Cynomolgus Monkeys with a Chimeric HIV-2/SIV$_{mac}$ Virus That Expresses the HIV-1 Envelope Glycoproteins," J. of AIDS, 5: 639-646, 1992.
Lifson et al., "The Extent of Early Viral Replication Is a Critical Determinant of the Nature History of Simian Immunodeficiency Virus Infection", J. Virol., 71: 9508-14, 1997.
Ourmanov et al., "Recombinant modified vaccinia virus ankara expressing the surface gpI20 of simian immunodeficiency virus (SIV) primes for a rapid neutralizing antibody response to SIV infection in macaques," J. Virol., 74: 2960-2965, 2000.
Pal et al., "Inhibition of HIV-1 infection by the β-Chemokine MDC", Science, 278: 695-8, 1997.
Pertmer and Robinson, "Studies on Antibody Responses Following Neonatal Immunization with Influenza Hemagglutinin DNA or Protein," Virology, 257: 406-414, (1999).
Pertmer et al., "Influenza Virus Ncleoprotein-Specific Immunoglobin G Subclass and Cytokine Responses Elicited by DNA Vaccination are Dependant on the Route of Vector DNA Delivery," J. Virol., 70: 6119-6125, 1996.
Pertmer et al., "Gene gun-based nucleis acid immunication: elicitation of humoral and cytotoxic T lymphocyte responses following epidermal delivery of nanogram quantities of DNA," Vaccine, 13: 1427-1430, 1995.

(56) References Cited

OTHER PUBLICATIONS

Poignard et al., "Neutralizing Antibodies Have Limited Effects of the Control of Established HIV-1 Infection In Vivo," Immunity, 10: 431-438, 1999.

Porgador et al., "Predominant Role for Directly Transfected Dendritic Cells in Antigen Presentation to CD8+ T Cells after Gene Gun Immunization," J. Exp. Med., 188: 1075-1082, 1998.

Power et al., "A valid ELISPOT essay for enumeration of ex vivo, antigen-specific, IFNγ-producing T cells," J. Immunol. Methods, 227: 99-107, 1999.

Quinn et al., "Viral Load and Heterosexual Transmission of Human Immunodeficiency Virus Type 1", N. Eng. J. Med., 342: 921-9, 2000.

Ramshaw and Ramsey, "The prime-boost strategy: exciting prospects for improved vaccination", Immunol. Today, 21: 163-5, 2000.

Reimann et al., "An *env* Gene Derived from a Primary Human Immunodeficiency Virus Type 1 Isolate Confers High In Vivo Replicative Capacity to a Chimeric Simian/Human Immunodeficiency Virus in Rhesus Monkeys," J. Virol., 70: 3198-3206, 1996.

Reimann et al., "A Chimeric Simian/Human Immunodeficiency Virus Expressing a Primary Patient Human Immunodeficiency Virus Type 1 Isolate *env* Causes as AIDS-Like Disease after In Vivo Passage in Rhesus Monkeys," J. Virol., 70: 6922-6928, 1996.

Richmond et al., "Studies of the Neutralizing Activity and Avidity of Anti-Human Immunodeficiency Virus Type 1 Env Antibody Elicited by DNA Priming and Protein Boosting," J. Virol., 72: 9092-9100, 1998.

Robinson and Pertmer, "DNA Vaccines: Basic Studies and Applications," in *Adv. Virus Res.*, 55: 1-74, 2000.

Robinson et al., "AIDS Vaccines: Heterologous Prime/Boost Strategies for raising Protective T Cell Reponses", AIDS Reviews, 2: 105-110, 2000.

Robinson and Pertmer, "Nucleic Acid Immunizations," in *Current Protocols in Immunology*, (R. Coico, Ed.), vol. 1, pp. 2.14.1-2.14.19.3 vols. John Wiley & Sons, Inc., New York, 2001.

Robinson et al., "Protection against a lethal influenza virus challenge by immunization with a haemagglutinin-expressing plasmid DNA," Vaccine, 11: 957-960, 1993.

Markrneyer et al., "The pAX plasmids: new gene-fusion vectors for sequencing, mutagenesis and expression of proteins in *E.coli*," *Gene* 93: 129-134 (1990).

Mizuno et al., "Mutational analysis of two zinc-finger motifs in HIV type 1 nucleocapsid proteins: effects on proteolytic processing of Gag precursors and particle formation," *Aides Research and Human Retroviruses* 12(9): 793-800 (1996).

Wang et al., "Mammalian cell/vaccinia virus expression vectors with increased stability of retroviral sequences in *E.coli*; production of feline immunodeficiency virus envelope protein," *Gene* 153: 197-202 (1995).

\* cited by examiner pGA1 Sequence

```
cgacaatattggctattggccattgcatacgttgtatctatatcataatatgtacatttatattggctcatgtccaatat
gaccgccatgttgacattgattattgactagttattaatagtaatcaattacgggttcattagttcatagcccatatatg
gagttccgcgttacataacttacggtaaatggcccgcctggctgacgcccaacgaccccgcccattgacgtcaataat
gacgtatgttcccatagtaacgccaatagggactttccattgacgtcaatgggtggagtatttacggtaaactgcccact
tggcagtacatcaagtgtatcatatgccaagtccgcccccctattgacgtcaatgacggtaaatgcccgcctggcattat
gcccagtacatgaccttacgggactttcctacttggcagtacatctacggtattagtcatcggctattaccatggtgatg
cggttttggcagtacaccaatgggcgtggatagcggtttgactcacggggatttccaagtctccacccattgacgtcaa
tgggagtttgttttggcaccaaaatcaacgggactttccaaaatgtcgtaataacccgccccgttgacgcaaatgggcg
gtaggcgtgtacggtgggaggtctatataagcagagctcgtttagtgaaccgtcagatcgcctggagacgccatccacgc
tgttttgacctccatagaagacaccgggaccgatccagcctccgcggccgggaacggtgcattggaacgcggattccccg
tgccaagagtgacgtaagtaccgcctatagactctataggcacacccctttggctcttatgcatgctatactgtttttgg
cttggggcctatacaccccgcttccttatgctataggtgatggtatagcttagcctataggtgtgggttattgaccatt
attgaccactcccctattggtgacgatactttccattactaatccataacatggctcttgccacaactatctctattgg
ctatatgccaatactctgtccttcagagactgacacggactctgtattttacaggatggggtcccatttattatttaca
aattcacatatacaacaacgccgtccccgtgcccgcagttttattaaacatagcgtgggatctccacgcgaatctcgg
gtaccgtgttccggacatgggtycttctccggtagcggcggagcttccacatccgagccctggtcccatgcctccagcgg
ctcatggtcgctcggcagctccttgctcctaacagtggaggccagacttaggcacagcacaatgccaccaccaccagtg
tgccgcacaaggccgtggcggtagggtatgtgtctgaaaatgagctcggagattgggctcgcaccgctgacgcagatgga
agacttaaggcagcggcagaagaagatgcaggcagctgagttgttgtattctgataagagtcagaggtaactcccgttgc
ggtgctgttaacggtggagggcagtgtagtctgagcagtactcgttgctgccgcgcgcgccaccagacataatagctgac
agactaacagactgttcctttccatgggtcttttctgcagtcaccatcgatgcttgcaatcatggatgcaatgaagagag
ggctctgctgtgtgctgctgctgtgtggagcagtcttcgtttcggctagcccgggtgataaacggaccggcaatccct
aggctgtgccttctagttgccagccatctgttgtttgcccctccccccgtgccttccttgaccctggaaggtgccactccc
actgtccttccctaataaaatgaggaaattgcatcgcattgtctgagtaggtgtcattctattctgggggtgggtggg
gcaggacagcaaggggggaggattgggaagacaatagcaggcatgctggggatgcggtgggctctatataaaaaacgcccg
gcggcaaccgagcgttctgaacgctagagtcgacaaattcagaagaactcgtcaagaaggcgatagaaggcgatgcgctg
cgaatcgggagcggcgataccgtaaagcacgaggaagcggtcagcccattcgccgccaagctcttcagcaatatcacggg
tagccaacgctatgtcctgatagcggtctgccacacccagccggccacagtcgatgaatccagaaaagcggccatttttcc
accatgatattcggcaagcaggcatcgccatgggtcacgacgagatcctcgccgtcgggcatgctcgccttgagcctggc
gaacagttcggctggcgcgagcccctgatgctcttcgtccagatcatcctgatcgacaagaccggcttccatccgagtac
gtgctcgctcgatgcgatgtttcgcttggtggtcgaatgggcaggtagccggatcaagcgtatgcagccgccgcattgca
tcagccatgatggatactttctcggcaggagcaaggtgagatgacaggagatcctgccccggcacttcgcccaatagcag
ccagtcccttcccgcttcagtgacaacgtcgagcacagctgcgcaaggaacgcccgtcgtggccagccacgatagccgcg
ctgcctcgtcttgcagttcattcagggcaccggacaggtcggtcttgacaaaagaaccgggcgcccctgcgctgacagc
cggaacacggcggcatcagagcagccgattgtctgttgtgccagtcatagccgaatagcctctccacccaagcggccgg
agaacctgcgtgcaatccatccttgttcaatcatgcgaaacgatcctcatcctgtctcttgatcagatcttgatccctgc
gccatcagatccttggcggcaagaaagccatccagtttacttttgcagggcttcccaacctttaccagagggcgccccagct
ggcaattccggttcgcttgctgtccataaaaccgcccagtctagctatcgccatgtaagcccactgcaagctacctgctt
tctctttgcgcttgcgtttccttgtccagatagcccagtagctgacattcatccggggtcagcaccgtttctgcggac
tggctttctacgtgaaaaggatctaggtgaagatccttttgataatctcatgaccaaaatccttaacgtgagttttcg
ttccactgagcgtcagaccccgtagaaaagatcaaaggatcttcttgagatccttttttctgcgcgtaatctgctgctt
gcaaacaaaaaaaccaccgctaccagcggtggtttgtttgccggatcaagagctaccaactcttttttccgaaggtaactg
gcttcagcagagcgcagataccaaatactgttcttctagtgtagccgtagttaggccaccacttcaagaactctgtagca
ccgcctacatacctcgctctgctaatcctgttaccagtggctgctgccagtggcgataagtcgtgtcttaccgggttgga
ctcaagacgatagttaccggataaggcgcagcggtcgggctgaacggggggttcgtgcacacagcccagcttggagcgaa
cgacctacaccgaactgagatacctacagcgtgagctatgagaaagcgccacgcttcccgaagggagaaaggcggacagg
tatccggtaagcggcagggtcggaacaggagagcgcacgagggagcttccaggggaaacgcctggtatctttatagtcc
tgtcgggtttcgccacctctgacttgagcgtcgatttttgtgatgctcgtcaggggggcggagcctatggaaaaacgcca
gcaacgcggcctttttacggttcctggccttttgctggccttttgctgcacatgttgt
```

FIG. 2A pGA1 Functional Regions

| Functional region | Position within sequence (starting-and ending pos.) | Origin of sequence |
|---|---|---|
| CMVIE promoter | 1-690 | pJW4303 |
| CMV intron A | 691-1638 | pJW4303 |
| tPA leader | 1659-1721 | pJW4303 |
| Multiple cloning site | 1648-1758 Cla I-Avr II | pJW4303; mutation of Hind III and Bam HI sites and addition of Cla I and Rsr II sites to the multiple cloning site of pJW4303 |
| BGHpA | 1761-1983 | pJW4303 |
| Lambda T0 terminator | 1984-2018 | Synthetic oligonucleotide |
| Kanamycin resistance | 2039-2833 | pZErO-2 (Invitrogen) |
| ColE1 origin of replication | 3219-3892 | pZErO-2 (Invitrogen) |

FIG. 2B pGA1.1 Functional Regions

| Functional region | Position within sequence (starting-and ending pos.) | Origin of sequence |
|---|---|---|
| CMVIE promoter | 1-690 | pGA1 |
| CMV intron A | 691-1638 | pGA1 |
| tPA leader | none | |
| Multiple cloning site | 1648-1786 (Cla I-Avr II) | pGA1, addition of two EcoR I sites to pGA1 multiple cloning site |
| BGHpA | 1789-2011 | pGA1 |
| Lambda T0 terminator | 2012-2046 | pGA1 |
| Kanamycin resistance | 2067-2861 | pGA1 |
| ColE1 origin of replication | 3247-3920 | pGA1 |

FIG. 3B pGA1.1 Sequence

```
cgacaatattggctattggccattgcatacgttgtatctatatcataatatgtacatttatattggctcatgtccaatat
gaccgccatgttgacattgattattgactagttattaatagtaatcaattacgggttcattagttcatagcccatatatg
gagttccgcgttacataacttacggtaaatggcccgcctggctgaccgcccaacgaccccgcccattgacgtcaataat
gacgtatgttcccatagtaacgccaatagggactttccattgacgtcaatgggtggagtatttacggtaaactgcccact
tggcagtacatcaagtgtatcatatgccaagtccgcccctattgacgtcaatgacggtaaatggcccgcctggcattat
gcccagtacatgaccttacgggactttcctacttggcagtacatctacggtattagtcatcggctattaccatggtgatg
cggtttttggcagtacaccaatgggcgtggatagcggtttgactcacggggatttccaagtctccacccattgacgtcaa
tgggagtttgttttggcaccaaaatcaacgggactttccaaaatgtcgtaataaccccgcccgttgacgcaaatgggcg
gtaggcgtgtacggtgggaggtctatataagcagagctcgtttagtgaaccgtcagatcgcctggagacgccatccacgc
tgttttgacctccatagaagacaccgggaccgatccagcctccgcggccgggaacggtgcattggaacgcggattcccg
tgccaagagtgacgtaagtaccgcctatagactctataggcacacccctttggctcttatgcatgctatactgttttttgg
cttggggcctatacaccccccgcttccttatgctataggtgatggtatagcttagcctataggtgtgggttattgaccatt
attgaccactcccctattggtgacgatactttccattactaatccataacatggctctttgccacaactatctctattgg
ctatatgccaatactctgtccttcagagactgacacggactctgtattttttacaggatggggtcccatttattatttaca
aattcacatatacaacaacgccgtcccccgtgcccgcagttttttattaaacatagcgtgggatctccacgcgaatctcgg
gtaccgtgttccggacatgggytcttctccggtagcggcggagcttccacatccgagccctggtcccatgcctccagcgg
ctcatggtcgctcggcagctccttgctcctaacagtggaggccagacttaggcacagcacaatgcccaccaccaccagtg
tgccgcacaaggccgtggcggtagggtatgtgtctgaaaatgagctcggagattgggctcgcaccgtgacgcagatgga
agacttaaggcagcggcagaagaagatgcaggcagctgagttgttgtattctgataagagtcagaggtaactcccgttgc
ggtgctgttaacggtggagggcagtgtagtctgagcagtactcgttgctgccgcgcgcgccaccagacataatagctgac
agactaacagactgttcctttccatgggtcttttctgcagtcaccatcgatgcttgcaatcatggatgcaatgaagagag
ggctctgctgtgtgctgctgctgtgtggagaattcttcgtttctgctgcgtgtgtggagaattcttcgtttcggctagcc
cgggtgataaacggaccgcgcaatccctaggctgtgccttctagttgccagccatctgttgtttgcccctccccccgtgcc
ttccttgaccctggaaggtgccactcccactgtccttcctaataaaatgaggaaattgcatcgcattgtctgagtaggt
gtcattctattctgggggggtggggtggggcaggacagcaaggggaggattgggaagacaatagcaggcatgctggggat
gcggtgggctctatataaaaaacgcccggcggcaaccgagcgttctgaacgctagagtcgacaaattcagaagaactcgt
caagaaggcgatagaaggcgatgcgctgcgaatcgggagcggcgataccgtaaagcacgaggaagcggtcagcccattcg
ccgccaagctcttcagcaatatcacgggtagcaacgctatgtcctgatagcggtctgccacacccagccggccacagtc
gatgaatccagaaaagcggccatttttccaccatgatattcggcaagcaggcatcgccatgggtcacgacgagatcctcgc
cgtcgggcatgctcgccttgagcctggcgaacagttcggctggcgcgagcccctgatgctcttcgtccagatcatcctga
tcgacaagaccggcttccatccgagtacgtgctcgctcgatgcgatgtttcgcttggtggtcgaatgggcaggtagccgg
atcaagcgtatgcagccgccgcattgcatcagccatgatggatactttctcggcaggagcaaggtgagatgacaggagat
cctgccccggcacttcgcccaatagcagtccctccgcttcagtgacaacgtcgagcacagctgcgcaaggaacg
cccgtcgtggccagccacgatagcgcgctgcctcgtcttgcagttcattcagggcaccggacaggtcggtcttgacaaa
aagaaccgggcgcccctgcgctgacagccggaacacggcggcatcagagcagccgattgtctgttgtgcccagtcatagc
cgaatagcctctccacccaagcggccggagaacctgcgtgcaatccatcttgttcaatcatgcgaaacgatcctcatcct
gtctcttgatcagatcttgatcccctgcgccatcagatccttggcggcaagaaagccatccagtttactttgcagggcttt
cccaaccttaccagagggcgccccagctggcaattccggttcgcttgctgtccataaaaccgcccagtctagctatcgcc
atgtaagcccactgcaagctacctgctttctcttttgcgttgcgttttccttgtccagatagcccagtagctgacattc
atccggggtcagcaccgtttctgcggactggctttctacgtgaaaaggatctaggtgaagatccttttttgataatctcat
gaccaaaatcccttaacgtgagttttcgttccactgagcgtcagaccccgtagaaaagatcaaaggatcttcttgagatc
cttttttttctgcgcgtaatctgctgcttgcaaacaaaaaaaccaccgctaccagcggtggtttgtttgccggatcaagag
ctaccaactctttttccgaaggtaactggcttcagcagagcgcagataccaaatactgttcttctagtgtagccgtagtt
aggccaccacttcaagaactctgtagcaccgcctacatacctcgctctgctaatcctgttaccagtggctgctgccagtg
gcgataagtcgtgtcttaccgggttggactcaagacgatagttaccggataaggcgcagcggtcgggctgaacgggggt
tcgtgcacacagcccagcttggagcgaacgacctacaccgaactgagatacctacagcgtgagctatgagaaagcgccac
gcttcccgaagggagaaaggcggacaggtatccggtaagcggcagggtcggaacaggagagcgcacgagggagcttccag
ggggaaacgcctggtatctttatagtcctgtcgggtttcgccacctctgacttgagcgtcgattttgtgatgctcgtca
ggggggcggagcctatggaaaaacgccagcaacgcggccttttacggttcctggccttttgctggccttttgctcacat
gttgt
```

FIG. 3A pGA1.2 Sequence

```
cgacaatattggctattggccattgcatacgttgtatctatatcataatatgtacatttatattggctcatgtccaatat
gaccgccatgttgacattgattattgactagttattaatagtaatcaattacgggttcattagttcatagcccatatatg
gagttccgcgttacataacttacggtaaatggcccgcctggctgaccgcccaacgaccccgcccattgacgtcaataat
gacgtatgttcccatagtaacgccaatagggactttccattgacgtcaatgggtggagtatttacggtaaactgcccact
tggcagtacatcaagtgtatcatatgccaagtccgcccctattgacgtcaatgacggtaaatggcccgcctggcattat
gcccagtacatgaccttacgggactttcctacttggcagtacatctacggtattagtcatcggctattaccatggtgatg
cggttttggcagtacaccaatgggcgtggatagcggtttgactcacggggatttccaagtctccacccattgacgtcaa
tgggagtttgttttggcaccaaaatcaacgggactttccaaaatgtcgtaataaccccgccccgttgacgcaaatgggcg
gtaggcgtgtacggtgggaggtctatataagcagagctcgtttagtgaaccgtcagatcgcctggagacgccatccacgc
tgttttgacctccatagaagacaccgggaccgatccagcctccgcggccgggaacggtgcattggaacgcggattccccg
tgccaagagtgacgtaagtaccgcctatagactctataggcacaccccttttggctcttatgcatgctatactgtttttgg
cttggggcctatacacccccgcttccttatgctataggtgatggtatagcttagcctataggtgtgggttattgaccatt
attgaccactccccctattggtgacgatactttccattactaatccataacatggctctttgccacaactatctctattgg
ctatatgccaatactctgtccttcagagactgacacggactctgtatttttacaggatggggtcccatttattatttaca
aattcacatatacaacaacgccgtccccgtgcccgcagttttttattaaacatagcgtgggatctccacgcgaatctcgg
gtaccgtgttccggacatgggytcttctccggtagcggcggagcttccacatccgagccctggtcccatgcctccagcgg
ctcatggtcgctcggcagctccttgctcctaacagtggaggccagacttaggcacagcacaatgcccaccaccaccagtg
tgccgcacaaggccgtggcggtagggtatgtgtctgaaaatgagctcggagattgggctcgcaccgctgacgcagatgga
agacttaaggcagcggcagaagaagatgcaggcagctgagttgttgtattctgataagagtcagaggtaactcccgttgc
ggtgctgttaacggtggagggcagtgtagtctgagcagtactcgttgctgccgcgcgcgccaccagacataatagctgac
agactaacagactgttcctttccatgggtcttttctgcagtcaccatggatccttgcactcgaggatgcaatgaagagag
ggctctgctgtgtgctgctgctgtgtggagaattcttcgtttctgctgctgtgtggagaattcttcgtttcggctagccc
cgggtgataaacggaccgcgcaatccctaggctgtgccttctagttgccagccatctgttgtttgcccctccccgtgcc
ttccttgaccctggaaggtgccactcccactgtcctttcctaataaaatgaggaaattgcatcgcattgtctgagtaggt
gtcattctattctgggggtgggtggggcaggacagcaaggggggaggattgggaagacaatagcaggcatgctgggat
gcggtgggctctatataaaaaacgccggcggcaaccgagcgttctgaacgctagagtcgacaaattcagaagaactcgt
caagaaggcgatagaaggcgatgcgctgcgaatcgggagcggcgataccgtaaagcacgaggaagcggtcagcccattcg
ccgccaagctcttcagcaatatcacgggtagccaacgctatgtcctgatagcggtctgccacacccagccggccacagtc
gatgaatccagaaaagcggccatttccaccatgatatttcggcaagcaggcatcgccatgggtcacgacgagatcctcgc
cgtcgggcatgctcgccttgagcctggcgaacagttcggctggcgcgagcccctgatgctcttcgtccagatcatcctga
tcgacaagaccggcttccatccgagtacgtgctcgctcgatgcgatgtttcgcttggtggtcgaatgggcaggtagccgg
atcaagcgtatgcagccgccgcattgcatcagccatgatggatactttctcggcaggagcaaggtgagatgacaggagat
cctgccccggcacttcgcccaatagcagccagtcccttcccgcttcagtgacaacgtcgagcacagctgcgcaaggaacg
cccgtcgtggccagccacgatagccgcgctgcctcgtcttgcagttcattcagggcaccggacaggtcggtcttgacaaa
aagaaccgggcgcccctgcgctgacagccggaacacggcggcatcagagcagccgattgtctgttgtgcccagtcatagc
cgaatagcctctcaccaagcggccggagaacctgcgtgcaatccatcttgttcaatcatgcgaaacgatcctcatcct
gtctcttgatcagatcttgatccctgcgccatcagatccttggcggcaagaaagccatccagtttactttgcagggctt
cccaaccttaccagagggcgcccagctggcaattccggttcgcttgctgtccataaaaccgcccagtctagctatcgcc
atgtaagcccactgcaagctacctgctttctctttgcgcttgcgttttcccttgtccagatagcccagtagctgacattc
atccggggtcagcaccgtttctgcggactggctttctacgtgaaaaggatctaggtgaagatcctttttgataatctcat
gaccaaaatcccttaacgtgagttttcgttccactgagcgtcagaccccgtagaaaagatcaaaggatcttcttgagatc
ctttttttctgcgcgtaatctgctgcttgcaaacaaaaaaaccaccgctaccagcggtggtttgtttgccggatcaagag
ctaccaactcttttttccgaaggtaactggcttcagcagagcgcagataccaaatactgttcttctagtgtagccgtagtt
aggccaccacttcaagaactctgtagcaccgcctacatacctcgctctgctaatcctgttaccagtggctgctgccagtg
gcgataagtcgtgtcttaccgggttggactcaagacgatagttaccggataaggcgcagcggtcgggctgaacgggggt
tcgtgcacacagcccagcttggagcgaacgacctacaccgaactgagatacctacagcgtgagctatgagaaagcgccac
gcttcccgaagggagaaaggcggacaggtatccggtaagcggcagggtcggaacaggagagcgcacgagggagcttccag
ggggaaacgcctggtatctttatagtcctgtcgggtttcgccacctctgacttgagcgtcgatttttgtgatgctcgtca
gggggcggagcctatggaaaaacgccagcaacgcggcccttttacggttcctggccttttgctggccttttgctcacat
gttgt
```

FIG. 4A pGA1.2 Functional Regions

| Functional region | Position within sequence (starting-and ending pos.) | Origin of sequence |
|---|---|---|
| CMVIE promoter | 1-690 | pGA1.1 |
| CMV intron A | 691-1638 | pGA1.1 |
| tPA leader | none | |
| Multiple cloning site | 1648-1786 (Bam HI-Avr II) | pGA1.1, addition of Bam HI and Xho I sites to pGA1.1 multiple cloning site |
| BGHpA | 1789-2011 | pGA1.1 |
| Lambda T0 terminator | 2012-2046 | pGA1.1 |
| Kanamycin resistance | 2067-2861 | pGA1.1 |
| ColE1 origin of replication | 3247-3920 | pGA1.1 |

FIG. 4B

PGA2 functional regions

| Functional region | Position within sequence (starting-and ending pos.) | Origin of sequence |
|---|---|---|
| CMVIE promoter | 1-687 | pGA1 |
| tPA leader | 712-774 | pGA1 |
| Multiple cloning site | 698-808 Cla I-Avr II | pGA1 |
| BGHpA | 814-1036 | pGA1 |
| Lambda T0 terminator | 1037-1071 | pGA1 |
| Kanamycin resistance | 1089-1883 | pGA1 |
| ColE1 origin of replication | 2269-2942 | pGA1 |

FIG. 6B pGA2 Sequence cgacaatattggctattggccattgcatacgttgtatctatatcataatatgtacatttatattggctcatgtccaatat
gaccgccatgttgacattgattattgactagttattaatagtaatcaattacggggtcattagttcatagcccatatatg
gagttccgcgttacataacttacggtaaatggcccgcctggctgaccgcccaacgaccccgcccattgacgtcaataat
gacgtatgttcccatagtaacgccaatagggactttccattgacgtcaatgggtggagtatttacggtaaactgcccact
tggcagtacatcaagtgtatcatatgccaagtccgcccctattgacgtcaatgacggtaaatggcccgcctggcattat
gcccagtacatgaccttacgggactttcctacttggcagtacatctacgtattagtcatcgctattaccatggtgatgcg
gtttggcagtacaccaatgggcgtggatagcggtttgactcacggggatttccaagtctccaccccattgacgtcaatg
ggagtttgttttggcaccaaaatcaacgggactttccaaaatgtcgtaataaccccgccccgttgacgcaaatgggcggt
aggcgtgtacggtgggaggtctatataagcagagctcgtttagtgaactcattctatcgatgcttgcaatcatggatgca
atgaagagagggctctgctgtgtgctgctgctgtgtggagcagtcttcgtttcggctagccccgggtgataaacggaccg
cgcaatccctaggctgtgccttctagttgccagccatctgttgtttgccccctccccccgtgccttccttgaccctggaagg
tgccactcccactgtccttcctaataaaatgaggaaattgcatcgcattgtctgagtaggtgtcattctattctgggggg
gtgggtggggcaggacagcaaggggggaggattgggaagacaatagcaggcatgctggggatgcggtgggctctatataa
aaaacgcccggcggcaaccgagcgttctgaacgctagagtcgacaaattcagaagaactcgtcaagaaggcgatagaagg
cgatgcgctgcgaatcgggagcggcgataccgtaaagcacgaggaagcggtcagcccattcgccgccaagctcttcagca
atatcacgggtagccaacgctatgtcctgatagcggtctgccacacccagccggccacagtcgatgaatccagaaaagcg
gccatttccaccatgatattcggcaagcaggcatcgccatgggtcacgacgagatcctcgccgtcgggcatgctcgcct
tgagcctggcgaacagttcggctggcgcgagcccctgatgctcttcgtccagatcatcctgatcgacaagaccggcttcc
atccgagtacgtgctcgctcgatgcgatgtttcgcttggtggtcgaatgggcaggtagccggatcaagcgtatgcagccg
ccgcattgcatcagccatgatggatactttctcggcaggagcaaggtgagatgacaggagatcctgccccggcacttcgc
ccaatagcagccagtccttcccgcttcagtgacaacgtcgagcacagctgcgcaaggaacgcccgtcgtggccagccac
gatagccgcgctgcctcgtcttgcagttcattcagggcaccggacaggtcggtcttgacaaaaagaaccgggcgcccctg
cgctgacagccggaacacggcggcatcagagcagccgattgtctgttgtgcccagtcatagccgaatagcctctccacc
aagcggccggagaacctgcgtgcaatccatccttgttcaatcatgcgaaacgatcctcatcctgtctcttgatcagatctt
gatcccctgcgccatcagatccttggcggcaagaaagccatccagtttactttgcagggcttcccaaccttaccagaggg
cgccccagctggcaattccggttcgcttgctgtccataaaaccgcccagtctagctatcgccatgtaagcccactgcaag
ctacctgctttctctttgcgcttgcgttttccccttgtccagatagcccagtagctgacattcatccgggtcagcaccgt
ttctgcggactggctttctacgtgaaaaggatctaggtgaagatccttttttgataatctcatgaccaaaatcccttaacg
tgagttttcgttccactgagcgtcagaccccgtagaaaagatcaaaggatcttcttgagatccttttttttctgcgcgtaa
tctgctgcttgcaaacaaaaaaaccaccgctaccagcggtggtttgtttgccggatcaagagctaccaactcttttttccg
aaggtaactggcttcagcagagcgcagataccaaatactgttcttctagtgtagccgtagttaggccaccacttcaagaa
ctctgtagcaccgcctacatacctcgctctgctaatcctgttaccagtggctgctgccagtggcgataagtcgtgtctta
ccgggttggactcaagacgatagttaccggataaggcgcagcggtcgggctgaacggggggttcgtgcacacagcccagc
ttggagcgaacgacctacaccgaactgagatacctacagcgtgagctatgagaaagcgccacgcttcccgaagggagaaa
ggcggacaggtatccggtaagcggcagggtcggaacaggagagcgcacgagggagcttccaggggggaaacgcctggtatc
tttatagtcctgtcgggtttcgccacctctgacttgagcgtcgatttttgtgatgctcgtcaggggggcggagcctatgg
aaaaacgccagcaacgcggccttttacggttcctggccttttgctggccttttgctcacatgttgt

FIG. 6A pGA2.1 Sequence

```
cgacaatattggctattggccattgcatacgttgtatctatatcataatatgtacatttatattggctcatgtccaatat
gaccgccatgttgacattgattattgactagttattaatagtaatcaattacggggtcattagttcatagcccatatatg
gagttccgcgttacataacttacggtaaatggcccgcctggctgaccgcccaacgaccccgcccattgacgtcaataat
gacgtatgttcccatagtaacgccaatagggactttccattgacgtcaatgggtggagtatttacggtaaactgcccact
tggcagtacatcaagtgtatcatatgccaagtccgcccccattgacgtcaatgacggtaaatggcccgcctggcattat
gcccagtacatgaccttacgggactttcctacttggcagtacatctacgtattagtcatcgctattaccatggtgatgcg
gtttggcagtacaccaatgggcgtggatagcggtttgactcacggggatttccaagtctccacccattgacgtcaatg
ggagtttgttttggcaccaaaatcaacgggactttccaaaatgtcgtaataaccccgccccgttgacgcaaatgggcggt
aggcgtgtacggtgggaggtctatataagcagagctcgtttagtgaactcattctatcgatgcttgcaatcatggatgca
atgaagagagggctctgctgtgtgctgctgctgtgtggagaattcttcgtttcggctgctgctgtgtggagaattcttcg
tttcggctagccccgggtgataaacggaccgcgcaatccctaggctgtgccttctagttgccagccatctgttgtttgcc
cctcccccgtgccttccttgaccctggaaggtgccactcccactgtcctttcctaataaaatgaggaaattgcatcgcat
tgtctgagtaggtgtcattctattctgggggtgggtgggcaggacagcaaggggggaggattgggaagacaatagcag
gcatgctggggatgcggtgggctctatataaaaaacgcccggcggcaaccgagcgttctgaacgctagagtcgacaaatt
cagaagaactcgtcaagaaggcgatagaaggcgatgcgctgcgaatcgggagcggcgataccgtaaagcacgaggaagcg
gtcagcccattcgccgccaagctcttcagcaatatcacgggtagccaacgctatgtcctgatagcggtctgccacaccca
gccggccacagtcgatgaatccagaaaagcggccattttccaccatgatattcggcaagcaggcatcgccatgggtcacg
acgagatcctcgccgtcgggcatgctcgccttgagcctggcgaacagttcggctggcgcgagcccctgatgctcttcgtc
cagatcatcctgatcgacaagaccggcttccatccgagtacgtgctcgctcgatgcgatgtttcgcttggtggtcgaatg
ggcaggtagccggatcaagcgtatgcagccgccgcattgcatcagccatgatggatactttctcggcaggagcaaggtga
gatgacaggagatcctgccccggcacttcgcccaatagcagccagtcccttcccgcttcagtgacaacgtcgagcacagc
tgcgcaaggaacgcccgtcgtggccagccacgatagccgcgctgcctcgtcttgcagttcattcagggcaccggacaggt
cggtcttgacaaaaagaaccgggcgcccctgcgctgacagccggaacacggcggcatcagagcagccgattgtctgttgt
gcccagtcatagccgaatagcctctccacccaagcggccggagaacctgcgtgcaatccatcttgttcaatcatgcgaaa
cgatcctcatcctgtctcttgatcagatcttgatccctgcgccatcagatccttggcggcaagaaagccatccagttta
ctttgcagggcttcccaaccttaccagagggcgccccagctggcaattccggttcgcttgctgtccataaaaccgcccag
tctagctatcgccatgtaagcccactgcaagctacctgctttctctttgcgcttgcgttttccttgtccagatagccca
gtagctgacattcatccggggtcagcaccgtttctgcggactggctttctacgtgaaaaggatctaggtgaagatccttt
ttgataatctcatgaccaaaatcccttaacgtgagttttcgttccactgagcgtcagaccccgtagaaaagatcaaagga
tcttcttgagatcctttttttctgcgcgtaatctgctgcttgcaaacaaaaaaaccaccgctaccagcggtggtttgttt
gccggatcaagagctaccaactcttttttccgaaggtaactggcttcagcagagcgcagataccaaatactgttcttctag
tgtagccgtagttaggccaccacttcaagaactctgtagcaccgcctacatacctcgctctgctaatcctgttaccagtg
gctgctgccagtggcgataagtcgtgtcttaccgggttggactcaagacgatagttaccggataaggcgcagcggtcggg
ctgaacggggggttcgtgcacacagcccagcttggagcgaacgacctacaccgaactgagatacctacagcgtgagctat
gagaaagcgccacgcttcccgaagggagaaaggcggacaggtatccggtaagcggcagggtcggaacaggagagcgcacg
agggagcttccaggggaaacgcctggtatctttatagtcctgtcgggtttcgccacctctgacttgagcgtcgatttt
gtgatgctcgtcaggggggcggagcctatggaaaaacgccagcaacgcggccttttacggttcctggccttttgctggc
cttttgctcacatgttgt
```

FIG. 7A

PGA2.1 functional regions

| Functional region | Position within sequence (starting-and ending pos.) | Origin of sequence |
|---|---|---|
| CMVIE promoter | 1-687 | PGA2 |
| tPA leader | None | |
| Multiple cloning site | 698-839 Cla I-Avr II | PGA2, addition of two EcoR I sites to pGA2 multiple cloning site |
| BGHpA | 842-1064 | PGA2 |
| Lambda T0 terminator | 1065-1099 | PGA2 |
| Kanamycin resistance | 1914-1120 | PGA2 |
| ColE1 origin of replication | 2300-2973 | PGA2 |

FIG. 7B

PGA2.2 functional regions

| Functional region | Position within sequence (starting-and ending pos.) | Origin of sequence |
|---|---|---|
| CMVIE promoter | 1-687 | PGA2.1 |
| tPA leader | None | |
| Multiple cloning site | 698-839 Bam HI-Avr II | PGA2.1, addition of Bam HI and Xho I sites to pGA2.1 multiple cloning site |
| BGHpA | 842-1064 | PGA2.1 |
| Lambda T0 terminator | 1065-1099 | PGA2.1 |
| Kanamycin resistance | 1914-1120 | PGA2.1 |
| ColE1 origin of replication | 2300-2973 | PGA2.1 |

FIG. 8B pGA2.2 Sequence

```
cgacaatattggctattggccattgcatacgttgtatctatatcataatatgtacatttatattggctcatgtccaatat
gaccgccatgttgacattgattattgactagttattaatagtaatcaattacggggtcattagttcatagcccatatatg
gagttccgcgttacataacttacggtaaatggcccgcctggctgaccgcccaacgaccccgcccattgacgtcaataat
gacgtatgttcccatagtaacgccaatagggactttccattgacgtcaatgggtggagtatttacggtaaactgcccact
tggcagtacatcaagtgtatcatatgccaagtccgcccccctattgacgtcaatgacggtaaatggcccgcctggcattat
gcccagtacatgaccttacgggactttcctacttggcagtacatctacgtattagtcatcgctattaccatggtgatgcg
gttttggcagtacaccaatgggcgtggatagcggtttgactcacggggatttccaagtctccaccccattgacgtcaatg
ggagtttgttttggcaccaaaatcaacgggactttccaaaatgtcgtaataaccccgccccgttgacgcaaatgggcggt
aggcgtgtacggtgggaggtctatataagcagagctcgtttagtgaactcattctatggatccttgctcgagtggatgca
atgaagagagggctctgctgtgtgctgctgctgtgtggagaattcttcgtttcggctgctgctgtgtggagaattcttcg
tttcggctagccccgggtgataaacggaccgcgcaatccctaggctgtgccttctagttgccagccatctgttgtttgcc
cctcccccgtgccttccttgaccctggaaggtgccactcccactgtcctttcctaataaaatgaggaaattgcatcgcat
tgtctgagtaggtgtcattctattctgggggtggggtggggcaggacagcaaggggggaggattgggaagacaatagcag
gcatgctggggatgcggtgggctctatataaaaaacgcccggcggcaaccgagcgttctgaacgctagagtcgacaaatt
cagaagaactcgtcaagaaggcgatagaaggcgatgcgctgcgaatcgggagcggcgataccgtaaagcacgaggaagcg
gtcagcccattcgccgccaagctcttcagcaatatcacgggtagccaacgctatgtcctgatagcggtctgccacaccca
gccggccacagtcgatgaatccagaaaagcggccattttccaccatgatattcggcaagcaggcatcgccatgggtcacg
acgagatcctcgccgtcgggcatgctcgccttgagcctggcgaacagttcggctggcgcgagcccctgatgctcttcgtc
cagatcatcctgatcgacaagaccggcttccatccgagtacgtgctcgctcgatgcgatgtttcgcttggtggtcgaatg
ggcaggtagccggatcaagcgtatgcagccgccgcattgcatcagccatgatggatactttctcggcaggagcaaggtga
gatgacaggagatcctgccccggcacttcgcccaatagcagccagtcccttcccgcttcagtgacaacgtcgagcacagc
tgcgcaaggaacgcccgtcgtggccagccacgatagccgcgctgcctcgtcttgcagttcattcagggcaccggacaggt
cggtcttgacaaaaagaaccgggcgcccctgcgctgacagccggaacacggcggcatcagagcagccgattgtctgttgt
gcccagtcatagccgaatagcctctccaccccaagcggccggagaacctgcgtgcaatccatcttgttcaatcatgcgaaa
cgatcctcatcctgtctcttgatcagatcttgatccctcgcgccatcagatccttggcggcaagaaagccatccagttta
ctttgcagggcttcccaaccttaccagagggcgcccagctggcaattccggttcgcttgctgtccataaaaccgcccag
tctagctatcgccatgtaagcccactgcaagctacctgctttctctttgcgcttgcgttttcccttgtccagatagccca
gtagctgacattcatccggggtcagcaccgtttctgcggactggctttctacgtgaaaaggatctaggtgaagatcctt
ttgataatctcatgaccaaaatcccttaacgtgagttttcgttccactgagcgtcagaccccgtagaaaagatcaaagga
tcttcttgagatccttttttttctgcgcgtaatctgctgcttgcaaacaaaaaaaccaccgctaccagcggtggttttgttt
gccggatcaagagctaccaactctttttccgaaggtaactggcttcagcagagcgcagataccaaatactgttcttctag
tgtagccgtagttaggccaccacttcaagaactctgtagcaccgcctacatacctcgctctgctaatcctgttaccagtg
gctgctgcagtggcgataagtcgtgtcttaccgggttggactcaagacgatagttaccggataaggcgcagcggtcggg
ctgaacggggggttcgtgcacacagcccagcttggagcgaacgacctacaccgaactgagatacctacagcgtgagctat
gagaaagcgccacgcttcccgaagggagaaaggcggacaggtatccggtaagcggcagggtcggaacaggagagcgcacg
agggagcttccaggggggaaacgcctggtatctttatagtcctgtcgggtttcgccacctctgacttgagcgtcgatttt
gtgatgctcgtcagggggcggagcctatggaaaaacgccagcaacgcggccttttacggttcctggccttttgctggc
cttttgctcacatgttgt
```

FIG. 8A

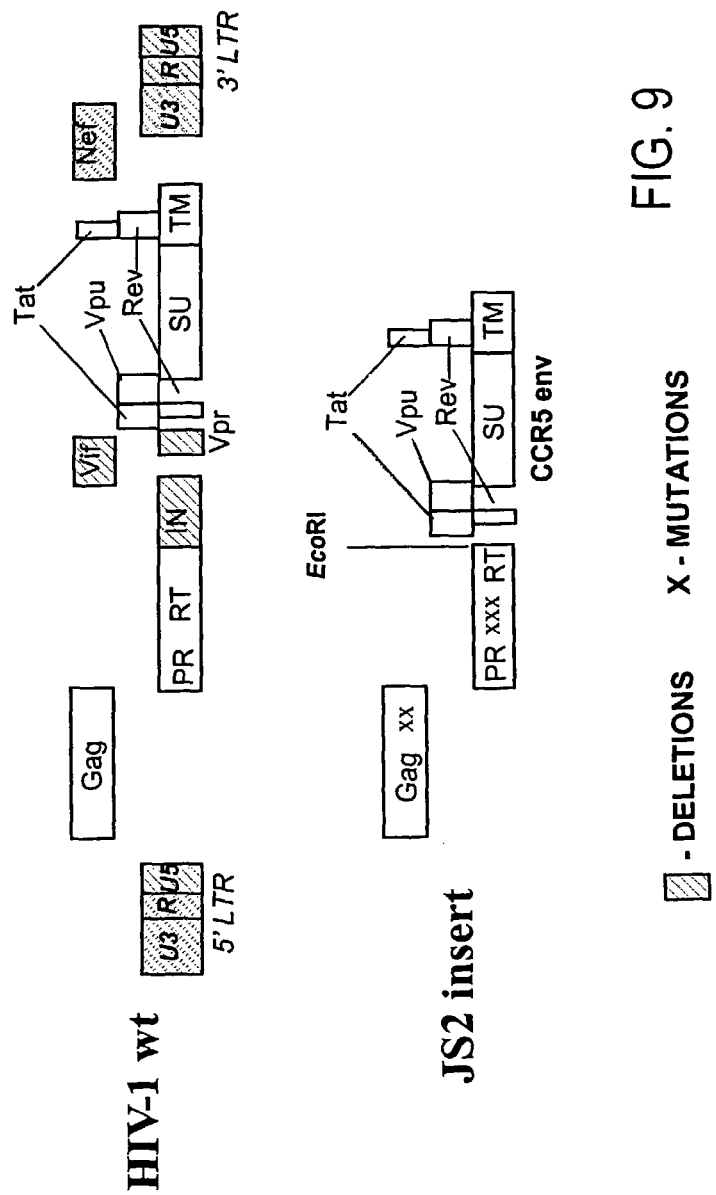

pGA2/JS2 sequence

```
atcgatgcaggactcggcttgctgaagcgcgcacggcaagaggcgaggggcggcgactggtgggtacgccaaaaattttg
actagcggaggctagaaggagagagatgggtgcgagagcgtcagtattaagcgggggagaattagatcgatgggaaaaaa
ttcggttaaggccagggggaaagaaaaaatataaattaaaacatatagtatgggcaagcagggagctagaacgattcgca
gttaatcctggcctgttagaaacatcagaaggctgtagacaaatactgggacagctacaaccatccttcagacaggatc
agaagaacttagatcattatataatacagtagcaaccctctattgtgtgcatcaaaggatagagataaaagacaccaagg
aagctttagacaagatagaggaagagcaaaacaaaagtaagaaaaaagcacagcaagcagcagctgacacaggacacagc
agtcaggtcagccaaaattaccctatagtgcagaacatccaggggcaaatggtacatcaggccatatcacctagaacttt
aaatgcatgggtaaaagtagtagaagagaaggctttcagcccagaagtaatacccatgttttcagcattatcagaaggag
ccaccccacaagatttaaacaccatgctaaacacagtggggggacatcaagcagccatgcaaatgttaaaagagaccatc
aatgaggaagctgcagaatgggatagagtacatccagtgcatgcagggcctattgcaccaggccagatgagagaaccaag
gggaagtgacatagcaggaactactagtacccttcaggaacaaataggatggatgacaaataatccacctatcccagtag
gagaaatttataaaagatggataatcctgggattaaataaaatagtaagaatgtatagccctaccagcattctggacata
agacaaggaccaaaagaacctttttagagactatgtagaccggttctataaaactctaagagccgagcaagcttcacagga
ggtaaaaaattggatgacagaaaccttgttggtccaaaatgcgaacccagattgtaagactattttaaaagcattgggac
cagcggctacactagaagaaatgatgacagcatgtcagggagtaggaggaccggccataaggcaagagttttggctgaa
gcaatgagccaagtaacaaatacagctaccataatgatgcagagaggcaattttaggaaccaaagaaagatggttaagag
cttcaatagcggcaaagaagggcacacagccagaaattgcagggcccctaggaaaaagggcagctggaaaagcggaaagg
aaggacaccaaatgaaagattgtactgagagacaggctaatttttagggaagatctggccttcctacaagggaaggcca
gggaattttcttcagagcagaccagagccaacagccccaccatttcttcagagcagaccagagccaacagccccaccaga
agagagcttcaggtctggggtagagacaacaactccccctcagaagcaggagccgatagacaaggaactgtatccttaa
cttccctcagatcactctttggcaacgaccctctcgtcacaataaagataggggggcaactaaaggaagctctattagata
caggagcagatgatacagtattagaagaaatgagtttgccaggaagatggaaaccaaaaatgatagggggaattggaggt
tttatcaaagtaagacagtatgatcagatactcatagaaatctgtggacataaagctataggtacagtattagtaggacc
tacacctgtcaacataattggaagaaatctgttgactcagattggttgcactttaaattttcccattagccctattgaga
ctgtaccagtaaaattaaagccaggaatggatggcccaaaagttaaacaagttaaaacactaccactaaccagaagaagca
ttagtagaaatttgtacagaaatggaaaaggaaggaaaaatttcaaaaattgggcctgagaatccatacaatactccagt
atttgccataaagaaaaaagacagtactaaatggagaaaattagtagatttcagagaacttaataagagaactcaagact
tctgggaagttcaattaggaataccacatcccgcaggggttaaaaagaaaaaatcagtaacagtactggatgtgggtgat
gcatatttttcagttcccttagatgaagacttcaggaagtatactgcatttaccatacctagtataaacaatgagacacc
agggattagatatcagtacaatgtgcttccacaggatggaaaggatccaccagcaatattccaaagtagcatgacaaaaa
tcttagagcctttttaaaaaacaaaatccagacatagttatctatcaatacatgaacgatttgtatgtaggatctgactta
gaaatagggcagcatagaacaaaaatagaggagctgagacaacatctgttgaggtggggacttaccacaccagacaaaaa
acatcagaaagaacctccattcctttggatgggttatgaactccatcctgataaatggacagtacagcctatagtgctgc
cagaaaaagacagctggactgtcaatgacatacagaagttagtggggaaattgaataccgcaagtcagatttacccaggg
attaaagtaaggcaattatgtaaactccttagaggaaccaaagcactaacagaagtaataccactaacagaagaagcaga
gctagaactggcagaaaacagagagattctaaaagaaccagtacatggtgtattatgacccatcaaaagacttaatag
cagaaatacagaagcaggggcaaggccaatggacatatcaaatttatcaagagccatttaaaaatctgaaaacaggaaaa
tatgcaagaatgaggggtgcccacactaatgatgtaaaacaattaacagaggcagtgcaaaaaataaccacagaaagcat
agtaatatggggaaagactcctaaatttaaactacccatacaaaaggaaacatgggaaacatggtggacagagtattggc
aagccacctggattcctgagtgggagtttgttaatacccctcctttagtgaaattatggtaccagttagagaaagaaccc
atagtaggagcagaaaccttctatgtagatggggcagctaacagggagactaaattaggaaaagcaggatatgttactaa
caaaggaagacaaaaggttgtccccctaactaacacaacaaatcagaaaactcagttacaagcaatttatctagctttgc
aggattcaggattagaagtaaacatagtaacagactcacaatatgcattaggaatcattcaagcacaaccagataaaagt
gaatcagagttagtcaatcaaataatagagcagttaataaaaaaggaaaaggtctatctggcatgggtaccagcacacaa
aggaattggaggaaatgaacaagtagataaattagtcagtgctggaatcaggaaaatactatttttagatggaatagata
aggcccaagatgaacattagaattctgcaacaactgctgtttatccatttttcagaatttgggtgtcgacatagcagaatag
gcgttactcgacagaggagagcaagaaatggagccagtagatcctagactagagccctggaagcatccaggaagtcagcc
taaaactgcttgtaccaattgctattgtaaaaagtgttgctttcattgccaagtttgtttcataacaaaagccttaggca
tctcctatggcaggaagaagcggagacagcgacgaagacctcctcaagacagtcagactcatcaagtttctctatcaaag
cagtaagtagtaaatgtaatgcaacctttacaaatattagcaatagtagcattagtagtagcagcaataatagcaatagt
tgtgtggaccatagtattcatagaatataggaaaatattaagacaaagaaaaatagacaggttaattgataggataacag
aaagagcagaagacagtggcaatgaaagtgaagggggatcaggaagaattatcagcacttgtggaaatggggcatcatgct
ccttgggatgttgatgatctgtagtgctgtagaaaattgtgggtcacagtttattatgggtacctgtgtggaaagaag
caaccaccactctattttgtgcatcagatgctaaagcatatgatacagaggtacataatgtttgggccacacatgcctgt
gtacccacagaccccaacccacaagaagtagtattggaaaatgtgacagaaaattttaacatgtgaaaaataacatggt
agaacagatgcatgaggatataatcagtttatgggatcaaagcctaaagccatgtgtaaaattaaccccactctgtgtta
ctttaaattgcactgatttgaggaatgttactaatatcaataatagtagtgagggaatgagaggagaaataaaaaactgc
tcttttcaatatcaccacaagcataagagataaggtgaagaaagactatgcactttttttatagacttgatgtagtaccaat
agataatgataatactagtaggttgataaattgtaatacctcaaccattacacaggcctgtccaaaggtatccttttg
agccaattcccatacattattgtaccccggctggttttgcgattctaaagtgtaaagacaagaagttcaatggaacaggg
ccatgtaaaaatgtcagcacagtacaatgtacacatggaattaggccagtagtgtcaactcaactgctgttaaatggcag
```

FIG. 10A-1

```
tctagcagaagaagaggtagtaattagatctagtaatttcacagacaatgcaaaaaacataatagtacagttgaaagaat
ctgtagaaattaattgtacaagacccaacaacaatacaaggaaaagtatacatataggaccaggaagagcattttataca
acaggagaaataataggagatataagacaagcacattgcaacattagtagaacaaaatggaataacacttttaaatcaaat
agctacaaaattaaaagaacaatttgggaataataaaacaatagtctttaatcaatcctcaggaggggacccagaaattg
taatgcacagttttaattgtggagggaattttctactgtaattcaacacaactgtttaatagtacttggaattttaat
ggtacttggaatttaacacaatcgaatggtactgaaggaaatgacactatcacactcccatgtagaataaaacaaattat
aaatatgtggcaggaagtaggaaaagcaatgtatgcccctcccatcagaggacaaattagatgctcatcaaatattacag
ggctaatattaacaagagatggtggaactaacagtagtgggtccgagatcttcagacctggggggaggagatatgagggac
aattggagaagtgaattatataaatataaagtagtaaaaattgaaccattaggagtagcacccaccaaggcaaaaagaag
agtggtgcagagagaaaaaagagcagtgggaacgataggagctatgttccttgggttcttgggagcagcaggaagcacta
tgggcgcagcgtcaataacgctgacggtacaggccagactattattgtctggtatagtgcaacagcagaacaatttgctg
agggctattgaggcgcaacagcatctgttgcaactcacagtctggggcatcaagcagctccaggcaagagtcctggctct
ggaaagatacctaagggatcaacagctcctagggatttggggttgctctggaaaactcatctgcaccactgctgtgcctt
ggaatgctagttggagtaataaaactctggatatgatttgggataacatgacctggatggagtgggaaagagaaatcgaa
aattacacaggcttaatatacaccttaattgaagaatcgcagaaccaacaagaaaagaatgaacaagacttattagcatt
agataagtgggcaagtttgtggaattggtttgacatatcaaattggctgtggtgtataaaaaatcttcataatgatagtag
gaggcttgataggtttaagaatagttttttactgtactttctatagtaaatagagtaggcagggatactccaccattgtca
tttcagacccacctcccagccccgaggggacccgacaggcccgaaggaatcgaagaagaaggtggagacagagacagaga
cagatccgtcgcgattagtggatggatcccttagcacttatctgggacgatctgcggagcctgtgcctcttcagctaccacc
gcttgagagacttactcttgattgtaacgaggattgtggaacttctgggacgcaggggggtgggaagccctcaaatattgg
tggaatctcctacagtattggagtcaggagctaaagaatagtgctgttagcttgctcaatgccacagctatagcagtagc
tgaggggacagataggttatagaagtagtacaaggagcttatagagctattcgccacatacctagaagaataagacagg
gcttggaaaggattttgctataagatgggtggctagccccgggtgataaacggaccgcgcaatcctaggctgtgccttc
tagttgccagccatctgttgtttgccctcccccgtgccttccttgaccctggaaggtgccactcccactgtcctttcct
aataaaatggagaaattgcatcgcattgtctgagtaggtgtcattctattctgggggtgggggtggggcaggacagcaag
ggggaggattgggaagacaatagcaggcatgctggggatgcggtgggctctatataaaaaacgcccggcggcaaccgagc
gttctgaacgctagagtcgacaaattcagaagaactcgtcaagaaggcgatagaaggcgatgcgctgcgaatcgggagcg
gcgataccgtaaagcacgaggaagcggtcagccccattcgccgccaagctcttcagcaatatcacgggtagccaacgctat
gtcctgatagcggtctgccacacccagccggccacagtcgatgaatccagaaaagcggccattttccaccatgatattcg
gcaagcaggcatcgccatgggtcacgacgagatcctcgccgtcgggcatgctcgccttgagcctggcgaacagttcggct
ggcgcgagccctgatgctcttcgtccagatcatcctgatcgacaagaccggcttccatccgagtacgtgctcgctcgat
gcgatgtttcgcttggtggtcgaatgggcaggtagccggatcaagcgtatgcagccgccgcattgcatcagccatgatgg
atactttctcggcaggagcaaggtgagatgacaggagatcctgccccggcacttcgcccaatagcagccagtccctccc
gcttcagtgacaacgtcgagcacagctgcgcaaggaacgcccgtcgtggccagccacgatagccgcgctgcctcgtcttg
cagttcattcagggcaccggacaggtcggtcttgacaaaaagaaccgggcgcccctgcgctgacagccggaacacggcgg
catcagagcagccgattgtctgttgtgcccagtcatagccgaatagcctctccaccaagcggccggagaacctgcgtgc
aatccatcttgttcaatcatgcgaaacgatcctcatcctgtctcttgatcagatcttgatccctgcgccatcagatcct
tggcggcgagaaagccatccagttttactttgcagggcttcccaacctaccagagggcgcccccagctggcaattccggtt
cgcttgctgtccataaaaccgcccagtctagctatcgccatgtaagcccactgcaagctacctgctttctctttgcgctt
gcgtttcccttgtccagatagcccagtagctgacattcatccgggtcagcaccgtttctgcggactggctttctacgt
gaaaaggatctaggtgaagatcctttttgataatctcatgaccaaaatccccttaacgtgagttttcgttccactgagcgt
cagaccccgtagaaaagatcaaaggatcttcttgagatcctttttttctgcgcgtaatctgctgcttgcaaacaaaaaa
ccaccgctaccagcgctggtttgtttgccggatcaagagctaccaactcttttccgaaggtaactggcttcagcagagc
gcagataccaaatactgtccttctagtgtagccgtagttaggccaccacttcaagaactctgtagcaccgcctacatacc
tcgctctgctaatcctgttaccagtggctgctgccagtggcgataagtcgtgtcttaccgggttggactcaagacgatag
ttaccggataaggcgcagcggtcgggctgaacggggggttcgtgcacacagcccagcttggagcgaacgacctacaccga
actgagatacctacagcgtgagctatgagaaagcgccacgcttcccgaagggagaaaggcggacaggtatccggtaagcg
gcagggtcggaacaggagagcgcacgagggagcttccaggggggaaacgcctggtatctttatagtcctgtcgggtttcgc
cacctctgacttgagcgtcgatttttgtgatgctcgtcaggggggcggagcctatggaaaacgccagcaacgcggccttt
ttacggttcctggccttttgctggccttttgctcacatgttgtcgaccgacaatattggctattggccattgcatacgtt
gtatctatatcataatatgtacatttatattggctcatgtccaatatgaccgccatgttgacattgattattgactagtt
attaatagtaatcaattacgggtcattagttcatagcccatatatggagttccgcgttacataacttacggtaaatggc
ccgcctcgtgaccgccaacgaccccgcccattgacgtcaataatgacgtatgttcccatagtaacgccaatagggact
ttccattgacgtcaatgggtggagtatttacggtaaactgcccacttggcagtacatcaagtgtatcatatgccaagtcc
gcccctattgacgtcaatgacggtaaatggcccgcctggcattatgcccagtacatgaccttacgggactttcctacttg
gcagtacatctacgtattagtcatcgctattaccatggtgatgcggttttggcagtacaccaatgggcgtggatagcggt
ttgactcacggggatttccaagtctccaccccattgacgtcaatgggagtttgttttggcaccaaaatcaacgggacttt
ccaaaatgtcgtaataaccccgccccgttgacgcaaatgggcggtaggcgtgtacggtgggaggtctatataagcagagc
tcgtttagtgaaccgtcagatcgc
```

FIG. 10A-2 pGA2/JS2 Functional Regions

| Position within sequence (starting-and ending pos.) | Gene/ORF (indicate complete name of the gene and the expressed gene product) | Origin of sequence (organism) |
|---|---|---|
| 106-1644 | Gag, inactivating point mutations in zinc finger packaging sequences for viral RNA | HIV-1 IIIb (BH10) |
| 1401-3620 | Pol, inactivating point mutations in reverse transcriptase, deletion of integrase | HIV-1 IIIb (BH10) |
| 3708-3922 and 6247-6337 | Tat exons #1 and #2 | |
| 3847-3922 and 6247-6521 | Rev exons #1 and #2 | |
| 3939-4184 | Vpu | |
| 4102-6663 | Env | HIV-1 ADA |
| 6664-9544 | Plasmid vector | PGA2, Gen Bank accession # AF425298 |

FIG. 10B

JS2 Mutation chart

| Codon change | Amino acid change | Region | Function |
|---|---|---|---|
| to AGC Position 1279-1281 | C392S | Gag | Ablation of zinc finger used in packaging |
| to AGC Position 1288-1290 | C395S | Gag | Ablation of zinc finger used in packaging |
| to AGC Position 1342-1344 | C413S | Gag | Ablation of zinc finger used in packaging |
| to AGC Position 1351-1353 | C416S | Gag | Ablation of zinc finger used in packaging |
| to AAC Position 2454-2456 | D185N | Reverse Transcriptase | Inactivation of Polymerase active site |
| to ACC Position 2697-2699 | W266T | Reverse Transcriptase | Ablation of strand transfer activity |
| to CAG Position 3333-3335 | E478Q | Rnase H | Inactivation of RNase H activity |

FIG. 10C pGA2/JS7 Sequence

```
ATCGATGCAGGACTCGGCTTGCTGAAGCGCGCACGGCAAGAGGCGAGGGGCGGCGACTGGTGAGTACGCCAAAAATTTTG
ACTAGCGGAGGCTAGAAGGAGAGAGATGGGTGCGAGAGCGTCAGTATTAAGCGGGGGAGAATTAGATCGATGGGAAAAAA
TTCGGTTAAGGCCAGGGGGAAAGAAAAAATATAAATTAAAACATATAGTATGGGCAAGCAGGGAGCTAGAACGATTCGCA
GTTAATCCTGGCCTGTTAGAAACATCAGAAGGCTGTAGACAAATACTGGGACAGCTACAACCATCCCTTCAGACAGGATC
AGAAGAACTTAGATCATTATATAATACAGTAGCAACCCTCTATTGTGTGCATCAAAGGATAGAGATAAAAGCACCAAGG
AAGCTTTAGACAAGATAGAGGAAGAGCAAAACAAAAGTAAGAAAAAAGCACAGCAAGCAGCAGCTGACACAGGACACAGC
AATCAGGTCAGCCAAAATTACCCTATAGTGCAGAACATCCAGGGGCAAATGGTACATCAGGCCATATCACCTAGAACTTT
AAATGCATGGGTAAAAGTAGTAGAAGAGAAGGCTTTCAGCCCAGAAGTGATACCCATGTTTTCAGCATTATCAGAAGGAG
CCACCCCACAAGATTTAAACACCATGCTAAACACAGTGGGGGGACATCAAGCAGCCATGCAAATGTTAAAAGAGACCATC
AATGAGGAAGCTGCAGAATGGGATAGAGTGCATCCAGTGCATGCAGGGCCTATTGCACCAGGCCAGATGAGAGAACCAAG
GGGAAGTGACATAGCAGGAACTACTAGTACCCTTCAGGAACAAATAGGATGGATGACAAATAATCCACCTATCCCAGTAG
GAGAAATTTATAAAAGATGGATAATCCTGGGATTAAATAAAATAGTAAGAATGTATAGCCCTACCAGCATTCTGGACATA
AGACAAGGACCAAAAGAACCCTTTAGAGACTATGTAGACCGGTTCTATAAAACTCTAAGAGCCGAGCAAGCTTCACAGGA
GGTAAAAAATTGGATGACAGAAACCTTGTTGGTCCAAAATGCGAACCCAGATTGTAAGACTATTTTAAAAGCATTGGGAC
CAGCGGCTACACTAGAAGAAATGATGACAGCATGTCAGGGAGTAGGAGGACCCGGCCATAAGGCAAGAGTTTTGGCTGAA
GCAATGAGCCAAGTAACAAATTCAGCTACCATAATGATGCAGAGAGGCAATTTTAGGAACCAAAGAAAGATTGTTAAGAG
CTTCAATAGCGGCAAAGAAGGGCACACAGCCAGAAATTGCAGGGCCCCTAGGAAAAAGGGCAGCTGGAAAAGCGGAAAGG
AAGGACACCAAATGAAAGATTGTACTGAGAGACAGGCTAATTTTTTAGGGAAGATCTGGCCTTCCTACAAGGGAAGGCCA
GGGAAtTTTCTTCAGAGCAGACCAGAGCCAACAGCCCCACCAGAAGAGAGCTTCAGGTCTGGGGTAGAGACAACAACTCC
CCCTCAGAAGCAGGAGCCGATAGACAAGGAACTGTATCCTTTAACTTCCCTCAGATCACTCTTTGGCAACGACCCCTCGT
CACAATAAAGATAGGGGGGCAACTAAAGGAAGCTCTATTAGCCACAGGAGCAGATGATACAGTATTAGAAGAAATGAGTT
TGCCAGGAAGATGGAAACCAAAAATGATAGGGGGAATTGGAGGTTTTATCAAAGTAAGACAGTATGATCAGATACTCATA
GAAATCTGTGGACATAAAGCTATAGGTACAGTATTAGTAGGACCTACACCTGTCAACATAATTGGAAGAAATCTGTTGAC
TCAGATTGGTTGCACTTTAAATTTTCCCATTAGCCCTATTGAGACTGTACCAGTAAAATTAAAGCCAGGAATGGATGGCC
CAAAAGTTAAACAATGGCCATTGACAGAAGAAAAGATAAAAGCATTAGTAGAAATTTGTACAGAGATGGAAAAGGAAGGG
AAAATTTCAAAAATTGGGCCTGAAAATCCATACAATACTCCAGTATTTGCCATAAAGAAAAAAGACAGTACTAAATGGAG
AAAATTAGTAGATTTCAGAGAACTTAATAAGAGAACTCAAGACTTCTGGGAAGTTCAATTAGGAATACCACATCCCGCAG
GGTTAAAAAAGAAAAAATCAGTAACAGTACTGGATGTGGGTGATGCATATTTTTCAGTTCCCTTAGATGAAGACTTCAGG
AAATATACTGCATTTACCATACCTAGTATAAACAATGAGACACCAGGGATTAGATATCAGTACAATGTGCTTCCACAGGG
ATGGAAAGGATCACCAGCAATATTCCAAAGTAGCATGACAAAAATCTTAGAGCCTTTTAGAAAACAAAATCCAGACATAG
TTATCTATCAATACATGAACGATTTGTATGTAGGATCTGACTTAGAAATAGGGCAGCATAGAACAAAAATAGAGGAGCTG
AGACAACATCTGTTGAGGTGGGGACTTACCACACCAGACAAAAAACATCAGAAAGAACCTCCATTCCTTTGGATGGGTTA
TGAACTCCATCCTGATAAATGGACAGTACAGCCTATAGTGCTGCCAGAAAAAGACAGCTGGACTGTCAATGACATACAGA
AGTTAGTGGGGAAATTGAATACCGCAAGTCAGATTTACCCAGGGATTAAAGTAAGGCAATTATGTAAACTCCTTAGAGGA
aCCAAAGCACTAACAGAAGTAATACCACTAACAGAAGAAGCAGAGCTAGAACTGGCAGAAAACAGAGAGATTCTAAAAGA
ACCAGTACATGGAGTGTATTATGACCCATCAAAAGACTTAATAGCAGAAATACAGAAGCAGGGGCAAGGCCAATGGACAT
ATCAAATTTATCAAGAGCCATTTAAAAATCTGAAAACAGGAAAATATGCAAGAATGAGGGGTGCCCACACTAATGATGTA
AAACAATTAACAGAGGCAGTGCAAAAAATAACCACAGAAAGCATAGTAATATGGGGAAAGACTCCTAAATTTAAACTGCC
CATACAAAAGGAAACATGGGAAACATGGTGGACAGAGTATTGGCAAGCCACCTGGATTCCTGAGTGGGAGTTTGTTAATA
CCCCTCCTTTAGTGAAATTATGGTACCAGTTAGAGAAAGAACCCATAGTAGGAGCAGAAACCTTCTATGTAGATGGGGCA
GCTAACAGGGAGACTAAATTAGGAAAAGCAGGATATGTTACTAATAGAGGAAGACAAAAAGTTGTCACCCTAACTAACAC
AACAAATCAGAAAACTCAGTTACAAGCAATTTATCTAGCTTTGCAGGATTCGGGATTAGAAGTAAACATAGTAACAGACT
CACAATATGCATTAGGAATCATTCAAGCACAACCAGATCAAAGTGAATCAGAGTTAGTCAATCAAATAATAGAGCAGTTA
ATAAAAAAGGAAAAGGTCTATCTGGCATGGGTACCAGCACACAAAGGAATTGGAGGAAATGAACAAGTAGATAAATTAGT
CAGTGCTGGAATCAGGAAAGTACTATTTTTAGATGGAATAGATAAGGCCCAAGATGAACATTAGAATTCTGCAACAACTG
CTGTTTATCCATTTCAGAATTGGGTGTCGACATAGCAGAATAGGCGTTACTCGACAGAGGAGAGCAAGAAATGGAGCCAG
TAGATCCTAGACTAGAGCCCTGGAAGCATCCAGGAAGTCAGCCTAAAACTGCTTGTACCAATTGCTATTGTAAAAAGTGT
TGCTTTCATTGCCAAGTTTGTTTCATAACAAAAGCCTTAGGCATCTCCTATGGCAGGAAGAAGCGGAGACAGCGACGAAG
AGCTCCTCAAGACAGTCAGACTCATCAAGTTTCTCTATCAAAGCAGTAAGTAGTAAATGTAATGCAACCTTTACAAATAT
TAGCAATAGTAGCATTAGTAGTAGCAGCAATAATAGCAATAGTTGTGTGGACCATAGTATTCATAGAATATAGGAAAATA
TTAAGACAAAGAAAAATAGACAGGTTAATTGATAGGATAACAGAAAGAGCAGAAGACAGTGGCAATGAAAGTGAAGGGGA
TCAGGAAGAATTATCAGCACTTGTGGAAATGGGGCATCATGCTCCTTGGGATGTTGATGATCTGTAGTGCTGTAGAAAAT
TTGTGGGTCACAGTTTATTATGGGGTACCTGTGTGGAAAGAAGCAACCACCACTCTATTTTGTGCATCAGATGCTAAAGC
ATATGATACAGAGGTACATAATGTTTGGGCCACACATGCCTGTGTACCCACAGACCCCAACCCACAAGAAGTAGTATTGG
AAAATGTGACAGAAAATTTTAACATGTGGAAAAATAACATGGTAGAACAGATGCATGAGGATATAATCAGTTTATGGGAT
CAAAGCCTAAAGCCATGTGTAAAATTAACCCCACTCTGTGTTACTTTAAATTGCACTGATTTGAGGAATGTTACTAATAT
CAATAATAGTAGTGAGGGAATGAGAGGAGAAATAAAAAACTGCTCTTTCAATATCACCACAAGCATAAGAGATAAGGTGA
AGAAAGACTATGCACTTTTTTATAGACTTGATGTAGTACCAATAGATAATGATAATACTAGCTATAGGTTGATAAATTGT
AATACCTCAACCATTACACAGGCCTGTCCAAAGGTATCCTTTGAGCCAATTCCCATACATTATTGTACCCCGGCTGGTTT
TGCGATTCTAAAGTGTAAAGACAAGAAGTTCAATgGAACAGGGCCATGTAAAAATGTCAGCACAGTACAATGTACACATG
GAATTAGGCCAGTAGTGTCAACTCAACTGCTGTTAAATGGCAGTCTAGCAGAAGAAGAGGTAGTAATTAGATCTAGTAAT
```

FIG. 11A-1

```
TTCACAGACAATGCAAAAAACATAATAGTACAGTTGAAAGAATCTGTAGAAATTAATTGTACAAGACCCAACAACAATAC
AAGGAAAAGTATACATATAGGACCAGGAAGAGCATTTTATACAACAGGAGAAATAATAGGAGATATAAGACAAGCACATT
GCAACATTAGTAGAACAAAATGGAATAACACTTTAAATCAAATAGCTACAAAATTAAAAGAACAATTTGGGAATAATAAA
ACAATAGTCTTTAATCAATCCTCAGGAGGGGACCCAGAAATTGTAATGCACAGTTTTAATTGTGGAGGGGAATTTTTCTA
CTGTAATTCAACACAACTGTTTAATAGTACTTGGAATTTTAATGGTACTTGGAATTTAACACAATCGAATGGTACTGAAG
GAAATGACACTATCACACTCCCATGTAGAATAAAACAAATTATAAATATGTGGCAGGAAGTAGGAAAAGCAATGTATGCC
CCTCCCATCAGAGGACAAATTAGATGCTCATCAAATATTACAGGGCTAATATTAACAAGAGATGGTGGAACTAACAGTAG
TGGGTCCGAGATCTTCAGACCTGGGGGAGGAGATATGAGGGACAATTGGAGAAGTGAATTATATAAATATAAAGTAGTAA
AAATTGAACCATTAGGAGTAGCACCCACCAAGGCAAAAGAAGAGTGGTGCAGAGAGAAAAAAGAGCAGTGGGAACGATA
GGAGCTATGTTCCTTGGGTTCTTGGGAGCAGCAGGAAGCACTATGGGCGCAGCGTCAATAACGCTGACGGTACAGGCCAG
ACTATTATTGTCTGGTATAGTGCAACAGCAGAACAATTTGCTGAGGGCTATTGAGGCGCAACAGCATCTGTTGCAACTCA
CAGTCTGGGGCATCAAGCAGCTCCAGGCAAGAGTCCTGGCTGTGGAAAGATACCTAAGGGATCAACAGCTCCTAGGGATT
TGGGGTTGCTCTGGAAAACTCATCTGCACCACTGCTGTGCCTTGGAATGCTAGTTGGAGTAATaAAACTCTGGATATGAT
TTGGGATAACATGACCTGGATGGAGTGGGAAAGAGAAATCGAAAATTACACAGGCTTAATATACACCTTAATTGAAGAAT
CGCAGAACCAACAAGAAAAGAATGAACAAGACTTATTAGCATTAGATAAGTGGGCAAGTTTGTGGAATTGGTTTGACATA
TCAAATTGGCTGTGGTATGTAAAAATCTTCATAATGATAGTAGGAGGCTTGATAGGTTTAAGAATAGTTTTTACTGTACT
TTCTATAGTAAATAGAGTTAGGCAGGGATACTCACCATTGTCATTTCAGACCCACCTCCCAGCCCCGAGGGGACCCGACA
GGCCCGAAGGAATCGAAGAAGAAGGTGGAGACAGAGACAGAGACAGATCCGTGCGATTAGTGGATGGATCCTTAGCACTT
ATCTGGGACGATCTGCGGAGCCTGTGCCTCTTCAGCTACCACCGCTTGAGAGACTTACTCTTGATTGTAACGAGGATTGT
GGAACTTCTGGGACGCAGGGGGTGGGAAGCCCTCAAATATTGGTGGAATCTCCTACAGTATTGGAGTCAGGAGCTAAAGA
ATAGTGCTGTTAGCTTGCTCAATGCCACAGCTATAGCAGTAGCTGAGGGGACAGATAGGGTTATAGAAGTAGTACAAGGA
GCTTATAGAGCTATTCGCCACATACCTAGAAGAATAAGACAGGGCTTGGAAAGGATTTTGCTATAAGATGGGTGGCTAGC
CCCGGGTGATAAACGGACCGCGCAATCCCTAGGCTGTGCCTTCTAGTTGCCAGCCATCTGTTGTTTGCCCCTCCCCGTG
CCTTCCTTGACCCTGGAAGGTGCCACTCCCACTGTCCTTTCCTAATAAAATGAGGAAATTGCATCGCATTGTCTGAGTAG
GTGTCATTCTATTCTGGGGGGTGGGGTGGGGCAGGACAGCAAGGGGGAGGATTGGGAAGACAATAGCAGGCATGCTGGGG
ATGCGGTGGGCTCTATATAAAAAACGCCCGGCGGCAACCGAGCGTTCTGAACGCTAGAGTCGACAAATTCAGAAGAACTC
GGCAAGAAGGCGATAGAAGGCGATGCGCTGCGAATCGGGAGCGGCGATACCGTAAAGCACGAGGAAGCGGTCAGCCCATT
CGCCGCCAAGCTCTTCAGCAATATCACGGGTAGCCAACGCTATGTCCTGATAGCGGTCTGCCACACCCAGCCGGCCACAG
TCGATGAATCCAGAAAAGCGGCCATTTTCCACCATGATATTCGGCAAGCAGGCATCGCCATGGGTCACGACGAGATCCTC
GCCGTCGGGCATGCTCGCCTTGAGCCTGGCGAACAGTTCGGCTGGCGCGAGCCCCTGATGCTCTTCGTCCAGATCATCCT
GATCGACAAGACCGGCTTCCATCCGAGTACGTGCTCGCTCGATGCGATGTTTCGCTTGGTGGTCGAATGGGCAGGTAGCC
GGATCAAGCGTATGCAGCCGCCGCATTGCATCAGCCATGATGGATACTTTCTCGGCAGGAGCAAGGTGAGATGACAGGAG
ATCCTGCCCCGGCACTTCGCCCAATAGCAGCCAGTCCCTTCCCGCTTCAGTGACAACGTCGAGCACAGCTGCGCAAGGAA
CGCCCGTCGTGGCCAGCCACGATAGCCGCGCTGCCTCGTCTTGCAGTTCATTCAGGGCACCGGACAGGTCGGTCTTGACA
AAAAGAACCGGGCGCCCCTGCGCTGACAGCCGGAACACGGCGGCATCAGAGCAGCCGATTGTCTGTTGTGCCCAGTCATA
GCCGAATAGCCTCTCCACCCAAGCGGCCGGAGAACCTGCGTGCAATCCATCTTGTTCAATCATGCGAAACGATCCTCATC
CTGTCTCTTGATCAGATCTTGATCCCCTGCGCCATCAGATCCTTGGCGGCAAGAAAGCCATCCAGTTTACTTTGCAGGGC
TTCCCAACCTTACCAGAGGGCGCCCCAGCTGGCAATTCCGGTTCGCTTGCTGTCCATAAAACCGCCCAGTCTAGCTATCG
CCATGTAAGCCCACTGCAAGCTACCTGCTTTCTCTTTGCGCTTGCGTTTTCCCTTGTCCAGATAGCCCAGTAGCTGACAT
TCATCCGGGGTCAGCACCGTTTCTGCGGACTGGCTTTCTACGTGAAAAGGATCTAGGTGAAGATCCTTTTTGATAATCTC
ATGACCAAAATCCCTTAACGTGAGTTTTCGTTCCACTGAGCGTCAGACCCCGTAGAAAAGATCAAAGGATCTTCTTGAGA
TCCTTTTTTTCTGCGCGTAATCTGCTGCTTGCAAACAAAAAAACCACCGCTACCAGCGGTGGTTTGTTTGCCGGATCAAG
AGCTACCAACTCTTTTTCCGAAGGTAACTGGCTTCAGCAGAGCGCAGATACCAAATACTGTTCTTCTAGTGTAGCCGTAG
TTAGGCCACCACTTCAAGAACTCTGTAGCACCGCCTACATACCTCGCTCTGCTAATCCTGTTACCAGTGGCTGCTGCCAG
TGGCGATAAGTCGTGTCTTACCGGGTTGGACTCAAGACGATAGTTACCGGATAAGGCGCAGCGGTCGGGCTGAACGGGGG
GTTCGTGCACACAGCCCAGCTTGGAGCGAACGACCTACACCGAACTGAGATACCTACAGCGTGAGCTATGAGAAAGCGCC
ACGCTTCCCGAAGGGAGAAAGGCGGACAGGTATCCGGTAAGCGGCAGGGTCGGAACAGGAGAGCGCACGAGGGAGCTTCC
AGGGGGAAACGCCTGGTATCTTTATAGTCCTGTCGGGTTTCGCCACCTCTGACTTGAGCGTCGATTTTGTGATGCTCGT
CAGGGGGGCGGAGCCTATGGAAAAACGCCAGCAACGCGGCCTTTTACGGTTCCTGGCCTTTTGCTGGCCTTTTGCTCAC
ATGTTGTCGACAATATTGGCTATTGGCCATTGCATACGTTGTATCTATATCATAATATGTACATTTATATTGGCTCATGT
CCAATATGACCGCCATGTTGACATTGATTATTGACTAGTTATTAATAGTAATCAATTACGGGTTCATTAGTTCATAGCCC
ATATATGGAGTTCCGCGTTACATAACTTACGGTAAATGGCCCGCCTGGCTGACCGCCCAACGACCCCCGCCCATTGACGT
CAATAATGACGTATGTTCCCATAGTAACGCCAATAGGGACTTTCCATTGACGTCAATGGGTGGAGTATTTACGGTAAACT
GCCCACTTGGCAGTACATCAAGTGTATCATATGCCAAGTCCGCCCCCTATTGACGTCAATGACGGTAAATGGCCCGCCTG
GCATTATGCCCAGTACATGACCTTACGGGACTTTCCTACTTGGCAGTACATCTACGTATTAGTCATCGCTATTACCATGG
TGATGCGGTTTTGGCAGTACACCAATGGGCGTGGATAGCGGTTTGACTCACGGGGATTTCCAAGTCTCCACCCCATTGAC
GTCAATGGGAGTTTGTTTTGGCACCAAAATCAACGGGACTTTCCAAAATGTCGTAATAACCCCGCCCCGTTGACGCAAAT
GGGCGGTAGGCGTGTACGGTGGGAGGTCTATATAAGCAGAGCTCGTTTAGTGAACCGTCAGATCGC
```

FIG. 11A-2 pGA2/JS7 functional regions

| Position within sequence (starting-and ending pos.) | Gene/ORF (indicate complete name of the gene and the expressed gene product) | Origin of sequence (organism) |
|---|---|---|
| 106-1608 | Gag, inactivating point mutations in zinc finger packaging sequences for viral RNA | HIV-1 HXB2 |
| 1401-3584 | Pol, inactivating point mutations in protease and reverse transcriptase, deletion of integrase | HIV-1 HXB2 |
| 3671-3885 and 6210-6300 | Tat exons #1 and #2 | |
| 3810-3885 and 6210-6884 | Rev exons #1 and #2 | |
| 3902-4147 | Vpu | |
| 4165-6626 | Env | HIV-1 ADA |
| 6627-9506 | Plasmid vector | PGA2, Gen Bank accession # AF425298 |

FIG. 11B

JS7 Mutation Chart

| Codon change | Amino acid change | Region | Function |
|---|---|---|---|
| to AGC Position 1279-1281 | C392S | Gag | Ablation of zinc finger used in packaging |
| to AGC Position 1288-1290 | C395S | Gag | Ablation of zinc finger used in packaging |
| to AGC Position 1342-1344 | C413S | Gag | Ablation of zinc finger used in packaging |
| to AGC Position 1351-1353 | C416S | Gag | Ablation of zinc finger used in packaging |
| To ACA position 1641-1643 | D25A | Protease | Inactivation of Protease active site |
| to AAC Position 2418-2420 | D185N | Reverse Transcriptase | Inactivation of Polymerase active site |
| to ACC Position 2661-2663 | W266T | Reverse Transcriptase | Ablation of strand transfer activity |
| to CAG Position 3297-3299 | E478Q | RNase H | Inactivation of RNase H activity |

FIG. 11C pGA2/JS7.1 Sequence

```
atcgatgcaggactcggcttgctgaagcgcgcacggcaagaggcgaggggcggcgactggtgagtacgccaaaaatt
ttgactagcggaggctagaaggagagagatgggtgcgagagcgtcagtattaagcgggggagaattagatcgatggg
aaaaaattcggttaaggccaggggggaaagaaaaaatataaattaaaacatatagtatgggcaagcagggagctagaa
cgattcgcagttaatcctggcctgttagaaacatcagaaggctgtagacaaatactgggacagctacaaccatccct
tcagacaggatcagaagaacttagatcattatataatacagtagcaaccctctattgtgtgcatcaaaggatagaga
taaaagacaccaaggaagctttagacaagatagaggaagagcaaaacaaaagtaagaaaaaagcacagcaagcagca
gctgacacaggacacagcaatcaggtcagccaaaattaccctatagtgcagaacatccaggggcaaatggtacatca
ggccatatcacctagaactttaaatgcatgggtaaaagtagtagaagagaaggctttcagcccagaagtgatacca
tgttttcagcattatcagaaggagccaccccacaagatttaaacaccatgctaaacacagtggggggacatcaagca
gccatgcaaatgttaaaagagaccatcaatgaggaagctgcagaatgggatagagtgcatccagtgcatgcagggcc
tattgcaccaggccagatgagagaaccaaggggaagtgacatagcaggaactactagtacccttcaggaacaaatag
gatggatgacaaataatccacctatcccagtaggagaaatttataaaagatggataatcctgggattaaataaaata
gtaagaatgtatagccctaccagcattctggacataagacaaggaccaaaagaaccctttagagactatgtagaccg
gttctataaaactctaagagccgagcaagcttcacaggaggtaaaaaattggatgacagaaaccttgttggtccaaa
atgcgaacccagattgtaagactatttttaaaagcattgggaccagcggctacactagaagaaatgatgacagcatgt
cagggagtaggaggacccggccataaggcaagagttttggctgaagcaatgagccaagtaacaaattcagctaccat
aatgatgcagagaggcaattttaggaaccaaagaaagattgttaaggacttctgggaagttcaattaggaataccacacag
ccagaaattgcagggcccctaggaaaaagggcagctggaaaagcggaaaggaaggacaccaaatgaaagattgtact
gagagacaggctaatttttagggaagatctggccttcctacaagggaaggccagggaattttcttcagagcagacc
agagccaacagccccaccagaagagagcttcaggtctggggtagagacaacaactcccccctcagaagcaggagccga
tagacaaggaactgtatcctttaacttccctcagatcactctttggcaacgacccctcgtcacaataaagataggggg
ggcaactaaaggaagctctattagccacaggagcagatgatacagtattagaagaaatgagtttgccaggaagatgg
aaaccaaaaatgataggggggaattggaggtttttatcaaagtaagacagtatgatcagatactcatagaaatctgtgg
acataaagctataggtacagtattagtaggacctacacctgtcaacataattggaagaaatctgttgactcagattg
gttgcacttttaaattttcccattagccctattgagactgtaccagtaaaattaaagccaggaatggatggcccaaaa
gttaaacaatggccattgacagaagaaaagataaaagcattagtagaaatttgtacagagatggaaaaggaagggaa
aatttcaaaaattgggcctgaaaatccatacaatactccagtatttgccataaagaaaaagacagtactaaatgga
gaaaattagtagatttcagagaacttaataagagaactcaagacttctgggaagttcaattaggaataccacatccc
gcaggg tt aaaaaagaaaaaatcagtaacagtactggatgtgggtgatgcatatttttcagttcccttagatgaaga
cttcaggaaatatactgcatttaccatacctagtataaacaatgagacaccagggattagatatcagtacaatgtgc
ttccacagggatggaaaggatcaccagcaatattccaaagtagcatgacaaaaatcttagagccttttagaaaacaa
aatccagacatagttatctatcaatacatgaacgatttgtatgtaggatctgacttagaaatagggcagcatagaac
aaaaatagaggagctgagacaacatctgttgaggtggggacttaccacacaacaaaaatcagaaagaacctc
cattcctttggatggttatgaactccatcctgataaatggacagtacagcctatagtgctgccagaaaaagacagc
tggactgtcaatgacatacagaagttagtggggaaattgaataccgcaagtcagatttacccaggattaaagtaag
gcaattatgtaaactccttagaggaaccaaagcactaacagaagtaataccactaacagaagaagcagagctagaac
tggcagaaaacagagagattctaaaagaaccagtacatggagtgtattatgacccatcaaaagacttaatagcagaa
atacagaagcaggggcaaggccaatggacatatcaaatttatcaagagccatttaaaaatctgaaaacaggaaaata
tgcaagaatgaggggtgcccacactaatgatgtaaaacaattaacagaggcagtgcaaaaaataaccacagaaagca
tagtaatatgggggaagactcctaaatttaaactgcccatacaaaaggaaacatgggaaacatggtggacagagtat
tggcaagccacctggattcctgagtgggagtttgttaatacccctcctttagtgaaattatggtaccagttagagaa
agaacccatagtaggagcagaaaccttctatgtagatggggcagctaacagggagactaaattaggaaaagcaggat
atgttactaatagaggaagacaaaaagttgtcaccctaactaacacaacaaatcagaaaactcagttacaagcaatt
tatctagctttgcaggattcgggattagaagtaaacatagtaacagactcacaatatgcattaggaatcattcaagc
acaaccagatcaaagtgaatcagagttagtcaatcaaataatagagcagttaataaaaaaggaaaaggtctatctgg
catgggtaccagcacacaaaggaattggaggaaatgaacaagtagataaattagtcagtgctggaatcaggaaagta
ctatttttagatggaatagataaggcccaagatgaacattagaattctgcaacaactgctgtttatccatttcagaa
ttgggtgtcgacatagcagaataggcgttactcgacagaggagagcaagaaatggagccagtagatcctagactaga
gccctggaagcatccaggaagtcagcctaaaactgcttgtaccaattgctattgtaaaagtgttgctttcattgcc
aagtttgtttcataacaaaagccttaggcatctcctatggcaggaagaagcggagacagcgacgaagagctcctcaa
gacagtcagactcatcaagtttctctatcaaagcagtaagtagtaaatctaatccaacctttacaaatattagcaat
agtagcattagtagtagcagcaataatagcaatagttgtgtggaccatagtattcatagaatataggaaaatattaa
gacaaagaaaaatagacaggttaattgataggataacaagaagcagaagacagtggcaatgaaagtgaagggat
caggaagaattatcagcacttgtggaaatggggcatcatgctccttgggatgttgatgatctgtagtgctgtagaaa
atttgtgggtcacagtttattatggggtacctgtgtggaaagaagcaaccaccactctattttgtgcatcagatgct
```

FIG. 12A-1

```
aaagcatatgatacagaggtacataatgtttgggccacacatgcctgtgtacccacagacccaacccacaagaagt
agtattggaaaatgtgacagaaaattttaacatgtggaaaaataacatggtagaacagatgcatgaggatataatca
gtttatgggatcaaagcctaaagccatgtgtaaaattaaccccactctgtgttactttaaattgcactgatttgagg
aatgttactaatatcaataatagtagtgagggaatgagaggagaaataaaaaactgctctttcaatatcaccacaag
cataagagataaggtgaagaaagactatgcactttttatagacttgatgtagtaccaatagataatgataatacta
gctataggttgataaattgtaatacctcaaccattacacaggcctgtccaaaggtatcctttgagccaattcccata
cattattgtaccccggctggttttgcgattctaaagtgtaaagacaagaagttcaatggaacagggccatgtaaaaa
tgtcagcacagtacaatgtacacatggaattaggccagtagtgtcaactcaactgctgttaaatggcagtctagcag
aagaagaggtagtaattagatctagtaatttcacagacaatgcaaaaaacataatagtacagttgaaagaatctgta
gaaattaattgtacaagacccaacaacaatacaaggaaaagtatacatataggaccaggaagagcattttatacaac
aggagaaaataataggagatataagacaagcacattgcaacattagtagaacaaaatggaataacactttaaatcaaa
tagctacaaaattaaaagaacaatttgggaataataaaacaatagtctttaatcaatcctcaggagggacccagaa
attgtaatgcacagttttaattgtggagggaattttttctactgtaattcaacacaactgtttaatagtacttggaa
ttttaatggtacttggaatttaacacaatcgaatggtactgaaggaaatgacactatcacactcccatgtagaataa
aacaaattataaatatgtggcaggaagtaggaaaagcaatgtatgccctcccatcagaggacaaattagatgctca
tcaaatattacagggctaatattaacaagagatggtggaactaacagtagtgggtccgagatcttcagacctggggg
aggagatatgagggacaattggagaagtgaattatataaatataaagtagtaaaaattgaaccattaggagtagcac
ccaccaaggcaaaagaagagtggtgcagagagaaaaagagcagtgggaacgataggagctatgttccttgggttc
ttgggagcagcaggaagcactatgggcgcagcgtcaataacgctgacggtacaggccagactattattgtctggtat
agtgcaacagcagaacaatttgctgagggctattgaggcgcaacagcatctgttgcaactcacagtctggggcatca
agcagctccaggcaagagtcctggctgtggaaagatacctaagggatcaacagctcctagggatttggggttgctct
ggaaaactcatctgccactgctgctgtgccttggaatgctagttggagtaataaaactctggatatgatttgggataa
catgacctggatggagtgggaaagagaaatcgaaaattacacaggcttaatatacaccttaattgaagaatcgcaga
accaacaagaaaagaatgaacaagacttattagcattagataagtgggcaagtttgtggaattggtttgacatatca
aattggctgtggtatgtaaaaatcttcataatgatagtaggaggcttgataggtttaagaatagtttttactgtact
ttctatagtaaatagagttaggcagggatactcaccattgtcatttcagacccacctcccagccccgaggggacccg
acaggcccgaaggaatcgaagaagaaggtggagacagagacagagacagatccgtgcgattagtggatggatccta
gcacttatctgggacgatctgcggagcctgtgcctcttcagctaccaccgcttgagagacttactcttgattgtaac
gaggattgtggaacttctgggacgcaggggtgggaagccctcaaatattggtggaatctcctacagtattggagtc
aggagctaaagaatagtgctgttagcttgctcaatgccacagctatagcagtagctgagggacagataggttata
gaagtagtacaaggagcttatagactattcgccacatacctagaagaataagacagggcttggaaaggattttgct
ataagatgggtggctagccccgggtgataaacggaccgcgcaatccctaggctgtgccttctagttgccagccatct
gttgtttgcccctccccgtgccttccttgacctggaaggtgccactcccactgtccttcctaataaaatgagga
aattgcatcgcattgtctgagtaggtgtcattctattctgggggtggggtggggcaggacagcaaggggaggatt
gggaagacaatagcaggcatgctgggatgcgtgggctctatataaaaaacgcccggcggcaaccgagcgttctga
acgctagagtcgacaaattcagaagaactcgtcaagaaggcgatagaaggcgatgcgctgcgaatcgggagcggcga
tacgtaaagcacgaggaagcggtcagcccattcgccgccaacctcttcagcaatatcacgggtagccaacgctatg
tcctgatagcggtctgccacacccagccggccacagtcgatgaatccagaaaagcggccatttccaccatgatatt
cggcaagcaggcatcgccatgggtcacgacgagatcctcgccgtcgggcatgctcgccttgagcctggcgaacagtt
cggctggcgcgagcccctgatgctcttcgtccagatcatcctgatcgacaagaccggcttccatccgagtacgtgct
cgctcgatgcgatgtttcgcttggtggtcgaatgggcaggtagccggatcaagcgtatgcagccgccgcattgcatc
agccatgatggatactttctcggcaggagcaaggtgagatgacaggagatcctgccccggcacttcgcccaatagca
gccagtcccttcccgcttcagtgacaacgtcgagcacagctgcgcaaggaacgcccgtcgtggccagccacgatagc
cgcgctgcctcgtcttgcagttcattcagggcaccggacaggtcggtcttgacaaaaagaaccgggcgcccctgcgc
tgacagccggaacaggcggcatcagagcagccgattgtctgttgtgcccagtcatagccgaatagcctctccaccc
aagcggccggagaacctgcgtgcaatccatcttgttcaatcatgcgaaacgatcctcatcctgtctcttgatcagat
cttgatcccctgcgccatcagatccttggcggcragaaagccatccagtttactttgcagggcttcccaaccttacc
agagggcgcccagctggcaattccggttcgcttgctgtccataaaaccgcccagtctagctatcgccatgtaagcc
cactgcaagctacctgctttctcttcgcgcttgcgttttcccttgtccagatagcccagtagctgacattcatccgg
ggtcagcaccgtttctgcggactggctttctacgtgaaaaggatctaggtgaagatccttttttgataatctcatgac
caaaatcccttaacgtgagttttcgttccactgagcgtcagacccgtagaaaagatcaaaggatcttcttgagatc
ctttttttctgcgcgtaatctgctgcttgcaaacaaaaaaaccaccgctaccagcggtggtttgtttgccggatcaa
gagctaccaactctttttccgaaggtaactggcttcagcagagcgcagataccaaatactgttcttctagtgtagcc
gtagttaggccaccacttcaagaactctgtagcaccgcctacatacctcgctctgctaatcctgttaccagtggctg
ctgccagtggcgataagtcgtgtcttaccgggttggactcaagacgatagttaccggataaggcgcagcggtcgggc
tgaacggggggttcgtgcacacagcccagcttggagcgaacgacctacaccgaactgagatacctacagcgtgagct
atgagaaagcgccacgcttcccgaagggagaaaggcggacaggtatccggtaagcggcagggtcggaacaggagagc
```

FIG. 12A-2 gcacgagggagcttccaggggggaaacgcctggtatctttatagtcctgtcgggtttcgccacctctgacttgagcgt
cgattttgtgatgctcgtcagggggcggagcctatggaaaaacgccagcaacgcggccctttttacggttcctggc
cttttgctggccttttgctcacatgttgtcgacaatattggctattggccattgcatacgttgtatctatatcataa
tatgtacatttatattggctcatgtccaatatgaccgccatgttgacattgattattgactagttattaatagtaat
caattacgggktcattagttcatagcccatatatggagttccgcgttacataacttacggtaaatggcccgcctggc
tgaccgcccaacgaccccgcccattgacgtcaataatgacgtatgttcccatagtaacgccaatagggactttcca
ttgacgtcaatgggtggagtatttacggtaaactgcccacttggcagtacatcaagtgtatcatatgccaagtccgc
ccctattgacgtcaatgacggtaaatggcccgcctggcattatgcccagtacatgaccttacgggactttcctactt
ggcagtacatctacgtattagtcatcgctattaccatggtgatgcggttttggcagtacaccaatgggcgtggatag
cggtttgactcacggggatttccaagtctccaccccattgacgtcaatgggagtttgttttkgscaccaaaatcaacg
ggactttccaaaatgtcgtaataaccccgccccgttgacgcaaatgggcggtaggcgtgtacggtgggaggtctata
taagcagagctcgtttagtgaaccgtcagatcgc

FIG. 12A-3 pGA2/JS7.1 functional regions

| Position within sequence (starting- and ending pos.) | Gene/ORF (indicate complete name of the gene and the expressed gene product) | Origin of sequence (organism) |
|---|---|---|
| 106-1608 | Gag, inactivating point mutations in zinc finger packaging sequences for viral RNA | HIV-1 HXB2 |
| 1401-3584 | Pol, inactivating point mutations in protease and reverse transcriptase, deletion of integrase | HIV-1 HXB2 |
| 3671-3885 and 6210-6300 | Tat exons #1 and #2 | HIV-1 ADA |
| 3810-3885 and 6210-6884 | Rev exons #1 and #2 | HIV-1 ADA |
| 3902-4147 | Vpu start site mutated (G3904C) and upstream ATG mutated (G3899C) | HIV-1 ADA |
| 4165-6626 | Env | HIV-1 ADA |
| 6627-9506 | Plasmid vector | PGA2, Gen Bank accession # AF425298 |

FIG. 12B

JS7.1 Mutation Chart

| Codon change | Amino acid change | Region | Function |
|---|---|---|---|
| to AGC Position 1279-1281 | C392S | Gag | Ablation of zinc finger used in packaging |
| to AGC Position 1288-1290 | C395S | Gag | Ablation of zinc finger used in packaging |
| to AGC Position 1342-1344 | C413S | Gag | Ablation of zinc finger used in packaging |
| to AGC Position 1351-1353 | C416S | Gag | Ablation of zinc finger used in packaging |
| to ACA position 1641-1643 | D25A | Protease | Inactivation of Protease active site |
| to AAC Position 2418-2420 | D185N | Reverse Transcriptase | Inactivation of Polymerase active site |
| to ACC Position 2661-2663 | W266T | Reverse Transcriptase | Ablation of strand transfer activity |
| to CAG Position 3297-3299 | E478Q | RNase H | Inactivation of RNase H activity |
| to ATC Position 3902-3904 | NA | Vpu | Vpu start site mutated |
| to ATC 3299 Position 3897-3899 | NA | Non-coding region | ATG upstream of Vpu mutated |

FIG. 12C pGA1/IC25 Sequence

```
atcgatgcaaggactcggcttgctgaggtgcacacagcaagaggcgagagcgacgactggtgagtacgccaattttttgac
tagcggaggctagaaggagagagatgggtgcgagagcgtcagtgttaacggggggaaaattagattcatgggagaaatt
aggttaaggccaggggggaaagaaaagatatagactaaaacacctagtatgggcaagcagggagctggagagattcgcact
taaccctggcctattagaaacagcagaaggatgtcaacaactaatgggacagttacaaccagctctcaggacaggatcag
aagagtttaaatcattatataatatagtagcaaccctttggtgcgtacatcaaagaatagacataaaagacacccaggag
gccttagataaagtagaggaaaaacaaaataagagcaagcaaaaggcacagcaggcagcagctgcaacagccgccacagg
aagcagcagccaaaattaccctatagtgcaaaatgcacaagggcaaatggtacatcagtccatgtcacctaggactttaa
atgcatgggtgaaggtaatagaagaaaaggcttttagcccagaggtaatacccatgttttcagcattatcagagggagcc
accccacaagatttaaatatgatgctaaacatagtgggggacaccaggcagcaatgcagatgttaaaagataccatcaa
tgatgaagctgcagaatgggacagagtacatccagtacatgcagggcctattccaccaggccaaatgagggaaccaaggg
gaagtgacatagcaggaactactagtaccccttcaagaacaaataggatggatgacaagtaatccacctatcccagtggga
gaaatctataaaagatggatagtcctgggattaaataaaatagtaagaatgtatagccctaccagcattttggacataag
acaagggccaaaagaacccttagagattatgtagacaggttctttaaaactttgagagctgaacaagctacgcaggagg
taaaaaactggatgacagaaaccttgttggtccaaaatgcgaatccagactgcaagtccatttaagagcattaggacca
gggctacattagaagaaatgatgacatcatgtcagggagtggaggacctggccataaagcaagggtttggctgaggc
aatgagtcaagtacaacagaccaatgtaatgatgcagagaggcaattttagaggccagagaataataaagagcttcaaca
gcggcaaagaaggcacctagccagaaattgcaaggctcctagaaaagagaggcagctggaaaagcggaaaggaaggacac
caaatgaaagactgtactgaaagacaggctaatttttagggaaaatttggccttcccacaaggggaggccaggaaattt
cctcagagcagaccagaaccaacagccccgccagcagagagctttggagtgggggaagagataccctcctctccgaagc
aggagccgagggacaagggactatatcctcccttaacttccctcaaatcactctttggcaacgaccagtagtcacagtaa
gaatagggggacagccaatagaagccctattaaacacaggagcagatgatacagtattagaagaaataagtttaccagga
aaatggaaaccaaaaatgataggggggaattggaggttttatcaaagtaagacagtatgatcagatatctatagaaatttg
tggaaaaagggccataggtacagtattagtaggacctacacctgtcaacataattggacgaaatatgttgactcagattg
gttgtactttaaattttccaattagtcctattgaaactgtgccagtaaaattaaagtcaggaatggatggcccaaaggtt
aaacaatggccattgacagaagaaaaaataaaagcattaaaagaaatttgtgcagagatggaaaaggaaggaaaaatttc
aaaaattgggcctgaaaaccccatacaatactccaatatttgccataaagaaaaaagatagtactaaatggagaaaattag
tagatttcagagagaactcaataagagaactcagggacttctgggaaggtccaattaggaataccctcatcctgcgggattaaaa
aagaaaaaatcagtaacagtactagatgtgggggatgcatatttttcagttccctttagatgaagactttagaaaatatac
tgcattcaccataccctagtttaaataatgagacaccagggattagatatcagtacaatgtactcccacagggatggaaag
gatcaccagcaatatttcaggcaagcatgacaaaaatcttagagccctttagagcaaaaaatccagagatagtgatctac
caatatatgaacgatttatatgtaggatctgacttagaaatagggcagcatagagcaaaaatagaggagttgagagaaca
tctattgaaatggggatttaccacaccagacaaaaaacatcagaaagaacctccatttcttttggatgggatatgaactcc
atcctgacaaatggacagtccagcctatacagctgccagaaaaagacagctggactgtcaatgatatacaaaaattagtg
ggaaaactaaataccgcaagtcagatttatgcaggaattaaagtaaagcaattgtgtagactcctcaggggagccaaagc
gctaacagatgtagtaacactgactgaggaagcagaattagaattggcagagaacagggaaattctaaaagaacctgtac
atggagtatattatgacccaacaaaagacttagtggcagaaatacagaaacaagggcaagatcaatggacatatcaaatt
tatcaagagccatttaaaaatctaaagacaggaaaatatgcaaaaaggaggtcggcccacactaatgatgtaaaacaatt
aacagaggtagtgcagaaaatagccatagaaagcatagtaatatgggggaagacccctaaatttagactacccatacaaa
gagaaacatgggaagcatggtggatggagtattggcaggctacctggattcctgaatgggagtttgtcaatacccctcct
ctagtaaaattatggtaccagttagagaaggaccccataatgggagcagaaactttctatgtagatgggggcagctaatag
ggagactaagctaggaaaagcagggtatgtcactgacagaggaagacaaaaggttgtttccctaactcagacaacaaatc
aaaagactcagttacatgcaattcatctagcctttgcaggattcaggatcagaagtaaatatagtaacagactcacagtat
gcattaggaatcattcaggcacaaccagacaggagtgaatcagagttagtcaatcaaataatagagaaactaatagaaaa
ggacaaagtctacctgtcatgggtaccagcacacaaagggattggaggaaatgaacaagtagataaattagtcagtagtg
gaatcagaaaggtactatttttagatggaatagataaagcccaagatgaacattagaattctgcaacagctactgtttgt
tcatttcagaattgggtgtcaacatagcagaataggcattattccagggagaagaggcaggaatggagctggtagatcct
agcctagagccctggaaccacccgggaagtcagcctacaactgcttgtagcaagtgttactgtaaaaaatgctgctggca
ttgccaattgtgctttctgaacaagggctttaggcatctcctatggcaggaagaagcggacgaggaactcctc
aggaccgtcaggttcatcaaaatcctgtaccaaaacagtaagtagtaattagtatatgtgatgcaatctttacaaat
agctgcaatagtaggactagtagtagcatccatagtagccatagttgtgtggtccatagtatttatagaatatagaaaaa
taaggaaacagaagaaaatagacaggttacttgagagaataagagaaagagcagaagatagtggcaatgagagtgatggg
gatacagaagaattatccactcttatggagaggggggtatgacaatattttggttaatgatgatttgtaatgctgaaagt
tgtgggtcacagtctactatggggtacctgtgtggagagacgcagagaccaccctattctgtgcatcagatgctaaagca
tatgacaaagaagcacacaatgtctgggctacgcatgcctgcgtacccacagaccctgacccacaagaattacctttggt
aaatgtaacagaagagtttaacatgtggaaaaataatatgtagaacagatgcatgaagatataattagtctatgggacc
aaagcttaaagccatgtgtacagctaacccctctctgcgttactttagggtgtgctgacgctcaaaacgtcaccgacacc
aacaccaccatatctaatgaaatgcaaggggaaataaaaaactgctctttcaatatgaccacagaattaagagataagaa
gcagaaagtgtatgcactttttttatagaccctgatgtaatagaaattaataaaactaagattaacaatagtaatagtagtc
agtatatgttaataaattgtaatacctcaaccattacacagacttgtccaaaggtatcctttgagccaattcccatacat
tattgtgccccagctggttttgcaattctaaagtgtaatgatacggagttcagtggaaaagggacatgcaagagtgtcag
cacagtacaatgcacacatggaatcaagccagtagtatcaactcaactgctgttaaatggcagtctagcagaaggaaaga
```

FIG. 13A-1

```
tagcgattagatctgagaatatctcaaacaatgccaaaactataatagtacaattgactgagcctgtagaaattaattgt
atcagacctggcaacaatacaagaaaaagtgtacgcataggaccaggacaaacattctatgcaacaggtgacataatagg
agatataagacaagcacactgtaatgttagtaaaatagcatgggaagaaactttacaaaaggtagctgcacaattaagga
agcactttcagaatgccacaataaaatttactaaacactcaggaggggatttagaaattacaacaaatagttttaattgt
ggaggagaattttctattgcaatacaacaaagctgtttaatagcacttggaataatgataactcaaacctcacagagga
aaagagaaaggaaaacataactctccactgcagaataaagcaaattgtaaatatgtggccaagagtaggacaagcaatat
atgcccctcccatcccaggaaacataacttgtggatcaaacattactgggctactattaacaagagatggagggaataat
ggtacaaatgatactgagaccttcaggcctggaggaggagatatgagggacaattggagaagtgaattatataaatataa
agtagtaaaaattgaaccactaggtgtagcaccaaccccctgcaaaaagaagagtggtggaaagagaaaaaagagcagttg
gaatgggagctttgatctttgagttcttaggagcagcaggaagcactatgggcgcggcgtcaatggcgctgacggtacag
gccagacaattattgtctggtatagtgcaacagcagagcaatctgctgaaggctatagaggctcaacaacatctgttgag
actcacggtctggggcattaaacagctccaggcaagagtcctggctctggaaagatacctaaaggatcaacagctcctag
gaatttggggctgctctggaaaactcatttgcaccactgctgtaccttggaactctagctggagtaataaaagttataat
gacatatgggataacatgacctggctgcaatggataaagaaattaacaattacacatacataatatataatctacttga
aaaatcgcagaaccagcaggaaattaatgaacaagacttattggcattagacaagtgggcaagtctgtggaattggtttg
acataacaagctggctatggtatataagattaggtataatgatagtaggaggcgtaataggcttaagaataattttgct
gtgcttactatagtgaatagagttaggcagggatactcacctttgtcattccagaccettgcccaccaccagagggaacc
cgacaggcccgaaagaatcgaagaaggaggtggcgagcaagacagagagagatccgtcgcgttagtgagcggattcttag
cacttgcctgggaagatctgcggagcctgtgcctcttcagctaccgccgattgagagacttagtcttgattgcagcaagg
actgtggaactcctgggacacagcagtctcaagggactgagactggggtgggaagccctcaaatatctgtggaaccttct
atcatactggggtcaggaactaaagaatagtgctattaatttgcttgatacaatagcaatagcagtagctaactggacag
atagagttataaaaatagtacaaagaactggtagagctattcttaacatacctagaaggatcagatagggctagccccgg
gtgataaacggaccgcgcaatccctaggctgtgccttctagttgccagccatctgttgtttgcccctccccgtgccttc
cttgacctggaaggtgccactcccactgtcctttcctaataaaatgaggaaattgcatcgcattgtctgagtaggtgtc
attctattctgggggtggggtggggcaggacagcaaggggggaggattgggaagacaatagcaggcatgctgggatgcg
gtgggctctatataaaaaacgccggcggcaaccgagcgttctgaacgctagagtcgacaaattcagaagaactcgtcaa
gaaggcgatagaaggcgatgcgctgcgaatcgggagcggcgataccgtaaagcacgaggaagcggtcagcccattcgccg
ccaagctcttcagcaatatcacgggtagccaacgctatgtcctgatagcggtctgccacacccagccggccacagtcgat
gaatccagaaaagcggccattttccaccatgatattcggcaagcaggcatcgccatgggtcacgacgagatcctcgccgt
cgggcatgctcgccttgagcctggcgaacagttcggctggcgcgagcccctgatgctcttcgtccagatcatcctgatcg
acaagaccggcttccatccgagtacgtgctcgctcgatgcgatgtttcgcttggtggtcgaatgggcaggtagccggatc
aagcgtatgcagccgccgcattgcatcagccatgatggatactttctcggcaggagcaaggtgagatgacaggagatcct
gccccggcacttcgcccaatagcagccagtccctteccgcttcagtgacaacgtcgagcacagctgcgcaaggaacgccc
gtcgtggccagccacgatagccgcgctgcctcgtcttgcagttcattcagggcaccggacaggtcggtcttgacaaaaag
aaccgggcgcccctgcgctgacagccggaacacggcggcatcagagcagccgattgtctgttgtgcccagtcatagccga
atagcctctccacccaagcggccggagaacctgcgtgcaatccatcttgttcaatcatgcgaaacgatcctcatcctgtc
tcttgatcagatcttgatccctgcgccatcagatccttggcggcaagaaagccatccagtttactttgcagggcttccc
aaccttaccagagggcgccccagctggcaattccggttcgcttgctgtccataaaaccgcccagtctagctatcgccatg
taagcccactgcaagctacctgctttctctttgcgcttgcgttttcccttgtccagatagcccagtagctgacattcatc
cggggtcagcaccgtttctgcggactggctttctacgtgaaaaggatctaggtgaagatcctttttgataatctcatgac
caaaatcccttaacgtgagttttcgttcctcactgagcgtcagaccccgtagaaaagatcaaaggatcttcttgagatcctt
ttttctgcgcgtaatctgctgcttgcaaacaaaaaaaccaccgctaccagcggtggtttgtttgccggatcaagagcta
ccaactctttttccgaaggtaactggcttcagcagagcgcagataccaaatactgttcttctagtgtagccgtagttagg
ccaccacttcaagaactctgtagcaccgcctacatacctcgctctgctaatcctgttaccagtggctgctgccagtggcg
ataagtcgtgtcttaccgggttggactcaagacgatagttaccggataaggcgcagcggtcgggctgaacggggggttcg
tgcacacagcccagcttggagcgaacgacctacaccgaactgagatacctacagcgtgagctatgagaaagcgccacgct
tcccgaagggagaaaggcggacaggtatccggtaagcggcagggtcggaacaggagagcgcacgagggagcttccagggg
gaaacgcctggtatctttatagtcctgtcgggtttcgccacctctgacttgagcgtcgatttttgtgatgctcgtcaggg
gggcggagcctatgggaaaacgccagcaacgcggccttttacggttcctggccttttgctggccttttgctcacatgtt
gtcgacaatattggctattggccattgcatacggttgtatctatatcataatatgtacatttatattggctcatgtccaat
atgaccgccatgttgacattgattattgactagttattaatagtaatcaattacgggttcattagttcatagcccatata
tggagttccgcgttacataacttacggtaaatggcccgcctggctgaccgcccaacgacccccgcccattgacgtcaata
atgacgtatgttcccatagtaacgccaatagggactttccattgacgtcaatgggtggagtatttacggtaaactgccca
cttggcagtacatcaagtgtatcatatgccaagtccgccccctattgacgtcaatgacggtaaatggcccgcctggcatt
atgcccagtacatgaccttacgggactttcctacttggcagtacatctacggtattagtcatcggctattaccatggtga
tgcggttttggcagtacaccaatgggcgtggatagcggtttgactcacggggatttccaagtctccaccccattgacgtc
aatgggagtttgttttggcaccaaaatcaacgggactttccaaaatgtcgtaataacccgccccgttgacgcaaatggg
cggtaggcgtgtacggtgggaggtctatataagcagagctcgtttagtgaaccgtcagatcgcctggagacgccatccac
gctgttttgacctccatagaagacaccgggaccgatccagcctccgcggccgggaacggtgcattggaacgcggattccc
cgtgccaagagtgacgtaagtaccgcctatagactctataggcacacccctttggctcttatgcatgctatactgttttt
ggcttggggcctatacaccccgcttccttatgctataggtgatggtatagcttagcctataggtgtgggttattgacca
ttattgaccactcccctattggtgacgatactttccattactaatccataacatggctctttgccacaactatctctatt
ggctatatgccaatactctgtccttcagagactgacacggactctgtattttacaggatggggtcccatttattatta
```

FIG. 13A-2

```
caaattcacatatacaacaacgccgtccccgtgcccgcagttttattaaacatagcgtgggatctccacgcgaatctc
gggtaccgtgttccggacatgggytcttctccggtagcggcggagcttccacatccgagccctggtcccatgcctccagc
ggctcatggtcgctcggcagctccttgctcctaacagtggaggccagacttaggcacagcacaatgcccaccaccaccag
tgtgccgcacaaggccgtggcggtagggtatgtgtctgaaaatgagctcggagattgggctcgcaccgctgacgcagatg
gaagacttaaggcagcggcagaagaagatgcaggcagctgagttgttgtattctgataagagtcagaggtaactcccgtt
gcggtgctgttaacggtggagggcagtgtagtctgagcagtactcgttgctgccgcgcgcgccaccagacataatagctg
acagactaacagactgttcctttccatgggtcttttctgcagtcacc
```

FIG. 13A-3 pGA1/IC25 Functional Regions

| Position within sequence (starting-and ending pos.) | Gene/ORF (indicate complete name of the gene and the expressed gene product) | Origin of sequence (organism) |
|---|---|---|
| 104-1591 | Gag, inactivating point mutations in zinc finger packaging sequences for viral RNA | AG HIV-1 isolate 928 |
| 1393-3576 | Pol, inactivating point mutations in protease and reverse transcriptase, deletion of integrase | AG HIV-1 isolate 928 |
| 3663-3877 and 6215-6305 | Tat exons #1 and #2 | AG HIV-1 isolate 928 |
| 3802-3877 and 6215-6510 | Rev exons #1 and #2 | AG HIV-1 isolate 928 |
| 3904-4149 | Vpu | AG HIV-1 isolate 928 |
| 4067-6628 | Env | AG HIV-1 isolate 928 |
| 6629-10447 | Plasmid vector | PGA1, Gen Bank accession # AF425297 |

FIG. 13B

IC25 Mutation Chart

| Codon change | Amino acid change | Region | Function |
|---|---|---|---|
| to AGC position 1271-1273 | C390S | Gag | Ablation of zinc finger used in packaging |
| to AGC position 1280-1282 | C393S | Gag | Ablation of zinc finger used in packaging |
| to AGC position 1334-1336 | C411S | Gag | Ablation of zinc finger used in packaging |
| to AGC position 1343-1336 | C414S | Gag | Ablation of zinc finger used in packaging |
| to AAC position 1633-1635 | R25N | Protease | Inactivation of Protease active site |
| to AAC position 2410-2412 | D185N | Reverse Transcriptase | Inactivation of Polymerase active site |
| to ACC position 2653-2655 | W266T | Reverse Transcriptase | Ablation of strand transfer activity |
| to CAG position 3289-3291 | E478Q | Rnase H | Inactivation of RNase H activity |

FIG. 13C pGA1/IC2 Sequence

```
atcgatgcaaggactcggcttgctgaggtgcacacagcaagaggcgagagcgacgactggtgagtacgccaattttttgac
tagcggaggctagaaggagagagatgggtgcgagagcgtcagtgttaacggggggaaaattagattcatgggagaaatt
aggttaaggccaggggggaaagaaaagatatagactaaaacacctagtatgggcaagcagggagctggagagattcgcact
taaccctggcctattagaaacagcagaaggatgtcaacaactaatgggacagttacaaccagctctcaggacaggatcag
aagagtttaaatcattatataatatagtagcaacccctttggtgcgtacatcaaagaatagacataaaagacacccaggag
gccttagataaagtagaggaaaaacaaaataagagcaagcaaaaggcacagcaggcagcagctgcaacagccgccacagg
aagcagcagccaaaattaccctatagtgcaaaatgcacaagggcaaatggtacatcagtccatgtcacctaggactttaa
atgcatgggtgaaggtaatagaagaaaaggcttttagcccagaggtaatacccatgttttcagcattatcagagggagcc
accccacaagatttaaatatgatgctaaacatagtgggggggacaccaggcagcaatgcagatgttaaaagataccatcaa
tgatgaagctgcagaatgggacagagtacatccagtacatgcagggcctattccaccaggccaaatgagggaaccaaggg
gaagtgacatagcaggaactactagtacccttcaagaacaaataggatggatgacaagtaatccacctatcccagtggga
gaaatctataaaagatggatagtcctgggattaaataaaatagtaagaatgtatagccctaccagcattttggacataag
acaagggccaaaagaacccttttagagattatgtagacaggttctttaaaactttgagagctgaacaagctacgcaggagg
taaaaaactggatgacagaaaccttgttggtccaaaatgcgaatccagactgcaagtccatttttaagagcattaggacca
ggggctacattagaagaaatgatgacatcatgtcagggagtgggaggacctggccataaagcaagggttttggctgaggc
aatgagtcaagtacaacagaccaatgtaatgatgcagagaggcaatttttagaggccagagaataataaagagcttcaaca
gcggcaaagaaggacacctagccagaaattgcaaggctcctagaaagagaggcagctggaaaagcggaaaggaaggacac
caaatgaaagactgtactgaaagacaggctaattttttagggaaaatttggccttcccacaaggggggaggccaggaaattt
tcctcagagcagaccagaaccaacagccccgccagcagagagctttggagtgggggaagagatacctcctctccgaagc
aggagccgagggacaagggactatatcctcccttaacttccctcaaatcactctttggcaacgaccagtagtcacagtaa
gaataggggggacagccaatagaagccctattagacacaggagcagatgatacagtattagaagaaataagtttaccagga
aaatggaaaccaaaaatgataggggggaattggaggtttttatcaaagtaagacagtatgatcagatatctatagaaatttg
tggaaaaaagggccataggtacagtattagtaggacctacacctgtcaacataattggacgaaatatgttgactcagattg
gttgtactttaaattttccaattagtcctattgaaactgtgccagtaaaattaaagtcaggaatggatggcccaaaggtt
aaacaatggccattgacagaagaaaaaataaaagcattaaaagaaatttgtgcagagatggaaaaggaaggaaaaatttc
aaaaattgggcctgaaaacccatacaatactccaatatttgccataaagaaaaagatagtactaaatggagaaaattag
tagatttcagagaactcaataagagaacttcaagacttctgggaggtccaattaggaatacctcatcctgcgggattaaaa
aagaaaaaatcagtaacagtactagatgtgggggatgcatattttcagttccctttagatgaagactttagaaaatatac
tgcattcaccatacctagttaaataatgagacaccagggattagatatcagtacaatgtactcccacagggatggaaag
gatcaccagcaatatttcaggcaagcatgacaaaaatcttagagcccttagagcaaaaaatccagagatagtgatctac
caatatatgaacgatttatatgtaggatctgacttagaaatagggcagcatagagcaaaaatagaggagttgagagaaca
tctattgaaatggggatttaccacaccagacaaaaaacatcagaaagaacctccatttctttggatgggatatgaactcc
atcctgacaaatggacagtccagcctatacagctgccagaaaaagacagctggactgtcaatgatatacaaaattagtg
ggaaaactaaataccgcaagtcagatttatgcaggaattaaagtaaagcaattgtgtagactcctcaggggagccaaagc
gctaacagatgtagtaacactgactgaggaagcagaattagaattggcagagaacagggaaattctaaaagaacctgtac
atggagtatattatgacccaacaaaagacttagtggcagaaatacagaaacaagggcaagatcaatggacatatcaaatt
tatcaagagccatttaaaaatctaaagacaggaaaatatgcaaaaaagaggtcggcccacactaatgatgtaaaacaatt
aacagaggtagtgcagaaaatagccatagaaagcatagtaatatggggaaagacccctaaatttagactacccatacaaa
gagaaacatgggaagcatggtggatggagtattggcaggctacctggattcctgaatgggagtttgtcaatacccctcct
ctagtaaaattatggtaccagttagagaaggaccccataatgggagcagaaactttctatgtagatggggcagctaatag
ggagactaagctaggaaaagcagggtatgtcactgacagaggaagacaaaaggttgtttcccctaattcagacaacaaatc
aaaagactcagttacatgcaattcatctagccttgcaggattcaggatcagaagtaaatatagtaacagactcacagtat
gcattaggaatcattcaggcacaaccagacaggagtgaatcagagttagtcaatcaaataatagagaaactaatagaaaa
ggacaaagtctacctgtcatgggtaccagcacacaaagggattggaggaaatgaacaagtagataaattagtcagtagtg
gaatcagaaaggtactatttttagatggaatagataaagcccaagatgaacattagaattctgcaacagctactgtttgt
tcatttcagaattgggtgtcaacatagcagaataggcattattccaggagaagaggcaggaatggagctggtagatcct
agcctagagccctggaaccacccgggaagtcagcctacaactgcttgtagcaagtgttactgtaaaaatgctgctggca
ttgccaattgtgctttctgaacaagggcttaggcatctcctatggcaggaagaagcggagacgccgacgaggaactcctc
aggaccgtcaggttcatcaaaatcctgtaccaaaacagtaagtagtagtaattagtatatgtgatgcaatctttacaaat
agctgcaataggtaggactagtagtagtagcatccatagtagcatagttgtgtggtccatagtatttatagaatagaaaaa
taaggaaacagaagaaaatagacaggttacttgagagaataagagaaagagcagaagatagtggcaatgagagtgatggg
gatacagaagaattatccactcttatggagaggggggtatgacaatattttggttaatgatgatttgtaatgctgaaaagt
tgtgggtcacagtctactatggggtacctgtgtggagagacgcagagaccaccctattctgtgcatcagatgctaaagca
tatgacaaagaagcacacaatgtctgggctacgcatgcctgcgtacccacagaccctgacccacaagaattacctttggt
aaatgtaacagaagagtttaacatgtggaaaaataatatggtagaacagatgcatgaagatataattagtctatgggacc
aaagcttaaagccatgtgtacagctaacccctctctgcgttacttTagggtgtgctgacgctcaaaacgtcaccgacacc
aacaccaccatatctaatgaaatgcaaggggaaataaaaaactgctctttcaatatgaccacagaattaagagataagaa
gcagaaagtgtatgcactttttttatagacctgatgtaatagaaattaataaaactaagattaacaatagtaatagtagtc
agtatatgttaataaattgtaatacctcaaccattacacagacttgtccaaaggtatcctttgagccaattcccatacat
tattgtgccccagctggttttgcaattctaaagtgtaatgatacggagttcagtggaaaagggacatgcaagagtgtcag
cacagtacaatgcacacatggaatcaagccagtagtatcaactcaactgctgttaaatggcagtctagcagaaggaaaga
```

FIG. 14A-1

```
tagcgattagatctgagaatatctcaaacaatgccaaaactataatagtacaattgactgagcctgtagaaattaattgt
atcagacctggcaacaatacaagaaaaagtgtacgcataggaccaggacaaacattctatgcaacaggtgacataatagg
agatataagacaagcacactgtaatgttagtaaaatagcatgggaagaaactttacaaaaggtagctgcacaattaagga
agcactttcagaatgccacaataaaatttactaaacactcaggaggggatttagaaattacaacaaatagttttaattgt
ggaggagaattttctattgcaatacaacaaagctgtttaatagcacttggaataatgataactcaaacctcacagagga
aaagagaaaggaaaacataactctccactgcagaataaagcaaattgtaaatatgtggccaagagtaggacaagcaatat
atgcccctcccatcccaggaaacataacctgtggatcaaacattactgggctactattaacaagagatggagggaataat
ggtacaaatgatactgagaccttcaggcctggaggaggagatatgagggacaattggagaagtgaattatataaatataa
agtagtaaaaattgaaccactaggtgtagcaccaaccctgcaaaagaagagtggtggaaagagaaaaagagcagttg
gaatgggagctttgatctttgagttcttaggagcagcaggaagcactatgggcgcggcgtcaatggcgctgacggtacag
gccagacaattattgtctggtatagtgcaacagcagagcaatctgctgaaggctatagaggctcaacaacatctgttgag
actcacggtctggggcattaaacagctccaggcaagagtcctggctctggaaagatacctaaaggatcaacagctcctag
gaatttggggctgctctggaaaactcatttgcaccactgctgtacctggaactctagctggagtaataaaagttataat
gacatatgggataacatgacctggctgcaatgggataaagaaattaacaattacacatacataatatataatctacttga
aaaatcgcagaaccagcaggaaattaatgaacaagacttattggcattagacaagtgggcaagtctgtggaattggtttg
acataacaagctggctatggtatataagattaggtataatgatagtaggaggcgtaataggcttaagaataatttttgct
gtgcttactatagtgaatagagttaggcagggatactcaccttttgtcattccagacccttgcccaccaccagagggaacc
cgacaggcccgaaagaatcgaagaaggaggtggcgagcaagacagagagagatccgtgcgcttagtgagcggattcttag
cacttgcctgggaagatctgcggagcctgtgcctcttcagctaccgccgattgagagacttagtcttgattgcagcaagg
actgtggaactcctgggacacacagtctcaagggactgagactggggtggaagccctcaaatatctgtggaaccttct
atcatactggggtcaggaactaaagaatagtgctattaatttgcttgatacaatagcaatagcagtagctaactggacag
atagagttataaaaatagtacaaagaactggtagagctattcttaacatacctagaaggatcagataggggctagcccgg
gtgataaacggaccgcgcaatccctaggctgtgccttctagttgccagccatctgttgtttgccctccccgtgccttc
cttgaccctggaaggtgccactcccactgtcctttcctaataaaatgaggaaattgcatcgcattgtctgagtaggtgtc
attctattctggggggtggggtggggcaggacagcaaggggggaggattgggaagacaatagcaggcatgctggggatgcg
gtgggctctatataaaaaacgcccggcggcaaccgagcgttctgaacgctagagtcgacaaattcagaagaactcgtcaa
gaaggcgatagaaggcgatgcgctgcgaatcgggagcggcgataccgtaaagcacgaggaagcggtcagcccattcgccg
ccaagctcttcagcaatatcacgggtagccaacgctatgtcctgatagcggtctgccacacccagccggccacagtcgat
gaatccagaaaagcggccattttccaccatgatattcggcaagcaggcatcgccatgggtcacgacgagatcctcgccgt
cgggcatgctcgccttgagcctggcgaacagttcggctggcgcgagcccctgatgctcttcgtccagatcatcctgatcg
acaagaccggcttccatccgagtacgtgctcgctcgatgcgatgtttcgcttggtggtcgaatgggcaggtagccggatc
aagcgtatgcagccgccgcattgcatcagccatgatggatactttctcggcaggagcaaggtgagatgacaggagatcct
gccccggcacttcgcccaatagcagccagtcccttcccgcttcagtgacaacgtcgagcacagctgcgcaaggaacgccc
gtcgtggccagccacgatagccgcgctgcctcgtcttgcagttcattcagggcaccggacaggtcggtcttgacaaaaag
aaccgggcgcccctgcgctgacagccggaacacggcggcatcagagcagccgattgtctgttgtgcccagtcatagccga
atagcctctccacccaagcggccggagaacctgcgtgcaatccatcttgttcaatcatgcgaaacgatcctcatcctgtc
tcttgatcagatcttgatccctgcgccatcagatccttggcggcaagaaagccatccagtttactttgcagggcttccc
aaccttaccagagggcgccccagctggcaattccggttcgcttgctgtccataaaaccgcccagtctagctatcgccatg
taagcccactgcaagctacctgctttctctttgcgcttgcgttttcccttgtccagatagcccagtagctgacattcatc
cggggtcagcaccgtttctgcggactggctttctacgtgaaaaggatctaggtgaagatcctttttgataatctcatgac
caaaatcccttaacgtgagttttcgttccactgagcgtcagacccgtagaaaagatcaaaggatcttcttgagatcctt
ttttctgcgcgtaatctgctgcttgcaaacaaaaaaaccaccgctaccagcggtggtttgtttgccggatcaagagcta
ccaactcttttccgaaggtaactggcttcagcagagcgcagataccaaatactgttcttctagtgtagccgtagttagg
ccaccacttcaagaactctgtagcaccgcctacatacctcgctctgctaatcctgttaccagtggctgctgccagtggcg
ataagtcgtgtcttaccgggttggactcaagacgatagttaccggataaggcgcagcggtcgggctgaacggggggttcg
tgcacacagcccagcttggagcgaacgacctacaccgaactgagataccacagcgtgagctatgagaaagcgccacgct
tcccgaagggagaaaggcggacaggtatccggtaagcggcagggtcggaacaggagagcgcacgagggagcttccagggg
gaaacgcctggtatctttatagtcctgtcgggtttcgccacctctgacttgagcgtcgatttttgtgatgctcgtcaggg
gggcggagcctatggaaaaacgccagcaacgcggccttttacggttcctggccttttgctggccttttgctcacatgtt
gtcgacaatattggctattggccattgcatacgttgtatctatatcataatatgtacatttatattggctcatgtccaat
atgaccgccatgttgacattgattattgactagttattaatagtaatcaattacgggttcattagttcatagcccatata
tggagttccgcgttacataacttacggtaaatggcccgcctggctgaccgcccaacgacccccgcccattgacgtcaata
atgacgtatgttcccatataacgccaataggggacttttccattgacgtcaatgggtggagtatttacggtaaactgccca
cttggcagtacatcaagtgtatcatatgccaagtccgccccctattgacgtcaatgacggtaaatggcccgcctggcatt
atgcccagtacatgaccttacgggactttcctacttggcagtacatctacggtattagtcatcggctattaccatggtga
tgcggttttggcagtacaccaatgggcgtggatagcggtttgactcacggggatttccaagtctccaccccattgacgtc
aatgggagtttgttttggcaccaaaatcaacgggactttccaaaatgtcgtaataaccccgccccgttgacgcaaatggg
cggtaggcgtgtacggtgggaggtctatataagcagagctcgtttagtgaaccgtcagatcgcctggagacgccatccac
gctgttttgacctccatagaagacaccgggaccgatccagcctccgcggccgggaacggtgcattggaacgcggattccc
cgtgccaagagtgacgtaagtaccgcctatagactctataggcacaccctttggctcttatgcatgctatactgttttt
ggcttggggcctatacaccccgcttccttatgctataggtgatggtatagcttagcctataggtgtgggttattgacca
ttattgaccactcccctattggtgacgatactttccattactaatccataacatggctctttgccacaactatctctatt
ggctatatgccaatactctgtccttcagagactgacacggactctgtattttacaggatggggtcccatttatttta
```

FIG. 14A-2

```
caaattcacatatacaacaacgccgtccccgtgcccgcagttttttattaaacatagcgtgggatctccacgcgaatctc
gggtaccgtgttccggacatgggytcttctccggtagcggcggagcttccacatccgagccctggtcccatgcctccagc
ggctcatggtcgctcggcagctccttgctcctaacagtggaggccagacttaggcacagcacaatgcccaccaccaccag
tgtgccgcacaaggccgtggcggtagggtatgtgtctgaaaatgagctcggagattgggctcgcaccgctgacgcagatg
gaagacttaaggcagcggcagaagaagatgcaggcagctgagttgttgtattctgataagagtcagaggtaactcccgtt
gcggtgctgttaacggtggagggcagtgtagtctgagcagtactcgttgctgccgcgcgcgccaccagacataatagctg
acagactaacagactgttcctttccatgggtcttttctgcagtcacc
```

FIG. 14A-3 pGA1/IC2 Functional Regions

| Position within sequence (starting-and ending pos.) | Gene/ORF (indicate complete name of the gene and the expressed gene product) | Origin of sequence (organism) |
|---|---|---|
| 104-1591 | Gag, inactivating point mutations in zinc finger packaging sequences for viral RNA | AG HIV-1 isolate 928 |
| 1393-3576 | Pol, inactivating point mutations in reverse transcriptase, deletion of integrase | AG HIV-1 isolate 928 |
| 3663-3877 and 6215-6305 | Tat exons #1 and #2 | AG HIV-1 isolate 928 |
| 3802-3877 and 6215-6510 | Rev exons #1 and #2 | AG HIV-1 isolate 928 |
| 3904-4149 | Vpu | AG HIV-1 isolate 928 |
| 4067-6628 | Env | AG HIV-1 isolate 928 |
| 6629-10447 | Plasmid vector | PGA1, Gen Bank accession # AF425297 |

FIG. 14B

IC2 Mutation Chart

| Codon change | Amino acid change | Region | Function |
|---|---|---|---|
| to AGC position 1271-1273 | C390S | Gag | Ablation of zinc finger used in packaging |
| to AGC position 1280-1282 | C393S | Gag | Ablation of zinc finger used in packaging |
| to AGC position 1334-1336 | C411S | Gag | Ablation of zinc finger used in packaging |
| to AGC position 1343-1336 | C414S | Gag | Ablation of zinc finger used in packaging |
| to AAC position 2410-2412 | D185N | Reverse Transcriptase | Inactivation of Polymerase active site |
| to ACC position 2653-2655 | W266T | Reverse Transcriptase | Ablation of strand transfer activity |
| to CAG position 3289-3291 | E478Q | RNase H | Inactivation of RNase H activity |

FIG. 14C pGA1/IC48 sequence

```
atcgatgcaaggactcggcttgctgaggtgcacacagcaagaggcgagagcgacgactggtgagtacgccaattttttgac
tagcggaggctagaaggagagagatgggtgcgagagcgtcagtgttaacggggggaaaattagattcatgggagaaaatt
aggttaaggccaggggggaaagaaaagatatagactaaaacacctagtatgggcaagcagggagctggagagattcgcact
taaccctggcctattagaaacagcagaaggatgtcaacaactaatgggacagttacaaccagctctcaggacaggatcag
aagagtttaaatcattatataatatagtagcaacccttggtgcgtacatcaaagaatagacataaaagacacccaggag
gccttagataaagtagaggaaaaacaaaataagagcaagcaaaaggcacagcaggcagcagctgcaacagccgccacagg
aagcagcagcagccaaaattaccctatagtgcaaaatgcacaagggcaaatggtacatcagtccatgtcacctaggactttaa
atgcatgggtgaaggtaatagaagaaaaggcttttagcccagaggtaatacccatgttttcagcattatcagagggagcc
accccacaagatttaaatatgatgctaaacatagtgggggacaccaggcagcaatgcagatgttaaaagataccatcaa
tgatgaagctgcagaatgggacagagtacatccagtacatgcagggcctattccaccaggccaaatgagggaaccaaggg
gaagtgacatagcaggaactactagtaccttcaagaacaaataggatggatgacaagtaatccacctatcccagtggga
gaaatctataaaagatggatagtcctgggattaaataaaatagtaagaatgtatagcccctaccagcatttgggacataag
acaaggggccaaaagaacccctttagagattatgtagacaggttctttaaaactttgagagctgaacaagctacgcaggagg
taaaaaactggatgacagaaaccttgttggtccaaaatgcgaatccagactgcaagtccatttttaagagcattaggacca
ggggctacattagaagaaatgatgacatcatgtcaggagtgggaggacctggccataaagcaagggtttggctgaggc
aatgagtcaagtacaacagaccaatgtaatgatgcagagaggcaattttagaggccagagaataataaagagcttcaaca
gcggcaaagaaggacacctagccagaaattgcaaggctcctagaaagagaggcagctggaaaagcggaaaggaaggacac
caaatgaaagactgtactgaaagacaggctaatttttttagggaaaatttggccttcccacaaggggaggccaggaaattt
tcctcagagcagaccagaaccaacagccccgccagcagagagctttggagtgggggaagagatacctcctctccgaagc
aggagccgagggacaagggactatatcctcccttaacttccctcaaatcactctttggcaacgaccagtagtcacagtaa
gaataggggggacagccaatagaagcccctattagacacaggagcagatgatacagtattagaagaaataagtttaccagga
aaatggaaaccaaaaatgataggtggaattggaggttttatcaaagtaagacagtatgatcagatatctatagaaatttg
tggaaaaagggccataggtacagtattagtaggacctacacctgtcaacataattggacgaaatatgttgactcagattg
gttgtactttaaattttccaattagtcctattgaaactgtgccagtaaaattaaagtcaggaatggatggcccaaaggtt
aaacaatggccattgacagaagaaaaaataaaagcattaaaagaaatttgtgcagagatggaaaaggaaggaaaaatttc
aaaaattgggcctgaaaacccatacaatactccaatatttgccataaagaaaaaagatagtactaaatggagaaaattag
tagatttcagagaactcaataagagaactcaagacttctgggaggtccaattaggaataccctcatcctgcgggattaaaa
aagaaaaaatcagtaacagtactagatgtgggggatgcatatttttcagttcccttagatgaagactttagaaaatatac
tgcattccaccatacctagttaataatgagaacaccagggattagatatcagtacaatgtactcccacagggatggaaag
gatcaccagcaatatttcaggcaagcatgacaaaaatcttagagccctttagagcaaaaatccagagatagtgatctac
caatatatgaacgatttatatgtaggatctgacttagaaatagggcagcatagagcaaaaatagaggagttgagagaaca
tctattgaaatggggatttaccacaccagacaaaaaacatcagaaagaacctccatttctttggatgggatatgaactcc
atcctgacaaatggacagtccagcctatacagctgccagaaaaagacagctggactgtcaatgatatacaaaaattagtg
ggaaaactaaataccgcaagtcagatttatgcaggaattaaagtaaagcaattgtgtagactcctcaggggagccaaagc
gctaacagatgtagtaacactgactgaggaagcagaattagaattggcagagaacagggaaattctaaaagaacctgtac
atggagtatattatgacccaacaaaagacttagtgcagaaatacaggctcaattcaatggacatatcaaatt
tatcaagagccatttaaaaatctaaagacaggaaaatatgcaaaaagaggtcggcccacactaatgatgtaaaacaatt
aacagaggtagtgcagaaaatagccatagaaagcatagtaatatgggggaagaccccctaaatttagactacccatacaaa
gagaaacatgggaagcatggtggatggagtattggcaggctacctggattcctgaatgggagtttgtcaatacccctcct
ctagtaaaattatggtaccagttagagaaggaccccataatgggagcagaaactttctatgtagatggggcagctaatag
ggagactaagctaggaaaagcagggtatgtcactgacagaggaagacaaaaggttgtttccctaattcagacaacaaatc
aaaagactcagttacatgcaattcatctagccttgcaggattcaggatcagaagtaaatatagtaacagactcacagtat
gcattaggaatcattcaggcacaaccagacagagtaatcagagttagtcaataaataatagagaaactaatagaaaaa
ggacaaagtctacctgtcatgggtaccagcacacaaaggattggaggaaatgaacaagtagataaaattagtcagtagtg
gaatcagaaaggtactatttttagatggaatagataaagcccaagatgaacattagaattctgcaacagctactgtttgt
tcatttcagaattgggtgtcaacatagcagaataggcattattccagggagaagaggcaggaatggagctggtagatcct
agcctagagccctggaaccacccgggaagtcagcctacaactgcttgtagcaagtgttactgtaaaaatgctgctggca
ttgccaattgtgctttctgaacaagggcttaggcatctcctatggcaggaagaagcggagacgccgacgaggaactcctc
aggaccgtcaggttcatcaaaatcctgtaccaaaacagtaagtagtagtaattagtatatgtgatgcaatctttacaaat
agctgcaatagtaggactagtagtagcatccatagtagccatagttgtgtggtccatagtatttatagaatatagaaaaa
taaggaaacagaagaaaatagacaggttacttgagaataagaaagacagaggcagaagatagtggcaatgagagtgatggg
gatacagaagaattatccactcttatggagagggggtatgacaatattttggttaatgatgatttgtaatgctgaaaagt
tgtgggtcacagtctactatggggtacctgtgtggagagacgcagagaccacccctattctgtgcatcagatgctaaagca
tatgacaaagaagcacacaatgtctgggctacgcatgcctgcgtacccacagaccctgacccacaagaattaccttttggt
aaatgtaacagaagagtttaacatgtggaaaaataatatggtagaacagatgcatgaagatataattagtctatgggacc
aaagcttaaagccatgtgtacagctaaccccctctctgcgttactttagggtgtgctgacgctcaaaacgtcaccgacacc
aacaccaccatatctaatgaaatgcaaggggaaataaaaaactgctcttcaatatgaccacagaattaagagataagaa
gcagaaagtgtatgccactttttttatagacctgatgtaatagaaattaataaaactaagattaacaatagtaatagtagtc
agtatatgttaataaattgtaatacctcaaccattacacagactgtcccaaaggtatcctttgagccaattcccatacat
tattgtgccccagctggttttgcaattctaaagtgtaatgatacggagttcagtggaaaaagggacatgcaagagtgtcag
cacagtacaatgcacacatggaatcaagccagtagtatcaactcaactgctgttaaatggcagtctagcagaaggaaaga
```

FIG. 15A-1

```
tagcgattagatctgagaatatctcaaacaatgccaaaactataatagtacaattgactgagcctgtagaaattaattgt
atcagacctggcaacaatacaagaaaaagtgtacgcataggaccaggacaaacattctatgcaacaggtgacataatagg
agatataagacaagcacactgtaatgttagtaaaatagcatgggaagaaactttacaaaaggtagctgcacaattaagga
agcactttcagaatgccacaataaaatttactaaacactcaggaggggatttagaaattacaacaaatagttttaattgt
ggaggagaattttctattgcaatacaacaaagctgtttaatagcacttggaataatgataactcaaacctcacagagga
aaagagaaaggaaaacataactctccactgcagaataaagcaaattgtaaatatgtggccaagagtaggacaagcaatat
atgcccctcccatcccaggaaacataacttgtggatcaaacattactgggctactattaacaagagatggagggaataat
ggtacaaatgatactgagaccttcaggcctggaggaggagatatgagggacaattggagaagtgaattatataaatataa
agtagtaaaaattgaaccactaggtgtagcaccaaccctgcaaaagaagagtggtggaaagagaaaaaagagcagttg
gaatgggagctttgatctttgagttcttaggagcagcaggaagcactatgggcgcggcgtcaatggcgctgacggtacag
gccagacaattattgtctggtatagtgcaacagcagagcaatctgctgaaggctatagaggctcaacaacatctgttgag
actcacggtctggggcattaaacagctccaggcaagagtcctggctctgaaagatacctaaaggatcaacagctcctag
gaatttggggctgctctggaaaactcatttgcaccactgctgtaccttggaactctagctggagtaataaaagttataat
gacatatgggataacatgacctggctgcaatgggataaagaaattaacaattacacatacataatatataatctacttga
aaaatcgcagaaccagcaggaaattaatgaacaagacttattggcattagacaagtgggcaagtctgtggaattggttg
acataacaagctggctatggtatataagattaggtataatgatagtaggaggcgtaataggcttaagaataattttgct
gtgcttactatagtgaatagagttaggcagggatactcaccttgtcattccagacccttgcccaccaccagagggaacc
cgacaggcccgaaagaatcgaagaaggaggtggcgagcaagacagagagatccgtgcgcttagtgagcggattcttag
cacttgcctgggaagatctgcggagcctgtgcctcttcagctaccgccgattgagagacttagtcttgattgcagcaagg
actgtggaactcctgggacacagcagtctcaagggactgagactggggtgggaagccctcaaatatctgtggaaccttct
atcatactgggtcaggaactaaagaatagtgctattaatttgcttgatacaatagcaatagcagtagctaactggacag
atagagttataaaatagtacaaagaactggtagagctattcttaacatacctagaaggatcagataggctagcccgg
gtgataaacggaccgcgcaatccctaggctgtgccttctagttgccagccatctgttgtttgcccctcccccgtgccttc
cttgaccctggaaggtgccactcccactgtcctttcctaataaaatgaggaaattgcatcgcattgtctgagtaggtgtc
attctattctggggggtggggtggggcaggacagcaaggggaggattgggaagacaatagcaggcatgctggggatgcg
gtgggctctatataaaaaaacgcccggccggcaaccgagcgttctgaacgctagagtcgacaaattcagaagaactcgtcaa
gaaggcgatagaaggcgatgcgctgcgaatcgggagcggcgataccgtaaagcacgaggaagcggtcagcccattcgccg
ccaagctcttcagcaatatcacgggtagccaacgctatgtcctgatagcggtctgccacacccagccggccacagtcgat
gaatccagaaaagcggccatttccaccatgatattcggcaagcaggcatcgccatgggtcacgacgagatcctcgccgt
cgggcatgctcgccttgagcctggcgaacagttcggctggcgcgagccctgatgctcttcgtccagatcatcctgatcg
acaagaccggcttccatccgagtacgtgctcgctcgatgcgatgtttcgcttggtggtcgaatgggcaggtagccggatc
aagcgtatgcagccgccgcattgcatcagccatgatggatactttctcggcaggagcaaggtgagatgacaggagatcct
gccccggcacttcgcccaatagcagccagtcccttcccgcttcagtgacaacgtcgagcacagctgcgcaaggaacgccc
gtcgtgcagccagccacgatagccgcgctgcctcgtcttgcagttcattcagggcaccggacaggtcggtcttgacaaaaag
aaccgggcgcccctgcgctgacagccggaacacggcggcatcagagcagccgattgtctgttgtgcccagtcatagccga
atagcctctccacccaagcggccggagaacctgcgtgcaatccatcttgttcaatcatgcgaaacgatcctcatcctgtc
tcttgatcagatcttgatcccctgcgccatcagatccttggcggcaagaaagccatccagtttactttgcagggcttccc
aaccttaccagagggcgccccagctggcaattccggttcgcttgctgtccataaaaccgcccagtctagctatcgccatg
taagcccactgcaagctacctgctttctctttgcgcttgcgttttcccttgtccagatagcccagtagctgacattcatc
cggggtcagcaccgtttctgcggactggctttctacgtgaaaaggatctaggtgaagatccttttttgataatctcatgac
caaaatcccttaacgtgagttttcgttccactgagcgtcagaccccgtagaaaagatcaaaggatcttcttgagatcctt
ttttctgcgcgtaatctgctgcttgcaaacaaaaaaaccaccgctaccagcggtggtttgtttgccggatcaagagcta
ccaactctttttccgaaggtaactggcttcagcagagcgcagataccaaatactgttcttctagtgtagccgtagttagg
ccaccacttcaagaactctgtagcaccgcctacatacctcgctctgctaatcctgttaccagtggctgctgccagtggcg
ataagtcgtgtcttaccgggttggactcaagacgatagttaccggataaggcgcagcggtcgggctgaacggggggttcg
tgcacacagcccagcttggagcgaacgacctacaccgaactgagatacctacagcgtgagctatgagaaagcgccacgct
tcccgaagggagaaaggcggacaggtatccggtaagcggcagggtcggaacaggagagcgcacgagggagcttccagggg
gaaacgcctggtatctttatagtcctgtcgggtttcgccacctctgacttgagcgtcgatttttgtgatgctcgtcaggg
gggcggagcctatggaaaaacgccagcaacgcggcctttttacggttcctggccttttgctggccttttgctcacatgtt
gtcgacaatattggctcattggccattgcatacgttgtatctatatcataatatgtacatttatattggctcatgtccaat
atgaccgccatgttgacattgattattgactagttattaatagtaatcaattacggggtcattagttcatagcccatata
tggagttccgcgttacataacttacggtaaatggcccgcctggctgaccgcccaacgacccccgcccattgacgtcaata
atgacgtatgttcccatagtaacgccaataggactttccattgacgtcaatgggtggagtatttacggtaaactgccca
cttggcagtacatcaagtgtatcatatgccaagtccgccccctattgacgtcaatgacggtaaatggcccgcctggcatt
atgcccagtacatgaccttacgggactttcctacttggcagtacatctacggtattagtcatcggctattaccatggtga
tgcggttttggcagtacaccaatgggcgtggatagcggtttgactcacggggatttccaagtctccaccccattgacgtc
aatgggagtttgttttggcaccaaaatcaacgggactttccaaaatgtcgtaataaccccgccccgttgacgcaaatggg
cggtaggcgtgtacggtgggaggtctatataagcagagctcgtttagtgaaccgtcagatcgcctggagacgccatccac
gctgttttgacctccatagaagacaccgggaccgatccagcctccgcggccgggaacggtgcattggaacgcggattccc
cgtgccaagagtgacgtaagtaccgcctatagactctataggcacaccccttggctcttatgcatgctatactgttttt
ggcttggggcctatacaccccgcttccttatgctataggtgatggtatagcttagcctataggtgtgggttattgacca
ttattgaccactcccctattggtgacgatactttccattactaatccataacatggctctttgccacaactatctctatt
ggctatatgccaatactctgtccttcagagactgacacggactctgtatttttacaggatggggtcccatttattattta
```

FIG. 15A-2

```
caaattcacatatacaacaacgccgtcccccgtgcccgcagttttattaaacatagcgtgggatctccacgcgaatctc
gggtaccgtgttccggacatgggytcttctccggtagcggcggagcttccacatccgagccctggtcccatgcctccagc
ggctcatggtcgctcggcagctccttgctcctaacagtggaggccagacttaggcacagcacaatgcccaccaccaccag
tgtgccgcacaaggccgtggcggtagggtatgtgtctgaaaatgagctcggagattgggctcgcaccgctgacgcagatg
gaagacttaaggcagcggcagaagaagatgcaggcagctgagttgttgtattctgataagagtcagaggtaactcccgtt
gcggtgctgttaacggtggagggcagtgtagtctgagcagtactcgttgctgccgcgcgcgccaccagacataatagctg
acagactaacagactgttcctttccatgggtcttttctgcagtcacc
```

FIG. 15A-3 pGA1/IC48 Functional Regions

| Position within sequence (starting- and ending pos.) | Gene/ORF (indicate complete name of the gene and the expressed gene product) | Origin of sequence (organism) |
|---|---|---|
| 104-1591 | Gag, inactivating point mutations in zinc finger packaging sequences for viral RNA | AG HIV-1 isolate 928 |
| 1393-3

FIG. 15C

IC48 Mutation Chart

| Codon change | Amino acid change | Region | Function |
|---|---|---|---|
| to AGC position 1271-1273 | C390S | Gag | Ablation of zinc finger used in packaging |
| to AGC position 1280-1282 | C393S | Gag | Ablation of zinc finger used in packaging |
| to AGC position 1334-1336 | C411S | Gag | Ablation of zinc finger used in packaging |
| to AGC position 1343-1345 | C414S | Gag | Ablation of zinc finger used in packaging |
| to GTG position 1703-1705 | G48V | Protease | Partial inactivation of Protease |
| to AAC position 2410-2412 | D185N | Reverse Transcriptase | Inactivation of Polymerase active site |
| to ACC position 2653-2655 | W266T | Reverse Transcriptase | Ablation of strand transfer activity |
| to CAG position 3289-3291 | E478Q | Rnase H | Inactivation of RNase H activity |

```
atcgatgcaaggactcggcttgctgaggtgcacacagcaagaggcgagagcgacgactggtgagtacgccaattttt gac
tagcggaggctagaaggagagagatgggtgcgagagcgtcagtgttaacggggggaaaattagattcatgggagaaaatt
aggttaaggccaggggggaaagaaaagatatagactaaaacacctagtatgggcaagcagggagctggagagattcgcact
taaccctggcctattagaaacagcagaaggatgtcaacaactaatgggacagttacaaccagctctcaggacaggatcag
aagagtttaaatcattatataatatagtagcaaccctttggtgcgtacatcaaagaatagacataaaagacacccaggag
gccttagataaagtagaggaaaaacaaaataagagcaagcaaaaggcacagcaggcagcagctgcaacagccgccacagg
aagcagcagccaaaattaccctatagtgcaaaatgcacaagggcaaatggtacatcagtccatgtcacctaggactttaa
atgcatgggtgaaggtaatagaagaaaaaggcttttagcccagaggtaatacccatgttttt cagcattatcagagggagcc
accccacaagatttaaatatgatgctaaacatagtggggggacaccaggcagcaatgcagatgttaaaagataccatcaa
tgatgaagctgcagaatgggacagagtacatccagtacatgcagggcctattccaccaggccaaatgagggaaccaaggg
gaagtgacatagcaggaactactagtacccttcaagaacaaataggatggatgacaagtaatccacctatcccagtggga
gaaatctataaaagatggatagtcctgggattaaataaaatagtaagaatgtatagccctaccagcattttggacataag
acaagggccaaaagaacccttt agagattatgtagacaggttcttt aaaactttgagagctgaacaagctacgcaggagg
taaaaaactggatgacagaaaccttgttggtccaaaatgcgaatccagactgcaagtccatttt aagagcattaggacca
ggggctacattagaagaaatgatgacatcatgtcagggagtggggaggacctggccataaagcaagggttttggctgaggc
aatgagtcaagtacaacagaccaatgtaatgatgcagagaggcaattttt agaggccagagaataataaagagcttcaaca
gcggcaaagaaggacacctagccagaaattgcaaggctcctagaaagagaggcagctggaaaagcggaaaggaaggacac
caaatgaaagactgtactgaaagacaggctaattttttt agggaaaatttggccttcccacaaggggaggccaggaaattt
tcctcagagcagaccagaaccaacagccccgccagcagagagctttggagtgggggaagagataccctcctctccgaagc
aggagccgagggacaagggactatatcctcccttaacttccctcaaatcactctttggcaacgaccagtagtcacagtaa
gaataggggacagccaatagaagccctattagacacaggagcagatgatacagtattagaagaaataagtttaccagga
aaatggaaaccaaaaatgatagggggaattggaggttttatcaaagtaagacagtatgatcagatatctatagaaatttg
tggaaaaagggccataggtacagtattagtaggacctacacctgtcaacataattggacgaaatatgatgactcagattg
gttgtacttt aaattttt ccaattagtcctattgaaactgtgccagtaaaattaaagtcaggaatggatggcccaaaggtt
aaacaatggccattgacagaagaaaaaataaaagcattaaaagaaatttgtgcagagatggaaaaggaaggaaaaatttc
aaaaattgggcctgaaaacccatacaatactccaatatttgccataaagaaaaaagatagtactaaatggagaaaattag
tagatttcagagaactcaataagagaactcaagacttctgggaggtccaattaggaataccttcatcctgcgggattaaaa
aagaaaaaatcagtaacagtactagatgtgggggatgcatattttt cagttcccttagatgaagactttagaaaatatac
tgcattcaccatacctagtttaaataatgagacaccaggggattagatatcagtacaatgtactcccacagggatggaaag
gatcaccagcaatatttcaggcaagcatgacaaaaatcttagagccctttagagcaaaaaatccagagatagtgatctac
caatatatgaacgatttatatgtaggatctgacttagaaatagggcagcatagagcaaaaatagaggagttgagagaaca
tctattgaaatggggatttaccacaccagacaaaaaacatcagaaagaacctccatttctttggatgggatatgaactcc
atcctgacaaatggacagtccagcctatacagctgccagaaaaagacagctggactgtcaatgatatacaaaaattagtg
ggaaaactaaataccgcaagtcagatttt atgcaggaattaaagtaaagcaattgtgtagactcctcagggagccaaagc
gctaacagatgtagtaacactgactgaggaagcagaattagaattggcagagaacagggaaattctaaaagaacctgtac
atggagtatattatgacccaacaaaagacttagtggcagaaatacagaaacaagggcaagatcaatggacatatcaatt
tatcaagagccatttaaaaatctaaagacaggaaaatatgcaaaaaagaggtcggcccacactaatgatgtaaaacaatt
aacagaggtagtgcagaaaatagccatagaaagcatagtaatatggggaaagacccctaaatttagactacccatacaaa
gagaaacatgggaagcatggtggatggagtattggcaggctacctggattcctgaatgggagtttgtcaatacccctcct
ctagtaaaattatggtaccagttagagaaggaccccataatgggagcagaaactttctatgtagatggggcagctaatag
ggagactaagctaggaaaagcagggtatgtcactgacagaggaagacaaaaggttgtttccctaattcagacaacaaatc
aaaagactcagttacatgcaattcatctagccttgcaggattcaggatcagaagtaaatatagtaacagactcacagtat
gcattaggaatcattcaggcacaaccagacaggagtgaatcagagttagtcaatcaaataatagagaaactaatagaaaaa
ggacaaagtctacctgtcatgggtaccagcacacaaagggattggaggaaatgaacaagtagataaattagtcagtagtg
gaatcagaaaggtactattttt agatggaatagataaagcccaagatgaacattagaattctgcaacagctactgtttgt
tcatttcagaattgggtgtcaacatagcagaataggcattattccagggagaagaggcaggaatggagctggtagatcct
agcctagagccctggaaccacccgggaagtcagcctacaactgcttgtagcaagtgttactgtaaaaatgctgctggca
ttgccaattgtgctttctgaacaagggcttaggcatctcctatggcaggaagaagcggagacgccgacgaggaactcctc
aggaccgtcaggttcatcaaaatcctgtaccaaaacagtaagtagtagtaattagtatatgtgatgcaatcttt acaaat
agctgcaatagtaggactagtagtagcatccatagtagccatagttgtgtggtccatagtatttt atagaatatagaaaaa
taaggaaacagaagaaaatagacaggttacttgagagaataagagaagaagtagtggcaatgagagtgatggg
gatacagaagaattatccactcttatggagagggggtatgacaatattttt ggttaatgatgatttgtaatgctgaaaagt
tgtgggtcacagtctactatggggtacctgtgtggagagacgcagagaccacccttattctgtgcatcagatgctaaagca
tatgacaaagaagcacacaatgtctgggctacgcatgcctgcgtacccacagaccctgacccacaagaattacctttggt
aaatgtaacagaagagtttaacatgtggaaaaataatatggtagaacagatgcatgaagatataattagtctatgggacc
aaagcttaaagccatgtgtacagctaaccccctctctgcgttactt agggtgtgctgacgctcaaaacgtcaccgacacc
aacaccaccatatctaatgaaatgcaggggaaataaaaaactgctcttt caatatgaccacagaattaagagataagaa
gcagaaagtgtatgcacttttttt atagacctgatgtaatagaaattaataaaactaagattaacaatagtaatagtagtc
agtatatgttaataaattgtaatacctcaaccattacacagacttgtccaaaggtatcctttgagccaattcccatacat
tattgtgccccagctggttttgcaattctaaagtgtaatgatacggagttcagtggaaaagggacatgcaagagtgtcag
cacagtacaatgcacacatggaatcaagccagtagtatcaactcaactgctgttaaatggcagtctagcagaaggaaaga
```

FIG. 16A-1

```
tagcgattagatctgagaatatctcaaacaatgccaaaactataatagtacaattgactgagcctgtagaaattaattgt
atcagacctggcaacaatacaagaaaaagtgtacgcataggaccaggacaaacattctatgcaacaggtgacataatagg
agatataagacaagcacactgtaatgttagtaaaatagcatgggaagaaactttacaaaaggtagctgcacaattaagga
agcactttcagaatgccacaataaaatttactaaacactcaggaggggatttagaaattacaacaaatagtttttaattgt
ggaggagaattttttctattgcaatacaacaaagctgtttaatagcacttggaataatgataactcaaacctcacagagga
aaagagaaaggaaaacataactctccactgcagaataaagcaaattgtaaatatgtggccaagagtaggacaagcaatat
atgcccctcccatcccaggaaacataacttgtggatcaaacattactgggctactattaacaagagatggagggaataat
ggtacaaatgatactgagaccttcaggcctggaggaggagatatgagggacaattggagaagtgaattatataaatataa
agtagtaaaaattgaaccactaggtgtagcaccaacccctgcaaaaagaagagtggtggaaagagaaaaaagagcagttg
gaatgggagctttgatctttgagttcttaggagcagcaggaagcactatgggcgcggcgtcaatggcgctgacggtacag
gccagacaattattgtctggtatagtgcaacagcagagcaatctgctgaaggctatagaggctcaacaacatctgttgag
actcacggtctggggcattaaacagctccaggcaagagtcctggctctggaaagataccctaaaggatcaacagctcctag
gaatttggggctgctctggaaaactcatttgcaccactgctgtaccttggaactctagctggagtaataaaagttataat
gacatatgggataacatgacctggctgcaatgggataaagaaattaacaattacacatacataatatataatctacttga
aaaatcgcagaaccagcaggaaattaatgaacaagacttattggcattagacaagtgggcaagtctgtggaattggtttg
acataacaagctggctatggtatataagattaggtataatgatagtaggaggcgtaataggcttaagaataattttttgct
gtgcttactatagtgaatagagttaggcagggatactcacctttgtcattccagacccttgcccaccaccagagggaacc
cgacaggcccgaaagaatcgaagaaggaggtggcgagcaagacagagagagatccgtgcgcttagtgagcggattcttag
cacttgcctgggaagatctgcggagcctgtgcctcttcagctaccgccgattgagagacttagtcttgattgcagcaagg
actgtggaactcctgggacacagcagtctcaagggactgagactggggtggggaagccctcaaatatctgtggaaccttct
atcatactgggtcaggaactaaagaatagtgctattaatttgcttgatacaatagcaatagcagtagctaactggacag
atagagttataaaaatagtacaaagaactggtagagctattcttaacatacctagaaggatcagatagggctagccccgg
gtgataaacggaccgcgcaatccctaggctgtgccttctagttgccagccatctgttgtttgcccctcccccgtgccttc
cttgaccctggaaggtgccactcccactgtcctttcctaataaaatgaggaaattgcatcgcattgtctgagtaggtgtc
attctattctgggggtggggtggggcaggacagcaaggggggaggattgggaagacaatagcaggcatgctggggatgcg
gtgggctctatataaaaaacgcccggcggcaaccgagcgttctgaacgctagagtcgacaaattcagaagaactcgtcaa
gaaggcgatagaaggcgatgcgctgcgaatcgggagcggcgataccgtaaagcacgaggaagcggtcagcccattcgccg
ccaagctcttcagcaatatcacgggtagccaacgctatgtcctgatagcggtctgccacacccagccggccacagtcgat
gaatccagaaaagcggccattttccaccatgatattcggcaagcaggcatcgccatgggtcacgacgagatcctcgccgt
cgggcatgctcgccttgagcctggcgaacagttcggctggcgcgagcccctgatgctcttcgtccagatcatcctgatcg
acaagaccggcttccatccgagtacgtgctcgctcgatgcgatgtttcgcttggtggtcgaatgggcaggtagccggatc
aagcgtatgcagccgccgcattgcatcagccatgatggatactttctcggcaggagcaaggtgagatgacaggagatcct
gccccggcacttcgcccaatagcagccagtcccttcccgcttcagtgacaacgtcgagcacagctgcgcaaggaacgccc
gtcgtggccagccacgatagccgcgctgcctcgtcttgcagttcattcagggcaccggacaggtcggtcttgacaaaaag
aaccgggcgcccctgcgctgacagccggaacacggcggcatcagagcagccgattgtctgttgtgcccagtcatagccga
atagcctctccacccaagcggccggagaacctgcgtgcaatccatcttgttcaatcatgcgaaacgatcctcatcctgtc
tcttgatcagatcttgatccccctgcgccatcagatccttggcggcaagaaaagccatccagtttactttgcagggcttccc
aaccttaccagagggcgccccagctgcaattccggttcgcttgctgtccataaaaccgcccagtctagctatcgccatg
taagcccactgcaagctacctgctttctctttgcgcttgcgttttcccttgtccagatagcccagtagctgacattcatc
cggggtcagcaccgtttctgcggactggctttctacgtgaaaaggatctaggtgaagatcctttttgataatctcatgac
caaaatcccttaacgtgagttttcgttccactgagcgtcagaccccgtagaaaagatcaaaggatcttcttgagatcctt
ttttctgcgcgtaatctgctgcttgcaaacaaaaaaaccaccgctaccagcggtggtttgtttgccggatcaagagcta
ccaactcttttttccgaaggtaactggcttcagcagagcgcagataccaaatactgttcttctagtgtagccgtagttagg
ccaccacttcaagaactctgtagcaccgcctacatacctcgctctgctaatcctgttaccagtggctgctgccagtggcg
ataagtcgtgtcttaccgggttggactcaagacgatagttaccggataaggcgcagcggtcgggctgaacggggggttcg
tgcacacagcccagcttggagcgaacgacctacaccgaactgagatacctacagcgtgagctatgagaaagcgccacgct
tcccgaagggagaaaggcggacaggtatccggtaagcggcagggtcggaacaggagagcgcacgagggagcttccagggg
gaaacgcctggtatctttatagtcctgtcgggtttcgccacctctgacttgagcgtcgatttttgtgatgctcgtcaggg
gggcggagcctatggaaaaacgccagcaacgcggcctttttacggttcctggccttttgctggccttttgctcacatgtt
gtcgacaatattggctattggccattgcatacgttgtatctatatcataatatgtacatttatattggctcatgtccaat
atgaccgccatgttgacattgattattgactagttattaatagtaatcaattacgggttcattagttcatagcccatata
tggagttccgcgttacataacttacggtaaatggcccgcctggctgaccgcccaacgacccccgcccattgacgtcaata
atgacgtatgttcccatagtaacgccaataggactttccattgacgtcaatgggtggagtatttacggtaaactgccca
cttggcagtacatcaagtgtatcatatgccaagtccgccccctattgacgtcaatgacggtaaatggcccgcctggcatt
atgcccagtacatgaccttacgggactttcctacttggcagtacatctacgtattagtcatcggctattaccatggtga
tgcggttttggcagtacaccaatgggcgtggatagcggtttgactcacggggatttccaagtctccaccccattgacgtc
aatgggagtttgttttggcaccaaaatcaacgggactttccaaaatgtcgtaataaccccgccccgttgacgcaaatggg
cggtaggcgtgtacggtggaggtctatataagcagagctcgtttagtgaaccgtcagatcgcctggagacgccatccac
gctgttttgacctccatagaagacaccgggaccgatccagcctccgcggccgggaacggtgcattggaacgcggattccc
cgtgccaagagtgacgtaagtaccgcctatagactctataggcacacccctttggctcttatgcatgctatactgtttt
ggcttggggcctatacaccccgcttccttatgctataggtgatggtatagcttagcctataggtgtgggttattgacca
ttattgaccactcccctattggtgacgatactttccattactaatccataacatggctctttgccacaactatctctatt
ggctatatgccaatactctgtccttcagagactgacacggactctgtatttttacaggatggggtcccatttattattta
```

FIG. 16A-2

```
caaattcacatatacaacaacgccgtcccccgtgcccgcagttttttattaaacatagcgtgggatctccacgcgaatctc
gggtaccgtgttccggacatgggytcttctccggtagcggcggagcttccacatccgagccctggtcccatgcctccagc
ggctcatggtcgctcggcagctccttgctcctaacagtggaggccagacttaggcacagcacaatgcccaccaccaccag
tgtgccgcacaaggccgtggcggtagggtatgtgtctgaaaatgagctcggagattgggctcgcaccgctgacgcagatg
gaagacttaaggcagcggcagaagaagatgcaggcagctgagttgttgtattctgataagagtcagaggtaactcccgtt
gcggtgctgttaacggtggagggcagtgtagtctgagcagtactcgttgctgccgcgcgcgccaccagacataatagctg
acagactaacagactgttcctttccatgggtcttttctgcagtcacc
```

FIG. 16A-3 pGA1/IC90 Functional Regions

| Position within sequence (starting-and ending pos.) | Gene/ORF (indicate complete name of the gene and the expressed gene product) | Origin of sequence (organism) |
|---|---|---|
| 104-1591 | Gag, inactivating point mutations in zinc finger packaging sequences for viral RNA | AG HIV-1 isolate 928 |
| 1393-3576 | Pol, inactivating point mutations in protease and reverse transcriptase, deletion of integrase | AG HIV-1 isolate 928 |
| 3663-3877 and 6215-6305 | Tat exons #1 and #2 | AG HIV-1 isolate 928 |
| 3802-3877 and 6215-6510 | Rev exons #1 and #2 | AG HIV-1 isolate 928 |
| 3904-4149 | Vpu | AG HIV-1 isolate 928 |
| 4067-6628 | Env | AG HIV-1 isolate 928 |
| 6629-10447 | Plasmid vector | PGA1, Gen Bank accession # AF425297 |

FIG. 16B

IC90 Mutation Chart

| Codon change | Amino acid change | Region | Function |
|---|---|---|---|
| to AGC position 1271-1273 | C390S | Gag | Ablation of zinc finger used in packaging |
| to AGC position 1280-1282 | C393S | Gag | Ablation of zinc finger used in packaging |
| to AGC position 1334-1336 | C411S | Gag | Ablation of zinc finger used in packaging |
| to AGC position 1343-1345 | C414S | Gag | Ablation of zinc finger used in packaging |
| to ATG position 1828-1830 | L90M | Protease | Partial inactivation of Protease |
| to AAC position 2410-2412 | D185N | Reverse Transcriptase | Inactivation of Polymerase active site |
| to ACC position 2653-2655 | W266T | Reverse Transcriptase | Ablation of strand transfer activity |
| to CAG position 3289-3291 | E478Q | Rnase H | Inactivation of RNase H activity |

FIG. 16C

PGA1/IN3 Sequence

```
ggatccggcttgctgaagtgcactcggcaagaggcgagggtggcggctggtgagtacgccaaattttatttgactagcg
gaggctagaaggagagagatgggtgcgagagcgtcaatattaagaggggaaaattagataaatgggaaaagattaggtt
aaggccaggggaaagaaacactatatgctaaaacacctagtatgggcaagcagggagctggaaagatttgcacttaacc
ctggcctttagagacatcagaaggctgtaaacaaataataaaacagctacaaccagctcttcagacaggaacagaggaa
cttaggtcattattcaatgcagtagcaactctctattgtgtacatgcagacatagaggtacgagacaccaaagaagcatt
agacaagatagaggaagaacaaaacaaaagtcagcaaaaaacgcagcaggcaaaagaggctgacaaaaaggtcgtcagtc
aaaattatcctatagtgcagaatcttcaagggcaaatggtacaccaggcactatcacctagaactttgaatgcatgggta
aaagtaatagaagaaaaagcctttagcccggaggtaatacccatgttcacagcattatcagaaggagccaccccacaaga
tttaaacaccatgttaaataccgtgggggacatcaagcagccatgcaaatgttaaaagataccatcaatgaggaggctg
cagaatgggatagattacatccagtacatgcagggcctgttgcaccaggccaaatgagagaaccaagggaagtgacata
gcaggaactactagtaaccttcaggaacaaatagcatggatgacaagtaacccacctattccagtgggagatatctataa
aagatggataattctggggttaaataaaatagtaagaatgtatagccctgtcagcattttagacataagacaagggccaa
aggaaccctttagagattatgtagaccggttctttaaaactttaagagctgaacaagcttcacaagatgtaaaaaattgg
atggcagacacttgttggtccaaaatgcgaacccagattgtaagaccattttaagagcattaggaccaggagctacatt
agaagaaatgatgacagcatgtcaaggagtgggaggacctagccacaaagcaagagtgttggctgaggcaatgagccaaa
caggcagtaccataatgatgcagagaagcaatttaaaggctctaaaagaactgttaaatccttcaactctggcaaggaa
gggcacatagctagaaattgcagggcccctaggaaaaaaggctcttggaaatctggaaaggaaggacaccaaatgaaaga
ctgtgctgagaggcaggctaattttttagggaaaatttggccttcccacaagggaggccagggaattccttcagaaca
ggccagagccaacagcccccaccagcagagagcttcaggttcgaggagacaaccccctgctccgaagcaggagctgaaagac
agggaaccctaacctccctcaaatcactctttggcagcgacccttgtctcaataaaaataggggccagataaaggag
gctctcttagccacaggagcagatgatacagtattagaagaaatgaatttgccaggaaaatggaaaccaaaaatgatagg
aggaattggaggttttatcaaagtaagacagtatgatcaaatacttatagaaatttgtggaaaaaaggctataggtacag
tattagtaggacccacacctgtcaacataattggaagaaatatgctgactcagattggatgcacgctaaattttccaatt
agtcccattgaaactgtaccagtaaaattaaagccaggaatggatggcccaaaggttaaacaatggccattgacagagga
gaaaataaaagcattaacagcaatttgtgatgaaatggagaaggaaggaaaattacaaaaattgggcctgaaaatccat
ataacactccaatattcgccataaaaaagaaggacagtactaagtggagaaaattagtagatttcagagaacttaataaa
agaactcaagacttctgggaagttcaattaggaataccacacccagcagggttaaaaaagaaaaaatcagtgacagtact
agatgtgggggatgcatattttcagttcctttagatgaaagctttaggaggtatactgcattcaccataccctagtagaa
acaatgaaacaccagggattagatatcaatataatgtgcttccacaaggatggaaaggatcaccagcaatattccagagt
agcatgacaaaaatcttagagcccttagagcacaaaatccagaaaatagtcatctatcaatatatgaatgacttgtatgt
aggatctgacttagaaatagggcaacatagagcaaagatagaggaattaagagaacatctattaaggtggggatttacca
caccagacaagaaacatcagaaagaacccccatttctttggatgggtatgaactccatcctgacaaatggacagtacag
cctatacagctgccagaaaaggagagctggactgtcaatgatatacagaagttagtgggaaaattaaacacggcaagcca
gatttacccagggattaaagtaagacaactttgtagactccttagaggggccaaagcactaacagacatagtaccactaa
ctgaagaagcagaattagaattggcagagaacagggaaattctaaaagaaccagtacatggagtatattatgaccccttca
aaagacttgatagctgaaatacagaaacagggacatgaccaatggacatatcaaatttaccaagaaccattcaaaaatct
gaaaacagggaagtatgcaaaaatgaggactgcccacactaatgatgtaaaacggttaacagaggcagtgcaaaaaatag
ccttagaaagcatagtaatatggggaaagattcctaaacttaggttacccatccaaaaagaaacatgggagacatggtgg
actgactattggcaagccacctggattcctgagtgggaatttgttaatactcctcccctagtaaaattatggtaccagct
agagaaggaacccataataggagtagaaactttctatgtagatggagcagctaatagggaaccaaaataggaaaagcag
ggtatgttactgacgaggaaggcagaaaattgtttctctaactgaaacaacaaatcagaagactcaattacaagcaatt
tatctagctttgcaagattcaggatcagaagtaaacatagtaacagactcacagtatgcattaggaattattcaagcaca
accagataagagtgaatcagggttagtcaaccaaataatagaacaattaataaaaaaggaaagggtctacctgtcatggg
taccagcacataaaggtattggaggaaatgaacaagtagacaaattagtaagtagtggaatcaggagagtgctataataa
gctcgagatacttggacaggagttgaaactatcataagaatgctgcaacaactactgttatttcatttcagaatttgggtg
ccagcataggcaataggcattatgagacagagaagaggcaagaaattggagccagtagatcctaacctagagccctggaac
catccaggaagtcagcctgaaactgcttgcaataactgttattgtaaacgctatagctaccattgtctagtttgctttca
gagaaaggcttaggcatttcctatggcaggaagaagcggagacagcgacgaagcgctcctcagagcagtgaggatcatc
agaattttgtatcaaagcagtaagtatctgtaatgttagatttagattataaattagcagtaggagcatttatagtagca
ctactcatagcaatagttgtgtggaccatagtatttatagaatatagggaaattgttaagacaaagaaaaatagactggtt
aattaaaagaattagggaaagagcagaagacagtggcaatgagagtgagggggatactgaggaattatcgacaatggtgg
atatgggcatcttaggcttttggatgttaatgatttgtaatggaaacttgtgggtcacagtctattatggggtacctgt
gtggaaagaagcaaaaactactctattctgtgcatcaaatgctaaagcatatgagaagaagtacataatgtctggcta
cacatgcctgtgtacccacagaccccaacccacaagaaatggttttggaaaacgtaacagaaaatttaacatgtggaaa
aatgacatggtgaatcagatgcatgaggatgtaatcagcttatgggatcaaagcctaaagccatgtgtaaagttgacccc
actctgtgtcactttagaatgtagaaaggttaatgctacccataatgctaccaataatggggatgctacccataatgtta
ccaataatgggcaagaaatacaaaattgctctttcaatgcaaccacagaaataagagataggaagcagagagtgtatgca
cttttttatagacttgatatagtaccacttgataagaacaactctagtaagaacaactctagtgagtattatagattaat
aaattgtaatacctcagccataacacaagcatgtccaaaggtcagttttgatccaattcctatacactattgtgctccag
ctggttatgcgattctaaagtgtaacaataagacattcaatgggacaggaccatgcaataatgtcagcacagtacaatgt
acacatggaattaagccagtggtatcaactcagctattgttaaacggtagcctagcagaaggagagataataattagatc
```

FIG. 17A-1

```
tgaaaatctgacagacaatgtcaaaacaataatagtacatcttgatcaatctgtagaaattgtgtgtacaagacccaaca
ataatacaagaaaaagtataaggatagggccaggacaaacattctatgcaacaggaggcataatagggaacatacgacaa
gcacattgtaacattagtgaagacaaatggaatgaaactttacaaagggtgggtaaaaaattagtagaacacttccctaa
taagacaataaaatttgcaccatcctcaggagggacctagaaattacaacacatagctttaattgtagaggagaatttt
tctattgcagcacatcaagactgtttaatagtacatacatgcctaatgatacaaaaagtaagtcaaacaaaaccatcaca
atcccatgcagcataaaacaaattgtaaacatgtggcaggaggtaggacgagcaatgtatgcccctcccattgaaggaaa
cataacctgtagatcaaatatcacaggaatactattggtacgtgatggaggagtagattcagaagatccagaaaataata
agacagagacattccgacctggaggaggagatatgaggaacaattggagaagtgaattatataaatataaagcggcagaa
attaagccattgggagtagcacccactccagcaaaaaggagagtggtggagagagaaaaaagagcagtaggattaggagc
tgtgttccttggattcttgggagcagcaggaagcactatgggcgcagcgtcaataacgctgacggtacaggccagacaat
tgttgtctggtatagtgcaacagcaaagcaatttgctgagggctatcgaggcgcaacagcatctgttgcaactcacggtc
tggggcattaagcagctccagacaagagtcctggctatcgaaagatacctaaaggatcaacagctcctagggctttgggg
ctgctctggaaaactcatctgcaccactaatgtaccttggaactccagttggagtaacaaatctcaaacagatatttggg
aaaacatgacctggatgcagtgggataaagaagttagtaattacacagacacaatatacaggttgcttgaagactcgcaa
acccagcaggaaagaaatgaaaaggattattattagcattggacaattggaaaaatctgtggaattggtttagtataacaaa
ctggctgtggtatataaaaatattcataatgatagtaggaggcttgataggcttaagaataattttgctgtgctttcta
tagtgaatagagttaggcagggatactcacctttgtcgtttcagacccttaccccaaacccaaggggacccgacaggctc
ggaagaatcgaagaagaaggtggagggcaagacagagacagatctgattcgattagtgaacagattcttagcacttgcctg
ggacgacctgtggagcctgtgcctcttcagctaccaccgattgagagacttaatattggtgacagcgagagcggtggaac
ttctgggacacagcagtctcagggggactacagagggggtgggaagcccttaagtatctgggaggtattgtgcagtattgg
ggtctggaactaaaaagagggctattagtctgcttgatactgtagcaatagcagtagctgaaggcacagataggattat
agaattcctccaaagaatttgtagagctatccgcaacatacctagaaggataagacagggctttgaagcagctttgcagt
aaaatggctagccccgggtgataaacggaccgcgcaatccctaggctgtgccttctagttgccagccatctgttgtttgc
ccctccccgtgccttccttgaccctggaaggtgccactcccactgtcctttcctaataaaatgaggaaattgcatcgca
ttgtctgagtaggtgtcattctattctgggggtggggtggggcaggacagcaaggggggaggattgggaagacaatagca
ggcatgctggggatgcggtgggctctatataaaaaacgcccggcggcaaccgagcgttctgaacgctagagtcgacaaat
tcagaagaactcgtcaagaaggcgatagaaggcgatgcgctgcgaatcgggagcggcgataccgtaaagcacgaggaagc
ggtcagcccattcgccgccaagctcttcagcaatatcacgggtagccaacgctatgtcctgatagcggtctgccacaccc
agccggccacagtcgatgaatccagaaaagcggccattttccaccatgatattcggcaagcaggcatcgccatgggtcac
gacgagatcctcgccgtcgggcatgctcgccttgagcctggcgaacagttcggctggcgcgagcccctgatgctcttcgt
ccagatcatcctgatcgacaagaccggcttccatccgagtacgtgctcgctcgatgcgatgtttcgcttggtggtcgaat
gggcaggtagccggatcaagcgtatgcagccgccgcattgcatcagccatgatggatacttctcggcaggagcaaggtg
agatgacaggagatcctgccccggcacttcgcccaatagcagccagtcccttcccgcttcagtgacaacgtcgagcacag
ctgcgcaaggaacgcccgtcgtggccagccacgatagccgcgctgcctcgtcttgcagttcattcagggcaccggacagg
tcggtcttgacaaaagaaccgggcgcccctgcgctgacagccggaacacggcggcatcagagcagccgattgtctgttg
tgcccagtcatagccgaatagcctctccacccaagcggccggagaacctgcgtgcaatccatcttgttcaatcatgcgaa
acgatcctcatcctgtctcttgatcagatcttgatccctgcgccatcagatccttggcggcaagaaagccatccagttt
actttgcagggcttcccaaccttaccagagggcgccccagctggcaattccggttcgcttgctgtccataaaaccgccca
gtctagctatcgccatgtaagcccactgcaagctacctgctttctctttgcgcttgcgttttcccttgtccagatagccc
agtagctgacattcatccggggtcagcaccgtttctgcggactggctttctacgtgaaaaggatctaggtgaagatccttt
tttgataatctcatgaccaaaatccttaacgtgagttttcgttccactgagcgtcagacccccgtagaaaagatcaaagg
atcttcttgagatcctttttttctgcgcgtaatctgctgcttgcaaacaaaaaaaccaccgctaccagcggtggtttgtt
tgccggatcaagagctaccaactctttttccgaaggtaactggcttcagcagagcgcagataccaaatactgttcttcta
gtgtagccgtagttaggccaccacttcaagaactctgtagcaccgcctacatacctcgctctgctaatcctgttaccagt
ggctgctgccagtggcgataagtcgtgtcttaccgggttggactcaagacgatagttaccggataaggcgcagcggtcgg
gctgaacggggggttcgtgcacacagcccagcttggagcgaacgacctacaccgaactgagatacctacagcgtgagcta
tgagaaagcgccacgcttcccgaagggagaaaggcggacaggtatccggtaagcggcagggtcggaacaggagagcgcac
gagggagcttccaggggggaaacgcctggtatctttatagtcctgtcgggtttcgccacctctgacttgagcgtcgatttt
tgtgatgctcgtcaggggggcggagcctatggaaaaacgccagcaacgcggcctttttacggttcctggccttttgctgg
ccttttgctcacatgttgtcgacaatattggctattggccattgcatacgttgtatctatatcataatatgtacatttat
attggctcatgtccaatatgaccgccatgttgacattgattattgactagttattaatagtaatcaattacgggttcatt
agttcatagcccatatatggagttccgcgttacataacttacggtaaatggcccgcctggctgaccgcccaacgacccc
gcccattgacgtcaataatgacgtatgttcccatagtaacgccaatagggactttccattgacgtcaatgggtggagtat
ttacgtaaactgcccacttggcagtacatcaagtgtatcatatgccaagtccgcccccattgacgtcaatgacggtaa
atggcccgcctggcattatgcccagtacatgaccttacgggactttcctacttggcagtacatctacggtattagtcatc
ggctattaccatggtgatgcggttttggcagtacaccaatgggcgtggatagcggtttgactcacggggatttccaagtc
tccaccccattgacgtcaatgggagtttgttttggcaccaaaatcaacgggactttccaaaatgtcgtaataacccgcc
ccgttgacgcaaatgggcggtaggcgtgtacggtgggaggtctatataagcagagctcgttagtgaaccgtcagatcgc
ctggagacgccatccacgctgttttgacctccatagaagacaccgggaccgatccagcctccgcggccgggaacggtgca
ttggaacgcggattccccgtgccaagagtgacgtaagtaccgcctatagactctataggcacacccctttggctcttatg
catgctatactgttttggcttggggcctatacaccccgcttccttatgctataggtgatggtatagcttagcctatag
gtgtgggttattgaccattattgaccactccctattggtgacgatacttccattactaatccataacatggctctttg
ccacaactatctctattggctatatgccaatactctgtccttcagagactgacacggactctgtatttttacaggatggg
```

```
gtcccatttattatttacaaattcacatatacaacaacgccgtcccccgtgcccgcagttttattaaacatagcgtggg
atctccacgcgaatctcgggtaccgtgttccggacatgggytcttctccggtagcggcggagcttccacatccgagccct
ggtcccatgcctccagcggctcatggtcgctcggcagctccttgctcctaacagtggaggccagacttaggcacagcaca
atgcccaccaccaccagtgtgccgcacaaggccgtggcggtagggtatgtgtctgaaaatgagctcggagattgggctcg
caccgctgacgcagatggaagacttaaggcagcggcagaagaagatgcaggcagctgagttgttgtattctgataagagt
cagaggtaactcccgttgcggtgctgttaacggtggagggcagtgtagtctgagcagtactcgttgctgccgcgcgcgcc
accagacataatagctgacagactaacagactgttcctttccatgggtcttttctgcagtcaccat
```

FIG. 17A-3 pGA1 IN3 Functional Regions

| Position within sequence (starting-and ending pos.) | Gene/ORF (indicate complete name of the gene and the expressed gene product) | Origin of sequence (organism) |
|---|---|---|
| 99-1577 | Gag, inactivating point mutations in zinc finger packaging sequences for viral RNA | C HIV-1 isolate 98IN012 |
| 1382-3520 | Pol, inactivating point mutations in protease and reverse transcriptase, deletion of integrase | C HIV-1 isolate 98IN012 |
| 3645-3859 and 6205-6295 | Tat exons #1 and #2 | C HIV-1 isolate 98IN012 |
| 3784-3859 and 6205-6452 | Rev exons #1 and #2 | C HIV-1 isolate 98IN012 |
| 3873-4121 | Vpu | C HIV-1 isolate 98IN012 |
| 4039-6642 | Env | C HIV-1 isolate 98IN012 |
| 6643-10466 | Plasmid vector | pGA1, Gen Bank accession # AF425297 |

FIG. 17B

IN3 Mutation Chart

| Codon change | Amino acid change | Region | Function |
|---|---|---|---|
| to TCC position 1260-1262 | C390S | Gag | Ablation of zinc finger used in packaging |
| to TCT position 1269-1271 | C393S | Gag | Ablation of zinc finger used in packaging |
| to TCT position 1323-1325 | C411S | Gag | Ablation of zinc finger used in packaging |
| to TCT position 1332-1334 | C414S | Gag | Ablation of zinc finger used in packaging |
| to GCC position 1610-1612 | D25N | Protease | Inactivation of Protease active site |
| to AAT position 2387-2389 | D185N | Reverse Transcriptase | Inactivation of Polymerase active site |
| to ACG position 2630-2632 | W266T | Reverse Transcriptase | Ablation of strand transfer activity |
| to CAA position 3266-3268 | E478Q | Rnase H | Inactivation of RNase H activity |

FIG. 17C pGA1/IN2 Sequence

```
ggatccggcttgctgaagtgcactcggcaagaggcgagggtggcggctggtgagtacgccaaatttatttgactagcg
gaggctagaaggagagatgggtgcgagagcgtcaatattaagaggggaaaattagataaatgggaaaagattaggtt
aaggccaggggaaagaaacactatatgctaaaacacctagtatgggcaagcagggagctggaaagatttgcacttaacc
ctggcctttagagacatcagaaggctgtaaacaaataataaaacagctacaaccagctcttcagacaggaacagaggaa
cttaggtcattattcaatgcagtagcaactctctattgtgtacatgcagacatagaggtacgagacaccaaagaagcatt
agacaagatagaggaagaacaaaacaaaagtcagcaaaaaacgcagcaggcaaaagaggctgacaaaaaggtcgtcagtc
aaaattatcctatagtgcagaatcttcaagggcaaatggtacaccaggcactatcacctagaactttgaatgcatggta
aaagtaatagaagaaaaagcctttagcccggaggtaatacccatgttcacagcattatcagaaggagccacccacaaga
tttaaacaccatgttaaataccgtgggggacatcaagcagccatgcaaatgttaaaagataccatcaatgaggaggctg
cagaatgggatagattacatccagtacatgcagggcctgttgcaccaggccaaatgagagaaccaaggggaagtgacata
gcaggaactactagtaaccttcaggaacaaatagcactggatgacaagtaacccacctattccagtgggagatatctataa
aagatggataattctggggttaaataaaatagtaagaatgtatagccctgtcagcatttagacataagacaagggccaa
aggaacccttagagattatgtagaccggttcttaaaactttaagagctgaacaagcttcacaagatgtaaaaaattgg
atggcagacaccttgttggtccaaaatgcgaacccagattgtaagaccattttaagagcattaggaccaggagctacatt
agaagaaatgatgacagcatgtcaaggagtggaggacctagccacaaagcaagagtgttggctgaggcaatgagccaaa
caggcagtaccataatgatgcagagaagcaattttaaaggctctaaaagaactgttaaatgcttcaactgtggcaaggaa
gggcacatagctagaaattgcagggcccctaggaaaaaaggctgttggaaatgtggaaaggaaggacaccaaatgaaaga
ctgtgctgagaggcaggctaatttttagggaaaatttggccttcccacaggggggaggccagggaatttccttcagaaca
ggccagagccaacagccccaccagcagagagcttcaggttcgaggagacaacccctgctccgaagcaggagctgaaagac
agggaaccccttaacctccctcaaatcactctttggcagcgaccccttgtctcaataaaaatagggggccagataaaggag
gctctcttagacacaggagcagatgatacagtattagaagaaatgaatttgccaggaaaatggaaaccaaaaatgatagg
aggaattggaggttttatcaaagtaagacagtatgatcaaatacttatagaaatttgtggaaaaaaggctataggtacag
tattagtaggacccacacctgtcaacataattggaagaaatatgctgactcagattggatgcacgctaaattttccaatt
agtcccattgaaactgtaccagtaaaattaaagccaggaatggatggcccaaaggttaaacaatggccattgacagagga
gaaaataaaagcattaacagcaatttgtgatgaaatggagaaggaaggaaaaattacaaaaattgggcctgaaaatccat
ataacactccaatattcgccataaaaaagaaggacagtactaagtggagaaaattagtagatttcagagaacttaataaa
agaactcaagacttctgggaagttcaattaggaataccacacccagcagggttaaaaaagaaaaaatcagtgacagtact
agatgtgggggatgcatatttttcagttcctttagatgaaagctttaggaggtatactgcattcaccatacctagtagaa
acaatgaaacaccagggattagatatcaatataatgtgcttccacaaggatggaaaggatcaccagcaatattccagagt
agcatgacaaaaatcttagagcccttagagcacaaaatccagaaaatagtcatctatcaatatatggatgacttgtatgt
aggatctgacttagaaatagggcaacatagacaaagatagaggaattaagagaacatctattaaggtggggatttacca
caccagacaagaaacatcagaaagaaccccccatttctttggatggggtatgaactccatcctgacaaatggacagtacag
cctatacagctgccagaaaaggagagctggactgtcaatgatatacagaagttagtgggaaaattaaacacggcaagcca
gatttacccagggattaaagtaagacaactttgtagactccttagaggggccaaagcactaacagacatagtaccactaa
ctgaagaagcagaattagaattggcagagaacagggaaattctaaaagaaccagtacatggagtatattatgaccccttca
aaagacttgatagctgaaatacagaaacaggggcatgaccaatggacatatcaaatttaccaagaaccattcaaaaatct
gaaaacagggaagtatgcaaaaatgaggactgcccacactaatgatgtaaaacggttaacagaggcagtgcaaaaaatag
ccttagaaagcatagtaatatggggaaagattcctaaacttaggttacccatccaaaaagaaacatgggagacatggtgg
actgactattggcaagccacctggattcctgagtgggaatttgttaatactcctcccctagtaaaattatggtaccagct
agagaaggaacccataataggagtagaaactttctatgtagatggagcagctaatagggaaaccaaaataggaaaagcag
ggtatgttactgacagaggaaggcagaaaattgtttctctaactgaaacaacaaatcagaagactcaattacaagcaatt
tatctagctttgcaagattcaggatcagaagtaaacatagtaacagactcacagtatgcattaggaattattcaagcaca
accagataagagtgaatcagggttagtcaaccaaataatagaacaattaataaaaaggaaagggtctacctgtcatggg
taccagcacataaaggtattggaggaaatgaacaagtagacaaattagtaagtagtggaatcaggagagtgctataataa
gctcgagatacttggacaggagttgaaactatcataagaatgctgcaacaactactgtttattcatttcagaattggggtg
ccagcatagcagaataggcattatgagacagagaagagcaagaaatggagccagtagatcctaacctagagccctggaac
catccaggaagtcagcctgaaactgcttgcaataactgttattgtaaacgctatagctaccattgtctagtttgctttca
gagaaaaggcttaggcatttcctatggcaggaagaagcggagacagcgacgaagcgctcctcagagcagtgaggatcatc
agaattttgtatcaaagcagtaagtatctgtaatgttagatttagattataaattagcagtaggagcatttatagtagca
ctactcatagcaatagttgtgtggaccatagtatttatagaataggaaattgttaagacaaagaaaaatagactggtt
aattaaaagaattaggggaagagcagaagacagtggcaatgagagtgaaggggatactgaggaattatcgacaatggtgg
atatgggcatcttaggcttttggatgttaatgatttgtaatggaaacttgtgggtcacagtctattatggggtacctgt
gtggaaagaagcaaaaactactctattctgtgcatcaaatgctaaagcatatgagaagaagtacataatgtctggcta
cacatgcctgtgtacccacagaccccaacccacaagaaatggttttggaaaacgtaacagaaaattttaacatgtggaaa
aatgacatggtgaatcagatgcatgaggatgtaatcagcttatgggatcaaagcctaaagccatgtgtaaagttgacccc
actctgtgtcactttagaatgtagaaaggttaatgctacccataatgctaccaataatggggatgctacccataatgtta
ccaataatgggcagaaatacaaaattgctctttcaatgcaaccacagaaataagagataggaagcagagagtgtatgca
ctttttatagacttgatatagtaccacttgataagaacaactctagtaagaacaactctagtgagtattatagattaat
aaattgtaatacctcagccataacacaagcatgtccaaaggtcagttttgatccaattcctatacactattgtgctccag
ctggttatgcgattctaaagtgtaacaataagacattcaatgggacaggaccatgcaataatgtcagcacagtacaatgt
acacatggaattaagccagtggtatcaactcagctattgttaaacggtagcctagcagaaggagagataataattagatc
```

FIG. 18A-1

```
tgaaaatctgacagacaatgtcaaaacaataatagtacatcttgatcaatctgtagaaattgtgtgtacaagacccaaca
ataatacaagaaaaagtataaggatagggccaggacaaacattctatgcaacaggaggcataatagggaacatacgacaa
gcacattgtaacattagtgaagacaaatggaatgaaactttacaaagggtgggtaaaaaattagtagaacacttccctaa
taagacaataaaatttgcaccatcctcaggagggggacctagaaattacaacacatagctttaattgtagaggagaatttt
tctattgcagcacatcaagactgtttaatagtacatacatgcctaatgatacaaaaagtaagtcaaacaaaaccatcaca
atcccatgcagcataaaacaaattgtaaacatgtggcaggaggtaggacgagcaatgtatgccctcccattgaaggaaa
cataacctgtagatcaaatatcacaggaatactattggtacgtgatggaggagtagattcagaagatccagaaaataata
agacagagacattccgacctggaggaggagatatgaggaacaattggagaagtgaattatataaatataaagcggcagaa
attaagccattgggagtagcacccactccagcaaaaaggagagtggtggagagagaaaaaagagcagtaggattaggagc
tgtgttccttggattcttgggagcagcaggaagcactatgggcgcagcgtcaataacgctgacggtacaggccagacaat
tgttgtctggtatagtgcaacagcaaagcaatttgctgagggctatcgagggcgaacagcatctgttgcaactcacggtc
tggggcattaagcagctccagacaagagtcctggctatcgaaagatacctaaaggatcaacagctcctagggctttgggg
ctgctctggaaaactcatctgcaccactaatgtaccttggaactccagttggagtaacaaatctcaaacagatatttggg
aaaacatgacctggatgcagtgggataaagaagttagtaattacacagacacaatatacaggttgcttgaagactcgcaa
acccagcaggaaagaaatgaaaggatttattagcattggacaattggaaaaatctgtggaattggtttagtataacaaa
ctggctgtggtatataaaatattcataatgatagtaggaggcttgataggcttaagaataattttttgctgtgctttcta
tagtgaatagagttaggcagggatactcacctttgtcgtttcagaccccttaccccaaacccaaggggacccgacaggctc
ggaagaatcgaagaagaaggtggagggcaagacagagacagatcgattcgattagtgaacggattcttagcacttgcctg
ggacgacctgtggagcctgtgcctcttcagctaccaccgattagagacttaatattggtgacagcgagagcggtggaac
ttctgggacacagcagtctcagggactacagaggggtgggaagcccttaagtatctgggaggtattgtgcagtattgg
ggtctggaactaaaaaagagggctattagtctgcttgatactgtagcaatagcagtagctgaaggcacagataggattat
agaattcctccaaagaatttgtagagctatccgcaacatacctagaaggataagacagggctttgaagcagctttgcagt
aaaatggctagcccggggtgataaacggaccgcgcaatccctaggctgtgccttctagttgccagccatctgttgtttgc
ccctcccccgtgccttccttgaccctggaaggtgccactcccactgtccttcctaataaaatgaggaaattgcatcgca
ttgtctgagtaggtgtcattctattctgggggtgggtgtgggcaggacagcaaggggaggattgggaagacaatagca
ggcatgctggggatgcggtgggctctatataaaaaacgcccggcggcaaccgagcgttctgaacgctagagtcgacaaat
tcagaagaactcgtcaagaaggcgatagaaggcgatgcgctgcgaatcgggagcggcgataccgtaaagcacgaggaagc
ggtcagcccattcgccgccaagtcttcagcaatatcacggtagccaacgctatgtcctgatagcggtctgccacaccc
agccggccacagtcgatgaatccagaaaagcggccattttccaccatgatattcggcaagcaggcatcgccatgggtcac
gacgagatcctcgccgtcgggcatgctcgccttgagcctggcgaacagttcggctggcgcgagcccctgatgctcttcgt
ccagatcatcctgatcgacaagaccggcttccatccgagtacgtgctcgctcgatgcgatgtttcgcttggtggtcgaat
gggcaggtagccggatcaagcgtatgcagccgccgcattgcatcagccatgatggatactttctcggcaggagcaaggtg
agatgacaggagatcctgccccggcacttcgcccaatagcagccagtcccttcccgcttcagtgacaacgtcgagcacag
ctgcgcaaggaacgcccgtcgtggccagccacgatagccgcgctgcctcgtcttgcagttcattcagggcaccggacagg
tcggtcttgacaaaaagaaccgggcgcccctgcgctgacagccggaacacggcggcatcagagcagccgattgtctgttg
tgcccagtcatagccgaatagcctctccacccaagcggccgggagaacctcgtgcaatccatcttgttcaatcatgcgaa
acgatcctcatcctgtctcttgatcagatcttgatccctgcgccatcagatccttggcggcaagaaagccatccagttt
actttgcagggcttcccaaccttaccagagggcgccccagctggcaattccggttcgcttgctgtccataaaaccgccca
gtctagctatcgccatgtaagcccactgcaagctacctgctttctctttgcgcttgcgttttcccttgtccagatagccc
agtagctgacattcatccgggtcagcaccgtttctgcggactggctttctacgtgaaaaggatctaggtgaagatcctt
tttgataatctcatgaccaaaatcccttaacgtgagttttcgttccactgagcgtcagaccccgtagaaaagatcaaagg
atcttcttgagatcctttttttctgcgcgtaatctgctgcttgcaaacaaaaaaaccaccgctaccaggcggtttttgtt
tgccggatcaagagctaccaactctttttccgaaggtaactggcttcagcagagcgcagataccaaatactgttcttcta
gtgtagccgtagttaggccaccacttcaagaactctgtagcaccgcctacatacctcgctctgctaatcctgttaccagt
ggctgctgccagtggcgataagtcgtgtcttaccgggttggactcaagacgatagttaccggataaggcgcagcggtcgg
gctgaacggggggttcgtgcacacagcccagcttggagcgaacgacctacaccgaactgagatacctacagcgtgagcta
tgagaaagcgccacgcttcccgaagggagaaaggcggacaggtatccggtaagcggcagggtcggaacaggagagcgcac
gagggagcttccaggggggaaacgcctggtatctttatagtcctgtcgggtttcgccacctctgacttgagcgtcgatttt
tgtgatgctcgtcaggggggcggagcctatggaaaaacgccagcaacgcggccttttacggttcctggccttttgctgg
ccttttgctcacatgttgtcgacaatattggctattggccattgcatacgttgtatctatatcataatatgtacatttat
attggctcatgtccaatatgaccgccatgttgacattgattattgactagttattaatagtaatcaattacggggtcatt
agttcatagcccatatatggagttccgcgttacataacttacggtaaatggcccgcctggctgaccgcccaacgacccc
gcccattgacgtcaataatgacgtatgttcccatagtaacgccaatagggactttccattgacgtcaatgggtggagtat
ttacggtaaactgcccacttggcagtacatcaagtgtatcatatgccaagtccgcccccattgacgtcaatgacggtaa
atggcccgcctggcattatgcccagtacatgaccttacgggactttcctacttggcagtacatctacggtattagtcatc
ggctattaccatggtgatgcggttttggcagtacaccaatgggcgtggatagcggtttgactcacggggatttccaagtc
tccacccccattgacgtcaatgggagtttgttttggcaccaaaatcaacgggactttccaaaatgtcgtaataaccccgcc
ccgttgacgcaaatgggcggtaggcgtgtacggtggaggtctatataagcagagctcgtttagtgaaccgtcagatcgc
ctggagacgccatccacgctgttttgacctccatagaagacaccgggaccgatccagcctccgcggccgggaacggtgca
ttggaacgcggattcccgtgccaagagtgacgtaagtacgcctatagactctataggcacaccctttggctcttatg
catgctatactgtttttgggcctatacacccgcttcctatgctataggtgatggtatagctagcctatag
gtgtgggttattgaccattattgaccactccccattggtgacgatactttccattactaatccataacatggctctttg
ccacaactatctctattggctatatgccaatactctgtccttcagagactgacacggactctgtattttacaggatggg
```

FIG. 18A-2

```
gtcccatttattatttacaaattcacatatacaacaacgccgtcccccgtgcccgcagtttttattaaacatagcgtggg
atctccacgcgaatctcgggtaccgtgttccggacatgggytcttctccggtagcggcggagcttccacatccgagccct
ggtcccatgcctccagcggctcatggtcgctcggcagctccttgctcctaacagtggaggccagacttaggcacagcaca
atgcccaccaccaccagtgtgccgcacaaggccgtggcggtagggtatgtgtctgaaaatgagctcggagattgggctcg
caccgctgacgcagatggaagacttaaggcagcggcagaagaagatgcaggcagctgagttgttgtattctgataagagt
cagaggtaactcccgttgcggtgctgttaacggtggagggcagtgtagtctgagcagtactcgttgctgccgcgcgcgcc
accagacataatagctgacagactaacagactgttcctttccatgggtctttctgcagtcaccat
```

FIG. 18A-3

FIG. 18B pGA1/IN2 Functional Regions

| Position within sequence (starting- and ending pos.) | Gene/ORF (indicate complete name of the gene and the expressed gene product) | Origin of sequence (organism) |
|---|---|---|
| 99-1577 | Gag | C HIV-1 isolate 98IN012 |
| 1382-3520 | Pol, inactivating point mutations in reverse transcriptase, deletion of integrase | C HIV-1 isolate 98IN012 |
| 3645-3859 and 6205-6295 | Tat exons #1 and #2 | C HIV-1 isolate 98IN012 |
| 3784-3859 and 6205-6452 | Rev exons #1 and #2 | C HIV-1 isolate 98IN012 |
| 3873-4121 | Vpu | C HIV-1 isolate 98IN012 |
| 4039-6642 | Env | C HIV-1 isolate 98IN012 |
| 6643-10466 | Plasmid vector | pGA1, Gen Bank accession # AF425297 |

IN2 Mutation Chart

| Codon change | Amino acid change | Region | Function |
|---|---|---|---|
| to TCC position 1260-1262 | C390S | Gag | Ablation of zinc finger used in packaging |
| to TCT position 1269-1271 | C393S | Gag | Ablation of zinc finger used in packaging |
| to TCT position 1323-1325 | C411S | Gag | Ablation of zinc finger used in packaging |
| to TCT position 1332-1334 | C414S | Gag | Ablation of zinc finger used in packaging |
| To AAT position 2387-2389 | D185N | Reverse Transcriptase | Inactivation of Polymerase active site |
| To ACG position 2630-2632 | W266T | Reverse Transcriptase | Ablation of strand transfer activity |
| to CAA position 3266-3268 | E478Q | Rnase H | Inactivation of RNase H activity |

FIG. 18C

```
  1  GAATTCGTTG GTGGTCGCCA TGGATGGTGT TATTGTATAC TGTCTAAACG CGTTAGTAAA ACATGGGCAG
     CTTAAGCAAC CACCAGCGGT ACCTACCACA ATAACATATG ACAGATTTGC GCAATCATTT TGTACCGCTC

71  GAAATAAATC ATATAAAAAA TGATTTCATG ATTAAACCAT GTTCTGAAAA AGTCAAGAAC GTTCACATTG
     CTTTATTTAG TATATTTTTT ACTAAAGTAC TAATTTGGTA CAAGACTTTT TCAGTTCTTG CAAGTGTAAC

141  GCGGACAATC TAAAAACAAT ACAGTGATTG CAGATTTGCC ATATATGGAT AATGCGGTAT CCGATGTATG
     CGCCTGTTAG ATTTTTGTTA TGTCACTAAC GTCTAAACGG TATATACCTA TTACGCCATA GGCTACATAC

211  CAATTCACTG TATAAAAAGA ATGTATCAAG AATATCCAGA TTTGCTAATT TGATAAAGAT AGATGACGAT
     GTTAAGTGAC ATATTTTTCT TACATAGTTC TTATAGGTCT AAACGATTAA ACTATTTCTA TCTACTGCTA

281  GACAAGACTC CTACTGGTGT ATATAATTAT TTTAAACCTA AAGATGCCAT TCCTGTTATT ATATCCATAG
     CTGTTCTGAG GATGACCACA TATATTAATA AAATTTGGAT TTCTACGGTA AGGACAATAA TATAGGTATC

351  GAAAGGATAG AGATGTTTGT GAACTATTAA TCTCATCTGA TAAAGGCGTG GCGTGTATAG AGTTAAATTC
     CTTTCCTATC TCTACAAACA CTTGATAATT AGAGTAGACT ATTTCGCCAC CGCACATATC TCAATTTAAG
```

FIG. 20B

Text File of pLW-48 and the Included Individual HIV Genes And Their Promoters

Entire pLW-48 plasmid sequences:

```
GAATTCGTTGGTGGTCGCCATGGATGGTGTTATTGTATACTGTCTAAACGCG
TTAGTAAAACATGGCGAGGAAATAAATCATATAAAAAATGATTTCATGATTAA
ACCATGTTGTGAAAAAGTCAAGAACGTTCACATTGGCGGACAATCTAAAAAC
AATACAGTGATTGCAGATTTGCCATATATGGATAATGCGGTATCCGATGTAT
GCAATTCACTGTATAAAAGAATGTATCAAGAATATCCAGATTTGCTAATTTG
ATAAAGATAGATGACGATGACAAGACTCCTACTGGTGTATATAATTATTTTAA
ACCTAAAGATGCCATTCCTGTTATTATATCCATAGGAAAGGATAGAGATGTTT
GTGAACTATTAATCTCATCTGATAAAGCGTGTGCGTGTATAGAGTTAAATTCA
TATAAAGTAGCCATTCTTCCCATGGATGTTTCCTTTTTTACCAAAGGAAATGC
ATCATTGATTATTCTCCTGTTTGATTTCTATCGATGCGGCACCTCTCTTAA
GAAGTGTAACCGATAATAATGTTATTATATCTAGACACCAGCGTCTACATGA
CGAGCTTCCGAGTTCCAATTGGTTCAAGTTTTACATAAGTATAAAGTCCGAC
TATTGTTCTATATTATATATGGTTGTTGATGGATCTGTGATGCATGCAATAGC
TGATAATAGAACTTACGCAAATATTAGCAAAAATATATTAGACAATACTACAA
TTAACGATGAGTGTAGATGCTGTTATTTTGAACCACAGATTAGGATTCTTGAT
AGAGATGAGATGCTCAATGGATCATCGTGTGATATGAACAGACATTGTATTA
TGATGAATTTACCTGATGTAGGCGAATTTGGATCTAGTATGTTGGGGAAATA
TGAACCTGACATGATTAAGATTGCTCTTTCGGTGGCTGGGTACCAGGCGCG
CCTTTCATTTTGTTTTTTTCTATGCTATAAATGGTACGTCCTGTAGAAACCCC
AACCCGTGAAATCAAAAAACTCGACGGCCTGTGGGCATTCAGTCTGGATCG
CGAAAACTGTGGAATTGATCAGCGTTGGTGGGAAAGCGCGTTACAAGAAAG
CCGGGCAATTGCTGTGCCAGGCAGTTTTAACGATCAGTTCGCCGATGCAGA
TATTCGTAATTATGCGGGCAACGTCTGGTATCAGCGCGAAGTCTTTATACCG
AAAGGTTGGGCAGGCCAGCGTATCGTGCTGCGTTTCGATGCGGTCACTCAT
TACGGCAAAGTGTGGGTCAATAATCAGGAAGTGATGGAGCATCAGGGCGG
CTATACGCCATTTGAAGCCGATGTCACGCCGTATGTTATTGCCGGGAAAAG
TGTACGTATCACCGTTTGTGTGAACAACGAACTGAACTGGCAGACTATCCC
GCCGGGAATGGTGATTACCGACGAAAACGGCAAGAAAAGCAGTCTTACTT
CCATGATTTCTTTAACTATGCCGGAATCCATCGCAGCGTAATGCTCTACACC
ACGCCGAACACCTGGGTGGACGATATCACCGTGGTGACGCATGTCGCGCA
AGACTGTAACCACGCGTCTGTTGACTGGCAGGTGGTGGCCAATGGTGATGT
CAGCGTTGAACTGCGTGATGCGGATCAACAGGTGGTTGCAACTGGACAAG
GCACTAGCGGGACTTTGCAAGTGGTGAATCCGCACCTCTGGCAACCGGGT
GAAGGTTATCTCTATGAACTGTGCGTCACAGCCAAAAGCCAGACAGAGTGT
GATATCTACCCGCTTCGCGTCGGCATCCGGTCAGTGGCAGTGAAGGGCGA
ACAGTTCCTGATTAACCACAAACCGTTCTACTTTACTGGCTTTGGTCGTCAT
GAAGATGCGGACTTGCGTGGCAAAGGATTCGATAACGTGCTGATGGTGCAC
GACCACGCATTAATGGACTGGATTGGGGCCAACTCCTACCGTACCTCGCAT
TACCCTTACGCTGAAGAGATGCTCGACTGGGCAGATGAACATGGCATCGTG
```

FIG. 21-1

```
GTGATTGATGAAACTGCTGCTGTCGGCTTTAACCTCTCTTTAGGCATTGGTT
TCGAAGCGGGCAACAAGCCGAAAGAACTGTACAGCGAAGAGGCAGTCAAC
GGGGAAACTCAGCAAGCGCACTTACAGGCGATTAAAGAGCTGATAGCGCGT
GACAAAAACCACCCAAGCGTGGTGATGTGGAGTATTGCCAACGAACCGGAT
ACCCGTCCGCAAGGTGCACGGGAATATTTCGCGCCACTGGCGGAAGCAAC
GCGTAAACTCGACCCGACGCGTCCGATCACCTGCGTCAATGTAATGTTCTG
CGACGCTCACACCGATACCATCAGCGATCTCTTTGATGTGCTGTGCCTGAA
CCGTTATTACGGATGGTATGTCCAAAGCGGCGATTTGGAAACGGCAGAGAA
GGTACTGGAAAAAGAACTTCTGGCCTGGCAGGAGAAACTGCATCAGCCGAT
TATCATCACCGAATACGGCGTGGATACGTTAGCCGGGCTGCACTCAATGTA
CACCGACATGTGGAGTGAAGAGTATCAGTGTGCATGGCTGGATATGTATCA
CCGCGTCTTTGATCGCGTCAGCGCCGTCGTCGGTGAACAGGTATGGAATTT
CGCCGATTTTGCGACCTCGCAAGGCATATTGCGCGTTGGCGGTAACAAGAA
AGGGATCTTCACTCGCGACCGCAAACCGAAGTCGGCGGCTTTTCTGCTGCA
AAAACGCTGGACTGGCATGAACTTCGGTGAAAAACCGCAGCAGGGAGGCA
AACAATGAGAGCTCGGTTGTTGATGGATCTGTGATGCATGCAATAGCTGATA
ATAGAACTTACGCAAATATTAGCAAAATATATTAGACAATACTACAATTAAC
GATGAGTGTAGATGCTGTTATTTTGAACCACAGATTAGGATTCTTGATAGAG
ATGAGATGCTCAATGGATCATCGTGTGATATGAACAGACATTGTATTATGAT
GAATTTACCTGATGTAGGCGAATTTGGATCTAGTATGTTGGGGAAATATGAA
CCTGACATGATTAAGATTGCTCTTTCGGTGGCTGGCGGCCCGCTCGAGTAA
AAAATGAAAAAATATTCTAATTTATAGGACGGTTTTGATTTTCTTTTTTCTAT
GCTATAAATAATAAATAGCGGCCGCACCATGAAAGTGAAGGGGATCAGGAA
GAATTATCAGCACTTGTGGAAATGGGGCATCATGCTCCTTGGGATGTTGATG
ATCTGTAGTGCTGTAGAAAATTTGTGGGTCACAGTTTATTATGGGGTACCTG
TGTGGAAAGAAGCAACCACCACTCTATTTTGTGCATCAGATGCTAAAGCATA
TGATACAGAGGTACATAATGTTTGGGCCACACATGCCTGTGTACCCACAGA
CCCCAACCCACAAGAAGTAGTATTGGAAAATGTGACAGAAAATTTTAACATG
TGGAAAAATAACATGGTAGAACAGATGCATGAGGATATAATCAGTTTATGGG
ATCAAAGCCTAAAGCCATGTGTAAAATTAACCCCACTCTGTGTTACTTTAAAT
TGCACTGATTTGAGGAATGTTACTAATATCAATAATAGTAGTGAGGGAATGA
GAGGAGAAATAAAAAACTGCTCTTTCAATATCACCACAAGCATAAGAGATAA
GGTGAAGAAAGACTATGCACTTTTCTATAGACTTGATGTAGTACCAATAGATA
ATGATAATACTAGCTATAGGTTGATAAATTGTAATACCTCAACCATTACACAG
GCCTGTCCAAAGGTATCCTTTGAGCCAATTCCCATACATTATTGTACCCCGG
CTGGTTTTGCGATTCTAAAGTGTAAAGACAAGAAGTTCAATGGAACAGGGCC
ATGTAAAAATGTCAGCACAGTACAATGTACACATGGAATTAGGCCAGTAGTG
TCAACTCAACTGCTGTTAAATGGCAGTCTAGCAGAAGAAGAGGTAGTAATTA
GATCTAGTAATTTCACAGACAATGCAAAAAACATAATAGTACAGTTGAAAGAA
TCTGTAGAAATTAATTGTACAAGACCCAACAACAATACAAGGAAAAGTATAC
ATATAGGACCAGGAAGAGCATTTTATACAACAGGAGAAATAATAGGAGATAT
AAGACAAGCACATTGCAACATTAGTAGAACAAAATGGAATAACACTTTAAAT
CAAATAGCTACAAAATTAAAAGAACAATTTGGGAATAATAAAACAATAGTCTT
TAATCAATCCTCAGGAGGGGACCCAGAAATTGTAATGCACAGTTTTAATTGT
GGAGGGGAATTCTTCTACTGTAATTCAACACAACTGTTTAATAGTACTTGGA
ATTTTAATGGTACTTGGAATTTAACACAATCGAATGGTACTGAAGGAAATGA
```

FIG. 21-2

```
CACTATCACACTCCCATGTAGAATAAAACAAATTATAAATATGTGGCAGGAA
GTAGGAAAAGCAATGTATGCCCCTCCCATCAGAGGACAAATTAGATGCTCAT
CAAATATTACAGGGCTAATATTAACAAGAGATGGTGGAACTAACAGTAGTGG
GTCCGAGATCTTCAGACCTGGGGGAGGAGATATGAGGGACAATTGGAGAA
GTGAATTATATAAATATAAAGTAGTAAAAATTGAACCATTAGGAGTAGCACCC
ACCAAGGCAAAAAGAAGAGTGGTGCAGAGAGAAAAAAGAGCAGTGGGAAC
GATAGGAGCTATGTTCCTTGGGTTCTTGGGAGCAGCAGGAAGCACTATGGG
CGCAGCGTCAATAACGCTGACGGTACAGGCCAGACTATTATTGTCTGGTAT
AGTGCAACAGCAGAACAATTTGCTGAGGGCTATTGAGGCGCAACAGCATCT
GTTGCAACTCACAGTCTGGGGCATCAAGCAGCTCCAGGCAAGAGTCCTGG
CTGTGGAAAGATACCTAAGGGATCAACAGCTCCTAGGGATTTGGGGTTGCT
CTGGAAAACTCATCTGCACCACTGCTGTGCCTTGGAATGCTAGTTGGAGTA
ATAAAACTCTGGATATGATTTGGGATAACATGACCTGGATGGAGTGGGAAA
GAGAAATCGAAAATTACACAGGCTTAATATACACCTTAATTGAGGAATCGCA
GAACCAACAAGAAAGAATGAACAAGACTTATTAGCATTAGATAAGTGGGCA
AGTTTGTGGAATTGGTTTGACATATCAAATTGGCTGTGGTATGTAAAATCTT
CATAATGATAGTAGGAGGCTTGATAGGTTTAAGAATAGTTTTTACTGTACTTT
CTATAGTAAATAGAGTTAGGCAGGGATACTCACCATTGTCATTTCAGACCCA
CCTCCCAGCCCCGAGGGGACCCGACAGGCCCGAAGGAATCGAAGAAGAAG
GTGGAGACAGAGACTAATTTTTATGCGGCCGCTGGTACCCAACCTAAAAATT
GAAAATAAATACAAAGGTTCTTGAGGGTTGTGTTAAATTGAAAGCGAGAAAT
AATCATAAATAAGCCCGGGGATCCTCTAGAGTCGACACCATGGGTGCGAGA
GCGTCAGTATTAAGCGGGGGAGAATTAGATCGATGGGAAAAAATTCGGTTA
AGGCCAGGGGGAAAGAAAAAATATAAATTAAAACATATAGTATGGGCAAGCA
GGGAGCTAGAACGATTCGCAGTTAATCCTGGCCTGTTAGAAACATCAGAAG
GCTGTAGACAAATACTGGGACAGCTACAACCATCCCTTCAGACAGGATCAG
AAGAACTTAGATCATTATATAATACAGTAGCAACCCTCTATTGTGTGCATCAA
AGGATAGAGATAAAAGACACCAAGGAAGCTTTAGACAAGATAGAGGAAGAG
CAAAACAAAAGTAAGAAAAAAGCACAGCAAGCAGCAGCTGACACAGGACAC
AGCAATCAGGTCAGCCAAAATTACCCTATAGTGCAGAACATCCAGGGGCAA
ATGGTACATCAGGCCATATCACCTAGAACTTTAAATGCATGGGTAAAAGTAG
TAGAAGAGAAGGCTTTCAGCCCAGAAGTGATACCCATGTTTTCAGCATTATC
AGAAGGAGCCACCCCACAAGATTTAAACACCATGCTAAACACAGTGGGGGG
ACATCAAGCAGCCATGCAAATGTTAAAAGAGACCATCAATGAGGAAGCTGC
AGAATGGGATAGAGTGCATCCAGTGCATGCAGGGCCTATTGCACCAGGCCA
GATGAGAGAACCAAGGGGAAGTGACATAGCAGGAACTACTAGTACCCTTCA
GGAACAAATAGGATGGATGACAAATAATCCACCTATCCCAGTAGGAGAAATT
TATAAAAGATGGATAATCCTGGGATTAAATAAAATAGTAAGAATGTATAGCCC
TACCAGCATTCTGGACATAAGACAAGGACCAAAAGAACCCTTTAGAGACTAT
GTAGACCGGTTCTATAAAACTCTAAGAGCCGAGCAAGCTTCACAGGAGGTA
AAAAATTGGATGACAGAAACCTTGTTGGTCCAAAATGCGAACCCAGATTGTA
AGACTATTTTAAAAGCATTGGGACCAGCGGCTACACTAGAAGAAATGATGAC
AGCATGTCAGGGAGTAGGAGGACCCGGCCATAAGGCAAGAGTTTTGGCTG
AAGCAATGAGCCAAGTAACAAATTCAGCTACCATAATGATGCAGAGAGGCA
ATTTTAGGAACCAAAGAAAGATTGTTAAGTGTTTCAATTGTGGCAAAGAAGG
GCACACAGCCAGAAATTGCAGGGCCCCTAGGAAAAAGGGCTGTTGGAAAT
```

FIG. 21-3

```
GTGGAAAGGAAGGACACCAAATGAAAGATTGTACTGAGAGACAGGCTAATT
TTTTAGGGAAGATCTGGCCTTCCTACAAGGGAAGGCCAGGGAATTTTCTTCA
GAGCAGACCAGAGCCAACAGCCCCACCAGAAGAGAGCTTCAGGTCTGGGG
TAGAGACAACAACTCCCCCTCAGAAGCAGGAGCCGATAGACAAGGAACTGT
ATCCTTTAACTTCCCTCAGATCACTCTTTGGCAACGACCCCTCGTCACAATA
AAGATAGGGGGGCAACTAAAGGAAGCTCTATTAGATACAGGAGCAGATGAT
ACAGTATTAGAAGAAATGAGTTTGCCAGGAAGATGGAAACCAAAAATGATAG
GGGGAATTGGAGGTTTTATCAAAGTAAGACAGTATGATCAGATACTCATAGA
AATCTGTGGACATAAAGCTATAGGTACAGTATTAGTAGGACCTACACCTGTC
AACATAATTGGAAGAAATCTGTTGACTCAGATTGGTTGCACTTTAAATTTTCC
CATTAGCCCTATTGAGACTGTACCAGTAAAATTAAAGCCAGGAATGGATGGC
CCAAAAGTTAAACAATGGCCATTGACAGAAGAAAAAATAAAAGCATTAGTAG
AAATTTGTACAGAAATGGAAAAGGAAGGGAAAATTTCAAAAATTGGGCCTGA
GAATCCATACAATACTCCAGTATTTGCCATAAAGAAAAAAGACAGTACTAAAT
GGAGGAAATTAGTAGATTTCAGAGAACTTAATAAGAGAACTCAAGACTTCTG
GGAAGTTCAATTAGGAATACCACATCCCGCAGGGTTAAAAAAGAAAAAATCA
GTAACAGTACTGGATGTGGGTGATGCATATTTTTCAGTTCCCTTAGATGAAG
ACTTCAGGAAGTATACTGCATTTACCATACCTAGTATAAACAATGAGACACC
AGGGATTAGATATCAGTACAATGTGCTTCCACAGGGATGGAAAGGATCACC
AGCAATATTCCAAAGTAGCATGACAAAAATCTTAGAGCCTTTTAAAAAACAAA
ATCCAGACATAGTTATCTATCAATACATGAACGATTTGTATGTAGGATCTGAC
TTAGAAATAGGGCAGCATAGAACAAAATAGAGGAGCTGAGACAACATCTG
TTGAGGTGGGGACTTACCACACCAGACAAAAACATCAGAAAGAACCTCCA
TTCCTTTGGATGGGTTATGAACTCCATCCTGATAAATGGACAGTACAGCCTA
TAGTGCTGCCAGAAAAAGACAGCTGGACTGTCAATGACATACAGAAGTTAG
TGGGGAAATTGAATACCGCAAGTCAGATTTACCCAGGGATTAAAGTAAGGC
AATTATGTAAACTCCTTAGAGGAACCAAAGCACTAACAGAAGTAATACCACT
AACAGAAGAAGCAGAGCTAGAACTGGCAGAAAACAGAGAGATTCTAAAAGA
ACCAGTACATGGAGTGTATTATGACCCATCAAAAGACTTAATAGCAGAAATA
CAGAAGCAGGGGCAAGGCCAATGGACATATCAAATTTATCAAGAGCCATTT
AAAAATCTGAAAACAGGAAAATATGCAAGAATGAGGGGTGCCCACACTAAT
GATGTAAAACAATTAACAGAGGCAGTGCAAAAAATAACCACAGAAAGCATAG
TAATATGGGGAAAGACTCCTAAATTTAAACTACCCATACAAAAGGAAACATG
GGAAACATGGTGGACAGAGTATTGGCAAGCCACCTGGATTCCTGAGTGGGA
GTTTGTTAATACCCCTCCTTTAGTGAAATTATGGTACCAGTTAGAGAAAGAA
CCCATAGTAGGAGCAGAAACCTTCTATGTAGATGGGGCAGCTAACAGGGAG
ACTAAATTAGGAAAAGCAGGATATGTTACTAACAAAGGAAGACAAAAGGTTG
TCCCCCTAACTAACACAACAAATCAGAAAACTCAGTTACAAGCAATTTATCTA
GCTTTGCAGGATTCAGGATTAGAAGTAAACATAGTAACAGACTCACAATATG
CATTAGGAATCATTCAAGCACAACCAGATAAAAGTGAATCAGAGTTAGTCAA
TCAAATAATAGAGCAGTTAATAAAAAAGGAAAAGGTCTATCTGGCATGGGTA
CCAGCACACAAAGGAATTGGAGGAAATGAACAAGTAGATAAATTAGTCAGT
GCTGGAATCAGGAAAATACTATTTTTAGATGGAATAGATAAGGCCCAAGATG
AACATTAGTTTTTATGTCGACCTGCAGGGAAAGTTTTATAGGTAGTTGATAG
AACAAAATACATAATTTTGTAAAAATAAATCACTTTTTATACTAATATGACACG
ATTACCAATACTTTTGTTACTAATATCATTAGTATACGCTACACCTTTTCCTCA
```

FIG. 21-4

```
GACATCTAAAAAAATAGGTGATGATGCAACTTTATCATGTAATCGAAATAATA
CAAATGACTACGTTGTTATGAGTGCTTGGTATAAGGAGCCCAATTCCATTAT
TCTTTTAGCTGCTAAAAGCGACGTCTTGTATTTTGATAATTATACCAAGGATA
AAATATCTTACGACTCTCCATACGATGATCTAGTTACAACTATCACAATTAAA
TCATTGACTGCTAGAGATGCCGGTACTTATGTATGTGCATTCTTTATGACATC
GCCTACAAATGACACTGATAAAGTAGATTATGAAGAATACTCCACAGAGTTG
ATTGTAAATACAGATAGTGAATCGACTATAGACATAATACTATCTGGATCTAC
ACATTCACCAGAAACTAGTTAAGCTTGTCTCCCTATAGTGAGTCGTATTAGA
GCTTGGCGTAATCATGGTCATAGCTGTTTCCTGTGTGAAATTGTTATCCGCT
CACAATTCCACACAACATACGAGCCGGAAGCATAAAGTGTAAAGCCTGGGG
TGCCTAATGAGTGAGCTAACTCACATTAATTGCGTTGCGCTCACTGCCCGCT
TTCGAGTCGGGAAACCTGTCGTGCCAGCTGCATTAATGAATCGGCCAACGC
GCGGGGAGAGGCGGTTTGCGTATTGGGCGCTCTTCCGCTTCCTCGCTCAC
TGACTCGCTGCGCTCGGTCGTTCGGCTGCGGCGAGCGGTATCAGCTCACT
CAAAGGCGGTAATACGGTTATCCACAGAATCAGGGGATAACGCAGGAAAGA
ACATGTGAGCAAAAGGCCAGCAAAAGGCCAGGAACCGTAAAAAGGCCGCG
TTGCTGGCGTTTTTCGATAGGCTCCGCCCCCTGACGAGCATCACAAAAAT
CGACGCTCAAGTCAGAGGTGGCGAAACCCGACAGGACTATAAAGATACCAG
GCGTTTCCCCCTGGAAGCTCCCTCGTGCGCTCTCCTGTTCCGACCCTGCCG
CTTACCGGATACCTGTCCGCCTTTCTCCCTTCGGGAAGCGTGGCGCTTTCT
CATAGCTCACGCTGTAGGTATCTCAGTTCGGTGTAGGTCGTTCGCTCCAAG
CTGGGCTGTGTGCACGAACCCCCGTTCAGCCCGACCGCTGCGCCTTATC
CGGTAACTATCGTCTTGAGTCCAACCCGGTAAGACACGACTTATCGCCACT
GGCAGCAGCCACTGGTAACAGGATTAGCAGAGCGAGGTATGTAGGCGGTG
CTACAGAGTTCTTGAAGTGGTGGCCTAACTACGGCTACACTAGAAGGACAG
TATTTGGTATCTGCGCTCTGCTGAAGCCAGTTACCTTCGGAAAAAGAGTTGG
TAGCTCTTGATCCGGCAAACAAACCACCGCTGGTAGCGGTGGTTTTTTTGTT
TGCAAGCAGCAGATTACGCGCAGAAAAAAAGGATCTCAAGAAGATCCTTTG
ATCTTTTCTACGGGGTCTGACGCTCAGTGGAACGAAAACTCACGTTAAGGG
ATTTTGGTCATGAGATTATCAAAAAGGATCTTCACCTAGATCCTTTTAAATTA
AAAATGAAGTTTTAAATCAATCTAAAGTATATATGAGTAAACTTGGTCTGACA
GTTACCAATGCTTAATCAGTGAGGCACCTATCTCAGCGATCTGTCTATTTCG
TTCATCCATAGTTGCCTGACTCCCCGTCGTGTAGATAACTACGATACGGGAG
GGCTTACCATCTGGCCCCAGTGCTGCAATGATACCGCGAGACCCACGCTCA
CCGGCTCCAGATTTATCAGCAATAAACCAGCCAGCCGGAAGGGCCGAGCG
CAGAAGTGGTCCTGCAACTTTATCCGCCTCCATCCAGTCTATTAATTGTTGC
CGGGAAGCTAGAGTAAGTAGTTCGCCAGTTAATAGTTTGCGCAACGTTGTT
GGCATTGCTACAGGCATCGTGGTGTCACGCTCGTCGTTTGGTATGGCTTCA
TTCAGCTCCGGTTCCCAACGATCAAGGCGAGTTACATGATCCCCCATGTTGT
GCAAAAAAGCGGTTAGCTCCTTCGGTCCTCCGATCGTTGTCAGAAGTAAGT
TGGCCGCAGTGTTATCACTCATGGTTATGGCAGCACTGCATAATTCTCTTAC
TGTCATGCCATCCGTAAGATGCTTTTCTGTGACTGGTGAGTACTCAACCAAG
TCATTCTGAGAATAGTGTATGCGGCGACCGAGTTGCTCTTGCCCGGCGTCA
ATACGGGATAATACCGCGCCACATAGCAGAACTTTAAAAGTGCTCATCATTG
GAAAACGTTCTTCGGGGCGAAAACTCTCAAGGATCTTACCGCTGTTGAGAT
CCAGTTCGATGTAACCCACTCGTGCACCCAACTGATCTTCAGCATCTTTTAC
```

FIG. 21-5

TTTCACCAGCGTTTCTGGGTGAGCAAAAACAGGAAGGCAAAATGCCGCAAA
AAAGGGAATAAGGGCGACACGGAAATGTTGAATACTCATACTCTTCCTTTTT
CAATATTATTGAAGCATTTATCAGGGTTATTGTCTCATGAGCGGATACATATT
TGAATGTATTTAGAAAAATAAACAAATAGGGGTTCCGCGCACATTTCCCCGA
AAAGTGCCACCTGACGTCTAAGAAACCATTATTATCATGACATTAACCTATAA
AAATAGGCGTATCACGAGGCCCTTTCGTCTCGCGCGTTTCGGTGATGACGG
TGAAAACCTCTGACACATGCAGCTCCCGGAGACGGTCACAGCTTGTCTGTA
AGCGGATGCCGGGAGCAGACAAGCCCGTCAGGGCGCGTCAGCGGGTGTT
GGCGGGTGTCGGGGCTGGCTTAACTATGCGGCATCAGAGCAGATTGTACT
GAGAGTGCACCATATGCGGTGTGAAATACCGCACAGATGCGTAAGGAGAAA
ATACCGCATCAGGCGCCATTCGCCATTCAGGCTGCGCAACTGTTGGGAAGG
GCGATCGGTGCGGGCCTCTTCGCTATTACGCCAGCTGGCGAAAGGGGGAT
GTGCTGCAAGGCGATTAAGTTGGGTAACGCCAGGGTTTTCCCAGTCACGAC
GTTGTAAAACGACGGCCAGTGAATTGGATTTAGGTGACACTATA

New Psyn II Promoter which controls ADA envelope expression:

TAAAAAATGAAAAAATATTCTAATTTATAGGACGGTTTTGATTTTCTTTTTTTC
TATGCTATAAATAATAAATA

ADA envelope truncated:

ATGAAAGTGAAGGGGATCAGGAAGAATTATCAGCACTTGTGGAAATGGGGC
ATCATGCTCCTTGGGATGTTGATGATCTGTAGTGCTGTAGAAAATTTGTGGG
TCACAGTTTATTATGGGGTACCTGTGTGGAAAGAAGCAACCACCACTCTATT
TTGTGCATCAGATGCTAAAGCATATGATACAGAGGTACATAATGTTTGGGCC
ACACATGCCTGTGTACCCACAGACCCCAACCCACAAGAAGTAGTATTGGAA
AATGTGACAGAAAATTTTAACATGTGGAAAAATAACATGGTAGAACAGATGC
ATGAGGATATAATCAGTTTATGGGATCAAAGCCTAAAGCCATGTGTAAAATT
AACCCCACTCTGTGTTACTTTAAATTGCACTGATTTGAGGAATGTTACTAATA
TCAATAATAGTAGTGAGGGAATGAGAGGAGAAATAAAAAACTGCTCTTTCAA
TATCACCACAAGCATAAGAGATAAGGTGAAGAAAGACTATGCACTTTTCTAT
AGACTTGATGTAGTACCAATAGATAATGATAATACTAGCTATAGGTTGATAAA
TTGTAATACCTCAACCATTACACAGGCCTGTCCAAAGGTATCCTTTGAGCCA
ATTCCCATACATTATTGTACCCCGGCTGGTTTTGCGATTCTAAAGTGTAAAG
ACAAGAAGTTCAATGGAACAGGGCCATGTAAAAATGTCAGCACAGTACAAT
GTACACATGGAATTAGGCCAGTAGTGTCAACTCAACTGCTGTTAAATGGCAG
TCTAGCAGAAGAAGAGGTAGTAATTAGATCTAGTAATTTCACAGACAATGCA
AAAAACATAATAGTACAGTTGAAAGAATCTGTAGAAATTAATTGTACAAGACC
CAACAACAATACAAGGAAAAGTATACATATAGGACCAGGAAGAGCATTTTAT
ACAACAGGAGAAATAATAGGAGATATAAGACAAGCACATTGCAACATTAGTA
GAACAAAATGGAATAACACTTTAAATCAAATAGCTACAAAATTAAAAGAACAA
TTTGGGAATAATAAAACAATAGTCTTTAATCAATCCTCAGGAGGGGACCCAG
AAATTGTAATGCACAGTTTTAATTGTGGAGGGGAATTCTTCTACTGTAATTCA
ACACAACTGTTTAATAGTACTTGGAATTTTAATGGTACTTGGAATTTAACACA

FIG. 21-6

ATCGAATGGTACTGAAGGAAATGACACTATCACACTCCCATGTAGAATAAAA
CAAATTATAAATATGTGGCAGGAAGTAGGAAAAGCAATGTATGCCCCTCCCA
TCAGAGGACAAATTAGATGCTCATCAAATATTACAGGGCTAATATTAACAAG
AGATGGTGGAACTAACAGTAGTGGGTCCGAGATCTTCAGACCTGGGGGAG
GAGATATGAGGGACAATTGGAGAAGTGAATTATATAAATATAAAGTAGTAAA
AATTGAACCATTAGGAGTAGCACCCACCAAGGCAAAAGAAGAGTGGTGCA
GAGAGAAAAAAGAGCAGTGGGAACGATAGGAGCTATGTTCCTTGGGTTCTT
GGGAGCAGCAGGAAGCACTATGGGCGCAGCGTCAATAACGCTGACGGTAC
AGGCCAGACTATTATTGTCTGGTATAGTGCAACAGCAGAACAATTTGCTGAG
GGCTATTGAGGCGCAACAGCATCTGTTGCAACTCACAGTCTGGGGCATCAA
GCAGCTCCAGGCAAGAGTCCTGGCTGTGGAAAGATACCTAAGGGATCAACA
GCTCCTAGGGATTTGGGGTTGCTCTGGAAAACTCATCTGCACCACTGCTGT
GCCTTGGAATGCTAGTTGGAGTAATAAAACTCTGGATATGATTTGGGATAAC
ATGACCTGGATGGAGTGGGAAAGAGAAATCGAAAATTACACAGGCTTAATAT
ACACCTTAATTGAGGAATCGCAGAACCAACAAGAAAAGAATGAACAAGACTT
ATTAGCATTAGATAAGTGGGCAAGTTTGTGGAATTGGTTTGACATATCAAATT
GGCTGTGGTATGTAAAAATCTTCATAATGATAGTAGGAGGCTTGATAGGTTT
AAGAATAGTTTTTACTGTACTTTCTATAGTAAATAGAGTTAGGCAGGGATACT
CACCATTGTCATTTCAGACCCACCTCCCAGCCCCGAGGGGACCCGACAGG
CCCGAAGGAATCGAAGAAGAAGGTGGAGACAGAGAC

PmH5 promoter (which controls HXB2 gag pol expression):

AAAAATTGAAAATAAATACAAAGGTTCTTGAGGGTTGTGTTAAATTGAAAGC
GAGAAATAATCATAAATA

HXB2 gag pol (with safety mutations, Δintegrase):

ATGGGTGCGAGAGCGTCAGTATTAAGCGGGGGAGAATTAGATCGATGGGA
AAAAATTCGGTTAAGGCCAGGGGGAAAGAAAAAATATAAATTAAAACATATA
GTATGGGCAAGCAGGGAGCTAGAACGATTCGCAGTTAATCCTGGCCTGTTA
GAAACATCAGAAGGCTGTAGACAAATACTGGGACAGCTACAACCATCCCTT
CAGACAGGATCAGAAGAACTTAGATCATTATATAATACAGTAGCAACCCTCT
ATTGTGTGCATCAAAGGATAGAGATAAAAGACACCAAGGAAGCTTTAGACAA
GATAGAGGAAGAGCAAAACAAAAGTAAGAAAAAAGCACAGCAAGCAGCAGC
TGACACAGGACACAGCAATCAGGTCAGCCAAAATTACCCTATAGTGCAGAA
CATCCAGGGGCAAATGGTACATCAGGCCATATCACCTAGAACTTTAAATGCA
TGGGTAAAAGTAGTAGAAGAGAAGGCTTTCAGCCCAGAAGTGATACCCATG
TTTTCAGCATTATCAGAAGGAGCCACCCCACAAGATTTAAACACCATGCTAA
ACACAGTGGGGGGACATCAAGCAGCCATGCAAATGTTAAAAGAGACCATCA
ATGAGGAAGCTGCAGAATGGGATAGAGTGCATCCAGTGCATGCAGGGCCT
ATTGCACCAGGCCAGATGAGAGAACCAAGGGGAAGTGACATAGCAGGAAC
TACTAGTACCCTTCAGGAACAAATAGGATGGATGACAAATAATCCACCTATC
CCAGTAGGAGAAATTTATAAAAGATGGATAATCCTGGGATTAAATAAAATAG
TAAGAATGTATAGCCCTACCAGCATTCTGGACATAAGACAAGGACCAAAAGA
ACCCTTTAGAGACTATGTAGACCGGTTCTATAAAACTCTAAGAGCCGAGCAA

FIG. 21-7

```
GCTTCACAGGAGGTAAAAAATTGGATGACAGAAACCTTGTTGGTCCAAAATG
CGAACCCAGATTGTAAGACTATTTTAAAAGCATTGGGACCAGCGGCTACACT
AGAAGAAATGATGACAGCATGTCAGGGAGTAGGAGGACCCGGCCATAAGG
CAAGAGTTTTGGCTGAAGCAATGAGCCAAGTAACAAATTCAGCTACCATAAT
GATGCAGAGAGGCAATTTTAGGAACCAAAGAAAGATTGTTAAGTGTTTCAAT
TGTGGCAAAGAAGGGCACACAGCCAGAAATTGCAGGGCCCCTAGGAAAAA
GGGCTGTTGGAAATGTGGAAGGAAGGACACCAAATGAAAGATTGTACTGA
GAGACAGGCTAATTTTTTAGGGAAGATCTGGCCTTCCTACAAGGGAAGGCC
AGGGAATTTTCTTCAGAGCAGACCAGAGCCAACAGCCCCACCAGAAGAGAG
CTTCAGGTCTGGGGTAGAGACAACAACTCCCCCTCAGAAGCAGGAGCCGAT
AGACAAGGAACTGTATCCTTTAACTTCCCTCAGATCACTCTTTGGCAACGAC
CCCTCGTCACAATAAAGATAGGGGGGCAACTAAAGGAAGCTCTATTAGATA
CAGGAGCAGATGATACAGTATTAGAAGAAATGAGTTTGCCAGGAAGATGGA
AACCAAAAATGATAGGGGGAATTGGAGGTTTTATCAAAGTAAGACAGTATGA
TCAGATACTCATAGAAATCTGTGGACATAAAGCTATAGGTACAGTATTAGTA
GGACCTACACCTGTCAACATAATTGGAAGAAATCTGTTGACTCAGATTGGTT
GCACTTTAAATTTTCCCATTAGCCCTATTGAGACTGTACCAGTAAAATTAAAG
CCAGGAATGGATGGCCCAAAAGTTAAACAATGGCCATTGACAGAAGAAAAA
ATAAAAGCATTAGTAGAAATTTGTACAGAAATGGAAAAGGAAGGGAAAATTT
CAAAAATTGGGCCTGAGAATCCATACAATACTCCAGTATTTGCCATAAAGAA
AAAAGACAGTACTAAATGGAGGAAATTAGTAGATTTCAGAGAACTTAATAAG
AGAACTCAAGACTTCTGGGAAGTTCAATTAGGAATACCACATCCCGCAGGG
TTAAAAAAGAAAAAATCAGTAACAGTACTGGATGTGGGTGATGCATATTTTTC
AGTTCCCTTAGATGAAGACTTCAGGAAGTATACTGCATTTACCATACCTAGT
ATAAACAATGAGACACCAGGGATTAGATATCAGTACAATGTGCTTCCACAGG
GATGGAAAGGATCACCAGCAATATTCCAAAGTAGCATGACAAAAATCTTAGA
GCCTTTTAAAAAACAAAATCCAGACATAGTTATCTATCAATACATGAACGATT
TGTATGTAGGATCTGACTTAGAAATAGGGCAGCATAGAACAAAAATAGAGGA
GCTGAGACAACATCTGTTGAGGTGGGGACTTACCACACCAGACAAAAAACA
TCAGAAAGAACCTCCATTCCTTTGGATGGGTTATGAACTCCATCCTGATAAA
TGGACAGTACAGCCTATAGTGCTGCCAGAAAAAGACAGCTGGACTGTCAAT
GACATACAGAAGTTAGTGGGGAAATTGAATACCGCAAGTCAGATTTACCCA
GGGATTAAAGTAAGGCAATTATGTAAACTCCTTAGAGGAACCAAAGCACTAA
CAGAAGTAATACCACTAACAGAAGAAGCAGAGCTAGAACTGGCAGAAAACA
GAGAGATTCTAAAAGAACCAGTACATGGAGTGTATTATGACCCATCAAAAGA
CTTAATAGCAGAAATACAGAAGCAGGGGCAAGGCCAATGGACATATCAAAT
TTATCAAGAGCCATTTAAAAATCTGAAAACAGGAAAATATGCAAGAATGAGG
GGTGCCCACACTAATGATGTAAAACAATTAACAGAGGCAGTGCAAAAAATAA
CCACAGAAAGCATAGTAATATGGGGAAAGACTCCTAAATTTAAACTACCCAT
ACAAAAGGAAACATGGGAAACATGGTGGACAGAGTATTGGCAAGCCACCTG
GATTCCTGAGTGGGAGTTTGTTAATACCCCTCCTTTAGTGAAATTATGGTAC
CAGTTAGAGAAAGAACCCATAGTAGGAGCAGAAACCTTCTATGTAGATGGG
GCAGCTAACAGGGAGACTAAATTAGGAAAAGCAGGATATGTTACTAACAAA
GGAAGACAAAAGGTTGTCCCCCTAACTAACACAACAAATCAGAAAACTCAGT
TACAAGCAATTTATCTAGCTTTGCAGGATTCAGGATTAGAAGTAAACATAGTA
ACAGACTCACAATATGCATTAGGAATCATTCAAGCACAACCAGATAAAAGTG
AATCAGAGTTAGTCAATCAAATAATAGAGCAGTTAATAAAAAGGAAAGGT
CTATCTGGCATGGGTACCAGCACACAAAGGAATTGGAGGAAATGAACAAGT
AGATAAATTAGTCAGTGCTGGAATCAGGAAAATACTATTTTTAGATGGAATA
GATAAGGCCCAAGATGAACATTAG
```

FIG. 21-8

Sequence of new Psyn II promoter:

Early part of promoter

Early start site

Critical region
TAAAAATGAAAAATATTCTAATTTATAGGACGGT

Late part of promoter
TTTGATTTCTTTTTCTATGCTATAAATAAATA

FIG. 24

COMPOSITIONS AND METHODS FOR GENERATING AN IMMUNE RESPONSE

RELATED APPLICATIONS

This application is a continuation-in-part of U.S. Ser. No. 10/093,953 (pending), which was filed on Mar. 8, 2002, and which is a continuation-in-part of U.S. Ser. No. 09/798,675 (which is pending and was published Aug. 8, 2002, under publication number 20020106798), which was filed on Mar. 2, 2001, and which claims the benefit under 35 U.S.C. §119 (e) of the filing dates of four provisional applications (U.S. Ser. No. 60/251,083, filed Dec. 1, 2000, U.S. Ser. No. 60/186, 364, filed Mar. 2, 2000, U.S. Ser. No. 60/324,845, filed Sep. 25, 2001, and U.S. Ser. No. 60/325,004, filed Sep. 26, 2001). U.S. Ser. No. 10/093,953 is also a continuation-in-part of International Application No. PCT/US01/06795, which was filed on Mar. 2, 2001, and was published in English under International Publication No. WO01/92470 on Dec. 6, 2001. The contents of all applications listed above are hereby incorporated by reference in their entirety. The instant application is also a continuation-in-part of International Application No. PCT/US02/06713, which was filed on Mar. 1, 2002, and was published in English under International Publication No. WO 02/072754 on Sep. 19, 2002, which claims the benefit under 35 U.S.C. §119(e) of U.S. Provisional Application U.S. Ser. No. 60/274,434, filed Mar. 8, 2001.

GOVERNMENT SUPPORT

The work described herein was supported, at least in part, by grants from the National Institutes of Health (P01 AI43045, P01 AI49364, and R21 AI44325). The United States Government may therefore have certain rights in this invention.

FIELD OF THE INVENTION

The present invention is directed generally to the fields of molecular genetics and immunology. More particularly, the present invention features expression vectors and methods of administering those vectors to animals.

BACKGROUND OF THE INVENTION

Vaccines have had profound and long lasting effects on world health. Smallpox has been eradicated, polio is near elimination, and diseases such as diphtheria, measles, mumps, pertussis, and tetanus are contained. Nonetheless, current vaccines address only a handful of the infections suffered by people and domesticated animals. Common infectious diseases for which there are no vaccines cost the United States alone about $120 billion dollars per year (Robinson et al., American Academy of Microbiology, May 31-Jun. 2, 1996). In first world countries, emerging infections such as immunodeficiency viruses, as well as reemerging diseases like drug resistant forms of tuberculosis, pose new threats and challenges for vaccine development. The need for both new and improved vaccines is even more pronounced in third world countries where effective vaccines are often unavailable or cost-prohibitive.

The prevalence of HIV-1 infection has made vaccine development for this recently emergent agent a high priority for world health. Pre-clinical trials on DNA vaccines have demonstrated that DNA alone can protect against highly attenuated HIV-1 challenges in chimpanzees (Boyer et al., Nature Med. 3:526-532, 1997), but not against more virulent SIV challenges in macaques (Lu et al., Vaccine 15:920-923, 1997). A combination of DNA priming plus an envelope glycoprotein boost has raised neutralizing antibody-associated protection against a homologous challenge with a non-pathogenic chimera between SIV and HIV (SHIV-IIIB) (Letvin et al., Proc. Natl. Acad. Sci. USA 94:9378-9383, 1997). A comparative trial testing eight different protocols for the ability to protect against a series of challenges with SHIVs (chimeras between simian and human immunodeficiency viruses) revealed the best containment of challenge infections by an immunization protocol that included priming by intradermal inoculation of DNA and boosting with recombinant fowl pox virus vectors (Robinson et al., Nature Med. 5:526, 1999). This containment of challenge infections was independent of the presence of neutralizing antibody to the challenge virus. Despite these and many other efforts, a vaccine for containing HIV infection is still not commercially available.

SUMMARY OF THE INVENTION

The continuing force of the AIDS epidemic illustrates the pressing need for effective vaccines against human immunodeficiency viruses (HIV), which frequently mutate and exist in several different clades (or subtypes) and recombinant forms. These subtypes and recombinant forms, which may arise either naturally or as the result of human intervention, can be distinguished by differences in the sequences of their nucleic acid. We have developed DNA and viral vectors (described at length below) that can be used, alone or in combination, as a vaccine against one HIV clade, subtype, or recombinant form of HIV or against multiple HIV clades, subtypes, or recombinant forms (unless otherwise specified, the term "clade(s)" is meant to encompass subtypes or recombinant forms of HIV). Moreover, the vectors can encode a variety of antigens, which may be obtained from one clade or from two or more different clades, and the antigens selected and/or the manner in which the vectors are formulated (e.g., mixed) can be manipulated to generate a protective immune response against a variety of clades (e.g., the clades to which a patient is most likely to be exposed).

There is also a need for an effective vaccine against poxviruses, such as the variola virus that causes smallpox; the current smallpox vaccine carries a small risk of substantial adverse side effects. Although smallpox has been eradicated, the population is still threatened by smallpox as a biological weapon. The viral vectors described herein can be used to generate an immune response against poxviruses. Thus, methods in which such vectors are administered (regardless of the precise protocol followed) can also elicit an immune response that confers protective or therapeutic effects against conditions such as smallpox (i.e., a pox viral vector can be administered before or after (e.g., 1-4 or more days after) a subject has been exposed to an agent that causes a viral disease such as smallpox). These methods can be effective regardless of whether the vectors contain vaccine inserts or what that insert encodes (e.g., proteins obtained from an HIV or proteins that elicit an immune response against one or more HIV clades).

The present invention provides plasmid vectors as well as viral vectors that can be used to deliver nucleic acids to a cell; while the invention encompasses vectors that do not contain vaccine "inserts," when immunizing or treating a patient, the vectors will include nucleic acids that encode protein antigens that induce or enhance an immune response against a pathogen (e.g., one or more HIV clades (or subtypes or recombinant forms)). The nucleic acids or polynucleotides described herein include those having linear arrays of naturally occurring and/or synthetic nucleotides (or nucleosides) derived from cDNA (or mRNA) or genomic DNA, or derivatives thereof (the pyrimidine or purine rings can be attached to a pentose sugar, such as a ribose or deoxyribose). The sequence of the nucleic acid may or may not be identical to a sequence occurring in nature (e.g., the sequence can encode a mutant form of an HIV protein that may make the vaccine safer). Specific characteristics and specific sequences of the proteins that can be expressed by way of the vectors described herein are discussed below.

Plasmid or viral vectors can include nucleic acids representing one or more genes found in one or more HIV clades or any fragments or derivatives thereof that, when expressed, elicit an immune response against the virus (or viral clade) from which the nucleic acid was derived or obtained. The nucleic acids may be purified from HIV or they may have been previously cloned, subcloned, or synthesized and, in any event, can be the same as or different from a naturally occurring nucleic acid sequence. The plasmid vectors of the present invention may be referred to herein as, inter alia, expression vectors, expression constructs, plasmid vectors or, simply, as plasmids, regardless of whether or not they include a vaccine insert (i.e., a nucleic acid sequence that encodes an antigen or immunogen). Similar variations of the term "viral vector" may appear as well (e.g., we may refer to the "viral vector" as a "poxvirus vector," a "vaccinia vector," a "modified vaccinia Ankara vector," or an "MVA vector"). The viral vector may or may not include a vaccine insert.

Accordingly, in one aspect, the invention features compositions (including pharmaceutically or physiologically acceptable compositions) that contain, but are not limited to, a vector, which may be a plasmid or viral vector, having a vaccine insert. The insert can include one or more of the sequences described herein (the features of the inserts and representative sequences are described at length below; any of these, or any combination of these, can be used as the insert). When the insert is expressed, the expressed protein(s) may generate an immune response against one or more HIV clades. One can increase the probability that the immune response will be effective against more than one clade by including sequences from more than one clade in the insert of a single vector (multi-vector vaccines are also useful and are described further below). For example, to increase the probability of generating an immune response against clade B and clade C, one can administer, to a subject, vectors that each includes an insert that encodes proteins of clade B and clade C. The subject may be a person who lives in, or travels between, parts of the world where HIV clades B and C are prevalent. Of course, expressing one or more proteins of a single clade is also beneficial and vectors that do so are within the scope of the invention (again, any inserts having the features or sequences of the exemplary inserts described herein can be used, and the inserts per se are features of the invention).

In another aspect, the invention features compositions (including pharmaceutically or physiologically acceptable compositions) that contain, but are not limited to, two vectors: a first vector that encodes one or more antigens (i.e., a vector that includes a vaccine insert) that elicit (e.g., induces or enhances) an immune response against an HIV of a first clade and a second vector that encodes one or more antigens that elicit (e.g., induces or enhances) an immune response against an HIV of a second clade. However, the compositions can contain more than first and second vectors; they can contain three, four, five, six, or more different vectors (by "different" vectors, we mean vectors that contain different regulatory elements (e.g. different promoters), or that encode different antigens or combinations of antigens, or that otherwise vary (e.g., that vary in their "backbone" sequence)). In some embodiments, the compositions can contain as many vectors as are required to elicit an immune response against two, three, four, or a majority of, if not all, HIV clades. While one vector can encode one antigen (e.g., Gag-Pol), one or more of the vectors (i.e., the first vector, the second vector, or both; the first, second, third, or all three vectors; etc.) can include nucleic acids encoding at least three antigens (e.g. Gag-Pol and Env), each of which can elicit an immune response directed primarily against the same HIV clade (i.e., the first vector can express three antigens, each of which generates a response against, primarily, clade A and a second vector can express three antigens, each of which generates a response against, primarily, clade B). In other embodiments, one or more of the vectors can elicit an immune response against more than one HIV clade (i.e., the first vector can express a first antigen (e.g., Gag-Pol) that generates a response against clade A and a second antigen (e.g., Env) that generates a response against clade B). Thus, one or more of the vectors can elicit an immune response against more than one HIV clade. Any of the types of vectors described herein, whether they are plasmid or viral vectors, or whether they individually encode antigens that elicit immune responses against primarily one, or more than one, HIV clade, can be used alone or in combination with one another, depending on the particular HIV clades to which one wishes to generate immunity.

The vaccine inserts per se (i.e., the sequences encoding HIV proteins that serve as antigens or immunogens) are also within the scope of the invention. While these inserts are described at length below, we note here that the invention features a variety of isolated nucleic acids that represent modified HIV genomes (e.g., fragments or recombinant forms of a genome or one or more HIV genes that are recombined or mutated in some way). For example, one or more nucleic acids can be deleted from one or more genes or replaced with other nucleic acids (i.e., the sequences can be fragments of a gene or genes and can contain point mutations). More specifically, the invention features isolated nucleic acids that represent HIV genomes having safety mutations (e.g., deletion of the LTRs and of sequences encoding integrase (IN), Vif, Vpr and Nef). The nucleic acids can encode Gag, PR, RT, Env, Tat, Rev, and Vpu proteins, one or more of which may contain safety mutations (particular mutations are described at length below). Moreover, the isolated nucleic acids can be of any HIV clade and nucleic acids from different clades can be used in combination (as described further below). In the work described herein, clade B inserts are designated JS (e.g., JS2, JS7, and JS7.1), clade AG inserts are designated IC (e.g., IC2, IC25, IC48, and IC90), and clade C inserts are designated IN (e.g., IN2 and IN3). These inserts are within the scope of the present invention, as are vectors (whether plasmid or viral) containing them (particular vector/insert combinations are referred to below as, for example, pGA1/JS2, pGA2/JS2 etc.

Expression vectors that carry DNA are necessarily limited in that they can only be used to immunize patients with products (i.e., proteins) encoded by DNA, and it is possible that bacterial and parasitic proteins may be atypically processed by eukaryotic cells. Another problem with existing DNA vaccines is that some vaccine insert sequences are unstable during the growth and amplification of DNA vaccine plasmids in bacteria. Instability can arise during plasmid growth where the secondary structure of the vaccine insert or of the plasmid vector (the "backbone") can be altered by bacterial endonucleases. The expression vectors of the present invention can include a termination sequence that improves stability. The termination sequence and other regulatory components (e.g., promoters and polyadenylation sequences) are discussed at length below.

The compositions of the invention can be administered to humans, including children. Accordingly, the invention features methods of immunizing a patient (or of eliciting an immune response in a patient, which may include multi-epitope $CD8^+$ T cell responses) by administering one or more types of vectors (e.g., one or more plasmids, which may or may not have identical sequences, components, or inserts (i.e., sequences that can encode antigens) and/or one or more viral vectors, which may or may not be identical or express identical antigens). As noted above, the vectors, whether plasmid or viral vectors, can include one or more nucleic acids obtained from or derived from (e.g., a mutant sequence is a derivative sequence) one or more HIV clades. When these sequences are expressed, they produce an antigen or antigens that elicit an immune response to one or more HIV clades. In particular embodiments, patients receive a first vector and a second vector. The first vector can encode one or more antigens of a first HIV clade (these antigens can elicit (e.g., induce or enhance) an immune response against that HIV clade) and the second vector can encode one or more antigens of a second HIV clade (here again, these antigens can elicit (e.g., induce or enhance) an immune response against the second HIV clade). In alternative embodiments, the subject can receive a third, fourth, fifth, etc. vector encoding one or more antigens from a third, fourth, fifth, etc. HIV clade (or mutants thereof). Moreover, and as in other embodiments, the antigen(s) can be from any clade (e.g., from one or more of clades A-L) or any HIV isolate.

Where the compositions contain vectors that differ either in their backbone, regulatory elements, or insert(s), the ratio of the vectors in the compositions, and the routes by which they are administered, can vary. The ratio of one type of vector to another can be equal or roughly equal (e.g., roughly 1:1 or 1:1:1, etc.). Alternatively, the ratio can be in any desired proportion (e.g., 1:2, 1:3, 1:4 ... 1:10; 1:2:1, 1:3:1, 1:4:1 ... 1:10:1; etc.). Thus, the invention features compositions containing a variety of vectors, the relative amounts of antigen-expressing vectors being roughly equal or in a desired proportion. While preformed mixtures may be made (and may be more convenient), one can, of course, achieve the same objective by administering two or more vector-containing compositions (on, for example, the same occasion (e.g., within minutes of one another) or nearly the same occasion (e.g., on consecutive days)).

Plasmid vectors can be administered alone (i.e., a plasmid can be administered on one or several occasions with or without an alternative type of vaccine formulation (e.g., with or without administration of protein or another type of vector, such as a viral vector)) and, optionally, with an adjuvant or in conjunction with (e.g., prior to) an alternative booster immunization (e.g., a live-vectored vaccine such as a recombinant modified vaccinia Ankara vector (MVA)) comprising an insert that may be distinct from that of the "prime" portion of the immunization or may be a related vaccine insert(s). For example, the viral vector can contain at least some of the sequence contained with the plasmid administered as the "prime" portion of the inoculation protocol (e.g., sequences encoding one or more, and possibly all, of the same antigens). The adjuvant can be a "genetic adjuvant" (i.e., a protein delivered by way of a DNA sequence). Similarly, as described further below, one can immunize a patient (or elicit an immune response, which can include multi-epitope $CD8^+$ T cell responses) by administering a live-vectored vaccine (e.g., an MVA vector) without administering a plasmid-based (or "DNA") vaccine. Thus, in alternative embodiments, the invention features compositions having only viral vectors (with, optionally, one or more of any of the inserts described here, or inserts having their features) and methods of administering them. The viral-based regimens (e.g., "MVA only" or "MVA-MVA" vaccine regimens) are the same as those described herein for "DNA-MVA" regimens, and the MVAs in any vaccine can be in any proportion desired. For example, in any case (whether the immunization protocol employs only plasmid-based immunogens, only viral-carried immunogens, or a combination of both), one can include an adjuvant and administer a variety of antigens, including those obtained from any HIV clade, by way of the plurality of vectors administered.

As implied by the term "immunization" (and variants thereof), the compositions of the invention can be administered to a subject who has not yet become infected with a pathogen (thus, the terms "subject" or "patient," as used herein encompasses apparently healthy or non-HIV-infected individuals), but the invention is not so limited; the compositions described herein can also be administered to treat a subject or patient who has already been exposed to, or who is known to be infected with, a pathogen (e.g., an HIV of any clade, including those presently known as clades A-L or mutant or recombinant forms thereof).

An advantage of DNA and rMVA immunizations is that the immunogen may be presented by both MHC class I and class II molecules. Endogenously synthesized proteins readily enter processing pathways that load peptide epitopes onto MHC I as well as MHC II molecules. MHC I-presented epitopes raise CD8 cytotoxic T cell (Tc) responses, whereas MHC II-presented epitopes raise CD4 helper T cells (Th). By contrast, immunogens that are not synthesized in cells are largely restricted to the loading of MHC II epitopes and therefore raise CD4 Th but not CD8 Tc. In addition, DNA plasmids express only the immunizing antigens in transfected cells and can be used to focus the immune response on only those antigens desired for immunization. In contrast, live virus vectors express many antigens (e.g., those of the vector as well as the immunizing antigens) and prime immune responses against both the vector and the immunogen. Thus, we believed these vectors could be highly effective at boosting a DNA-primed response by virtue of the large amounts of antigen that can be expressed by a live vector preferentially boosting the highly targeted DNA-primed immune response. The live virus vectors also stimulate the production of pro-inflammatory cytokines that augment immune responses. Thus, administering one or more of the DNA vectors described herein (as a "prime") and subsequently administering one or more of the viral vectors (as a "boost"), could be more effective than DNA-alone or live vectors-alone at raising both cellular and humoral immunity. Insofar as these vaccines may be administered by DNA expression vectors and/or recombinant viruses, there is a need for plasmids that are stable in bacterial hosts and safe in animals. Plasmid-based vaccines that may have this added stability are disclosed herein, together with methods for administering them to animals, including humans.

The antigens encoded by DNA or rMVA are necessarily proteinaceous. The terms "protein," "polypeptide," and "peptide" are generally interchangeable, although the term "peptide" is commonly used to refer to a short sequence of amino acid residues or a fragment of a larger protein. In any event, serial arrays of amino acid residues, linked through peptide bonds, can be obtained by using recombinant techniques to express DNA (e.g., as was done for the vaccine inserts described and exemplified herein), purified from a natural source, or synthesized.

Other advantages of DNA-based vaccines (and of viral vectors, such as pox virus-based vectors) are described below. The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIGS. 2a and 2b relate to pGA1. FIG. 2a is an illustration of the nucleotide sequence of pGA1 (SEQ ID NO:1), and FIG. 2b is a table listing the functional regions of pGA1, their positions within the SEQ ID NO:1, and the origins of the sequences.

FIGS. 3a and 3b relate to pGA1.1. FIG. 3a is an illustration of pGA1.1 (SEQ ID NO:2), and FIG. 3b is a table listing the functional regions of pGA1.1, their positions within SEQ ID NO:2, and the origins of the sequences. pGA1.1 differs from pGA1 in that it includes an EcoR I restriction site in its multiple cloning site.

FIGS. 4a and 4b relate to pGA1.2. FIG. 4a is an illustration of pGA1.2 (SEQ ID NO:3) and FIG. 4b is a table listing the functional regions of pGA1.2, their positions within SEQ ID NO:3, and the origins of the sequences. pGA1.2 differs from pGA1.1 in that it includes a BamHI site in its multiple cloning site.

FIGS. 6a and 6b relate to pGA2. FIG. 6a is an illustration of the nucleotide sequence of pGA2 (SEQ ID NO:4), and FIG. 6b is a table listing the functional regions of pGA2, their positions within SEQ ID NO:4, and the origins of the sequences.

FIGS. 7a and 7b relate to pGA2.1. FIG. 7a is an illustration of pGA2.1 (SEQ ID NO:5) and FIG. 7b is a table listing the functional regions of pGA2.1, the positions within SEQ ID NO:5, and the origins of the sequences. pGA2.1 differs from pGA2 in having an EcoR I site in its multiple cloning site.

FIGS. 8a and 8b relate to pGA2.2. FIG. 8a is an illustration of pGA2.2 (SEQ ID NO:6), and FIG. 8b is a table listing the functional regions of pGA2.2, their positions with SEQ ID NO:6, and the origins of the sequences. pGA2.2 differs from pGA2.1 in having a BamH I site in its multiple cloning site.

FIG. 9 is a schematic representation of the proviral (integrated DNA) form of the HIV genome (HIV-1 wt) and a representative vaccine insert. This representative insert has safety mutations that include deletion of the LTRs, deletion of sequences encoding integrase (IN), Vif, Vpr and Nef. The insert encodes Gag, PR, RT, Env, Tat, Rev, and Vpu proteins.

Figure 1:
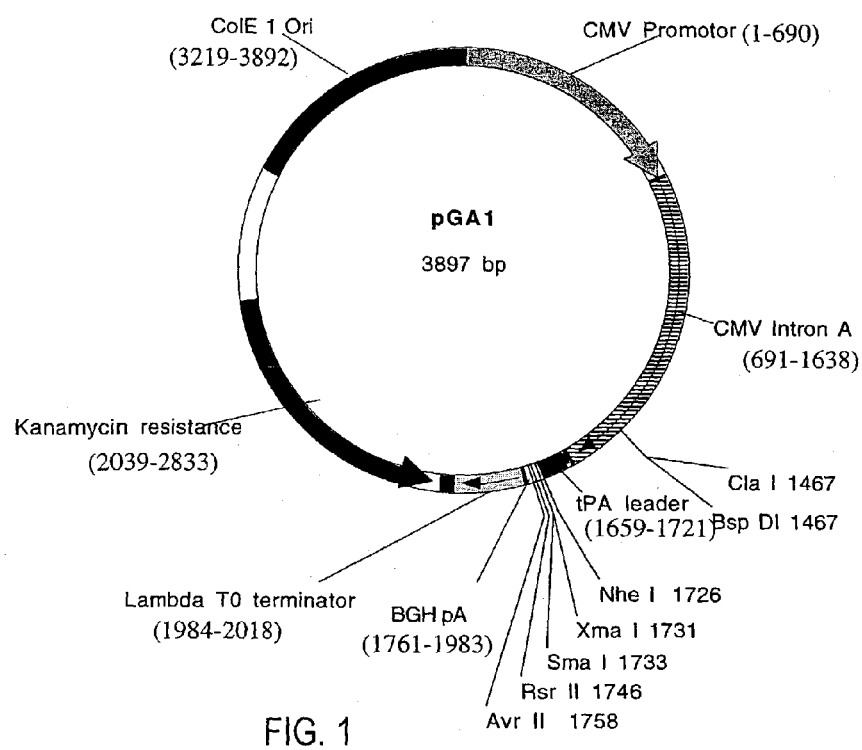
FIG. 1 is a schematic illustration of the plasmid construct pGA1. The identities and positions of elements present in the vector (e.g., the promoter (here, a CMV promoter including intron A), the multiple-cloning site, a terminator sequence (here, the lambda T0 terminator), and a selection gene (here, the kanamycin resistance gene) are shown. Unique restriction endonuclease sites, which are useful for cloning vaccine inserts into the plasmid, are also shown.

Clade B inserts are designated JS (clade B), IC (clade AG) and IN (clade C) with arabic numerals designating the specific vaccine constructs (e.g., JS2, JS7 and JS7.1 are examples of specific clade B vaccine constructs; IC2, IC25, IC48 and IC90, examples of specific AG vaccine constructs; and IN2 and IN3 are examples of specific clade C vaccine constructs). When inserted into the pGA1 vector, the insert-bearing plasmids are referred to as pGA1/JS2 etc; when inserted into the pGA2 vector, plasmids are referred to as pGA2/JS2 etc.

FIGS. 10a-10c relate to pGA2/JS2. FIG. 10a is an illustration of the sequence of the pGA2/JS2 clade B vaccine vector (SEQ ID NO:7), and FIG. 10b is a table listing the positions of seven functional regions of pGA2/JS2, the gene sequences within those regions (describing mutations, where present), and the origins of their sequences. FIG. 10c is a table listing codons that were changed, the resulting amino acid change (e.g., C392S indicates a substitution of serine for cysteine at amino acid residue 392), the region of the genome where the mutation resides, and the mutation's function.

FIGS. 11a-11c relate to pGA2/JS7. FIG. 12a is an illustration of the sequence of the pGA2/JS7 clade B vaccine vector (SEQ ID NO:8), and FIG. 11b is a table listing the positions of seven functional regions of pGA2/JS7, the gene sequences within those regions (describing mutations, where present), and the origins of their sequences. FIG. 11c is a table listing codons that were changed, the resulting amino acid change (e.g., C395S indicates a substitution of serine for cysteine at amino acid residue 395), the region of the genome where the mutation resides, and the mutation's function.

FIGS. 12a-12c relate to pGA2/JS7.1. FIG. 12a is an illustration of the sequence of the pGA2/JS7.1 clade B vaccine vector (SEQ ID NO:9), and FIG. 12b is a table listing the positions of functional regions of pGA2/JS7.1, the gene sequences within those regions (describing mutations, where present), and the origins of their sequences. FIG. 12c is a table listing codons that were changed, the resulting amino acid change, the region of the genome where the mutation resides, and the mutation's function.

FIGS. 13a-13c relate to pGA1/IC25. FIG. 13a is an illustration of the sequence of the pGA1/IC25 clade AG vaccine vector (SEQ ID NO:10), and FIG. 13b is a table listing the positions of functional regions within pGA1/IC25, the gene sequences within those regions (describing mutations, where present), and the origins of their sequences. FIG. 13c is a table listing codons that were changed, the resulting amino acid change, the region of the genome where the mutation resides, and the mutation's function.

FIGS. 14a-14c relate to pGA1/IC2. FIG. 14a is an illustration of the sequence of the pGA1/IC2 clade AG vaccine vector (SEQ ID NO:11), and FIG. 14b is a table listing the positions of functional regions within pGA1/IC2, the gene sequences within those regions (describing mutations, where present), and the origins of their sequences. FIG. 14c is a table listing codons that were changed, the resulting amino acid change, the region of the genome where the mutation resides, and the mutation's function.

FIGS. 15a-15c relate to pGA1/IC48. FIG. 15a is an illustration of the sequence of the pGA1/IC48 clade AG vaccine vector (SEQ ID NO:12), and FIG. 15b is a table listing the positions of functional regions within pGA1/IC48, the gene sequences within those regions (describing mutations, where present), and the origins of their sequences. FIG. 15c is a table listing codons that were changed, the resulting amino acid change, the region of the genome where the mutation resides, and the mutation's function.

FIGS. 16a-16c relate to pGA1/IC90. FIG. 16a is an illustration of the sequence of the pGA1/IC90 clade AG vaccine vector (SEQ ID NO:13), and FIG. 16b is a table listing the positions of functional regions within pGA1/IC90, the gene sequences within those regions (describing mutations, where present), and the origins of their sequences. FIG. 16c is a table listing codons that were changed, the resulting amino acid change, the region of the genome where the mutation resides, and the mutation's function.

FIGS. 17a-17c relate to pGA1/IN3. FIG. 17a is an illustration of the sequence of the pGA1/IN3 clade C vaccine vector (SEQ ID NO:14), and FIG. 17b is a table listing the positions of functional regions within pGA1/IN3, the gene sequences within those regions (describing mutations, where present), and the origins of their sequences. FIG. 17c is a table listing codons that were changed, the resulting amino acid change, the region of the genome where the mutation resides, and the mutation's function.

FIGS. 18a-18c relate to pGA1/IN2. FIG. 18a is an illustration of the sequence of the pGA1/IN2 clade C vaccine vector (SEQ ID NO:15), and FIG. 18b is a table listing the positions of functional regions within pGA1/IN2, the gene sequences within those regions (describing mutations, where present), and the origins of their sequences. FIG. 18c is a table listing codons that were changed, the resulting amino acid change, the region of the genome where the mutation resides, and the mutation's function.

Figure 19:
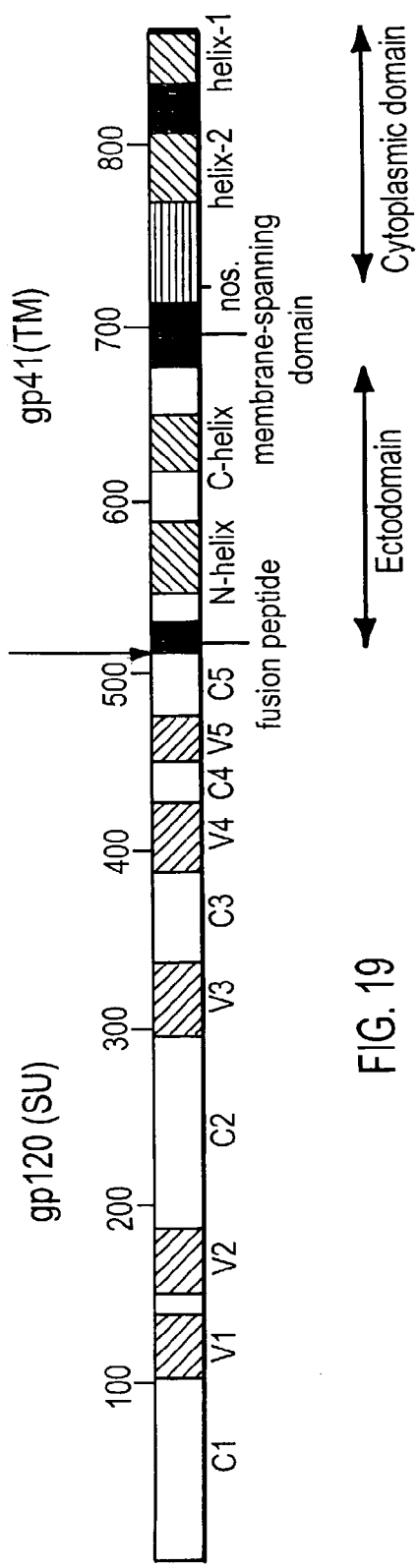

FIG. 19 is a schematic representation of an HIV-1 Env glycoprotein. The arrow indicates the site of gp160 cleavage to gp120 and gp41. In gp120, cross-hatched areas represent variable domains ($V_1$ to $V_2$) and open boxes depict conserved sequences ($C_1$ to $C_5$). In the gp41 ectodomain, several domains are indicated: the N-terminal fusion peptide and the two ectodomain helices (N- and C-helices). The membrane-spanning domain is represented by a black box. In the gp41 cytoplasmic domain, the Tyr-X-X-Leu (YXXL) endocytosis motif and two predicted helical domains (helix-1 and helix-2) are shown. Amino acid residues are numbered at intervals of 100.

Figure 20A:
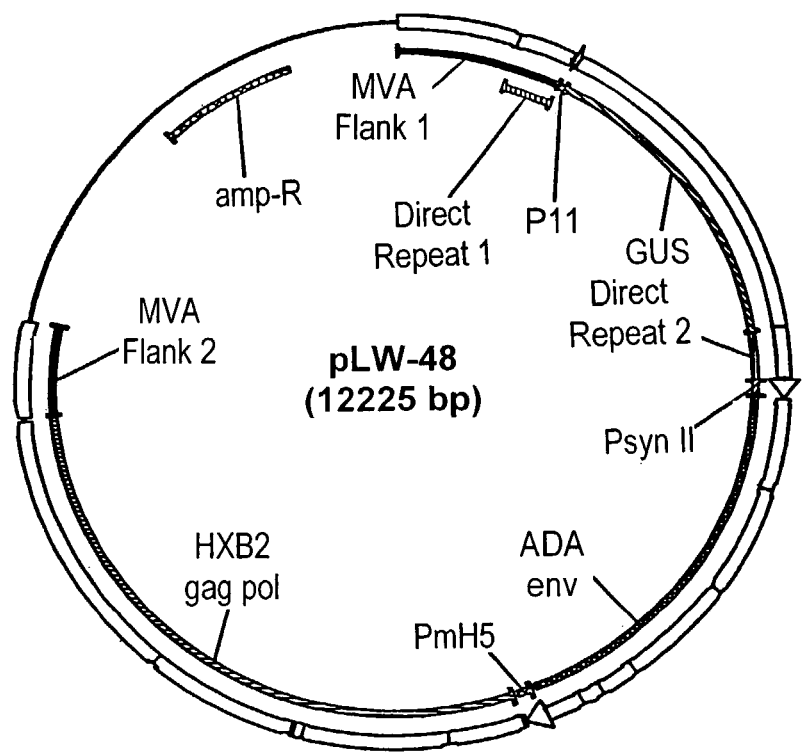

FIGS. 20A and 20B relate to the plasmid transfer vector pLW-48. FIG. 20A is a map of pLW-48 and FIG. 20B is a representation of its sequence.

FIG. 21 is a representation of the sequences of the plasmid transfer vector pLW-48, the Psy II promoter (which controls ADA envelope expression), the ADA envelope (truncated), the PmH5 promoter (which controls HXB2 gag and pol expression), and HXB2 gag-pol (with safety mutations, inactivating point mutations in RT and the deletion of integrase).

Figure 22:
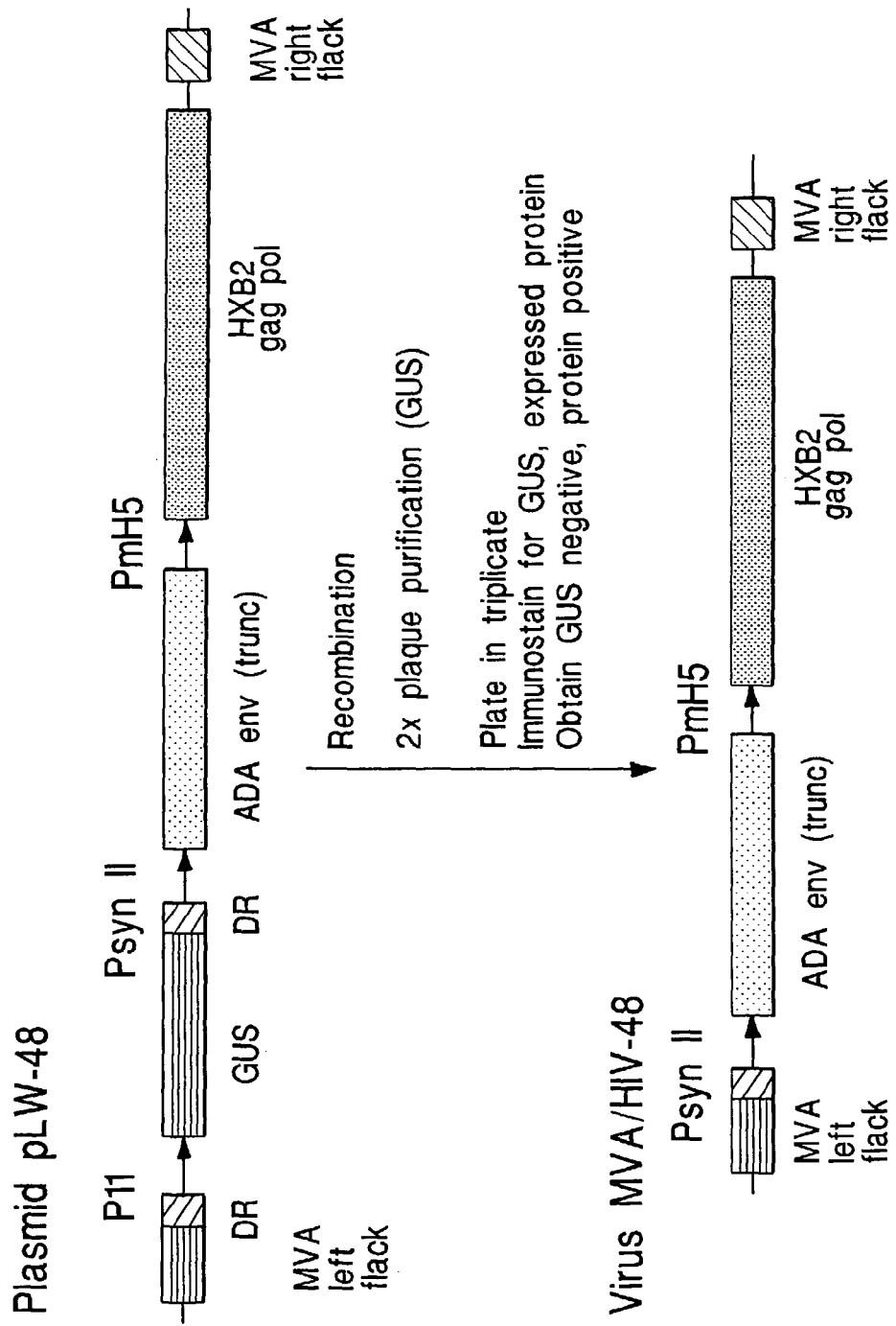

FIG. 22 is a representation of the plasmid transfer vector pLW-48 and a scheme for making an MVA recombinant virus (MVA/HIV 48).

Figure 23:
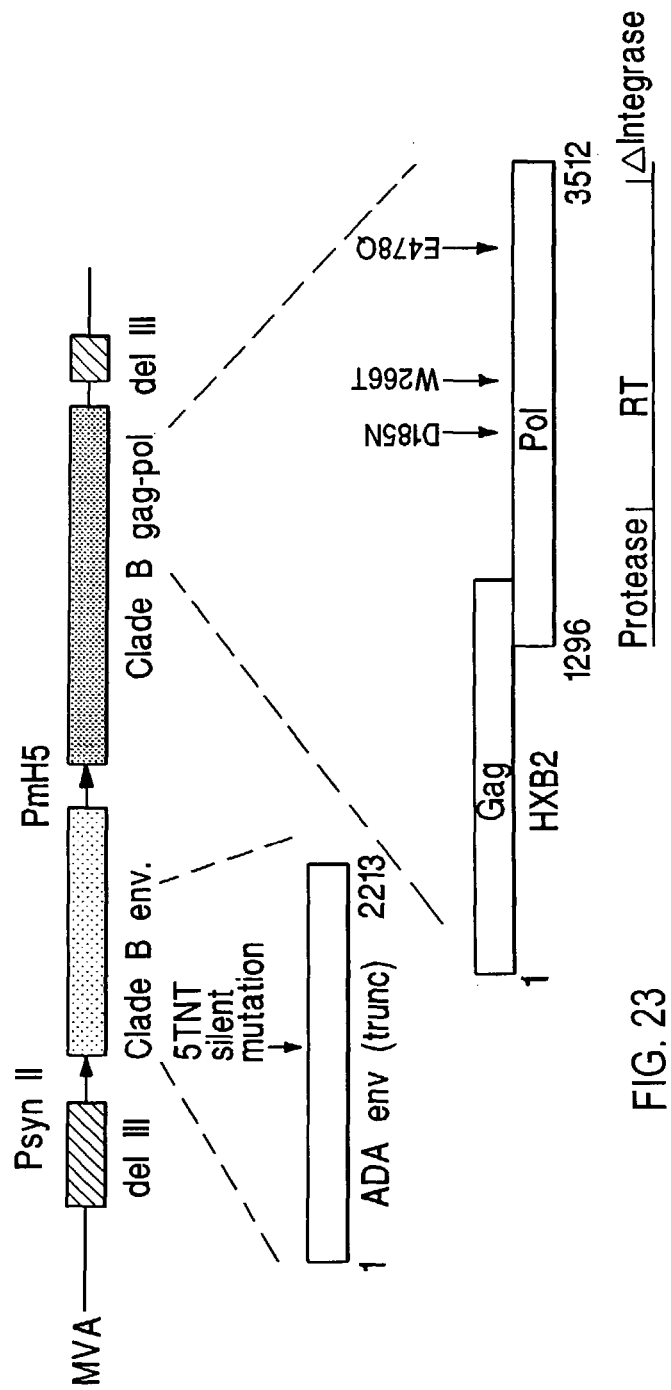

FIG. 23 is a representation of a clade B gag pol.

FIG. 24 is a representation of a Psyn II promoter.

DETAILED DESCRIPTION

This invention encompasses a wide variety of vectors and types of vectors (e.g., plasmid and viral vectors), each of which can, but do not necessarily, include one or more nucleic acid sequences that encode one or more antigens that elicit (e.g., that induce or enhance) an immune response against the pathogen from which the antigen was obtained or derived (the sequences encoding proteins that elicit an immune response may be referred to herein as "vaccine inserts" or, simply, "inserts"; when a mutation is introduced into a naturally occurring sequence, the resulting mutant is "derived" from the naturally occurring sequence). We point out that the vectors do not necessarily encode antigens to make it clear that vectors without "inserts" are within the scope of the invention and that the inserts per se are also compositions of the invention.

Accordingly, the invention features the nucleic acid sequences disclosed herein, analogs thereof, and compositions containing those nucleic acids (whether vector plus insert or insert only; e.g., physiologically acceptable solutions, which may include carriers such as liposomes, calcium, particles (e.g., gold beads) or other reagents used to deliver DNA to cells). The analogs can be sequences that are not identical to those disclosed herein, but that include the same or similar mutations (e.g., the same point mutation or a similar point mutation) at positions analogous to those included in the present sequences (e.g., any of the JS, IC, or IN sequences disclosed herein). A given residue or domain can be identified in various HIV clades even though it does not appear at precisely the same numerical position. The analogs can also be sequences that include mutations that, while distinct from those described herein, similarly inactivate an HIV gene product. For example, a gene that is truncated to a greater or lesser extent than one of the genes described here, but that is similarly inactivated (e.g., that loses a particular enzymatic activity) is within the scope of the present invention.

The pathogens and antigens, which are described in more detail below, include human immunodeficiency viruses of any clade (e.g. from any known clade or from any isolate (e.g., clade A, AG, B, C, D, E, F, G, H, I, J, K, or L)). When the vectors include sequences from a pathogen, they can be administered to a patient to elicit an immune response. Thus, methods of administering antigen-encoding vectors, alone or in combination with one another, are also described herein. These methods can be carried out to either immunize patients (thereby reducing the patient's risk of becoming infected) or to treat patients who have already become infected; when expressed, the antigens may elicit both cell-mediated and humoral immune responses that may substantially prevent the infection (e.g., immunization can protect against subsequent challenge by the pathogen) or limit the extent of its impact on the patient's health. While in many instances the patient will be a human patient, the invention is not so limited. Other animals, including non-human primates, domesticated animals and livestock can also be treated.

The compositions described herein, regardless of the pathogen or pathogenic subtype (e.g., the HIV clade(s)) they are directed against, can include a nucleic acid vector (e.g., a plasmid). As noted herein, vectors having one or more of the features or characteristics (particularly the oriented termination sequence and a strong promoter) of the plasmids designated pGA1, pGA2 (including, of course, those vectors per se), can be used as the basis for a vaccine or therapy. Such vectors can be engineered using standard recombinant techniques (several of which are illustrated in the examples, below) to include sequences that encode antigens that, when administered to, and subsequently expressed in, a patient will elicit (e.g., induce or enhance) an immune response that provides the patient with some form of protection against the pathogen from which the antigens were obtained or derived (e.g., protection against infection, protection against disease, or amelioration of one or more of the signs or symptoms of a disease). The encoded antigens can be of any HIV clade or subtype or any recombinant form thereof. With respect to inserts from immunodeficiency viruses, different isolates exhibit clustal diversity, with each isolate having overall similar diversity from the consensus sequence for the clade (see, e.g., Subbarao et al., AIDS 10(Suppl A):S13-23, 1996). Thus, any isolate can be used as a reasonable representative of sequences for other isolates of the same clade. Accordingly, the compositions of the invention can be made with, and the methods described herein can be practiced with, natural variants of genes or nucleic acid molecules that result from recombination events, alternative splicing, or mutations (these variants may be referred to herein simply as "recombinant forms" of HIV).

Moreover, one or more of the inserts within any construct can be mutated to decrease their natural biological activity (and thereby increase their safety) in humans (these human-made variants may also be referred to herein as "recombinant forms" of HIV (there are naturally occurring recombinant forms as well)). As noted above in the description of JS2, JS7 and JS7.1 and as described below (see, e.g., Examples 7-10), mutations can be introduced into sequences that participate in encapsidation. For example, one can mutate (by, for example, deletion of all or a part of) a cis-acting RNA encapsidation sequence in the non-coding regulatory sequence of an HIV (e.g., HIV-1). Alternatively, or in addition, one can mutate sequences that encode any antigenic proteins (e.g., any HIV antigen, including those listed above (e.g., the viral RT or protease).

For example, the compositions of the invention include those having two vectors: (a) a first vector comprising a vaccine insert encoding one or more antigens that elicit an immune response against a human immunodeficiency virus (HIV) of a first subtype or recombinant form and (b) a second vector comprising a vaccine insert encoding one or more antigens that elicit an immune response against an HIV of a second subtype or recombinant form. The compositions can be pharmaceutically acceptable and may include a carrier or adjuvant (discussed further below). Moreover, the insert of the first vector or the insert of the second vector can include the sequences of two or more of: (a) a gag, pol, env, tat, rev, nef, vif, vpr, or vpu gene or (b) mutants thereof and, optionally, (c) non-coding regulatory sequences (including the sequences of single promoters) of the HIV genome. At least one of the two or more sequences can be mutant or mutated so as to limit the encapsidation of viral RNA (preferably, the mutation(s) limit encapsidation appreciably).

One can introduce mutations and determine their effect (on, for example, expression or immunogenicity) using techniques known in the art; antigens that remain well expressed (e.g., antigens that are expressed about as well as or better than their wild type counterparts), but are less biologically active than their wild type counterparts, are within the scope of the invention. Techniques are also available for assessing the immune response. One can, for example, detect anti-viral antibodies or virus-specific T cells.

The mutant constructs (e.g., a vaccine insert) can include sequences encoding one or more of the substitution mutants described herein (see, e.g. the Examples) or an analogous mutation in another HIV clade. In addition to, or alternatively, HIV antigens can be rendered less active by deleting part of the gene sequences that encode them. Thus, the compositions of the invention can include constructs that encode antigens that, while capable of eliciting an immune response, are mutant (whether encoding a protein of a different length or content than a corresponding wild type sequence) and thereby less able to carry out their normal biological function when expressed in a patient. As noted above, expression, immunogenicity, and activity can be assessed using standard techniques for molecular biology and immunology.

Several plasmids have been constructed and used to express antigens (e.g., the pGA2/JS2 construct has gone through immunogenicity studies in macaques). The plasmids made and used include pGA1 and its derivatives pGA1.1 and pGA1.2; and pGA2, and its derivatives pGA2.1 and pGA2.2 (see Examples 1-8). The vaccine constructs we made are typically referred to with the "backbone" vector and the "insert" being separated by a backslash. These constructs express HIV-1 antigens, and those constructs can be administered to patients as described herein. While antigens (wild type and those containing mutations that render them safer for administration) are discussed at length below, we note here that, based upon our present evidence, plasmids containing JS7-like inserts appear to exhibit better immunogenicity and are more efficient in priming an immune response (as evidenced by anti-Env antibodies) than are plasmids containing JS2-like inserts. pGA2/JS7 and pGA2/JS7.1 differ from pGA2/JS2 in several ways, one of which is the source of their respective antigens. In pGA2/JS7 and pGA2/JS7.1, the Gag and Pol genes were obtained from HIV-1 HXB2, whereas in pGA2/JS2 those genes were obtained from a closely related isolate of HIV-1, HIV-1 BH10. Accordingly, the invention features inserts (as well as vectors and compositions containing them) that include Gag and Pol genes obtained from HIV-1 HXB2. Moreover, these inserts can contain mutations that inhibit one or more of the biological activities carried out by Gag-Pol. The vaccine inserts designated JS7 and JS2 also differ in that JS7 has an inactivating point mutation in its protease gene. This mutation facilitates the formation of viral like particles (VLPs) by, we believe, precluding premature intracellular cleavage of the pr55 Gag protein. pGA2/JS7 and pGA2/JS7.1 both contain this protease mutation and both constructs produce VLPs in abundance. Accordingly, the invention features inserts that include mutant gag and/or pol sequences (e.g., mutations (e.g., one or more deletions or point mutations) that inhibit the protease gene). Additional point mutations in the vpu gene in pGA2/JS7.1 resulted in a loss of Vpu expression and an increase in Env expression (in pGA2/JS7.1, the start site of Vpu is mutated along with a downstream ATG to eliminate translation of Vpu). The increase in Env expression does not compromise Gag expression.

Identical or analogous changes can be made in any vaccine insert that includes gag, pol; any vaccine insert that encodes a viral protease; or any vaccine insert that includes a vpu gene (regardless of the clade or isolate from which it was obtained). Moreover, these changes can be made in vaccine inserts that are placed in any of the plasmid or live-vectored vaccines (e.g., MVA) described herein (i.e., in any plasmid having one or more of the features or characteristics of the pGA vectors, the pGA vectors themselves, or the vaccinia vectors that may be used alone or in conjunction with (e.g., to boost) a DNA-primed patient).

Any plasmid within the scope of the invention can be tested for expression by transfecting cells, such as 293T cells (a human embryonic kidney cell line) and assessing the level of antigen expression (by, for example, an antigen-capture ELISA or a Western blot). Plasmids that express immunogens at a level comparable to, or higher than, the plasmids tested herein are strong therapeutic candidates and are within the scope of the invention (of course, any construct that elicits an effective immune response (e.g., any desirable degree of protection from infection or other therapeutic benefit) is within the scope of the invention, regardless of the level of antigen expression it generates). One can similarly assess the ability of candidate vectors to produce VLPs; the more the vectors' products resemble VLPs, the more likely they are to elicit a strong antibody response (while this is a desirable feature, vectors that fail to form VLPs are nevertheless useful and are within the scope of the present invention). In addition to assessing expression and VLP formation in cell culture, one can assess candidate vectors in vivo. For example, one can assess immunogenicity in animal models (and, eventually, in human patients). Plasmids that have substantially the same sequence as the pGA vectors described herein and that express one or more of the antigens described herein are within the scope of the invention so long as they are immunogenic enough to induce or enhance a therapeutically beneficial response in a patient (a plasmid can have substantially the same sequence as a pGA vector even if one or more of the component parts of the plasmid, such as the marker gene or antibiotic-resistance gene, has been deleted). In tests in animals for immunogenicity, one can perform an intracellular cytokine assay or an ELISPOT assay for IFN-γ production in response to stimulation with an antigenic peptide to evaluate the frequency of responding T cells to that peptide. Proliferation assays can also be carried out. Antigens produced by transient transfection can be used for stimulation, and supernatants from mock-transfected cultures can serve as controls. If desired, the data can be presented as a stimulation index (the growth of cultures in the presence of pathogenic (e.g., viral) antigens divided by the growth of cultures in the presence of mock antigen).

The nucleic acid vectors of the invention, including pGA1 and pGA2 and their derivatives can encode at least one antigen (which may also be referred to as an immunogen) obtained from, or derived from, any HIV clade or isolate (i.e., any subtype or recombinant form of HIV). The antigen (or immunogen) may be: a structural component of an HIV virus; glycosylated, myristoylated, or phosphorylated; one that is expressed intracellularly, on the cell surface, or secreted (antigens that are not normally secreted may be linked to a signal sequence that directs secretion). More specifically, the antigen can be all, or an antigenic portion of, Gag, gp120, Pol, Env (e.g., a CCR5-using Env; see, for example, FIG. 19), Tat, Rev, Vpu, Nef, Vif, Vpr, or a VLP (e.g., a polypeptide derived from a VLP that is capable of forming a VLP, including an Env-defective HIV VLP).

Particular inserts and insert-bearing compositions include the following. Where the composition includes either a vector with an insert or an insert alone, and that insert encodes a single antigen, the antigen can be a wild type or mutant gag sequence (e.g., a gag sequence having a mutation in one or more of the sequences encoding a zinc finger (e.g., a mutation at a nucleotide at any of positions 1279-1281, 1288-1290, 1342-1344, or 1351-1353 of SEQ ID NOs:7 or 8 or at an analogous position in an HIV gag sequence of another clade). As the mutation is intended to alter the encoded protein, it will not be a silent mutation (e.g., one at the third-base wobble position of a codon (this is true in the context of gag or any other HIV sequence included in an insert of the invention). A mutation at one or more of the positions just listed would change one or more of the cysteine residues at positions 392, 395, 413, or 416 to another residue (e.g., serine). Alternatively, the mutation can be at any of positions 1271-1273, 1280-1282, 1334-1336, or 1343-1345 of any of SEQ ID NOs: 10-13) or at an analogous position in an HIV gag sequence of another clade. Such a mutation would change one or more of the cysteine residues at positions 390, 393, 411, or 414 to another residue (e.g., serine). Alternatively, the mutation can be at any of positions 1260-1262, 1269-1271, 1323-1325, or 1332-1334 of SEQ ID NOs:14 or 15 or at an analogous position in an HIV gag sequence of another clade. Such a mutation would change one or more of the cysteine residues at positions 390, 393, 411, or 414 to another residue (e.g., serine).

Where the composition includes either a vector with an insert or an insert alone, and that insert encodes multiple protein antigens, one of the antigens can be a wild type or mutant gag sequence, including those described above. Similarly, where a composition includes more than one type of vector or more than one type of insert, at least one of the vectors or inserts (whether encoding a single antigen or multiple antigens) can include a wild type or mutant gag sequence, including those described above or analogous sequences from other HIV clades. For example, where the composition includes first and second vectors, the vaccine insert in either or both vectors (whether the insert encodes single or multiple antigens) can encode Gag; where both vectors encode Gag, the Gag sequence in the first vector can be from one HIV clade (e.g., clade B) and that in the second vector can be from another HIV clade (e.g., clade C).

Where the composition includes either a vector with an insert or an insert alone, and that insert encodes a single antigen, the antigen can be wild type or mutant Pol. The sequence can be mutated by deleting or replacing one or more nucleic acids, and those deletions or substitutions can result in a Pol gene product that has less enzymatic activity than its wild type counterpart (e.g., less integrase activity, less reverse transcriptase (RT) activity, or less protease activity). For example, one can inhibit RT by introducing a mutation at one or more of positions 2454-2456 or 2697-2699 of SEQ ID NO:7 or at an analogous position in a sequence of another subtype or recombinant form. While the invention is not limited to mutations that have any particular effect on enzyme activity, we believe the mutation at position 2454-2456 inhibits RT by inactivating the polymerase's active site and that the mutation at position 2697-2699 inhibits RT by ablating strand transfer activity. Accordingly, these mutations and others that have similar effects on the activity of the gene product are within the scope of the invention. More specifically, the mutation can change the amino acid encoded by the nucleotides at 2454-2456 of SEQ ID NO:7 (aspartic acid (D)) to any another amino acid (e.g., asparagine (N)). Alternatively, or in addition, one can inhibit the polymerase's RNase H activity by, for example, introducing a mutation at nucleotides 3333-3335 of SEQ ID NO:7 (e.g., a mutation that changes the glutamic acid residue (E) to tryptophan (W)). Alternatively, the mutation can be at any of positions 2418-2420, 2661-2663, or 3297-3299 of SEQ ID NOs:8 or 9 (other clade B inserts). Alternatively, the mutation can be at any of positions 2410-2412, 2653-2655, or 3289-3291 of any of SEQ ID NOs: 10-13 (for example, the aspartic acid (D), tryptophan (W) and glutamic acid (E) residues at those positions can be changed to asparagine (N), threonine (T), and/or glutamine (Q), respectively). Alternatively, the mutation can be at any of positions 2387-2389, 2630-2632, or 3266-3268 of SEQ ID NOs:14 or 15. Nucleic acids encoding analogous residues in other clades can be identified by one of ordinary skill in the art, even if those residues are not found at precisely the same position as they were in the clades tested here.

Where the composition includes either a vector with an insert or an insert alone, and that insert encodes multiple protein antigens, one of the antigens can be a wild type or mutant pol sequence, including those described above (these multi-protein-encoding inserts can also encode the wild type or mutant gag sequences described above). Similarly, where a composition includes more than one type of vector or more than one type of insert, at least one of the vectors or inserts (whether encoding a single antigen or multiple antigens) can include a wild type or mutantpol sequence, including those described above (and, optionally, a wild type or mutant gag sequence, including those described above (i.e., the inserts can encode Gag-Pol)). For example, where the composition includes first and second vectors, the vaccine insert in either or both vectors (whether the insert encodes single or multiple antigens) can encode Pol; where both vectors encode Pol, the Pol sequence in the first vector can be from one HIV clade (e.g., clade B) and that in the second vector can be from another HIV clade (e.g., clade AG).

Where an insert includes some or all of the pol sequence, another portion of the pol sequence that can be altered is the sequence encoding the protease activity (regardless of whether or not sequences affecting other enzymatic activities of Pol have been altered). For example, one can introduce a mutation at position 1641-1643 of SEQ ID NO:8 (e.g., a mutation that changes the glutamic acid residue normally encoded by this codon to another amino acid residue, such as alanine (A)). As with the other mutants (e.g., gag mutants) described herein, analogous mutations can be made in sequences obtained from other HIV clades. For example, one can introduce a mutation at position 1633-1635 of SEQ ID NO:10 (changing arginine (R) to another amino acid, such as asparagine (N)), at position 1703-1705 of SEQ ID NO:12 (changing glycine (G) to another residue, such as valine (V)), or at position 1828-1830 of SEQ ID NO:13 (changing leucine (L) to another residue, such as methionine (M) (SEQ ID NOs:10, 12, and 13 all represent clade AG sequences). In an insert from clade C, one can introduce a mutation at position 1610-1612 of SEQ ID NO:14 (changing aspartic acid (D) to another amino acid residue, such as asparagine (N)).

Where the composition includes either a vector with an insert or an insert alone, and that insert encodes a single antigen, the antigen can be a wild type or mutant Env, Tat, Rev, Nef, Vif, Vpr, or Vpu. Where the composition includes either a vector with an insert or an insert alone, and that insert encodes multiple protein antigens, one of the antigens can be a wild type or mutant Env. For example, multi-protein expressing inserts can encode wild type or mutant Gag-Pol and Env; they can also encode wild type or mutant Gag-Pol and Env and one or more of Tat, Rev, Nef, Vif, Vpr, or Vpu (each of which can be wild type or mutant). As with other antigens, Env, Tat, Rev, Nef, Vif, Vpr, or Vpu can be mutant by virtue of a deletion, addition, or substitution of one or more amino acid residues (e.g., any of these antigens can include a point mutation). With respect to Env, one or more mutations can be in any of the domains shown in FIG. 19. For example, one or more amino acids can be deleted from the gp120 surface and/or gp41 transmembrane cleavage products. With respect to Gag, one or more amino acids can be deleted from one or more of: the matrix protein (p17), the capsid protein (p24), the nucleocapsid protein (p7) and the C-terminal peptide (p6). For example, amino acids in one or more of these regions can be deleted (this may be especially desired where the vector is a viral vector, such as MVA). With respect to Pol, one or more amino acids can be deleted from the protease protein (p10), the reverse transcriptase protein (p66/p51), or the integrase protein (p32).

More specifically, the compositions of the invention can include a vector (e.g., a plasmid or viral vector) that encodes: (a) a Gag protein in which one or more of the zinc fingers has been inactivated to limit the packaging of viral RNA; (b) a Pol protein in which (i) the integrase activity has been inhibited by deletion of some or all of the pol sequence and (ii) the polymerase, strand transfer and/or RNase H activity of reverse transcriptase has been inhibited by one or more point mutations within the pol sequence; and (c) Env, Tat, Rev, and Vpu, with or without mutations. In this embodiment, as in others, the encoded proteins can be obtained or derived from a subtype A, B or C HIV (e.g., HIV-1) or recombinant forms thereof. Where the compositions include non-identical vectors, the sequence in each type of vector can be from a different HIV clade (or subtype or recombinant form thereof). For example, the invention features compositions that include plasmid vectors encoding the antigens just described (Gag-Pol, Env etc.), where some of the plasmids include antigens that are obtained from, or derived from, one clade and other plasmids include antigens that are obtained (or derived) from another clade. Mixtures representing two, three, four, five, six, or more clades (including all clades) are within the scope of the invention.

Where first and second vectors are included in a composition, either vector can be pGA1/JS2, pGA1/JS7, pGA1/JS7.1, pGA2/JS2, pGA2/JS7, pGA2/JS7.1 (pGA1.1 can be used in place of pGA1 and pGA2.1 or pGA2.2 can by used in place of pGA2). Similarly, either vector can be pGA1/IC25, pGA1/IC2, pGA1/IC48, pGA1/IC90, pGA2/IC25, pGA2/IC2, pGA2/IC48, or pGA2/IC90 (here again, pGA1.1 or pGA1.2 can be used in place of pGA1 and pGA2.1 or pGA2.2 can be used in place of pGA2). In alternative embodiments, the encoded proteins can be those of, or those derived from, a subtype C HIV (e.g., HIV-1) or a recombinant form thereof. For example, the vector can be pGA1/IN2, pGA1.1/IN2, pGA1.2/IN2, pGA1/IN3, pGA1.1/IN3, pGA1.2/IN3, pGA2/IN2, pGA2.1 pGA2.2/IN2, pGA2/IN3, pGA2.1/IN3, or pGA2.2/IN3.

The encoded proteins can also be those of, or those derived from, any of HIV clades (or subtypes) E, F, G, H, I, J, K or L or recombinant forms thereof. An HIV-1 classification system has been published by Los Alamos National Laboratory (HIV Sequence Compendium-2001, Kuiken et al, published by Theoretical Biology and Biophysics Group T-10, Los Alamos, N.M., (2001); http://hiv-web.lanl.gov).

The compositions of the invention can also include a vector (e.g., a plasmid vector) encoding: (a) a Gag protein in which one or both zinc fingers have been inactivated; (b) a Pol protein in which (i) the integrase activity has been inhibited by deletion of some or all of the pol sequence, (ii) the polymerase, strand transfer and/or RNase H activity of reverse transcriptase has been inhibited by one or more point mutations within the pol sequence and (iii) the proteolytic activity of the protease has been inhibited by one or more point mutations; and (c) Env, Tat, Rev, and Vpu, with or without mutations. As noted above, proteolytic activity can be inhibited by introducing a mutation at positions 1641-1643 of SEQ ID NO:8 or at an analogous position in the sequence of another HIV clade. For example, the plasmids can contain the inserts described herein as JS7, IC25, and IN3. As is true for plasmids encoding other antigens, plasmids encoding the antigens just described can be combined with (e.g., mixed with) other plasmids that encode antigens obtained from, or derived from, a different HIV clade (or subtype or recombinant form thereof). The inserts per se (sans vector) are also within the scope of the invention.

Other vectors of the invention include plasmids encoding a Gag protein (e.g., a Gag protein in which one or both of the zinc fingers have been inactivated); a Pol protein (e.g., a Pol protein in which integrase, RT, and/or protease activities have been inhibited; a Vpu protein (which may be encoded by a sequence having a mutant start codon); and Env, Tat, and/or Rev proteins (in a wild type or mutant form). As is true for plasmids encoding other antigens, plasmids encoding the antigens just described can be combined with (e.g., mixed with) other plasmids that encode antigens obtained from, or derived from, a different HIV clade (or subtype or recombinant form thereof). The inserts per se (sans vector) are also within the scope of the invention.

The plasmids described above, including those that express the JS2 or JS7 series of clade B HIV-1 sequences, can be administered to any subject, but may be most beneficially administered to subjects who have been, or who are likely to be, exposed to an HIV of clade B (the same is true for vectors other than plasmid vectors). Similarly, plasmids or other vectors that express an IN series of clades C HIV-1 sequences can be administered to a subject who has been, or who may be, exposed to an HIV of clade C. As vectors expressing antigens of various clades can be combined to elicit an immune response against more than one clade (this can be achieved whether one vector expresses multiple antigens from different clades or multiple vectors express single antigens from different clades), one can tailor the vaccine formulation to best protect a given subject. For example, if a subject is likely to be exposed to regions of the world where clades other than clade B predominate, one can formulate and administer a vector or vectors that express an antigen (or antigens) that will optimize the elicitation of an immune response to the predominant clade or clades.

The antigens they express are not the only parts of the plasmid vectors that can vary. Useful plasmids may or may not contain a terminator sequence that substantially inhibits transcription (the process by which RNA molecules are formed upon DNA templates by complementary base pairing). Useful terminator sequences include the lambda T0 terminator and functional fragments or variants thereof The terminator sequence is positioned within the vector in the same orientation and at the C terminus of any open reading frame that is expressed in prokaryotes (i.e., the terminator sequence and the open reading frame are operably linked). By preventing read through from the selectable marker into the vaccine insert as the plasmid replicates in prokaryotic cells, the terminator stabilizes the insert as the bacteria grow and the plasmid replicates.

Selectable marker genes are known in the art and include, for example, genes encoding proteins that confer antibiotic resistance on a cell in which the marker is expressed (e.g., resistance to kanamycin, ampicillin, or penicillin). The selectable marker is so-named because it allows one to select cells by virtue of their survival under conditions that, absent the marker, would destroy them. The selectable marker, the terminator sequence, or both (or parts of each or both) can be, but need not be, excised from the plasmid before it is administered to a patient. Similarly, plasmid vectors can be administered in a circular form, after being linearized by digestion with a restriction endonuclease, or after some of the vector "backbone" has been altered or deleted.

The nucleic acid vectors can also include an origin of replication (e.g., a prokaryotic ori) and a transcription cassette that, in addition to containing one or more restriction endonuclease sites, into which an antigen-encoding insert can be cloned, optionally includes a promoter sequence and a polyadenylation signal. Promoters known as strong promoters can be used and may be preferred. One such promoter is the cytomegalovirus (CMV) intermediate early promoter, although other (including weaker) promoters may be used without departing from the scope of the present invention. Similarly, strong polyadenylation signals may be selected (e.g., the signal derived from a bovine growth hormone (BGH) encoding gene, or a rabbit β globin polyadenylation signal (Bohm et al., *J. Immunol. Methods* 193:29-40, 1996; Chapman et al., *Nucl. Acids Res.* 19:3979-3986, 1991; Hartikka et al., *Hum. Gene Therapy* 7:1205-1217, 1996; Manthorpe et al., *Hum. Gene Therapy* 4:419-431, 1993; Montgomery et al., *DNA Cell Biol.* 12:777-783, 1993)).

The vectors can further include a leader sequence (a leader sequence that is a synthetic homolog of the tissue plasminogen activator gene leader sequence (tPA) is optional in the transcription cassette) and/or an intron sequence such as a cytomegalovirus (CMV) intron A or an SV40 intron. The presence of intron A increases the expression of many antigens from RNA viruses, bacteria, and parasites, presumably by providing the expressed RNA with sequences that support processing and function as a eukaryotic mRNA. Expression can also be enhanced by other methods known in the art including, but not limited to, optimizing the codon usage of prokaryotic mRNAs for eukaryotic cells (Andre et al., *J. Virol.* 72:1497-1503, 1998; Uchijima et al., *J. Immunol.* 161: 5594-5599, 1998). Multi-cistronic vectors may be used to express more than one immunogen or an immunogen and an immunostimulatory protein (Iwasaki et al., *J. Immunol.* 158: 4591-4601, 1997a; Wild et al., *Vaccine* 16:353-360, 1998). Thus (and as is true with other optional components of the vector constructs), vectors encoding one or more antigens from one or more HIV clades or isolates may, but do not necessarily, include a leader sequence and an intron (e.g., the CMV intron A).

The vectors of the present invention differ in the sites that can be used for accepting antigen-encoding sequences and in whether the transcription cassette includes intron A sequences in the CMVIE promoter. Accordingly, one of ordinary skill in the art may modify the insertion site(s) or cloning site(s) within the plasmid without departing from the scope of the invention. Both intron A and the tPA leader sequence have been shown in certain instances to enhance antigen expression (Chapman et al., *Nucleic Acids Research* 19:3979-3986, 1991).

As described further below, the vectors of the present invention can be administered with an adjuvant, including a genetic adjuvant. Accordingly, the nucleic acid vectors, regardless of the antigen they express, can optionally include such genetic adjuvants as GM-CSF, IL-15, IL-2, interferon response factors, secreted forms of flt-3, and mutated caspase genes. Genetic adjuvants can also be supplied in the form of fusion proteins, for example by fusing one or more C3d gene sequences (e.g., 1-3 (or more) C3d gene sequences) to an expressed antigen.

Figure 5:
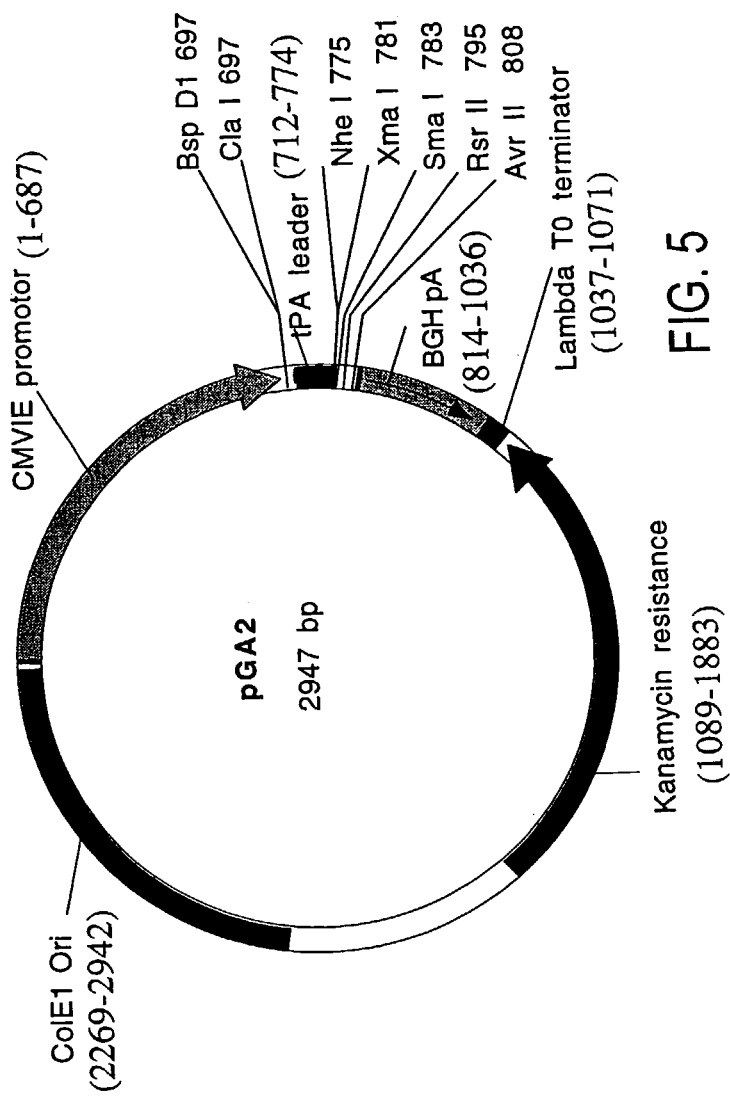
FIG. 5 is a schematic illustration of the plasmid construct pGA2. The identities and positions of elements present in the vector (e.g., a promoter (here the CMV promoter without intron A), the multi-cloning site, a terminator sequence (here, the lambda T0 terminator), and a selection gene (here, the kanamycin resistance gene) are shown. Unique restriction endonuclease sites, which are useful for cloning vaccine inserts into the plasmid, are also shown.

In the event the vector administered is a pGA vector, it can comprise the sequence of, for example, pGA1 (SEQ ID NO:1) or derivatives thereof (e.g., SEQ ID NOs:2 and 3) or pGA2 (SEQ ID NO:4) or derivatives thereof (e.g., SEQ ID NOs:5 and 6). The pGA vectors are described in more detail here (see also Examples 1-8). pGA1 is a 3897 bp plasmid that includes a promoter (bp 1-690), the CMV-intron A (bp 691-1638), a synthetic mimic of the tPA leader sequence (bp 1659-1721), the bovine growth hormone polyadenylation sequence (bp 1761-1983), the lambda T0 terminator (bp 1984-2018), the kanamycin resistance gene (bp 2037-2830) and the ColEI replicator (bp 2831-3890). The DNA sequence of the pGA1 construct (SEQ ID NO:1) is shown in FIG. 2. In FIG. 1, the indicated restriction sites are useful for cloning antigen-encoding sequences. The Cla I or BspD I sites are used when the 5' end of a vaccine insert is cloned upstream of the tPA leader. The Nhe I site is used for cloning a sequence in frame with the tPA leader sequence. The sites listed between Sma I and Bln I are used for cloning the 3' terminus of an antigen-encoding sequence.

pGA2 is a 2947 bp plasmid lacking the 947 bp of intron A sequences found in pGA1. pGA2 is the same as pGA1, except for the deletion of intron A sequences. pGA2 is valuable for cloning sequences which do not require an upstream intron for efficient expression, or for cloning sequences in which an upstream intron might interfere with the pattern of splicing needed for good expression. FIG. 5 presents a schematic map of pGA2 with useful restriction sites for cloning vaccine inserts. FIG. 6*a* shows the DNA sequence of pGA2 (SEQ ID NO:2). The use of restriction sites for cloning vaccine inserts into pGA2 is the same as that used for cloning fragments into pGA1. pGA2.1 and pGA2.2 are multiple cloning site derivatives of pGA2. FIGS. 7a and 8a show the DNA sequence of pGA2.1 (SEQ ID NO:5) and pGA2.2 (SEQ ID NO:6) respectively.

pGA plasmids having "backbone" sequences that differ from those disclosed herein are also within the scope of the invention so long as the plasmids retain substantially all of the characteristics necessary to be therapeutically effective (e.g., one can substitute nucleotides, add nucleotides, or delete nucleotides so long as the plasmid, when administered to a patient, induces or enhances an immune response against a given or desired pathogen). For example, 1-10, 11-20, 21-30, 31-40, 41-50, 51-60, 61-70, 71-80, 81-90, 91-100, or more than 100 nucleotides can be deleted or replaced.

In one embodiment, the methods of the invention (e.g., methods of eliciting an immune response in a patient) can be carried out by administering to the patient a therapeutically effective amount of a physiologically acceptable composition that includes a vector, which can contain a vaccine insert that encodes one or more antigens that elicit an immune response against an HIV. The vector can be a plasmid vector having one or more of the characteristics of the pGA constructs described above (e.g., a selectable marker gene, a prokaryotic origin of replication, a termination sequence (e.g., the lambda T0 terminator) and operably linked to the selectable gene marker, and a eukaryotic transcription cassette comprising a promoter sequence, a nucleic acid insert encoding at least one antigen derived from an immunodeficiency virus, and a polyadenylation signal sequence). Of course, the vaccine inserts of the invention may be delivered by plasmid vectors that do not have the characteristics of the pGA constructs (e.g., vectors other than pGA1 or pGA2). Alternatively, the composition can include any viral or bacterial vector that includes an insert described herein. The invention, therefore, encompasses administration of a single type of vector (i.e., plasmid or viral vectors that contain the same vaccine insert (i.e., an insert encoding the same antigens)). As is made clear elsewhere, the patient may receive two types of vectors, and each of those vectors can elicit an immune response against an HIV of a different clade. For example, the invention features methods in which a patient receives a composition that includes (a) a first vector comprising a vaccine insert encoding one or more antigens that elicit an immune response against a human immunodeficiency virus (HIV) of a first subtype or recombinant form and (b) a second vector comprising a vaccine insert encoding one or more antigens that elicit an immune response against an HIV of a second subtype or recombinant form. The first and second vectors can be any of those described herein. Similarly, the inserts in the first and second vectors can be any of those described herein.

A therapeutically effective amount of a vector (whether considered the first, second, third, etc. vector) can be administered by an intramuscular or an intradermal route, together with a physiologically acceptable carrier, diluent, or excipient, and, optionally, an adjuvant. A therapeutically effective amount of the same or a different vector can subsequently be administered by an intramuscular or an intradermal route, together with a physiologically acceptable carrier, diluent, or excipient, and, optionally, an adjuvant to boost an immune response. Such components can be readily selected by one of ordinary skill in the art, regardless of the precise nature of the antigens incorporated in the vaccine or the vector by which they are delivered.

The methods of eliciting an immune response can be carried out by administering only the plasmid vectors of the invention, by administering only the viral vectors of the invention, or by administering both (e.g., one can administer a plasmid vector (or a mixture or combination of plasmid vectors)) to "prime" the immune response and a viral vector (or a mixture or combination of viral vectors)) to "boost" the immune response. Where plasmid and viral vectors are administered, their inserts may be "matched." To be "matched," one or more of the sequences of the inserts (e.g., the sequences encoding Gag, or the sequences encoding Env, etc.) within the plasmid and viral vectors may be identical, but the term is not so limited. "Matched" sequences can also differ from one another. For example, inserts expressed by viral vectors are "matched" to those expressed by DNA vectors when the sequences used in the DNA vector are mutated or further mutated to allow (or optimize) replication of a viral vector that encodes those sequences and expression of the encoded antigens (e.g., Gag, Gag-Pol, or Env) in cells infected with the viral vector.

At least some of the immunodeficiency virus vaccine inserts of the present invention were designed to generate non-infectious VLPs (a term that can encompass true VLPs as well as aggregates of viral proteins) from a single DNA. This was achieved using the subgenomic splicing elements normally used by immunodeficiency viruses to express multiple gene products from a single viral RNA. The subgenomic splicing patterns are influenced by (i) splice sites and acceptors present in full length viral RNA, (ii) the Rev responsive element (RRE) and (iii) the Rev protein. The splice sites in retroviral RNAs use the canonical sequences for splice sites in eukaryotic RNAs. The RRE is an approximately 200 bp RNA structure that interacts with the Rev protein to allow transport of viral RNAs from the nucleus to the cytoplasm. In the absence of Rev, the approximately 10 kb RNA of immunodeficiency virus mostly undergoes splicing to the mRNAs for the regulatory genes Tat, Rev, and Nef. These genes are encoded by exons present between RT and Env and at the 3' end of the genome. In the presence of Rev, the singly spliced mRNA for Env and the unspliced mRNA for Gag and Pol are expressed in addition to the multiply spliced mRNAs for Tat, Rev, and Nef.

The expression of non-infectious VLPs from a single DNA affords a number of advantages to an immunodeficiency virus vaccine. The expression of a number of proteins from a single DNA affords the vaccinated host the opportunity to respond to the breadth of T- and B-cell epitopes encompassed in these proteins. The expression of proteins containing multiple epitopes allows epitope presentation by diverse histocompatibility types. By using whole proteins, one offers hosts of different histocompatibility types the opportunity to raise broad-based T cell responses. This may be essential for the effective containment of immunodeficiency virus infections, whose high mutation rate supports ready escape from immune responses (Evans et al., *Nat. Med.* 5:1270-1276, 1999; Poignard et al., *Immunity* 10:431-438, 1999, Evans et al., 1995). In the context of the present vaccination scheme, just as in drug therapy, multi-epitope T cell responses that require multiple mutations for escape will provide better protection than single epitope T cell responses (which require only a single mutation for escape).

Immunogens can also be engineered to be more or less effective for raising antibody or Tc by targeting the expressed antigen to specific cellular compartments. For example, antibody responses are raised more effectively by antigens that are displayed on the plasma membrane of cells, or secreted therefrom, than by antigens that are localized to the interior of cells (Boyle et al., *Int. Immunol.* 9:1897-1906, 1997; Inchauspe et al., *DNA Cell. Biol.* 16:185-195, 1997). Tc responses may be enhanced by using N-terminal ubiquitination signals which target the DNA-encoded protein to the proteosome causing rapid cytoplasmic degradation and more efficient peptide loading into the MHC I pathway (Rodriguez et al., *J. Virol.* 71:8497-8503, 1997; Tobery et al., *J. Exp. Med.* 185:909-920, 1997; Wu et al., *J. Immunol.* 159:6037-6043, 1997). For a review on the mechanistic basis for DNA-raised immune responses, refer to Robinson and Pertmer, *Advances in Virus Research*, vol. 53, Academic Press (2000).

Another approach to manipulating immune responses is to fuse immunogens to immunotargeting or immunostimulatory molecules. To date, the most successful of these fusions have targeted secreted immunogens to antigen presenting cells (APCs) or lymph nodes (Boyle et al., *Nature* 392:408-411, 1998). Accordingly, the invention features the HIV antigens described herein fused to immunotargeting or immunostimulatory molecules such as CTLA-4, L-selectin, or a cytokine (e.g., an interleukin such as IL-1, IL-2, IL-4, IL-7, IL-10, IL-15, or IL-21). Nucleic acids encoding such fusions and compositions containing them (e.g., vectors and physiologically acceptable preparations) are also within the scope of the present invention.

DNA can be delivered in a variety of ways, any of which can be used to deliver the plasmids of the present invention to a subject. For example, DNA can be injected in, for example, saline (e.g., using a hypodermic needle) or delivered biolistically (by, for example, a gene gun that accelerates DNA-coated beads). Saline injections deliver DNA into extracellular spaces, whereas gene gun deliveries bombard DNA directly into cells. The saline injections require much larger amounts of DNA (typically 100-1000 times more) than the gene gun (Fynan et al., *Proc. Natl. Acad. Sci. USA* 90:11478-11482, 1993). These two types of delivery also differ in that saline injections bias responses towards type 1 T-cell help, whereas gene gun deliveries bias responses towards type 2 T-cell help (Feltquate et al., *J. Immunol.* 158:2278-2284, 1997; Pertmer et al., *J. Virol.* 70:6119-6125, 1996). DNAs injected in saline rapidly spread throughout the body. DNAs delivered by the gun are more localized at the target site. Following either method of inoculation, extracellular plasmid DNA has a short half life of about 10 minutes (Kawabata et al., *Pharm. Res.* 12:825-830, 1995; Lew et al., *Hum. Gene Ther.* 6:553, 1995). Vaccination by saline injections can be intramuscular (i.m.) or intradermal (i.d.); gene gun deliveries can be administered to the skin or to surgically exposed tissue such as muscle.

While other routes of delivery are generally less favored, they can nevertheless be used to administer the compositions of the invention. For example, the DNA can be applied to the mucosa or by a parenteral route of inoculation. Intranasal administration of DNA in saline has met with both good (Asakura et al, *Scand. J. Immunol.* 46:326-330, 1997; Sasaki et al., *Infect. Immun.* 66:823-826, 1998b) and limited (Fynan et al., *Proc. Natl. Acad. Sci. USA* 90:11478-82, 1993) success. The gene gun has successfully raised IgG following the delivery of DNA to the vaginal mucosa (Livingston et al., *Ann. New York Acad. Sci.* 772:265-267, 1995). Some success at delivering DNA to mucosal surfaces has also been achieved using liposomes (McCluskie et al., *Antisense Nucleic Acid Drug Dev.* 8:401-414, 1998), microspheres (Chen et al., *J. Virol.* 72:5757-5761, 1998a; Jones et al., *Vaccine* 15:814-817, 1997) and recombinant Shigella vectors (Sizemore et al., *Science* 270:299-302, 1995; Sizemore et al., *Vaccine* 15:804-807, 1997). Agents such as these (liposomes, microspheres and recombinant Shigella vectors) can be used to deliver the nucleic acids of the present invention.

The dose of DNA needed to raise a response depends upon the method of delivery, the host, the vector, and the encoded antigen. The method of delivery may be the most influential parameter. From 10 µg to 5 mg of DNA is generally used for saline injections of DNA, whereas from 0.2 µg to 20 µg of DNA is used more typically for gene gun deliveries of DNA. In general, lower doses of DNA are used in mice (10-100 µg for saline injections and 0.2 µg to 2 µg for gene gun deliveries), and higher doses in primates (100 µg to 1 mg for saline injections and 2 µg to 20 µg for gene gun deliveries). The much lower amount of DNA required for gene gun deliveries reflect the gold beads directly delivering DNA into cells.

In addition to the DNA vectors described above, a number of different poxviruses can be used either alone (i.e., without a nucleic acid or DNA prime) or as the boost component of a vaccine regimen. MVA has been particularly effective in mouse models (Schneider et al., *Nat. Med.* 4:397-402, 1998). MVA is a highly attenuated strain of vaccinia virus that was developed toward the end of the campaign for the eradication of smallpox, and it has been safety tested in more than 100, 000 people (Mahnel et al., *Berl. Munch Tierarztl Wochenschr* 107:253-256, 1994; Mayr et al. *Zentralbl. Bakteriol.* 167: 375-390, 1978). During over 500 passages in chicken cells, MVA lost about 10% of its genome and the ability to replicate efficiently in primate cells. Despite its limited replication, MVA has proved to be a highly effective expression vector (Sutter et al., *Proc. Natl. Acad. Sci. USA* 89:10847-10851, 1992), raising protective immune responses in primates for parainfluenza virus (Durbin et al. *J. Infect. Dis.* 179:1345-1351, 1999), measles (Stittelaar et al. *J. Virol.* 74:4236-4243, 2000), and immunodeficiency viruses (Barouch et al., *J. Virol.* 75:5151-5158, 2001; Ourmanov et al., *J. Virol.* 74:2740-2751, 2000; Amara et al., *J. Virol.* 76:7625-7631, 2002). The relatively high immunogenicity of MVA has been attributed in part to the loss of several viral anti-immune defense genes (Blanchard et al., *J. Gen. Virol.* 79:1159-1167, 1998).

Vaccinia viruses have been used to engineer viral vectors for recombinant gene expression and as recombinant live vaccines (Mackett et al., *Proc. Natl. Acad. Sci. USA* 79:7415-7419; Smith et al., *Biotech. Genet. Engin. Rev.* 2:383-407, 1984). DNA sequences, which may encode any of the HIV antigens described herein, can be introduced into the genomes of vaccinia viruses. If the gene is integrated at a site in the viral DNA that is non-essential for the life cycle of the virus, it is possible for the newly produced recombinant vaccinia virus to be infectious (i.e., able to infect foreign cells) and to express the integrated DNA sequences. Preferably, the viral vectors featured in the compositions and methods of the present invention are highly attenuated. Several attenuated strains of vaccinia virus were developed to avoid undesired side effects of smallpox vaccination. The modified vaccinia Ankara (MVA) virus was generated by long-term serial passages of the Ankara strain of vaccinia virus on chicken embryo fibroblasts (CVA; see Mayr et al., *Infection* 3:6-14, 1975). The MVA virus is publicly available from the American Type Culture Collection (ATCC; No. VR-1508; Manassas, Va.). The desirable properties of the MVA strain have been demonstrated in clinical trials (Mayr et al., *Zentralbl Bakteriol.* 167:375-390, 1978; Stickl et al., *Dtsch. Med. Wschr.* 99:2386-2392, 1974; see also, Sutter and Moss, *Proc. Natl. Acad. Sci. USA* 89:10847-10851, 1992). During these studies in over 120,000 humans, including high-risk patients, no side effects were associated with the use of MVA vaccine.

The MVA vectors can be prepared as follows. A DNA construct that contains a DNA sequence that encodes a foreign polypeptide (e.g., any of the HIV antigens described herein) and that is flanked by MVA DNA sequences adjacent to a naturally occurring deletion with the MVA genome (e.g., deletion III or other non-essential site(s); six major deletions of genomic DNA (designated deletions I, II, III, IV, V, and VI) totaling 31,000 base pairs have been identified (Meyer et al., *J. Gen. Virol.* 72:1031-1038, 1991)) is introduced into cells infected with MVA under conditions that permit homologous recombination to occur. Once the DNA construct has been introduced into the eukaryotic cell and the foreign DNA has recombined with the viral DNA, the recombinant vaccinia virus can be isolated by methods known in the art (isolation can be facilitated by use of a detectable marker). The DNA constructed to be inserted can be linear or circular (e.g., a plasmid, linearized plasmid, gene, gene fragment, or modified HIV genome). The foreign DNA sequence is inserted between the sequences flanking the naturally occurring deletion. For better expression of a DNA sequence, the sequence can include regulatory sequences (e.g., a promoter, such as the promoter of the vaccinia 11 kDa gene or the 7.5 kDa gene). The DNA construct can be introduced into MVA-infected cells by a variety of methods, including calcium phosphate-assisted transfection (Graham et al., *Virol.* 52:456-467, 1973 and Wigler et al., *Cell* 16:777-785, 1979), electroporation (Neumann et al., *EMBO J.* 1:841-845, 1982) microinjection (Graessmann et al., *Meth. Enzymol.* 101:482-492, 1983), by means of liposomes (Straubinger et al., *Meth. Enzymol.* 101:512-527, 1983), by means of spheroplasts (Schaffner, *Proc. Natl. Acad. Sci. USA* 77:2163-2167, 1980), or by other methods known in the art.

One can arrive at an appropriate dosage when delivering DNA by way of a viral vector, just as one can when a plasmid vector is used. For example, one can deliver $1 \times 10^8$ pfu of an MVA-based vaccine, and administration can be carried out intramuscularly, intradermally, intravenously, or mucosally.

Accordingly, the invention features a composition comprising: (a) a first viral vector comprising a vaccine insert encoding one or more antigens that elicit an immune response against a human immunodeficiency virus (HIV) of a first subtype or recombinant form and (b) a second viral vector comprising a vaccine insert encoding one or more antigens that elicit an immune response against an HIV of a second subtype or recombinant form. The viral vector can be a recombinant poxvirus or a modified vaccinia Ankara (MVA) virus, and the insert can be any of the HIV antigens described herein from any clade (e.g., one can administer a prophylactically or therapeutically effective amount of an MVA that encodes a clade A, B, or C HIV (e.g., HIV-1 antigen). Moreover, when administered in conjunction with a plasmid vector (e.g., when administered subsequent to a "DNA prime"), the MVA-borne sequence can be "matched" to the plasmid-borne sequence. For example, a vaccinia virus (e.g., MVA) that expresses a recombinant clade B sequence can be matched to the JS series of plasmid inserts. Similarly, a vaccinia virus (e.g., MVA) that expresses a recombinant clade A sequence can be matched to the IC series of plasmid inserts; a vaccinia virus (e.g., MVA) that expresses a recombinant clade C sequence can be matched to the IN series of plasmid inserts. While particular clades are exemplified below, the invention is not so limited. The compositions that contain a viral vector, can include viral vectors that express an HIV antigen from any known clade (including clades A, B, C, D, E, F, G, H, I, J, K or L). Methods of eliciting an immune response can, of course, be carried out with compositions expressing antigens from any of these clades as well.

Either the plasmid or viral vectors described here can be administered with an adjuvant (i.e., any substance that is added to a vaccine to increase the vaccine's immunogenicity) and they can be administered by any conventional route of administration (e.g., intramuscular, intradermal, intravenous or mucosally; see below). The adjuvant used in connection with the vectors described here (whether DNA or viral-based) can be one that slowly releases antigen (e.g., the adjuvant can be a liposome), or it can be an adjuvant that is strongly immunogenic in its own right (these adjuvants are believed to function synergistically). Accordingly, the vaccine compositions described here can include known adjuvants or other substances that promote DNA uptake, recruit immune system cells to the site of the inoculation, or facilitate the immune activation of responding lymphoid cells. These adjuvants or substances include oil and water emulsions, *Corynebacterium parvum*, Bacillus Calmette Guerin, aluminum hydroxide, glucan, dextran sulfate, iron oxide, sodium alginate, Bacto-Adjuvant, certain synthetic polymers such as poly amino acids and co-polymers of amino acids, saponin, REGRESSIN (Vetrepharm, Athens, Ga.), AVRIDINE (N,N-dioctadecyl-N',N'-bis(2-hydroxyethyl)-propanediamine), paraffin oil, and muramyl dipeptide. Genetic adjuvants, which encode immunomodulatory molecules on the same or a co-inoculated vector, can also be used. For example, GM-CSF, IL-15, IL-2, interferon response factors, and mutated caspase genes can be included on a vector that encodes a pathogenic immunogen (such as an HIV antigen) or on a separate vector that is administered at or around the same time as the immunogen is administered. Expressed antigens can also be fused to an adjuvant sequence such as one, two, three or more copies of C3d.

The compositions described herein can be administered in a variety of ways including through any parenteral or topical route. For example, an individual can be inoculated by intravenous, intraperitoneal, intradermal, subcutaneous or intramuscular methods. Inoculation can be, for example, with a hypodermic needle, needleless delivery devices such as those that propel a stream of liquid into the target site, or with the use of a gene gun that bombards DNA on gold beads into the target site. The vector comprising the pathogen vaccine insert can be administered to a mucosal surface by a variety of methods including intranasal administration, i.e., nose drops or inhalants, or intrarectal or intravaginal administration by solutions, gels, foams, or suppositories. Alternatively, the vector comprising the vaccine insert can be orally administered in the form of a tablet, capsule, chewable tablet, syrup, emulsion, or the like. In an alternate embodiment, vectors can be administered transdermally, by passive skin patches, iontophoretic means, and the like.

Any physiologically acceptable medium can be used to introduce a vector (whether nucleic acid-based or live-vectored) comprising a vaccine insert into a patient. For example, suitable pharmaceutically acceptable carriers known in the art include, but are not limited to, sterile water, saline, glucose, dextrose, or buffered solutions. The media may include auxiliary agents such as diluents, stabilizers (i.e., sugars (glucose and dextrose were noted previously) and amino acids), preservatives, wetting agents, emulsifying agents, pH buffering agents, additives that enhance viscosity or syringability, colors, and the like. Preferably, the medium or carrier will not produce adverse effects, or will only produce adverse effects that are far outweighed by the benefit conveyed.

The present invention is further illustrated by the following examples, which are provided by way of illustration and should not be construed as limiting. The contents of all references, published patent applications and patents cited throughout the present application are hereby incorporated by reference in their entirety. A number of embodiments of the invention have been described. Nevertheless, it will be understood that various modifications may be made without departing from the spirit and scope of the invention.

EXAMPLE 1 pGA1 pGA1 (see FIGS. 1 and 2) contains (1) the ColE1 origin of replication (a 672 bp sequence that contains the origin of replication (ori) and encodes an RNA primer and two negative regulators of replication initiation) (2) the kanamycin resistance gene (an antibiotic resistance gene for plasmid selection in bacteria), (3) the lambda T0 terminator, and (4) a eukaryotic expression cassette that includes an upstream intron (here, CMV Intron A), the CMV immediate early (CMVIE) promoter, and termination sequences from the bovine growth hormone polyadenylation sequence (BGHpA). A synthetic mimic of the leader sequence for tissue plasminogen activator (tPA) can also be included within the expression cassette. The expression cassette can include multiple restriction sites, and those sites can be included or excluded as desired to facilitate inclusion of expression cassettes that encode antigens from any HIV clade. The cloning sites in pGA1 include a Cla I site upstream of the tPA leader, a Nhe I site for cloning in frame with the tPA leader, and Xmn I, Sma I, Rsr II, and Avr II sites for cloning prior to the BGHpA. The originally constructed plasmid containing the ColE1 replicator was pBR322 (Bolivar et al., *Gene* 2:95-113, 1977; Sutcliffe et al., *Cold Spring Harbor Quant. Biol.* 43:77-90, 1978).

The lambda T0 terminator (Scholtissek et al., *Nucleic Acids Res.* 15:3185, 1987) prevents read through from the kanamycin resistance gene into the eukaryotic expression cassette (in this case the vaccine transcription cassette) during prokaryotic growth of the plasmid. By preventing read through into the vaccine expression cassette, the terminator helps stabilize plasmid inserts during growth in bacteria.

The ColE1 replicator, the kanamycin resistance gene, and the transcriptional control elements for eukaryotic cells were combined in one plasmid using PCR fragments from the commercial vector pZErO-2.1 (Invitrogen, Carlsbad, Calif.) and a eukaryotic expression vector pJW4303 (Lu et al., *Vaccine* 15:920-923, 1997).

An 1859 bp fragment from pZErO-2.1 (nucleotides 1319 to 3178) included the ColE1 origin of replication and the kanamycin resistance gene. A 2040 bp fragment from pJW4303 (nucleotides 376 to 2416) included the CMVIE promoter with intron A, a synthetic homolog of the tissue plasminogen activator leader (tPA), and the bovine growth hormone polyadenylation site (BGHpA). Fragments were amplified by polymerase chain reaction (PCR) with oligonucleotide primers containing Sal I sites. A ligation product with the transcription cassettes for kanamycin resistance from pZErO2 and the eukaryotic transcription cassette form pJW4303 in opposite transcriptional orientations, was identified for further development. Nucleotide numbering for this parent of the pGA vectors was started from the first bp of the 5' end of the CMV promoter.

The T0 terminator was introduced into this parent for the pGA vectors by PCR amplification of a 391 bp fragment with a BamH I restriction endonuclease site at its 5' end and an Xba I restriction endonuclease site at its 3' end. The initial 355 bp of the fragment were sequences in the BGHpA sequence derived from the pJW4303 transcription cassette, the next 36 bases in a synthetic oligonucleotide introduced the T0 sequence and the Xba I site. The introduced T0 terminator sequences comprised the sequence: 5'-ATAAAAAACGC-CCGGCGGCAACCGAGCGTTCTGAA-3' (SEQ ID NO: 16).

The T0 terminator containing the BamH I-Xba I fragment was substituted for the homologous fragment without the T0 terminator in the plasmid created from pZErO-2 and pJW4303. The product was sequenced to verify the T0 orientation (FIG. 1).

A region in the eukaryotic transcription cassette between nucleotides 1755-1845 contained the last 30 bp of the reading frame for SIV nef. This region was removed from pGA by mutating the sequence at nt 1858 and generating an Avr II restriction endonuclease site. A naturally occurring Avr II site is located at nt 1755. Digestion with Avr II enzyme and then religation with T4 DNA ligase allowed for removal of the SIV segment of DNA between nucleotides 1755-1845. To facilitate cloning of HIV-1 sequences into pGA vectors, a Cla I site was introduced at bp 1648 and an Rsr II site at bp 1747 using standard techniques for site directed mutagenesis. Constructions were verified by sequence analyses.

EXAMPLE 2 pGA1.1 pGA1.1 (SEQ ID NO: 2) is identical to pGA1 except that the multiple cloning site has been altered to include an EcoRI site. This was accomplished by site directed mutagenesis using the following primers: 5'-GCTGCTGCTGTGTG-GAGAATTCTTCGTTTCGGC-3' (forward) and 5'-GC-CGAAACGAAGAATTCTCCACACAGCAGCAGC-3' (reverse) (SEQ ID NOs:17 and 18 respectively). Accordingly, the pGA1.1 vector is an embodiment of the invention; as are other vectors having one or more of the features or characteristics of a pGA plasmid (see the detailed description), but different restriction endonuclease sites in the multi-cloning site (e.g., the invention encompasses plasmids that are otherwise substantially similar to pGA1 but that have more, less, or different restriction endonuclease sites in their multi-cloning site).

EXAMPLE 3 pGA1.2 pGA1.2 (SEQ ID NO: 3) is identical to pGA1.1 except that the multiple cloning site has been altered to include BamHI and XhoI sites 5' to the EcoRI site. This was accomplished by site directed mutagenesis using the primer 5'-CTGCAGT-CACCATGGATCCTTGCACT-CGAGGATGCAATGAA-GAG-3' (SEQ ID NO:19) and the reverse primer

```
5'-CTCTTCATTGCATCCTCGAGTGCAAGGATCCATGGTGACTGCAG-3'.     (SEQ ID NO: 20)
```

EXAMPLE 4 pGA2 pGA2 is schematically illustrated in FIG. 5, and its nucleotide sequence is shown in FIG. 6 (SEQ ID NO: 4). pGA2 is identical to pGA1 except that the intron A sequence has been deleted from the CMV promoter of pGA2. pGA2 was created from pGA1 by introducing a Cla I site 8 bp downstream from the mRNA cap site in the CMV promoter; the Cla I site was introduced using oligonucleotide-directed mutagenesis using complimentary primers having the SEQuences: 5'-CCGT-CAGATCGCATCGATACGCCATCCACG-3' (SEQ ID NO: 19) and 5'-CGTGGATGGCGTATCGATGCGATCT-GACGG-3' (SEQ ID NO: 20). After insertion of the new Cla I site, pGA1 was digested with Cla I to remove the 946 bp Cla I fragment from pGA1, and then religated to yield pGA2.

EXAMPLE 5 pGA2.1

PGA2.1 (SEQ ID NO:5) is identical to pGA2 except that the multiple cloning site has been altered to include an EcoRI sites. This was accomplished by site directed mutagenesis using the following primers: forward 5'-GCTGCTGCTGT-GTGGAGAATTCTTCGTTTCGGC-3' (SEQ ID NO:17) and reverse 5'-GCCGAAACGAAGAATTCTCCACACAG-CAGCAGC-3' (SEQ ID NO:18). Accordingly, the pGA2.1 vector is an embodiment of the invention; as are other vectors having one or more of the features or characteristics of a pGA plasmid (see the detailed description), but different restriction endonuclease sites in the multi-cloning site (e.g., the invention encompasses plasmids that are otherwise substantially similar to pGA1 but that have more, less, or different restriction endonuclease sites in their multi-cloning site).

EXAMPLE 6 pGA2.2

PGA2.2 (SEQ ID NO: 6) is identical to pGA1.1 except that the multiple cloning site has been altered to include a BamHI and a XhoI site 5' to the EcoRI site. This was accomplished by site directed mutagenesis using the forward primer 5'-GAACTCATTCTATGGATCCTTGC-TCGAGTGGAT-GCAATGAAGAG-3' and the reverse primer 5'-CTCTTCAT-TGCATC-CACTCGAGCAAGGATCCATAGAAT-GAGTTC-3' (SEQ ID NOs:23 and 24 respectively)

EXAMPLE 7

Immunodeficiency Virus Vaccine Inserts

HIV-1 vaccine inserts for the pGA1 and pGA2 series of vectors were constructed to express multiple HIV-1 proteins from a single RNA transcript using the same subgenomic splicing mechanisms used by immunodeficiency viruses. To ensure that these multiprotein-expressing vectors did not form infectious virus, deletions and point mutations were introduced to cripple essential steps in the retrovirus life cycle. FIG. 9 presents schematics of the normal retroviral genome and a representative vaccine insert. Regions that have been deleted in the insert are stippled. X's indicate point mutations. The deletions included both of the long terminal repeat (LTR) sequences that encode cis-acting elements for reverse transcription, integration, and expression of proviral DNA. 5' sequences adjacent to the 5' LTR that promote encapsidation of viral RNA have been deleted. Coding sequences for the region of pol encoding integrase as well as the auxiliary genes vif and vpr have been deleted. And finally, nef, a gene encoding the Nef regulatory protein has been deleted. The seven point mutations that are common to all inserts described in the examples below are included in the schematic. These include four mutations in the zinc fingers in the nucleocapsid protein to limit zinc-finger-mediated packaging of viral RNA and three mutations in reverse transcriptase to prevent reverse transcription of viral RNA. Analogous changes can be made in any vaccine insert that includes gag and/or pol. Moreover, these changes (or analogous changes) can be made in vaccine inserts that are placed in any of the plasmid or live-vectored vaccines described herein (i.e., in any plasmid having one or more of the features or characteristics of the pGA vectors, the pGA vectors themselves, or the vaccinia vectors that may be used alone or in conjunction with (e.g., to boost) a DNA-primed patient).

The HIV-1 vaccine inserts described below can be expressed in any of the pGA vectors or further derivatives of these vectors. The examples for inserts that are given below are given with the example of the pGA vector that is planned for future use of that insert. However, any of these inserts can be used in any of the pGA vectors as well as other eukaryotic expression vectors.

EXAMPLE 8 pGA2/JS2, Multiprotein Clade B HIV-1 Insert

The sequence of pGA2/JS2 is shown in FIG. 7a (SEQ ID NO:7), its functional regions and the origins of these regions in FIG. 7b and the positions of its point mutations in FIG. 7c. The JS2 insert described here was designed with clade B HIV-1 sequences so that it would elicit an immune response against HIV-1 sequences that are endemic in the United States, Europe, and Japan. As noted above, any clade B isolate can be used as a reasonable representative for other clade B isolates. Since HIV-1 isolates use different chemokine receptors as co-receptors, and the vast majority of viruses that are undergoing transmission use the CCR-5 co-receptor (Berger, *AIDS* 11(*Suppl A*):S3-16, 1997), the vaccine insert we designed had a CCR-5-using Env. Of course, Envs that function through any other co-receptor or that have been constructed from naturally occurring or synthetic sequences so as to increase immunogenicity can be made and used as well.

To achieve a multiprotein-expressing clade B vaccine insert with high expression, candidate vaccines were constructed from seven different HIV-1 sequences, as shown in Table 1.

TABLE 1

Comparison of candidate vaccine inserts

| Plasmid designation | SEQuences tested | Ability to grow plasmid | Expression of Gag | Expression of Env | Comment |
|---|---|---|---|---|---|
| BH10-VLP | BH10 | Good | Good | Good | X4 Env |
| 6A-VLP | 6A env in BH10-VLP | Poor | Not tested | not tested | |

TABLE 1-continued

Comparison of candidate vaccine inserts

| Plasmid designation | SEQuences tested | Ability to grow plasmid | Expression of Gag | Expression of Env | Comment |
|---|---|---|---|---|---|
| BAL-VLP | BAL env in BH10-VLP | Good | Poor | Poor | |
| ADA-VLP | ADA env in BH10-VLP | Good | Good | Good | chosen for vaccine, renamed pGA1/JS1 |
| CDC-A-VLP | CDC-A env in BH10-VLP | Good | Good | Poor | |
| CDC-B-VLP | CDC-B-env in BH10-VLP | Good | Good | Good | not as favorable expression as ADA |
| CDC-C-VLP | CDC -C env in BH10-VLP | Good | Good | Good | not as favorable expression as ADA |

An initial construct, pBH10-VLP, was prepared from IIIB sequences that are stable in bacteria and have high expression in eukaryotic cells. The HIV-1-BH10 sequences were obtained from the NIH-sponsored AIDS Repository (catalog #90). The parental pHIV-1-BH10 was used as the template for PCR reactions to construct pBH10-VLP.

Primers were designed to yield a Gag-Rt PCR product (5' PCR product) encompassing (from 5' to 3') 105 bp of the 5' untranslated leader sequence and sequences from the start codon for Gag to the end of the RT coding sequence. The oligonucleotide primers introduced a Cla I site at the 5' end of the PCR product and EcoR I and Nhe I sites at the 3' end of the PCR product. Sense primer (5'-GAGCTCTATCGATGCAG-GACTCGGCTTGC-3' (SEQ ID NO:25 and antisense primer (5'-GGCAGGTTTTAATCGCTAGCCTATGCTCTCC-3' (SEQ ID NO:26) were used to amplify the 5' PCR product.

The PCR product for the env region of HIV-1 (3' PCR product) encompassed the vpu, tat, rev, and env sequences and the splice acceptor sites necessary for proper processing and expression of their respective mRNAs. An EcoR I site was introduced at the 5' end of this product and Nhe I and Rsr II sites were introduced into the 3' end. Sense primer (5'-GGGCAGGAGTGCTAGCC-3' (SEQ ID NO:27) and antisense primer 5'-CCACACTACTTTCGGACCGCTAGC-CACCC-3' (SEQ ID NO: 28)) were used to amplify the 3' PCR product. The 5' PCR product was cloned into pGA1 at the Cla I and Nhe I sites of pGA1 and the identity of the construct confirmed by sequencing. The 3' PCR product was then inserted into the 5' clone at the EcoR I and Nhe I sites to yield pBH10. The construction of this plasmid resulted in proviral sequences that lacked LTRs, integrase, vif. vpr and nef sequences (see FIG. 9).

Because pBH10-VLP encoded a CXCR-4 using Env, rather than a CCR-5 using Env, sequences encoding six different R5 Envs were substituted for env sequence in the pBH10 intermediate (Table 1). EcoR I to BamH I fragments encompassing tat, rev, vpu and env coding sequences from different viral genomes were substituted into pBH10. The resulting env and rev sequences were chimeras for the substituted sequences and HIV-1-BH10 sequences (see FIG. 9). In the case of the HIV-1-ADA envelope, a BamH I site was introduced into the HIV-1-ADA sequence to facilitate substituting an EcoR I to BamH I fragment for the EcoR I to BamH I region of pBH10. The results of these constructions are summarized in Table 1. Of the six sequences tested, one, the 6A-VLP gave poor plasmid growth in transformed bacteria. The plasmid 6A-VLP was not developed further. Among the other constructs, the pBH10/ADA chimera produced the best expression of viral Gag and Env proteins (Table 1). In transient transfections in 293T cells, the expression from the pBH10/ADA chimera was higher than that of wt proviruses for HIV-1-ADA or HIV-1-IIIB. Expression was also higher than for a previous multiprotein-expressing HIV-1 vaccine (dpol) (Richmond et al., *J. Virol.* 72:9092-9100, 1998) that had successfully primed cytotoxic T cell responses in rhesus macaques (Kent et al., *J. Virol.* 72:10180-10188, 1998). The pBH10/ADA chimera was now designated JS1. It should be recognized that plasmids having any given or desired HIV-1 inserts can be similarly assessed.

Next, inactivating point mutations were introduced into JS1 to further increase the safety of this construct for use in humans as a non-infectious vaccine agent (of course, mutations can be made preemptively, before any testing at all) (see FIG. 10c). Four codon mutations were introduced into the Zinc fingers in nucleocapsid to limit the encapsidation of viral RNA and three codon mutations were introduced into the reverse transcriptase region of pol to inactivate the viral reverse transcriptase. The JS1 insert with these mutations was designated JS2.

The mutations were made using a site directed mutagenesis kit (Stratagene) following the manufacturer's protocol. All mutations were confirmed by sequencing. Primer pairs used for the mutagenesis were:

```
(A) 5'-GGTTAAGAGCTTCAATAGCGGCAAAGAAGGGC-3' and          (C392S, C395S; SEQ ID NO: 29)
    5'-GCCCTTCTTTGCCGCTATTGAAGCTCTTAACC-3';             (C392S, C395S; SEQ ID NO: 30)

(B) 5'-GGGCAGCTGGAAAAGCGGAAAGGAAGG-3' and                (C413S, C416S; SEQ ID NO: 31
    5'-CCTTCCTTTCCGCTTTTCCAGCTGCCC-3';                   (C413S, C416S; SEQ ID NO: 32)

(C) 5'-CCAGACATAGTTATCTATCAATACATGAACGATTTGTATGTAGG-3'  (D185N; SEQ ID NO: 33)
    and
    5'-CCTACATACAAATCGTTCATGTATTGATAGATAACTATGTCTGG-3';  (D185N; SEQ ID NO: 34)

(D) 5'-GGGGAAATTGAATACCGCAAGTCAGATTTACCC-3'and          (W266T; SEQ ID NO: 35)
    5'-GGGTAAATCTGACTTGCGGTATTCAATTTCCCC-3';            (W266T; SEQ ID NO: 36)
```

-continued (E) 5'-CCCTAACTAACAACAAATCAGAAAACTCAGTTACAAGC-3' and  (E478Q; SEQ ID NO: 37)
    5'-GCTTGTAACTGAGTTTTCTGATTTGTTGTGTTAGTTAGGG-3'.    (E478Q; SEQ ID NO: 38)

EXAMPLE 9 pGA2/JS7 Vaccine Plasmid

The sequence of pGA2/JS7 is shown in FIG. 11a (SEQ ID NO:8), its functional regions and the origins of these regions in FIG. 11b and the positions of its codon mutations in FIG. 11c. In the JS7 insert, Gag sequences of HIV-1-HXB-2 are substituted for the Gag sequences of BH10. This was accomplished by PCR amplification of the HXB-2 sequence (p5' plasmid, NIH AIDS Research and Reference Program, catalog #3119) using the following primers:

```
forward     5'-GAGCTCTATCGATGCAGGACTCGGCTTGC-3'            (SEQ ID NO: 39)

and reverse 5'-CTCCAATTACTGTGAGAATTCTAATGTTCATCTTGGG-3'.  (SEQ ID NO: 40)
```

The forward primer introduced a Cla I site at the same position as that found in the JS2 insert and the reverse primer introduced a unique EcoR I site analogous to the same site in the JS2 insert. This PCR fragment was then inserted into pGA1.1 for mutagenesis. The safety mutations in the zinc finger regions and the RT mutations were then introduced as previously described for the JS2 insert. JS7 also differs from JS2 in having an inactivating codon mutation at the active site of protease. This mutation was introduced using the

```
primers:
5'-GGCAACTAAAGGAAGCTCTATTAGCCACAGGAGC-3' and  (D25A Prt1; forward; SEQ ID NO: 41)

5'-GCTCCTGTGGCTAATAGAGCTTCCTT-TAGTTGCC-3'.    (D25A Prt2; reverse; SEQ ID NO: 42)
```

Once the mutations were confirmed by sequencing, the HXB-2 Gag-Pol insert was introduced into pGA2/JS2 via the Cla I and EcoR I sites. In contrast to the JS2 insert that expresses aggregates of HIV-1 proteins due to premature cleavage of the pr55Gag polyprotein by the viral protease, the JS7 insert forms immature virus like particles (VLPs) that bud from the plasma membrane of DNA-expressing cells.

EXAMPLE 10 pGA2/JS7.1 Vaccine Plasmid

The sequence of pGA2/JS7.1 is shown in FIG. 12a (SEQ ID NO:9), its functional regions and the origins of these regions in FIG. 12b and the positions of its codon mutations in FIG. 12c. pGA2/JS7.1 is a derivative of pGA2/JS7 in which the start codon as well as an immediately upstream ATG have been mutated in vpu. These mutations were introduced to increase the level of the expression of Env. The mutations in the start codon for Vpu were accomplished using a site directed mutagenesis kit (Stratagene) and the oligonucleotides:

```
                                                          (SEQ ID NO: 43)
forward 5'-GCAGTAAGTAGTAAATCTAATCCAACCTTTAC-3' and (SEQ ID NO: 44)
reverse 5'-GTAAAGGTTGGATTAGATTTACTACTTACTGC-3'.
```

EXAMPLE 11 pGA1/IC25 Vaccine Plasmid

The sequence of pGA1/IC25 is shown in FIG. 13a (SEQ ID NO:10), its functional regions and the origins of these regions in FIG. 13b and the positions of its point mutations in FIG. 13c. The IC25 insert described here was designed with a circulating recombinant form of clades A and G (designated AG) so that it would elicit an immune response against HIV-1 sequences that predominate in West Africa. As noted above, any clade AG isolate from West Africa could be used as a reasonable representative for other clade AG isolates. Since HIV-1 isolates use different chemokine receptors as co-receptors, and the vast majority of viruses that are undergoing transmission use the CCR-5 co-receptor (Berger, *AIDS* 11(*SupplA*):S3-16, 1997), the AG vaccine insert we designed had a CCR-5-using Env. Of course, Envs that function through any other co-receptor or that have been constructed from naturally occurring or synthetic AG sequences so as to increase immunogenicity can be made and used as well.

To achieve a multiprotein-expressing clade AG vaccine insert with high expression, candidate vaccines were constructed from four different AG HIV-1 isolates, as shown in Table 2.

TABLE 2

Comparison of candidate AG vaccine inserts

| Plasmid designation | SEQuences tested | Ability to grow plasmid | Expression of Gag | Expression of Env | Comment |
|---|---|---|---|---|---|
| 418/928 | 418 gag in 928-VLP | Poor | Poor | not tested | |
| 421/928 | 421 gag in 928-VLP | Good | Good | Poor | |
| 896/928 | 896 gag in 928-VLP | Good | Good | Poor | |
| 928/928 | 928 | Good | Good | Good | chosen for vaccine, renamed pGA1/IC1 |

For each isolate, the forward primer 5'-AAGATCTATCGAT-GCAAGGACTCGGCTTGC-3' (SEQ ID NO:45) and the reverse primer 5'-TTCCAATTGCTGTGAGAATTCTCA-TGCTCTTCTTGGG-3' (SEQ ID NO:46) were used to amplify the 5' Gag-RT PCR product. The 3' PCR product for the Env region encompassed the vpu, tat, rev, and env sequences and the splice acceptor sites necessary for proper processing and expression of their respective mRNAs. An EcoR I site was introduced at the 5' end of this product and Nhe I and Rsr II sites were introduced into the 3' end. A forward primer 5'-AAGGGGTTAAAGCTATAATAAG-AATTCTGCA-3' (SEQ ID NO:47) and a reverse primer 5'-CCTTTGCTGCCCTATCTGA-TTCTTCTAGG-3' (SEQ ID NO:48) were used to amplify the 3' PCR product. Of these, those from patient 928 proved particularly favorable for further development (Table 2. The 928 sequences with deletions but not codon mutations were designated IC1.

The strategy used to construct IC25, a more disabled virus than IC1, was similar to that used to construct JS7 from JS1. Specifically four codon mutations were introduced into gag sequences to inactivate the zinc fingers that are involved in RNA packaging, three codon mutations were introduced into pol sequences to inactivate transcription, strand transfer and RNaseH activities of reverse transcriptase and the codon at the active site of the protease was mutated to limit proteolytic cleavage of viral Gag proteins and the maturation of viral particles. The protease mutations also limited premature cleavage of the Gag polyprotein and allowed budding of immature VLPs.

The inactivating codon mutations were made using a site directed mutagenesis kit (Stratagene) following the manufacturer's protocol. All mutations were confirmed by sequencing. Primer pairs used for the mutagenesis were:

(A) 5'-GCCAGAGAATAATAAAGAGCTTCAACAGCGGCAAAGAAGG-3' and (C3905, C393S; SEQ ID NO: 49)
    5'-CCTTCTTTGCCGCTGTTGAAGCTCTTTATTATTCTCTGGC-3';       (C390S, C393S; SEQ ID NO: 50)

(B) 5'-CCTAGAAAGAGAGGCAGCTGGAAAAGCGGAAAGGAAGG-3' and      (C411S, C414S; SEQ ID NO: 51)
    5'-CCTTCCTTTCCGCTTTTCCAGCTGCCTCTCTTTCTAGG-3';          (C414S 928 ZN4; SEQ ID NO: 52)

(C) 5'-CCAATATATGAACGATTTATATGTAGGATCTGAC-3' and           (D185N; SEQ ID NO: 53)
    5'-GTCAGATCCTACATATAAATCGTTCATATATTGG-3';              (D185N; SEQ ID NO: 54)

(D) 5'-GGGAAAACTAAATACCGCAAGTCAGATTTATGCAGG-3' and         (W266T; SEQ ID NO: 55)
    5'-CCTGCATAAATCTGACTTGCGGTATTTAGTTTTCCC-3'; and        (W266T; SEQ ID NO: 56)

(E) 5'-CCCTAATTGAGACAACAAATCAAAAGACTCAGTTACATGC-3' and     (E478Q; SEQ ID NO: 57)
    5'-GCATGTAACTGAGTCTTTTGATTTGTTGTCTCAATTAGGG-3'.        (E478Q; SEQ ID NO: 58)

(F) 5'-GCCAATAGAAGCCCTATTAAACACAGGAGC-3' and               (D25A; SEQ ID NO: 59)
    5'-GCTCCTGTGTTTAATAGGGCTTCTATTGGC-3'.                  (D25A; SEQ ID NO: 60)

EXAMPLE 12

PGA1/IC2

The sequence of pGA1/IC2 is shown in FIG. 14a (SEQ ID NO:11), its functional regions and the origins of these regions in FIG. 14b and the positions of its point mutations in FIG. 14c. pGA1/IC2 is identical to pGA1/IC25 except for not containing the inactivating point mutation in protease.

EXAMPLE 13

PGA1/IC48

The sequence of pGA1/IC48 is shown in FIG. 15a (SEQ ID NO:12), its functional regions and the origins of these regions in FIG. 15b and the positions of its point mutations in FIG. 15c. pGA1/IC48 is identical to pGA1/IC25 except that the codon mutation in protease is one that occurred in a drug resistant mutant mutant (Jacobsen et al., Virology 206:527-534, 1995). This mutation only partially inactivates the protease function. Mutagenesis was carried out using Stratagene kits and the following oligonucleotides: 5'-CCAAAAAT-GATAGtGGGAATTGGAGG-3' (G48V 928; SEQ ID NO:61) and 5'-CCTCCAATTCCCaCTATCATTTTTGG-3' (G48V 928; SEQ ID NO:62). This mutation only partially inactivates the protease function.

EXAMPLE 14

PGA1/IC90

The sequence of pGA1/IC90 is shown in FIG. 16a (SEQ ID NO:13), its functional regions and the origins of these regions in FIG. 16b and the positions of its point mutations in FIG. 16c. pGA1/IC90 is identical to pGA1/IC25 except that the codon mutation in protease is one that occurred in a drug resistant mutant (Jacobsen et al., *Virology* 206:527-534, 1995). This mutation only partially inactivates the protease function. Mutagenesis was carried out using Stratagene kits and the following oligonucleotides:

(M90L; SEQ ID NO: 63)
5'GGACGAAATATGaTGACTCAGATTGGT-3' and (M90L; SEQ ID NO: 64)
5'-ACCAATCTGAGTCAtCATATTTCGTCC-3'.

EXAMPLE 15 pGA1/IN3

The sequence of pGA1/IN3 is shown in FIG. 17a (SEQ ID NO:14), its functional regions and the origins of these regions in FIG. 17b and the positions of its point mutations in FIG. 17c. The IN3 insert described here was constructed from a clade C sequence recovered from a virus in India. As noted above, any clade C isolate could be used as a reasonable representative for other clade C isolates. Since HIV-1 isolates use different chemokine receptors as co-receptors, and the vast majority of viruses that are undergoing transmission use the CCR-5 co-receptor (Berger, *AIDS* 11(*Suppl A*):S3-16, 1997), the C vaccine insert we chose to construct had a CCR-5-using Env. Of course, Envs that function through any other co-receptor or that have been constructed from naturally occurring or synthetic C sequences so as to increase immunogenicity can be made and used as well.

To achieve a multiprotein-expressing clade C vaccine insert with high expression, candidate vaccines were constructed from four different clade C HIV-1 sequences that were obtained from the US NIAID AIDS repository, as shown in Table 3. Of these, those from the Indian clone proved particularly favorable for further development.

TABLE 3

Comparison of clade C candidate vaccine inserts

| Isolate and Genbank Accession # | Ability to grow plasmid | Expression of Gag | Expression of Env | Comment |
|---|---|---|---|---|
| South Africa AF286227 | Good | Good | Good | |
| Israel AF286233 | Good | Good | Good | |
| Tanzania AF286235 | Good | Good | Good | |
| India AF286231 | Good | Good | Very good | Chosen for vaccine, renamed pGA1/IN1 |

5' and 3' sequences from the Indian clone were cloned into pGA1.2 using oligonucleotides and PCR to generate 5' and 3' fragments. The 5' fragment encoding Gag and RT was generated using the forward primer 5'-CGCAGGATCCGGCT-TGCTGAAG-3' (SEQ ID NO:65), which incorporated a BamH I site at the 5' end of the fragment, and the reverse primer 5'-TCTACTCGAGCTTATTATAGCACTCTCCTG-3' (SEQ ID NO:66), which incorporated an Xho I site as well as two stop codons at the 3' end of the fragment. The 3' fragment encoding Tat, Rev, Vpu, and Env was generated using the forward primer 5'-CCTCTCGAGATACTTGGA-CAGGAG-3' (SEQ ID NO:67) and the reverse primer 5'-CACTTGCTAGCCATTTTACTGCAAAGC-3' (SEQ ID NO:68). These were designed such that Xho I and Nhe I restriction sites were incorporated at the 5' and 3' ends, respectively of the 3' fragment. These fragments were introduced into pGA1.2 using directed cloning to create pGA1.2/IN1.

The strategy used to construct IN3, a more disabled virus than IN1, was similar to that used to construct JS7 from JS1. Specifically four codon mutations were introduced into gag sequences to inactivate the zinc fingers that are involved in RNA packaging, three codon mutations were introduced into pol sequences to inactivate transcription, strand transfer and RNaseH activities of reverse transcriptase and the codon at the active site of the protease was mutated to limit proteolytic cleavage of viral Gag proteins and the maturation of viral particles. The protease mutations also limited premature cleavage of the Gag polyprotein and allowed budding of immature VLPs.

The inactivating codon mutations were made using a site directed mutagenesis kit (Stratagene) following the manufacturer's protocol. All mutations were confirmed by sequencing. Primer pairs used for the mutagenesis were:

EXAMPLE 16 pGA1/IN2

The sequence of pGA1/IN2 is shown in FIG. 18a (SEQ ID NO: 5), its functional regions and the origins of these regions in FIG. 18b and the positions of its point mutations in FIG. 18c. pGA1IN2 differs from pGA1/IN3 in not having the D25N Inactivating point mutation in protease.

EXAMPLE 17

Sequences Provided for Matched rMVAs

Sequences for the JS, IC, and IN inserts were used to prepare matched recombinant modified vaccinia Ankara (rMVA) vectors. These matched vectors can be used as booster inoculations for the various DNAs. They can also be used for both priming and boosting an anti-HIV immune response. The sequences provided to generate the viral vector included the three inactivating point mutations in reverse transcriptase. A representative study, in which a recombinant MVA vector was constructed and characterized, follows.

MVA virus (which may be obtained from the American Type Culture Collection) was plaque purified three times by terminal dilutions in chicken embryo fibroblasts (CEF), which were made from 9-day old SPF Premium SPAFAS fertile chicken eggs, distributed by B and E eggs (Stevens, Pa.). Secondary CEF cells were infected at an MOI of 0.05 of MVA and transfected with 2 pLW-48 (as described above; see FIGS. 20A and 20B). Following a two-day incubation at 37° C., the virus was harvested, frozen and thawed three times. It was then plated on CEF plates. At "four days," those foci of infection that stained blue after addition of X-gluc substrate, indicating that recombination had occurred between the plasmid and the infecting virus, were picked and inoculated on CEF plates. Again, those foci that stained blue were picked. These GUS-containing foci were plated out in triplicate and analyzed for GUS staining (which we wanted to now delete) and ADA envelope expression. Individual foci were picked from the third replicate plates of those samples that had about equal numbers of mixed populations of GUS staining and non-staining foci as well as mostly envelope staining foci. These foci were again plated out in triplicate and analyzed the same way. After five passages, a virus was derived that expressed the envelope protein but which had deleted the GUS gene because of the double repeat. By immunostaining, this virus also expressed the Gag-Pol protein.

```
(A) 5'-CTAAAAGAACTGTTAAATCCTTCAACTCTGGCAAGGAAGGGCAC-3' and (C390S, C393S; SEQ ID NO: 70)
    5'-GTGCCCTTCCTTGCCAGAGTTGAAGGATTTAACAGTTCTTTTAG-3';     (C390S, C393S; SEQ ID NO: 71)

(B) 5'-CTAGGAAAAAAGGCTCTTGGAAATCTGGAAAGGAAGGACAC-3' and    (C411S, C414S; SEQ ID NO: 72)
    5'-GTGTCCTTCCTTTCCAGATTTCCAAGAGCCTTTTTTCCTAG-3':        (C411S and C414S; SEQ ID NO:
                                                             73)

(C) 5'-GTCATCTATCAATATATGAATGACTTGTATGTAG-3' and           (D185N, SEQ ID NO: 74)
    5'-CTACATACAAGTCATTCATATATTGATAGATGAC-3';               (D185N, SEQ ID NO: 75)

(D) 5'-GTGGGAAAATTAAACACGGCAAGCCAGATTTAC-3' and            (W266T, SEQ ID NO: 76)
    5'-GTAAATCTGGCTTGCCGTGTTTAATTTTCCCAC-3';                (W266T, SEQ ID NO: 77)

(E) 5'-CAAATCAGAAGACTCAATTACAAGCAATTTATC-3' and            (E478Q, SEQ ID NO: 78)
    5'-GATAAATTGCTTGTAATTGAGTCTTCTGATTTG-3' and             (E478Q, SEQ ID NO: 79)

(F) 5'-GGAGGCTCTCTTAGcCACAGGAGCAGATG-3' and                (D25N, SEQ ID NO: 80)
    5'-CATCTGCTCCTGTGgCTAAGAGAGCCTCC-3'.                    (D25N, SEQ ID NO 81)
```

Aliquots of MVA/HIV48 infected cell lysates were analyzed by radio-immunoprecipitation and immunostaining with monoclonal antibodies for expression of both the Env and Gag-Pol protein. In both of these tests, each of these proteins was detected. The recombinant virus was shown to produce gag particles in the supernatant of infected cells by pelleting the $^{35}$S-labeled particles on a 20% sucrose cushion. By electron microscopy, gag particles were visualized both outside and budding from cells as well as within vacuoles of cells. The gag particles had envelope protein on their surface.

Thus, we made a recombinant MVA virus that expressed the ADA truncated envelope and the HXB2 Gag-Pol protein. The MVA recombinant virus is made using a transiently expressed GUS marker that is deleted in the final virus. High expression of the ADA envelope is possible because of a new hybrid early/late promoter (Psyn II; see, e.g., FIGS. 21, 22, and 24). In addition, the envelope has been truncated, as this may enhance the amount of protein on the surface of the infected cells and hence enhance immunogenicity. Stability of the recombinant may also be enhanced.

---

What is claimed is:

1. A method of eliciting a cellular and humoral immune response to an HIV antigen in a human subject comprising:
   (a) administering to the human subject a composition comprising a DNA vector encoding at least: HIV Gag, HIV Pol lacking the integrase domain, HIV Tat, HIV Rev, HIV Vpu, and HIV Env, all of which are of a selected HIV chosen from the group consisting of HIV clades A, B, C, D, E, F, G, H, I, J, K, L, and HIV AG, wherein the DNA vector comprises: nucleotides 6,627-9,506 of SEQ ID NO:8 or nucleotides 6,643-10,466 of SEQ ID NO:14; and
   (b) administering to the subject a composition comprising a modified vaccinia Ankara virus expressing at least one HIV antigen, wherein a cellular and humoral immune response to an HIV antigen is elicited in the human subject.

2. The method of claim 1 wherein the selected HIV is chosen from the group consisting of HIV clade B, HIV clade C, and HIV AG.

3. The method of claim 1 wherein the selected HIV clade is HIV clade B.

4. The method of claim 1 wherein the DNA vector comprises: an antibiotic resistance gene, a lambda T0 terminator and the CMV immediate early promoter.

5. The method of claim 1 wherein the modified vaccinia Ankara virus expresses HIV Gag.

6. The method of claim 1 wherein the modified Ankara virus expresses at least HIV Gag and HIV Pol, wherein the integrase domain of the HIV Pol is deleted.

7. The method of claim 6 wherein the modified Ankara virus expresses at least: HIV Gag; HIV Pol, wherein the integrase domain of the HIV Pol is deleted; and a truncated HIV Env.

8. The method of claim 1 wherein the HIV Gag has a mutation in a zinc finger domain that reduces RNA packaging activity.

9. The method of claim 1 wherein the HIV Pol has a mutation that reduces protease activity.

10. The method of claim 1 wherein the HIV Pol has a mutation that reduces polymerase activity.

11. The method of claim 1 wherein the HIV Pol has a mutation that reduces strand transfer activity.

12. The method of claim 1 wherein the HIV Pol has a mutation that reduces RNase H activity.

13. A method of eliciting a cellular and humoral immune response to an HIV antigen in a human subject comprising:
   (a) administering to the human subject a composition comprising a DNA vector selected from the group consisting of pGA2/JS7 (SEQ ID NO: 8), pGA1/IN3 (SEQ ID NO:14), pGA1/IN2 (SEQ ID NO: 15), pGA1/IC2 (SEQ ID NO: 11) and pGA1/IC25 (SEQ ID NO: 10); and
   (b) administering to the human subject a composition comprising a modified vaccinia Ankara virus expressing at least one HIV antigen,
wherein a cellular and humoral immune response to an HIV antigen is elicited in the human subject.

14. The method of claim 13 wherein the modified Ankara virus expresses at least HIV Gag and HIV Pol, wherein the integrase domain of the HIV Pol is deleted.

15. The method of claim 14 wherein the modified Ankara virus expresses at least: HIV Gag; HIV Pol, wherein the integrase domain of the HIV Pol is deleted; and a truncated HIV Env.

16. The method of claim 13 wherein the DNA vector is pGA2/JS7 (SEQ ID NO: 8).

17. The method of claim 14 wherein the DNA vector is pGA2/JS7 (SEQ ID NO: 8).

18. The method of claim 15 wherein the DNA vector is pGA2/JS7 (SEQ ID NO: 8).

* * * * *

UNITED STATES PATENT AND TRADEMARK OFFICE
CERTIFICATE OF CORRECTION

| | | |
|---|---|---|
| PATENT NO. | : 8,623,379 B2 | Page 1 of 1 |
| APPLICATION NO. | : 10/336566 | |
| DATED | : January 7, 2014 | |
| INVENTOR(S) | : Robinson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 449 days.

Signed and Sealed this
Twenty-first Day of April, 2015

Michelle K. Lee
*Director of the United States Patent and Trademark Office*

SEQUENCE LISTING

<160> NUMBER OF SEQ ID NOS: 87

<210> SEQ ID NO 1
<211> LENGTH: 3897
<212> TYPE: DNA
<213> ORGANISM: Artificial Sequence
<220> FEATURE:
<223> OTHER INFORMATION: Synthetically generated vector sequence-pGA-1

<400> SEQUENCE: 1

```
cgacaatatt ggctattggc cattgcatac gttgtatcta tatcataata tgtacattta      60
tattggctca tgtccaatat gaccgccatg ttgacattga ttattgacta gttattaata     120
gtaatcaatt acgggttcat tagttcatag cccatatatg gagttccgcg ttacataact     180
tacggtaaat ggcccgcctg gctgaccgcc caacgacccc cgcccattga cgtcaataat     240
gacgtatgtt cccatagtaa cgccaatagg gactttccat tgacgtcaat gggtggagta     300
tttacggtaa actgcccact tggcagtaca tcaagtgtat catatgccaa gtccgccccc     360
tattgacgtc aatgacggta aatggcccgc ctggcattat gcccagtaca tgaccttacg     420
ggactttcct acttggcagt acatctacgg tattagtcat cggctattac catggtgatg     480
cggttttggc agtacaccaa tgggcgtgga tagcggtttg actcacgggg atttccaagt     540
ctccacccca ttgacgtcaa tgggagtttg ttttggcacc aaaatcaacg ggactttcca     600
aaatgtcgta taaccccgc cccgttgacg caaatgggcg gtaggcgtgt acggtgggag     660
gtctatataa gcagagctcg tttagtgaac cgtcagatcg cctggagacg ccatccacgc     720
tgttttgacc tccatagaag acaccgggac cgatccagcc tccgcggccg ggaacggtgc     780
attggaacgc ggattccccg tgccaagagt gacgtaagta ccgcctatag actctatagg     840
cacacccctt tggctcttat gcatgctata ctgtttttgg cttggggcct atacaccccc     900
gcttccttat gctataggtg atggtatagc ttagcctata ggtgtgggtt attgaccatt     960
attgaccact cccctattgg tgacgatact ttccattact aatccataac atggctcttt    1020
gccacaacta tctctattgg ctatatgcca atactctgtc cttcagagac tgacacggac    1080
tctgtatttt tacaggatgg ggtcccattt attatttaca aattcacata tacaacaacg    1140
ccgtcccccg tgcccgcagt ttttattaaa catagcgtgg gatctccacg cgaatctcgg    1200
gtaccgtgtt ccggacatgg gytcttctcc ggtagcggcg gagcttccac atccgagccc    1260
tggtcccatg cctccagcgg ctcatggtcg ctcggcagct ccttgctcct aacagtggag    1320
gccagactta ggcacagcac aatgcccacc accaccagtg tgccgcacaa ggccgtggcg    1380
gtagggtatg tgtctgaaaa tgagctcgga gattgggctc gcaccgctga cgcagatgga    1440
agacttaagg cagcggcaga agaagatgca ggcagctgag ttgttgtatt ctgataagag    1500
tcagaggtaa ctcccgttgc ggtgctgtta acggtggagg gcagtgtagt ctgagcagta    1560
ctcgttgctg ccgcgcgcgc caccagacat aatagctgac agactaacag actgttcctt    1620
```

```
tccatgggtc ttttctgcag tcaccatcga tgcttgcaat catggatgca atgaagagag   1680
ggctctgctg tgtgctgctg ctgtgtggag cagtcttcgt ttcggctagc cccgggtgat   1740
aaacggaccg cgcaatccct aggctgtgcc ttctagttgc cagccatctg ttgtttgccc   1800
ctcccccgtg ccttccttga ccctggaagg tgccactccc actgtccttt cctaataaaa   1860
tgaggaaatt gcatcgcatt gtctgagtag gtgtcattct attctggggg gtggggtggg   1920
gcaggacagc aaggggagg attgggaaga caatagcagg catgctgggg atgcggtggg   1980
ctctatataa aaacgcccg gcggcaaccg agcgttctga acgctagagt cgacaaattc   2040
agaagaactc gtcaagaagg cgatagaagg cgatgcgctg cgaatcggga gcggcgatac   2100
cgtaaagcac gaggaagcgg tcagcccatt cgccgccaag ctcttcagca atatcacggg   2160
tagccaacgc tatgtcctga tagcggtctg ccacacccag ccggccacag tcgatgaatc   2220
cagaaaagcg gccattttcc accatgatat tcggcaagca ggcatcgcca tgggtcacga   2280
cgagatcctc gccgtcgggc atgctcgcct tgagcctggc gaacagttcg gctggcgcga   2340
gcccctgatg ctcttcgtcc agatcatcct gatcgacaag accggcttcc atccgagtac   2400
gtgctcgctc gatgcgatgt ttcgcttggt ggtcgaatgg gcaggtagcc ggatcaagcg   2460
tatgcagccg ccgcattgca tcagccatga tggatacttt ctcggcagga gcaaggtgag   2520
atgacaggag atcctgcccc ggcacttcgc ccaatagcag ccagtccctt cccgcttcag   2580
tgacaacgtc gagcacagct gcgcaaggaa cgcccgtcgt ggccagccac gatagccgcg   2640
ctgcctcgtc ttgcagttca ttcagggcac cggacaggtc ggtcttgaca aaaagaaccg   2700
ggcgcccctg cgctgacagc cggaacacgg cggcatcaga gcagccgatt gtctgttgtg   2760
cccagtcata gccgaatagc ctctccaccc aagcggccgg agaacctgcg tgcaatccat   2820
cttgttcaat catgcgaaac gatcctcatc ctgtctcttg atcagatctt gatccctgc   2880 gccatcagat cctggcggc aagaaagcca tccagtttac tttgcagggc ttcccaacct   2940
taccagaggg cgccccagct ggcaattccg gttcgcttgc tgtccataaa accgcccagt   3000
ctagctatcg ccatgtaagc ccactgcaag ctacctgctt tctctttgcg cttgcgtttt   3060
cccttgtcca gatagcccag tagctgacat tcatccgggg tcagcaccgt ttctgcggac   3120
tggcttccta cgtgaaaagg atctaggtga agatccttt tgataatctc atgaccaaaa   3180 tccctaacg tgagttttcg ttccactgag cgtcagaccc cgtagaaaag atcaaaggat   3240
cttcttgaga tcctttttt ctgcgcgtaa tctgctgctt gcaaacaaa aaaccaccgc   3300 taccagcggt ggtttgtttg ccggatcaag agctaccaac tcttttttccg aaggtaactg   3360 gcttcagcag agcgcagata ccaaatactg ttcttctagt gtagccgtag ttaggccacc   3420
acttcaagaa ctctgtagca ccgcctacat acctcgctct gctaatcctg ttaccagtgg   3480
ctgctgccag tggcgataag tcgtgtctta ccgggttgga ctcaagacga tagttaccgg   3540
ataaggcgca gcggtcgggc tgaacggggg gttcgtgcac acagcccagc ttggagcgaa   3600
cgacctacac cgaactgaga tacctacagc gtgagctatg agaaagcgcc acgcttcccg   3660
aagggagaaa ggcggacagg tatccggtaa gcggcagggt cggaacagga gagcgcacga   3720
gggagcttcc agggggaaac gcctggtatc tttatagtcc tgtcgggttt cgccacctct   3780
gacttgagcg tcgattttg tgatgctcgt caggggggcg gagcctatgg aaaaacgcca   3840
gcaacgcggc cttttacgg ttcctggcct tttgctggcc ttttgctcac atgttgt       3897
```

<210> SEQ ID NO 2
<211> LENGTH: 3925

<212> TYPE: DNA
<213> ORGANISM: Artificial Sequence
<220> FEATURE:
<223> OTHER INFORMATION: Synthetically generated vector sequence-pGA 1.1

<400> SEQUENCE: 2

| | | | | | |
|---|---|---|---|---|---|
| cgacaatatt | ggctattggc | cattgcatac | gttgtatcta | tatcataata | tgtacattta | 60 |
| tattggctca | tgtccaatat | gaccgccatg | ttgacattga | ttattgacta | gttattaata | 120 |
| gtaatcaatt | acgggttcat | tagttcatag | cccatatatg | gagttccgcg | ttacataact | 180 |
| tacggtaaat | ggcccgcctg | gctgaccgcc | caacgacccc | cgcccattga | cgtcaataat | 240 |
| gacgtatgtt | cccatagtaa | cgccaatagg | gactttccat | tgacgtcaat | gggtggagta | 300 |
| tttacggtaa | actgcccact | tggcagtaca | tcaagtgtat | catatgccaa | gtccgccccc | 360 |
| tattgacgtc | aatgacggta | aatggcccgc | ctggcattat | gcccagtaca | tgaccttacg | 420 |
| ggactttcct | acttggcagt | acatctacgt | attagtcat | cggctattac | catggtgatg | 480 |
| cggttttggc | agtacaccaa | tgggcgtgga | tagcggtttg | actcacgggg | atttccaagt | 540 |
| ctccacccca | ttgacgtcaa | tgggagtttg | ttttggcacc | aaaatcaacg | ggactttcca | 600 |
| aaatgtcgta | ataaccccgc | cccgttgacg | caaatgggcg | gtaggcgtgt | acggtgggag | 660 |
| gtctatataa | gcagagctcg | tttagtgaac | cgtcagatcg | cctggagacg | ccatccacgc | 720 |
| tgttttgacc | tccatagaag | acaccggac | cgatccagcc | tccgcggccg | gaacggtgc | 780 |
| attggaacgc | ggattccccg | tgccaagagt | gacgtaagta | ccgcctatag | actctatagg | 840 |
| cacacccctt | tggctcttat | gcatgctata | ctgttttgg | cttggggcct | atacaccccc | 900 |
| gcttccttat | gctataggtg | atggtatagc | ttagcctata | ggtgtgggtt | attgaccatt | 960 |
| attgaccact | cccctattgg | tgacgatact | ttccattact | aatccataac | atggctcttt | 1020 |
| gccacaacta | tctctattgg | ctatatgcca | atactctgtc | cttcagagac | tgacacggac | 1080 |
| tctgtatttt | tacaggatgg | ggtcccattt | attatttaca | aattcacata | tacaacaacg | 1140 |
| ccgtcccccg | tgcccgcagt | ttttattaaa | catagcgtgg | gatctccacg | cgaatctcgg | 1200 |
| gtaccgtgtt | ccggacatgg | gytcttctcc | ggtagcggcg | gagcttccac | atccgagccc | 1260 |
| tggtcccatg | cctccagcgg | ctcatggtcg | ctcggcagct | ccttgctcct | aacagtggag | 1320 |
| gccagactta | ggcacagcac | aatgcccacc | accaccagtg | tgccgcacaa | ggccgtggcg | 1380 |
| gtagggtatg | tgtctgaaaa | tgagctcgga | gattgggctc | gcaccgctga | cgcagatgga | 1440 |
| agacttaagg | cagcggcaga | agaagatgca | ggcagctgag | ttgttgtatt | ctgataagag | 1500 |
| tcagaggtaa | ctcccgttgc | ggtgctgtta | acggtggagg | gcagtgtagt | ctgagcagta | 1560 |
| ctcgttgctg | ccgcgcgcgc | caccagacat | aatagctgac | agactaacag | actgttcctt | 1620 |
| tccatgggtc | ttttctgcag | tcaccatcga | tgcttgcaat | catggatgca | atgaagagag | 1680 |
| ggctctgctg | tgtgctgctg | ctgtgtggag | aattcttcgt | ttctgctgct | gtgtggagaa | 1740 |
| ttcttcgttt | cggctagccc | cgggtgataa | acggaccgcg | caatccctag | gctgtgcctt | 1800 |
| ctagttgcca | gccatctgtt | gtttgcccct | ccccgtgcc | ttccttgacc | ctggaaggtg | 1860 |
| ccactcccac | tgtcctttcc | taataaaatg | aggaaattgc | atcgcattgt | ctgagtaggt | 1920 |
| gtcattctat | tctgggggt | ggggtgggc | aggacagcaa | ggggaggat | tgggaagaca | 1980 |
| atagcaggca | tgctggggat | gcggtgggct | ctatataaaa | acgcccggc | ggcaaccgag | 2040 |
| cgttctgaac | gctagagtcg | acaaattcag | aagaactcgt | caagaaggcg | atagaaggcg | 2100 |
| atgcgctgcg | aatcgggagc | ggcgataccg | taaagcacga | ggaagcggtc | agcccattcg | 2160 |
| ccgccaagct | cttcagcaat | atcacgggta | gccaacgcta | tgtcctgata | gcggtctgcc | 2220 |

```
acacccagcc ggccacagtc gatgaatcca gaaaagcggc catttccac catgatattc    2280 ggcaagcagg catcgccatg ggtcacgacg agatcctcgc cgtcgggcat gctcgccttg    2340
agcctggcga acagttcggc tggcgcgagc ccctgatgct cttcgtccag atcatcctga    2400
tcgacaagac cggcttccat ccgagtacgt gctcgctcga tgcgatgttt cgcttggtgg    2460
tcgaatgggc aggtagccgg atcaagcgta tgcagccgcc gcattgcatc agccatgatg    2520
gatactttct cggcaggagc aaggtgagat gacaggagat cctgcccgg cacttcgccc     2580 aatagcagcc agtcccttcc cgcttcagtg acaacgtcga gcacagctgc gcaaggaacg    2640
cccgtcgtgg ccagccacga tagccgcgct gcctcgtctt gcagttcatt cagggcaccg    2700
gacaggtcgg tcttgacaaa agaaccggg cgccctgcg ctgacagccg gaacacggcg      2760
gcatcagagc agccgattgt ctgttgtgcc cagtcatagc cgaatagcct ctccacccaa    2820
gcggccggag aacctgcgtg caatccatct tgttcaatca tgcgaaacga tcctcatcct    2880
gtctcttgat cagatcttga tccctgcgc catcagatcc ttggcggcaa gaaagccatc     2940
cagtttactt tgcagggctt cccaaccttaa ccagagggcg ccccagctgg caattccggt   3000
tcgcttgctg tccataaaac cgcccagtct agctatcgcc atgtaagccc actgcaagct    3060
acctgctttc tctttgcgct tgcgttttcc cttgtccaga tagcccagta gctgacattc    3120
atccggggtc agcaccgttt ctgcggactg gctttctacg tgaaaaggat ctaggtgaag    3180
atcctttttg ataatctcat gaccaaaatc ccttaacgtg agttttcgtt ccactgagcg    3240
tcagaccccg tagaaaagat caaaggatct tcttgagatc cttttttct gcgcgtaatc     3300 tgctgcttgc aaacaaaaaa accaccgcta ccagcggtgg tttgtttgcc ggatcaagag    3360
ctaccaactc ttttccgaa ggtaactggc ttcagcagag cgcagatacc aaatactgtt     3420
cttctagtgt agccgtagtt aggccaccac ttcaagaact ctgtagcacc gcctacatac    3480
ctcgctctgc taatcctgtt accagtggct gctgccagtg gcgataagtc gtgtcttacc    3540
gggttggact caagacgata gttaccggat aaggcgcagc ggtcgggctg aacggggggt    3600
tcgtgcacac agcccagctt ggagcgaacg acctacaccg aactgagata cctacagcgt    3660
gagctatgag aaagcgccac gcttcccgaa gggagaaagg cggacaggta tccggtaagc    3720
ggcagggtcg gaacaggaga gcgcacgagg gagcttccag ggggaaacgc ctggtatctt    3780
tatagtcctg tcgggtttcg ccacctctga cttgagcgtc gatttttgtg atgctcgtca    3840 gggggggcgga gcctatggaa aaacgccagc aacgcggccc ttttacggtt cctggccttt    3900
tgctggcctt ttgctcacat gttgt                                          3925
```

<210> SEQ ID NO 3
<211> LENGTH: 3925
<212> TYPE: DNA
<213> ORGANISM: Artificial Sequence
<220> FEATURE:
<223> OTHER INFORMATION: Synthetically generated vector sequence-pGA 1.2

<400> SEQUENCE: 3

```
cgacaatatt ggctattggc cattgcatac gttgtatcta tcataata tgtacattta       60 tattggctca tgtccaatat gaccgccatg ttgacattga ttattgacta gttattaata   120
gtaatcaatt acgggttcat tagttcatag cccatatatg gagttccgcg ttacataact    180
tacggtaaat ggcccgcctg gctgaccgcc caacgacccc cgcccattga cgtcaataat    240
gacgtatgtt cccatagtaa cgccaatagg gactttccat tgacgtcaat gggtggagta    300
tttacggtaa actgcccact tggcagtaca tcaagtgtat catatgccaa gtccgccccc    360
```

```
tattgacgtc aatgacggta aatggcccgc ctggcattat gcccagtaca tgaccttacg    420
ggactttcct acttggcagt acatctacgg tattagtcat cggctattac catggtgatg    480
cggttttggc agtacaccaa tgggcgtgga tagcggtttg actcacgggg atttccaagt    540
ctccacccca ttgacgtcaa tgggagtttg ttttggcacc aaaatcaacg ggactttcca    600
aaatgtcgta ataaccccgc cccgttgacg caaatgggcg gtaggcgtgt acggtgggag    660
gtctatataa gcagagctcg tttagtgaac cgtcagatcg cctggagacg ccatccacgc    720
tgttttgacc tccatagaag acaccggac cgatccagcc tccgcggccg gaacggtgc    780 attggaacgc ggattccccg tgccaagagt gacgtaagta ccgcctatag actctatagg    840 cacaccccctt tggctcttat gcatgctata ctgttttgg cttggggcct atacacccc    900 gcttccttat gctataggtg atggtatagc ttagcctata ggtgtgggtt attgaccatt    960
attgaccact cccctattgg tgacgatact ttccattact aatccataac atggctcttt    1020
gccacaacta tctctattgg ctatatgcca atactctgtc cttcagagac tgacacggac    1080
tctgtatttt tacaggatgg ggtcccattt attatttaca aattcacata tacaacaacg    1140 ccgtccccg tgcccgcagt ttttattaaa catagcgtgg gatctccacg cgaatctcgg    1200
gtaccgtgtt ccggacatgg gytcttctcc ggtagcggcg gagcttccac atccgagccc    1260
tggtcccatg cctccagcgg ctcatggtcg ctcggcagct ccttgctcct aacagtggag    1320
gccagactta ggcacagcac aatgcccacc accaccagtg tgccgcacaa ggccgtggcg    1380
gtagggtatg tgtctgaaaa tgagctcgga gattgggctc gcaccgctga cgcagatgga    1440
agacttaagg cagcggcaga agaagatgca ggcagctgag ttgttgtatt ctgataagag    1500
tcagaggtaa ctcccgttgc ggtgctgtta acggtggagg gcagtgtagt ctgagcagta    1560
ctcgttgctg ccgcgcgcgc caccagacat aatagctgac agactaacag actgttcctt    1620
tccatgggtc ttttctgcag tcaccatgga tccttgcact cgaggatgca atgaagagag    1680
ggctctgctg tgtgctgctg ctgtgtggag aattcttcgt ttctgctgct gtgtggagaa    1740
ttcttcgttt cggctagccc cgggtgataa acggaccgcg caatccctag gctgtgcctt    1800
ctagttgcca gccatctgtt gtttgcccct ccccgtgcc ttccttgacc ctggaaggtg    1860
ccactcccac tgtcctttcc taataaaatg aggaaattgc atcgcattgt ctgagtaggt    1920
gtcattctat tctgggggt ggggtggggc aggacagcaa gggggaggat tgggaagaca    1980
atagcaggca tgctggggat gcggtgggct ctatataaaa acgcccggc ggcaaccgag    2040 cgttctgaac gctagagtcg acaaattcag aagaactcgt caagaaggcg atagaaggcg    2100
atgcgctgcg aatcgggagc ggcgataccg taaagcacga ggaagcggtc agcccattcg    2160
ccgccaagct cttcagcaat atcacgggta gccaacgcta tgtcctgata gcggtctgcc    2220
acacccagcc ggccacagtc gatgaatcca gaaaagcggc cattttccac catgatattc    2280
ggcaagcagg catcgccatg ggtcacgacg agatcctcgc cgtcgggcat gctcgccttg    2340
agcctggcga acagttcggc tggcgcgagc ccctgatgct cttcgtccag atcatcctga    2400
tcgacaagac cggcttccat ccgagtacgt gctcgctcga tgcgatgttt cgcttggtgg    2460
tcgaatgggc aggtagccgg atcaagcgta tgcagccgcc gcattgcatc agccatgatg    2520
gatactttct cggcaggagc aaggtgagat gacaggagat cctgccccgg cacttcgccc    2580
aatagcagcc agtcccttcc cgcttcagtg acaacgtcga gcacagctgc gcaaggaacg    2640
cccgtcgtgg ccagccacga tagccgcgct gcctcgtctt gcagttcatt cagggcaccg    2700
gacaggtcgg tcttgacaaa aagaaccggg cgcccctgcg ctgacagccg gaacacggcg    2760
```

```
gcatcagagc agccgattgt ctgttgtgcc cagtcatagc cgaatagcct ctccacccaa    2820
gcggccggag aacctgcgtg caatccatct tgttcaatca tgcgaaacga tcctcatcct    2880
gtctcttgat cagatcttga tccctgcgc catcagatcc ttggcggcaa gaaagccatc    2940
cagtttactt tgcagggctt cccaaccta ccagagggcg ccccagctgg caattccggt    3000
tcgcttgctg tccataaaac cgcccagtct agctatcgcc atgtaagccc actgcaagct    3060
acctgctttc tctttgcgct tgcgttttcc cttgtccaga tagcccagta gctgacattc    3120
atccggggtc agcaccgttt ctgcggactg gctttctacg tgaaaaggat ctaggtgaag    3180
atcctttttg ataatctcat gaccaaaatc ccttaacgtg agttttcgtt ccactgagcg    3240
tcagaccccg tagaaaagat caaaggatct cttgagatc ctttttttct gcgcgtaatc    3300
tgctgcttgc aaacaaaaaa accaccgcta ccagcggtgg tttgtttgcc ggatcaagag    3360
ctaccaactc tttttccgaa ggtaactggc ttcagcagag cgcagatacc aaatactgtt    3420
cttctagtgt agccgtagtt aggccaccac ttcaagaact ctgtagcacc gcctacatac    3480
ctcgctctgc taatcctgtt accagtggct gctgccagtg gcgataagtc gtgtcttacc    3540
gggttggact caagacgata gttaccggat aaggcgcagc ggtcgggctg aacggggggt    3600
tcgtgcacac agcccagctt ggagcgaacg acctacaccg aactgagata cctacagcgt    3660
gagctatgag aaagcgccac gcttcccgaa gggagaaagg cggacaggta ccggtaagc    3720
ggcagggtcg gaacaggaga gcgcacgagg gagcttccag ggggaaacgc ctggtatctt    3780
tatagtcctg tcgggtttcg ccacctctga cttgagcgtc gatttttgtg atgctcgtca    3840
ggggggcgga gcctatggaa aaacgccagc aacgcggcc tttttacggtt cctggccttt    3900
tgctggcctt ttgctcacat gttgt                                          3925

<210> SEQ ID NO 4
<211> LENGTH: 2947
<212> TYPE: DNA
<213> ORGANISM: Artificial Sequence
<220> FEATURE:
<223> OTHER INFORMATION: Synthetically generated vector sequence-pGA 2

<400> SEQUENCE: 4
cgacaatatt ggctattggc cattgcatac gttgtatcta tatcataata tgtacattta      60
tattggctca tgtccaatat gaccgccatg ttgacattga ttattgacta gttattaata    120
gtaatcaatt acgggtcat tagttcatag cccatatatg gagttccgcg ttacataact    180
tacggtaaat ggcccgcctg gctgaccgcc caacgacccc cgcccattga cgtcaataat    240
gacgtatgtt cccatagtaa cgccaatagg gactttccat tgacgtcaat gggtggagta    300
tttacggtaa actgcccact tggcagtaca tcaagtgtat catatgccaa gtccgccccc    360
tattgacgtc aatgacggta aatggcccgc ctggcattat gcccagtaca tgaccttacg    420
ggactttcct acttggcagt acatctacgt attagtcatc gctattacca tggtgatgcg    480
gttttggcag tacaccaatg ggcgtggata gcggtttgac tcacgggat tccaagtct    540
ccacccatt gacgtcaatg ggagtttgtt ttggcaccaa aatcaacggg actttccaaa    600
atgtcgtaat aaccccgccc cgttgacgca aatgggcggt aggcgtgtac ggtgggaggt    660
ctatataagc agagctcgtt tagtgaactc attctatcga tgcttgcaat catggatgca    720
atgaagagag ggctctgctg tgtgctgctg ctgtgtggag cagtcttcgt ttcggctagc    780
cccgggtgat aaacgaccg cgcaatccct aggctgtgcc ttctagttgc agccatctg    840
ttgtttgccc ctcccccgtg ccttccttga ccctggaagg tgccactccc actgtccttt    900
```

```
cctaataaaa tgaggaaatt gcatcgcatt gtctgagtag gtgtcattct attctggggg      960
gtggggtggg gcaggacagc aaggggagg attgggaaga caatagcagg catgctgggg     1020
atgcggtggg ctctatataa aaaacgcccg gcggcaaccg agcgttctga acgctagagt     1080
cgacaaattc agaagaactc gtcaagaagg cgatagaagg cgatgcgctg cgaatcggga     1140
gcggcgatac cgtaaagcac gaggaagcgg tcagcccatt cgccgccaag ctcttcagca     1200
atatcacggg tagccaacgc tatgtcctga tagcggtctg ccacacccag ccggccacag     1260
tcgatgaatc cagaaaagcg gccatttttcc accatgatat cggcaagca ggcatcgcca     1320
tgggtcacga cgagatcctc gccgtcgggc atgctcgcct tgagcctggc gaacagttcg     1380
gctggcgcga gcccctgatg ctcttcgtcc agatcatcct gatcgacaag accggcttcc     1440
atccgagtac gtgctcgctc gatgcgatgt ttcgcttggt ggtcgaatgg gcaggtagcc     1500
ggatcaagcg tatgcagccc ccgcattgca tcagccatga tggatacttt ctcggcagga     1560
gcaaggtgag atgacaggag atcctgcccc ggcacttcgc ccaatagcag ccagtccctt     1620
cccgcttcag tgacaacgtc gagcacagct gcgcaaggaa cgcccgtcgt ggccagccac     1680
gatagccgcg ctgcctcgtc ttgcagttca ttcagggcac cggacaggtc ggtcttgaca     1740
aaaagaaccg ggcgcccctg cgctgacagc cggaacacgg cggcatcaga gcagccgatt     1800
gtctgttgtg cccagtcata gccgaatagc ctctccaccc aagcggccgg agaacctgcg     1860
tgcaatccat cttgttcaat catgcgaaac gatcctcatc ctgtctcttg atcagatctt     1920
gatccctgc gccatcagat ccttggcggc aagaaagcca tccagtttac tttgcagggc      1980
ttcccaacct taccagaggg cgccccagct ggcaattccg gttcgcttgc tgtccataaa     2040
accgcccagt ctagctatcg ccatgtaagc ccactgcaag ctacctgctt tctctttgcg     2100
cttgcgtttt cccttgtcca gatagcccag tagctgacat tcatccgggg tcagcaccgt     2160
ttctgcggac tggcttttcta cgtgaaaagg atctaggtga agatccttt tgataatctc     2220
atgaccaaaa tcccttaacg tgagttttcg ttccactgag cgtcagaccc cgtagaaaag     2280
atcaaaggat cttcttgaga tcctttttt ctgcgcgtaa tctgctgctt gcaaacaaaa     2340
aaaccaccgc taccagcggt ggtttgtttg ccggatcaag agctaccaac tctttttccg     2400
aaggtaactg gcttcagcag agcgcagata ccaaatactg ttcttctagt gtagccgtag     2460
ttaggccacc acttcaagaa ctctgtagca ccgcctacat acctcgctct gctaatcctg     2520
ttaccagtgg ctgctgccag tggcgataag tcgtgtctta ccgggttgga ctcaagacga     2580
tagttaccgg ataaggcgca gcggtcgggc tgaacggggg gttcgtgcac acagcccagc     2640
ttggagcgaa cgacctacac cgaactgaga tacctacagc gtgagctatg agaaagcgcc     2700
acgcttcccg aagggagaaa ggcggacagg tatccggtaa gcggcagggt cggaacagga     2760
gagcgcacga gggagcttcc agggggaaac gcctggtatc tttatagtcc tgtcgggttt     2820
cgccacctct gacttgagcg tcgatttttg tgatgctcgt caggggggcg gagcctatgg     2880
aaaaacgcca gcaacgcggc ctttttacgg ttcctggcct tttgctggcc ttttgctcac     2940
atgttgt                                                              2947
```

<210> SEQ ID NO 5
<211> LENGTH: 2978
<212> TYPE: DNA
<213> ORGANISM: Artificial Sequence
<220> FEATURE:
<223> OTHER INFORMATION: Synthetically generated vector sequence-pGA 2.1

<400> SEQUENCE: 5

-continued

```
cgacaatatt ggctattggc cattgcatac gttgtatcta tatcataata tgtacattta    60
tattggctca tgtccaatat gaccgccatg ttgacattga ttattgacta gttattaata   120
gtaatcaatt acggggtcat tagttcatag cccatatatg gagttccgcg ttacataact   180
tacggtaaat ggcccgcctg gctgaccgcc caacgacccc cgcccattga cgtcaataat   240
gacgtatgtt cccatagtaa cgccaatagg gactttccat tgacgtcaat gggtggagta   300
tttacggtaa actgcccact tggcagtaca tcaagtgtat catatgccaa gtccgccccc   360
tattgacgtc aatgacggta aatggcccgc ctggcattat gcccagtaca tgaccttacg   420
ggactttcct acttggcagt acatctacgt attagtcatc gctattacca tggtgatgcg   480
gttttggcag tacaccaatg ggcgtggata gcggtttgac tcacggggat ttccaagtct   540
ccaccccatt gacgtcaatg ggagtttgtt ttggcaccaa aatcaacggg actttccaaa   600
atgtcgtaat aaccccgccc cgttgacgca aatgggcggt aggcgtgtac ggtgggaggt   660
ctatataagc agagctcgtt tagtgaactc attctatcga tgcttgcaat catggatgca   720
atgaagagag ggctctgctg tgtgctgctg ctgtgtggag aattcttcgt ttcggctgct   780
gctgtgtgga gaattcttcg tttcggctag ccccgggtga taaacggacc cgcaatccc    840
taggctgtgc cttctagttg ccagccatct gttgtttgcc cctcccccgt gccttccttg   900
accctggaag gtgccactcc cactgtcctt tcctaataaa atgaggaaat tgcatcgcat   960
tgtctgagta ggtgtcattc tattctgggg ggtggggtgg ggcaggacag caaggggag   1020
gattgggaag acaatagcag gcatgctggg gatgcggtgg gctctatata aaaacgccc   1080
ggcggcaacc gagcgttctg aacgctagag tcgacaaatt cagaagaact cgtcaagaag   1140
gcgatagaag gcgatgcgct gcgaatcggg agcggcgata ccgtaaagca cgaggaagcg   1200
gtcagcccat tcgccgccaa gctcttcagc aatatcacgg gtagccaacg ctatgtcctg   1260
atagcggtct gccacaccca gccggccaca gtcgatgaat ccagaaaagc ggccattttc   1320
caccatgata ttcggcaagc aggcatcgcc atgggtcacg acgagatcct cgccgtcggg   1380
catgctcgcc ttgagcctgg cgaacagttc ggctggcgcg agccctgat gctcttcgtc   1440
cagatcatcc tgatcgacaa gaccggcttc catccgagta cgtgctcgct cgatgcgatg   1500
tttcgcttgg tggtcgaatg ggcaggtagc cggatcaagc gtatgcagcc gccgcattgc   1560
atcagccatg atggatactt tctcggcagg agcaaggtga gatgacagga gatcctgccc   1620
cggcacttcg cccaatagca gccagtccct tcccgcttca gtgacaacgt cgagcacagc   1680
tgcgcaagga acgcccgtcg tggccagcca cgatagccgc gctgcctcgt cttgcagttc   1740
attcagggca ccggacaggt cggtcttgac aaaaagaacc gggcgcccct gcgctgacag   1800
ccggaacacg gcggcatcag agcagccgat tgtctgttgt gcccagtcat agccgaatag   1860
cctctccacc caagcggccg gagaacctgc gtgcaatcca tcttgttcaa tcatgcgaaa   1920
cgatcctcat cctgtctctt gatcagatct tgatccctg cgccatcaga tccttggcgg   1980
caagaaagcc atccagttta ctttgcaggg cttcccaacc ttaccagagg gcgccccagc   2040
tggcaattcc ggttcgcttg ctgtccataa aaccgcccag tctagctatc gccatgtaag   2100
cccactgcaa gctacctgct ttctctttgc gcttgcgttt tcccttgtcc agatagccca   2160
gtagctgaca ttcatccggg gtcagcaccg tttctgcgga ctggctttct acgtgaaaag   2220
gatctaggtg aagatccttt ttgataatct catgaccaaa atcccttaac gtgagttttc   2280
gttccactga gcgtcagacc ccgtagaaaa gatcaaagga tcttcttgag atccttttt    2340
tctgcgcgta atctgctgct tgcaaacaaa aaaaccaccg ctaccagcgg tggtttgttt   2400
```

| | |
|---|---|
| gccggatcaa gagctaccaa ctcttttttcc gaaggtaact ggcttcagca gagcgcagat | 2460 |
| accaaatact gttcttctag tgtagccgta gttaggccac cacttcaaga actctgtagc | 2520 |
| accgcctaca tacctcgctc tgctaatcct gttaccagtg gctgctgcca gtggcgataa | 2580 |
| gtcgtgtctt accgggttgg actcaagacg atagttaccg gataaggcgc agcggtcggg | 2640 |
| ctgaacgggg ggttcgtgca cacagcccag cttggagcga acgacctaca ccgaactgag | 2700 |
| atacctacag cgtgagctat gagaaagcgc cacgcttccc gaagggagaa aggcggacag | 2760 |
| gtatccggta agcggcaggg tcggaacagg agagcgcacg agggagcttc caggggggaaa | 2820 |
| cgcctggtat ctttatagtc ctgtcgggtt tcgccacctc tgacttgagc gtcgattttt | 2880 |
| gtgatgctcg tcagggggc ggagcctatg gaaaaacgcc agcaacgcgg ccctttttacg | 2940 |
| gttcctggcc ttttgctggc cttttgctca catgttgt | 2978 |

<210> SEQ ID NO 6
<211> LENGTH: 2978
<212> TYPE: DNA
<213> ORGANISM: Artificial Sequence
<220> FEATURE:
<223> OTHER INFORMATION: Synthetically generated vector sequence-pGA 2.2

<400> SEQUENCE: 6

| | |
|---|---|
| cgacaatatt ggctattggc cattgcatac gttgtatcta tatcataata tgtacattta | 60 |
| tattggctca tgtccaatat gaccgccatg ttgacattga ttattgacta gttattaata | 120 |
| gtaatcaatt acggggtcat tagttcatag cccatatatg gagttccgcg ttacataact | 180 |
| tacggtaaat ggcccgcctg gctgaccgcc caacgacccc cgcccattga cgtcaataat | 240 |
| gacgtatgtt cccatagtaa cgccaatagg gactttccat tgacgtcaat gggtggagta | 300 |
| tttacggtaa actgcccact tggcagtaca tcaagtgtat catatgccaa gtccgccccc | 360 |
| tattgacgtc aatgacggta aatggcccgc ctggcattat gcccagtaca tgaccttacg | 420 |
| ggactttcct acttggcagt acatctacgt attagtcatc gctattacca tggtgatgcg | 480 |
| gttttggcag tacaccaatg ggcgtggata gcggtttgac tcacggggat ttccaagtct | 540 |
| ccaccccatt gacgtcaatg ggagtttgtt ttggcaccaa aatcaacggg actttccaaa | 600 |
| atgtcgtaat aaccccgccc cgttgacgca aatgggcggt aggcgtgtac ggtgggaggt | 660 |
| ctatataagc agagctcgtt tagtgaactc attctatgga tccttgctcg agtggatgca | 720 |
| atgaagagag ggctctgctg tgtgctgctg ctgtgtggag aattcttcgt ttcggctgct | 780 |
| gctgtgtgga gaattcttcg tttcggctag ccccgggtga taaacggacc gcgcaatccc | 840 |
| taggctgtgc cttctagttg ccagccatct gttgtttgcc cctccccgt gccttccttg | 900 |
| accctggaag gtgccactcc cactgtcctt tcctaataaa atgaggaaat tgcatcgcat | 960 |
| tgtctgagta ggtgtcattc tattctgggg gtgggtgg ggcaggacag caagggggag | 1020 |
| gattgggaag acaatagcag gcatgctggg gatgcggtgg gctctatata aaaaacgccc | 1080 |
| ggcggcaacc gagcgttctg aacgctagag tcgacaaatt cagaagaact cgtcaagaag | 1140 |
| gcgatagaag gcgatgcgct gcgaatcggg agcggcgata ccgtaaagca cgaggaagcg | 1200 |
| gtcagcccat tcgccgccaa gctcttcagc aatatcacgg gtagccaacg ctatgtcctg | 1260 |
| atagcggtct gccacaccca gccggccaca gtcgatgaat ccagaaaagc ggccattttc | 1320 |
| caccatgata ttcggcaagc aggcatcgcc atgggtcacg acgagatcct cgccgtcggg | 1380 |
| catgctcgcc ttgagcctgg cgaacagttc ggctggcgcg agcccctgat gctcttcgtc | 1440 |
| cagatcatcc tgatcgacaa gaccggcttc catccgagta cgtgctcgct cgatgcgatg | 1500 |

```
tttcgcttgg tggtcgaatg ggcaggtagc cggatcaagc gtatgcagcc gccgcattgc      1560
atcagccatg atggatactt tctcggcagg agcaaggtga gatgacagga gatcctgccc      1620
cggcacttcg cccaatagca gccagtccct tcccgcttca gtgacaacgt cgagcacagc      1680
tgcgcaagga acgcccgtcg tggccagcca cgatagccgc gctgcctcgt cttgcagttc      1740
attcagggca ccggacaggt cggtcttgac aaaaagaacc gggcgcccct cgcgctgacag      1800 ccggaacacg gcggcatcag agcagccgat tgtctgttgt gcccagtcat agccgaatag      1860
cctctccacc caagcggccg gagaacctgc gtgcaatcca tcttgttcaa tcatgcgaaa      1920
cgatcctcat cctgtctctt gatcagatct tgatccctg cgccatcaga tccttggcgg      1980
caagaaagcc atccagttta ctttgcaggg cttcccaacc ttaccagagg gcgccccagc      2040
tggcaattcc ggttcgcttg ctgtccataa accgcccag tctagctatc gccatgtaag      2100
cccactgcaa gctacctgct ttctctttgc gcttgcgttt tcccttgtcc agatagccca      2160
gtagctgaca ttcatccggg gtcagcaccg tttctgcgga ctggctttct acgtgaaaag      2220
gatctaggtg aagatccttt ttgataatct catgaccaaa atcccttaac gtgagttttc      2280
gttccactga gcgtcagacc ccgtagaaaa gatcaaagga tcttcttgag atcctttttt      2340
tctgcgcgta atctgctgct tgcaaacaaa aaaaccaccg ctaccagcgg tggtttgttt      2400
gccggatcaa gagctaccaa ctcttttcc gaaggtaact ggcttcagca gagcgcagat      2460
accaaatact gttcttctag tgtagccgta gttaggccac cacttcaaga actctgtagc      2520
accgcctaca tacctcgctc tgctaatcct gttaccagtg gctgctgcca gtggcgataa      2580
gtcgtgtctt accgggttgg actcaagacg atagttaccg gataaggcgc agcggtcggg      2640
ctgaacgggg ggttcgtgca cacagcccag cttggagcga acgacctaca ccgaactgag      2700
atacctacag cgtgagctat gagaaagcgc cacgcttccc gaagggagaa aggcggacag      2760
gtatccggta agcggcaggg tcggaacagg agagcgcacg agggagcttc caggggggaaa     2820 cgcctggtat ctttatagtc ctgtcgggtt tcgccacctc tgacttgagc gtcgattttt      2880
gtgatgctcg tcaggggggc ggagcctatg gaaaaacgcc agcaacgcgg ccctttttacg     2940 gttcctggcc ttttgctggc cttttgctca catgttgt                             2978
```

<210> SEQ ID NO 7
<211> LENGTH: 9544
<212> TYPE: DNA
<213> ORGANISM: Artificial Sequence
<220> FEATURE:
<223> OTHER INFORMATION: Synthetically generated vector sequence-pGA 2/
      JS2

<400> SEQUENCE: 7

```
atcgatgcag gactcggctt gctgaagcgc gcacggcaag aggcgagggg cggcgactgg       60
tgggtacgcc aaaattttg actagcggag gctagaagga gagagatggg tgcgagagcg      120
tcagtattaa gcgggggaga attagatcga tgggaaaaaa ttcggttaag gccagggggga     180 aagaaaaaat ataaattaaa acatatagta tgggcaagca gggagctaga acgattcgca      240
gttaatcctg gcctgttaga acatcagaa ggctgtagac aaatactggg acagctacaa       300
ccatcccttc agacaggatc agaagaactt agatcattat ataatacagt agcaaccctc      360
tattgtgtgc atcaaaggat agagataaaa gacaccaagg aagctttaga caagatagag      420
gaagagcaaa acaaaagtaa gaaaaaagca cagcaagcag cagctgacac aggacacagc      480
agtcaggtca gccaaaatta ccctatagtg cagaacatcc aggggcaaat ggtacatcag      540
```

```
gccatatcac ctagaacttt aaatgcatgg gtaaaagtag tagaagagaa ggctttcagc    600
ccagaagtaa tacccatgtt ttcagcatta tcagaaggag ccaccccaca agatttaaac    660
accatgctaa acacagtggg gggacatcaa gcagccatgc aaatgttaaa agagaccatc    720
aatgaggaag ctgcagaatg ggatagagta catccagtgc atgcagggcc tattgcacca    780
ggccagatga gagaaccaag gggaagtgac atagcaggaa ctactagtac ccttcaggaa    840
caaataggat ggatgacaaa taatccacct atcccagtag gagaaattta taaaagatgg    900
ataatcctgg gattaaataa aatagtaaga atgtatagcc ctaccagcat tctggacata    960
agacaaggac caaagaaacc ttttagagac tatgtagacc ggttctataa aactctaaga   1020
gccgagcaag cttcacagga ggtaaaaaat tggatgacag aaaccttgtt ggtccaaaat   1080
gcgaacccag attgtaagac tattttaaaa gcattgggac cagcggctac actagaagaa   1140
atgatgacag catgtcaggg agtaggagga cccggccata aggcaagagt tttggctgaa   1200
gcaatgagcc aagtaacaaa tacagctacc ataatgatgc agagaggcaa ttttaggaac   1260
caaagaaaga tggttaagag cttcaatagc ggcaaagaag gcacacagc  cagaaattgc   1320 agggccccta ggaaaaaggg cagctggaaa agcggaaagg aaggacacca aatgaaagat   1380
tgtactgaga gacaggctaa ttttttaggg aagatctggc cttcctacaa gggaaggcca   1440
gggaattttc ttcagagcag accagagcca acagccccac catttcttca gagcagacca   1500
gagccaacag ccccaccaga agagagcttc aggtctgggg tagagacaac aactcccccc   1560
cagaagcagg agccgataga caaggaactg tatccttta  acttccctcag atcactcttt   1620 ggcaacgacc cctcgtcaca ataaagatag ggggcaact  aaaggaagct ctattagata   1680
caggagcaga tgatacagta ttagaagaaa tgagtttgcc aggaagatgg aaaccaaaaa   1740
tgataggggg aattggaggt tttatcaaag taagacagta tgatcagata ctcatagaaa   1800
tctgtggaca taaagctata ggtacagtat tagtaggacc tacacctgtc aacataattg   1860
gaagaaatct gttgactcag attggttgca ctttaaattt tcccattagc cctattgaga   1920
ctgtaccagt aaaattaaag ccaggaatgg atggcccaaa agttaaacaa tggccattga   1980
cagaagaaaa aataaaagca ttagtagaaa tttgtacaga aatggaaaag gaagggaaaa   2040
tttcaaaaat tgggcctgag aatccataca atactccagt atttgccata agaaaaaag   2100 acagtactaa atggagaaaa ttagtagatt tcagagaact taataagaga actcaagact   2160
tctgggaagt tcaattagga ataccacatc ccgcagggtt aaaaaagaaa aaatcagtaa   2220
cagtactgga tgtgggtgat gcatattttt cagttccctt agatgaagac ttcaggaagt   2280
atactgcatt taccatacct agtataaaca atgagacacc agggattaga tatcagtaca   2340
atgtgcttcc acagggatgg aaaggatcac cagcaatatt ccaaagtagc atgacaaaaa   2400
tcttagagcc ttttaaaaaa caaaatccag acatagttat ctatcaatac atgaacgatt   2460
tgtatgtagg atctgactta gaaataggc  agcatagaac aaaaatagag gagctgagac   2520
aacatctgtt gaggtgggga cttaccacac cagacaaaaa acatcagaaa gaacctccat   2580
tcctttggat gggttatgaa ctccatcctg ataaatggac agtacagcct atagtgctgc   2640
cagaaaaaga cagctggact gtcaatgaca tacagaagtt agtggggaaa ttgaataccg   2700 caagtcgat  ttacccaggg attaaagtaa ggcaattatg taaactcctt agaggaacca   2760
aagcactaac agaagtaata ccactaacag aagaagcaga gctagaactg gcagaaaaca   2820
gagagattct aaaagaacca gtacatggag tgtattatga cccatcaaaa gacttaatag   2880
cagaaataca gaagcagggg caaggccaat ggacatatca aatttatcaa gagccattta   2940
```

```
aaaatctgaa aacaggaaaa tatgcaagaa tgaggggtgc ccacactaat gatgtaaaac    3000
aattaacaga ggcagtgcaa aaaataacca cagaaagcat agtaatatgg ggaaagactc    3060
ctaaatttaa actacccata caaaaggaaa catgggaaac atggtggaca gagtattggc    3120
aagccacctg gattcctgag tgggagtttg ttaatacccc tcctttagtg aaattatggt    3180
accagttaga gaaagaaccc atagtaggag cagaaacctt ctatgtagat ggggcagcta    3240
acagggagac taaattagga aaagcaggat atgttactaa caaaggaaga caaaaggttg    3300
tccccctaac taacacaaca atcagaaaa ctcagttaca agcaatttat ctagctttgc    3360
aggattcagg attagaagta aacatagtaa cagactcaca atatgcatta ggaatcattc    3420
aagcacaacc agataaaagt gaatcagagt tagtcaatca aataatagag cagttaataa    3480
aaaaggaaaa ggtctatctg gcatgggtac cagcacacaa aggaattgga ggaaatgaac    3540
aagtagataa attagtcagt gctggaatca ggaaaatact atttttagat ggaatagata    3600
aggcccaaga tgaacattag aattctgcaa caactgctgt ttatccattt tcagaattgg    3660
gtgtcgacat agcagaatag gcgttactcg acagaggaga gcaagaaatg gagccagtag    3720
atcctagact agagccctgg aagcatccag gaagtcagcc taaaactgct tgtaccaatt    3780
gctattgtaa aaagtgttgc tttcattgcc aagtttgttt cataacaaaa gccttaggca    3840
tctcctatgg caggaagaag cggagacagc gacgaagacc tcctcaagac agtcagactc    3900
atcaagtttc tctatcaaag cagtaagtag taaatgtaat gcaacctta caaatattag    3960 caatagtagc attagtagta gcagcaataa tagcaatagt tgtgtggacc atagtattca    4020
tagaatatag gaaaatatta agacaaagaa aaatagacag gttaattgat aggataacag    4080
aaagagcaga agacagtggc aatgaaagtg aaggggatca ggaagaatta tcagcacttg    4140
tggaaatggg gcatcatgct ccttgggatg ttgatgatct gtagtgctgt agaaaatttg    4200
tgggtcacag tttattatgg ggtacctgtg tggaaagaag caaccaccac tctattttgt    4260
gcatcagatg ctaaagcata tgatacagag gtacataatg tttgggccac acatgcctgt    4320
gtacccacag accccaaccc acaagaagta gtattggaaa atgtgacaga aaattttaac    4380
atgtggaaaa ataacatggt agaacagatg catgaggata taatcagttt atgggatcaa    4440
agcctaaagc catgtgtaaa attaacccca ctctgtgtta ctttaaattg cactgatttg    4500
aggaatgtta ctaatatcaa taatagtagt gagggaatga gaggagaaat aaaaaactgc    4560
tctttcaata tcaccacaag cataagagat aaggtgaaga aagactatgc acttttttat    4620
agacttgatg tagtaccaat agataatgat aatactagct ataggttgat aaaattgtaat    4680 acctcaacca ttacacaggc ctgtccaaag gtatcctttg agccaattcc catacattat    4740
tgtaccccgg ctggttttgc gattctaaag tgtaaagaca agaagttcaa tggaacaggg    4800
ccatgtaaaa atgtcagcac agtacaatgt acacatggaa ttaggccagt agtgtcaact    4860
caactgctgt taaatggcag tctagcagaa gaagaggtag taattagatc tagtaatttc    4920
acagacaatg caaaaaacat aatagtacag ttgaaagaat ctgtagaaat taattgtaca    4980
agacccaaca acaatacaag gaaaagtata catataggac caggaagagc attttataca    5040
acaggagaaa taataggaga tataagacaa gcacattgca acattagtag aacaaaatgg    5100
aataacactt taaatcaaat agctacaaaa ttaaagaaac aatttgggaa taataaaaca    5160
atagtcttta atcaatcctc aggaggggac ccagaaattg taatgcacag ttttaattgt    5220
ggaggggaat ttttctactg taattcaaca caactgttta atagtacttg gaattttaat    5280
ggtacttgga atttaacaca atcgaatggt actgaaggaa atgacactat cacactccca    5340
```

```
tgtagaataa acaaattat aaatatgtgg caggaagtag gaaaagcaat gtatgccct      5400 cccatcagag gacaaattag atgctcatca aatattacag ggctaatatt aacaagagat    5460
ggtggaacta acagtagtgg gtccgagatc ttcagacctg ggggaggaga tatgagggac    5520
aattggagaa gtgaattata taaatataaa gtagtaaaaa ttgaaccatt aggagtagca    5580
cccaccaagg caaaaagaag agtggtgcag agagaaaaaa gagcagtggg aacgatagga    5640
gctatgttcc ttgggttctt gggagcagca ggaagcacta tgggcgcagc gtcaataacg    5700
ctgacggtac aggccagact attattgtct ggtatagtgc aacagcagaa caatttgctg    5760
agggctattg aggcgcaaca gcatctgttg caactcacag tctggggcat caagcagctc    5820
caggcaagag tcctggctct ggaaagatac ctaagggatc aacagctcct agggatttgg    5880
ggttgctctg gaaaactcat ctgcaccact gctgtgcctt ggaatgctag ttggagtaat    5940
aaaactctgg atatgatttg gataacatg acctggatgg agtgggaaag agaaatcgaa     6000
aattacacag gcttaatata caccttaatt gaagaatcgc agaaccaaca agaaaagaat    6060
gaacaagact tattagcatt agataagtgg gcaagtttgt ggaattggtt tgacatatca    6120
aattggctgt ggtgtataaa aatcttcata atgatagtag gaggcttgat aggtttaaga    6180
atagttttta ctgtactttc tatagtaaat agagttaggc agggatactc accattgtca    6240
tttcagaccc acctcccagc cccgagggga cccgacaggc ccgaaggaat cgaagaagaa    6300
ggtggagaca gagacagaga cagatccgtg cgattagtgg atggatcctt agcacttatc    6360
tgggacgatc tgcggagcct gtgcctcttc agctaccacc gcttgagaga cttactcttg    6420
attgtaacga ggattgtgga acttctggga cgcaggggt gggaagccct caaatattgg    6480
tggaatctcc tacagtattg gagtcaggag ctaaagaata gtgctgttag cttgctcaat    6540
gccacagcta tagcagtagc tgaggggaca gataggtta tagaagtagt acaaggagct    6600
tatagagcta ttcgccacat acctagaaga ataagacagg gcttggaaag gattttgcta    6660
taagatgggt ggctagcccc gggtgataaa cggaccgcgc aatccctagg ctgtgccttc    6720
tagttgccag ccatctgttg tttgccccctc ccccgtgcct tccttgaccc tggaaggtgc    6780
cactcccact gtcctttcct aataaaatga ggaaattgca tcgcattgtc tgagtaggtg    6840
tcattctatt ctgggggtg gggtggggca ggacagcaag ggggaggatt gggaagacaa    6900
tagcaggcat gctgggatg cggtgggctc tatataaaaa acgcccggcg caaccgagc     6960 gttctgaacg ctagagtcga caaattcaga agaactcgtc aagaaggcga tagaaggcga    7020
tgcgctgcga atcgggagcg cgataccgt aaagcacgag gaagcggtca gcccattcgc     7080
cgccaagctc ttcagcaata tcacgggtag ccaacgctat gtcctgatag cggtctgcca    7140
cacccagccg gccacagtcg atgaatccag aaaagcggcc attttccacc atgatattcg    7200
gcaagcaggc atcgccatgg gtcacgacga gatcctcgcc gtcgggcatg ctcgccttga    7260
gcctggcgaa cagttcggct ggcgcgagcc cctgatgctc ttcgtccaga tcatcctgat    7320
cgacaagacc ggcttccatc cgagtacgtg ctcgctcgat gcgatgtttc gcttggtggt    7380
cgaatgggca ggtagccgga tcaagcgtat gcagccgccg cattgcatca gccatgatgg    7440
atactttctc ggcaggagca aggtgagatg acaggagatc ctgccccggc acttcgccca    7500
atagcagcca gtcccttccc gcttcagtga acaacgtcgag cacagctgcg caaggaacgc    7560
ccgtcgtggc cagccacgat agccgcgctg cctcgtcttg cagttcattc agggcaccgg    7620
acaggtcggt cttgacaaaa agaaccgggc gcccctgcgc tgacagccgg aacacggcgg    7680
catcagagca gccgattgtc tgttgtgccc agtcatagcc gaatagcctc tccacccaag    7740
```

| | |
|---|---|
| cggccggaga acctgcgtgc aatccatctt gttcaatcat gcgaaacgat cctcatcctg | 7800 |
| tctcttgatc agatcttgat ccctgcgcc atcagatcct tggcggcgag aaagccatcc | 7860 |
| agtttacttt gcagggcttc ccaaccttac cagagggcgc cccagctggc aattccggtt | 7920 |
| cgcttgctgt ccataaaacc gcccagtcta gctatcgcca tgtaagccca ctgcaagcta | 7980 |
| cctgctttct ctttgcgctt gcgttttccc ttgtccagat agcccagtag ctgacattca | 8040 |
| tccggggtca gcaccgtttc tgcggactgg ctttctacgt gaaaaggatc taggtgaaga | 8100 |
| tcctttttga taatctcatg accaaaatcc cttaacgtga gttttcgttc cactgagcgt | 8160 |
| cagaccccgt agaaaagatc aaaggatctt cttgagatcc ttttttctg cgcgtaatct | 8220 |
| gctgcttgca acaaaaaaa ccaccgctac cagcggtggt ttgtttgccg gatcaagagc | 8280 |
| taccaactct ttttccgaag gtaactggct tcagcagagc gcagatacca aatactgtcc | 8340 |
| ttctagtgta gccgtagtta ggccaccact tcaagaactc tgtagcaccg cctacatacc | 8400 |
| tcgctctgct aatcctgtta ccagtggctg ctgccagtgg cgataagtcg tgtcttaccg | 8460 |
| ggttggactc aagacgatag ttaccggata aggcgcagcg gtcgggctga acggggggtt | 8520 |
| cgtgcacaca gcccagcttg gagcgaacga cctacaccga actgagatac ctacagcgtg | 8580 |
| agctatgaga aagcgccacg cttcccgaag ggagaaaggc ggacaggtat ccggtaagcg | 8640 |
| gcagggtcgg aacaggagag cgcacgaggg agcttccagg gggaaacgcc tggtatcttt | 8700 |
| atagtcctgt cgggtttcgc cacctctgac ttgagcgtcg attttgtga tgctcgtcag | 8760 |
| gggggcggag cctatggaaa acgccagcaa cgcggccttt ttacggttcc tgggcttttg | 8820 |
| ctggcctttt gctcacatgt tgtcgaccga caatattggc tattggccat tgcatacgtt | 8880 |
| gtatctatat cataatatgt acatttatat tggctcatgt ccaatatgac cgccatgttg | 8940 |
| acattgatta ttgactagtt attaatagta atcaattacg gggtcattag ttcatagccc | 9000 |
| atatatggag ttccgcgtta cataacttac ggtaaatggc ccgcctcgtg accgcccaac | 9060 |
| gacccccgcc cattgacgtc aataatgacg tatgttccca tagtaacgcc aatagggact | 9120 |
| ttccattgac gtcaatgggt ggagtattta cggtaaactg cccacttggc agtacatcaa | 9180 |
| gtgtatcata tgccaagtcc gccctattg acgtcaatga cggtaaatgg cccgcctggc | 9240 |
| attatgccca gtacatgacc ttacgggact ttcctacttg gcagtacatc tacgtattag | 9300 |
| tcatcgctat taccatggtg atgcggtttt ggcagtacac caatgggcgt ggatagcggt | 9360 |
| ttgactcacg gggatttcca agtctccacc ccattgacgt caatgggagt tgttttggc | 9420 |
| accaaaatca acgggacttt ccaaaatgtc gtaataaccc cgccccgttg acgcaaatgg | 9480 |
| gcggtaggcg tgtacggtgg gaggtctata taagcagagc tcgtttagtg aaccgtcaga | 9540 |
| tcgc | 9544 |

<210> SEQ ID NO 8
<211> LENGTH: 9506
<212> TYPE: DNA
<213> ORGANISM: Artificial Sequence
<220> FEATURE:
<223> OTHER INFORMATION: Synthetically generated vector sequence-pGA 2/
      JS7

<400> SEQUENCE: 8

| | |
|---|---|
| atcgatgcag gactcggctt gctgaagcgc gcacggcaag aggcgagggg cggcgactgg | 60 |
| tgagtacgcc aaaaattttg actagcggag gctagaagga gagagatggg tgcgagagcg | 120 |
| tcagtattaa gcgggggaga attagatcga tgggaaaaaa ttcggttaag gccagggga | 180 |
| aagaaaaaat ataaattaaa acatatagta tgggcaagca gggagctaga acgattcgca | 240 |

-continued

```
gttaatcctg gcctgttaga aacatcagaa ggctgtagac aaatactggg acagctacaa        300
ccatcccttc agacaggatc agaagaactt agatcattat ataatacagt agcaaccctc        360
tattgtgtgc atcaaaggat agagataaaa gacaccaagg aagctttaga caagatagag        420
gaagagcaaa acaaaagtaa gaaaaaagca cagcaagcag cagctgacac aggacacagc        480
aatcaggtca gccaaaatta ccctatagtg cagaacatcc aggggcaaat ggtacatcag        540
gccatatcac ctagaacttt aaatgcatgg gtaaaagtag tagaagagaa ggctttcagc        600
ccagaagtga tacccatgtt ttcagcatta tcagaaggag ccaccccaca agatttaaac        660
accatgctaa acacagtggg gggacatcaa gcagccatgc aaatgttaaa agagaccatc        720
aatgaggaag ctgcagaatg ggatagagtg catccagtgc atgcagggcc tattgcacca        780
ggccagatga gagaaccaag gggaagtgac atagcaggaa ctactagtac ccttcaggaa        840
caaataggat ggatgacaaa taatccacct atcccagtag gagaaattta taaaagatgg        900
ataatcctgg gattaaataa aatagtaaga atgtatagcc ctaccagcat tctggacata        960
agacaaggac caaagaaacc ctttagagac tatgtagacc ggttctataa aactctaaga       1020
gccgagcaag cttcacagga ggtaaaaaat tggatgacag aaaccttgtt ggtccaaaat       1080
gcgaacccag attgtaagac tattttaaaa gcattgggac cagcggctac actagaagaa       1140
atgatgacag catgtcaggg agtaggagga cccggccata aggcaagagt tttggctgaa       1200
gcaatgagcc aagtaacaaa ttcagctacc ataatgatgc agagaggcaa ttttaggaac       1260
caaagaaaga ttgttaagag cttcaatagc ggcaaagaag gcacacagc cagaaattgc       1320 agggccccta ggaaaaaggg cagctggaaa agcggaaagg aaggacacca aatgaaagat       1380
tgtactgaga gacaggctaa ttttttaggg aagatctggc cttcctacaa gggaaggcca       1440
gggaattttc ttcagagcag accagagcca acagccccac cagaagagag cttcaggtct       1500
ggggtagaga caacaactcc ccctcagaag caggagccga tagacaagga actgtatcct       1560
ttaacttccc tcagatcact ctttggcaac gaccctcgt cacaataaag ataggggggc       1620
aactaaagga agctctatta gccacaggag cagatgatac agtattagaa gaaatgagtt       1680
tgccaggaag atggaaacca aaaatgatag ggggaattgg aggttttatc aaagtaagac       1740
agtatgatca gatactcata gaaatctgtg gacataaagc tataggtaca gtattagtag       1800
gacctacacc tgtcaacata attggaagaa atctgttgac tcagattggt tgcactttaa       1860
attttcccat tagccctatt gagactgtac cagtaaaatt aaagccagga atggatggcc       1920
caaaagttaa acaatggcca ttgacagaag aaaagataaa agcattagta gaaatttgta       1980
cagagatgga aaaggaaggg aaaatttcaa aaattgggcc tgaaaatcca tacaatactc       2040
cagtatttgc cataaagaaa aaagacagta ctaaatggag aaaattagta gatttcagag       2100
aacttaataa gagaactcaa gacttctggg aagttcaatt aggaatacca catcccgcag       2160
ggttaaaaaa gaaaaaatca gtaacagtac tggatgtggg tgatgcatat ttttcagttc       2220
ccttagatga agacttcagg aaatatactg catttaccat acctagtata acaatgagac       2280
caccagggat tagatatcag tacaatgtgc ttccacaggg atggaaagga tcaccagcaa       2340
tattccaaag tagcatgaca aaaatcttag agccttttag aaaacaaaat ccagacatag       2400
ttatctatca atacatgaac gatttgtatg taggatctga cttagaaata gggcagcata       2460
gaacaaaaat agaggagctg agacaacatc tgttgaggtg gggacttacc acaccagaca       2520
aaaaacatca gaaagaacct ccattccttt ggatgggtta tgaactccat cctgataaat       2580
ggacagtaca gcctatagtg ctgccagaaa aagacagctg gactgtcaat gacatacaga       2640
```

```
agttagtggg gaaattgaat accgcaagtc agatttaccc agggattaaa gtaaggcaat    2700
tatgtaaact ccttagagga accaaagcac taacagaagt aataccacta acagaagaag    2760
cagagctaga actggcagaa aacagagaga ttctaaaaga accagtacat ggagtgtatt    2820
atgacccatc aaaagactta atagcagaaa tacagaagca ggggcaaggc caatggacat    2880
atcaaattta tcaagagcca tttaaaaatc tgaaaacagg aaaatatgca agaatgaggg    2940
gtgcccacac taatgatgta aaacaattaa cagaggcagt gcaaaaaata accacagaaa    3000
gcatagtaat atggggaaag actcctaaat ttaaactgcc catacaaaag gaaacatggg    3060
aaacatggtg gacagagtat tggcaagcca cctggattcc tgagtgggag tttgttaata    3120
cccctccttt agtgaaatta tggtaccagt tagagaaaga acccatagta ggagcagaaa    3180
ccttctatgt agatggggca gctaacaggg agactaaatt aggaaaagca ggatatgtta    3240
ctaatagagg aagacaaaaa gttgtcaccc taactaacac aacaaatcag aaaactcagt    3300
tacaagcaat ttatctagct ttgcaggatt cgggattaga agtaaacata gtaacagact    3360
cacaatatgc attaggaatc attcaagcac aaccagatca aagtgaatca gagttagtca    3420
atcaaataat agagcagtta ataaaaaagg aaaaggtcta tctggcatgg gtaccagcac    3480
acaaaggaat tggaggaaat gaacaagtag ataaattagt cagtgctgga atcaggaaag    3540
tactattttt agatggaata dataaggccc aagatgaaca ttagaattct gcaacaactg    3600
ctgtttatcc atttcagaat tgggtgtcga catagcagaa taggcgttac tcgacagagg    3660
agagcaagaa atggagccag tagatcctag actagagccc tggaagcatc caggaagtca    3720
gcctaaaact gcttgtacca attgctattg taaaaagtgt tgctttcatt gccaagtttg    3780
tttcataaca aaagccttag gcatctccta tggcaggaag aagcggagac agcgacgaag    3840
agctcctcaa gacagtcaga ctcatcaagt ttctctatca aagcagtaag tagtaaatgt    3900
aatgcaacct ttacaaatat tagcaatagt agcattagta gtagcagcaa taatagcaat    3960
agttgtgtgg accatagtat tcatagaata taggaaaata ttaagacaaa gaaaaataga    4020
caggttaatt gataggataa cagaaagagc agaagacagt ggcaatgaaa gtgaagggga    4080
tcaggaagaa ttatcagcac ttgtggaaat ggggcatcat gctccttggg atgttgatga    4140
tctgtagtgc tgtagaaaat ttgtgggtca cagtttatta tggggtacct gtgtggaaag    4200
aagcaaccac cactctattt tgtgcatcag atgctaaagc atatgataca gaggtacata    4260
atgtttgggc cacacatgcc tgtgtaccca cagaccccaa cccacaagaa gtagtattgg    4320
aaaatgtgac agaaaatttt aacatgtgga aaaataacat ggtagaacag atgcatgagg    4380
atataatcag tttatgggat caaagcctaa agccatgtgt aaaattaacc ccactctgtg    4440
ttactttaaa ttgcactgat ttgaggaatg ttactaatat caataatagt agtgagggaa    4500
tgagaggaga aataaaaaac tgctctttca atatcaccac aagcataaga gataaggtga    4560
agaaagacta tgcactttt tatagacttg atgtagtacc aatagataat gataatacta    4620
gctataggtt gataaattgt aatacctcaa ccattacaca ggcctgtcca aaggtatcct    4680
ttgagccaat tcccatacat tattgtaccc cggctggttt tgcgattcta aagtgtaaag    4740
acaagaagtt caatggaaca gggccatgta aaaatgtcag cacagtacaa tgtacacatg    4800
gaattaggcc agtagtgtca actcaactgc tgttaaatgg cagtctagca gaagaagagg    4860
tagtaattag atctagtaat ttcacagaca atgcaaaaaa cataatagta cagttgaaag    4920
aatctgtaga aattaattgt acaagaccca acaacaatac aaggaaaagt atacatatag    4980
gaccaggaag agcatttat acaacaggag aaataatagg agatataaga caagcacatt    5040
```

```
gcaacattag tagaacaaaa tggaataaca ctttaaatca aatagctaca aaattaaaag   5100
aacaatttgg gaataataaa acaatagtct ttaatcaatc ctcaggaggg gacccagaaa   5160
ttgtaatgca cagttttaat tgtggagggg aattttctca ctgtaattca acacaactgt   5220
ttaatagtac ttggaatttt aatggtactt ggaatttaac acaatcgaat ggtactgaag   5280
gaaatgacac tatcacactc ccatgtagaa taaaacaaat tataaatatg tggcaggaag   5340
taggaaaagc aatgtatgcc cctcccatca gaggacaaat tagatgctca tcaaatatta   5400
cagggctaat attaacaaga gatggtgaaa ctaacagtag tgggtccgag atcttcagac   5460
ctgggggagg agatatgagg gacaattgga gaagtgaatt atataaatat aaagtagtaa   5520
aaattgaacc attaggagta gcacccacca aggcaaaaag aagagtggtg cagagagaaa   5580
aaagagcagt gggaacgata ggagctatgt tccttgggtt cttgggagca gcaggaagca   5640
ctatgggcgc agcgtcaata acgctgacgg tacaggccag actattattg tctggtatag   5700
tgcaacagca gaacaatttg ctgagggcta ttgaggcgca acagcatctg ttgcaactca   5760
cagtctgggg catcaagcag ctccaggcaa gagtcctggc tgtggaaaga tacctaaggg   5820
atcaacagct cctagggatt tggggttgct ctggaaaact catctgcacc actgctgtgc   5880
cttggaatgc tagttggagt aataaaactc tggatatgat ttgggataac atgacctgga   5940
tggagtggga aagagaaatc gaaaattaca caggcttaat atacacctta attgaagaat   6000
cgcagaacca acaagaaaag aatgaacaag acttattagc attagataag tgggcaagtt   6060
tgtggaattg gtttgacata tcaaattggc tgtggtatgt aaaaatcttc ataatgatag   6120
taggaggctt gataggttta agaatagttt ttactgtact ttctatagta aatagagtta   6180
ggcagggata ctcaccattg tcatttcaga cccacctccc agcccgagg ggacccgaca   6240 ggcccgaagg aatcgaagaa gaaggtggag acagagacag agacagatcc gtgcgattag   6300
tggatggatc cttagcactt atctgggacg atctgcggag cctgtgcctc ttcagctacc   6360
accgcttgag agacttactc ttgattgtaa cgaggattgt ggaacttctg gacgcaggg   6420 ggtgggaagc cctcaaatat tggtggaatc tcctacagta ttggagtcag gagctaaaga   6480
atagtgctgt tagcttgctc aatgccacag ctatagcagt agctgagggg acagataggg   6540
ttatagaagt agtacaagga gcttatagag ctattcgcca catacctaga agaataagac   6600
agggcttgga aaggattttg ctataagatg ggtggctagc cccgggtgat aaacggaccg   6660
cgcaatccct aggctgtgcc ttctagttgc cagccatctg ttgtttgccc ctcccccgtg   6720
ccttccttga ccctggaagg tgccactccc actgtccttt cctaataaaa tgaggaaatt   6780
gcatcgcatt gtctgagtag gtgtcattct attctggggg gtgggtggg gcaggacagc   6840 aaggggagg attgggaaga caatagcagg catgctgggg atgcggtggg ctctatataa   6900
aaaacgcccg gcggcaaccg agcgttctga acgctagagt cgacaaattc agaagaactc   6960
ggcaagaagg cgatagaagg cgatgcgctg cgaatcggga gcggcgatac cgtaaagcac   7020
gaggaagcgg tcagcccatt cgccgccaag ctcttcagca atatcacggg tagccaacgc   7080
tatgtcctga tagcggtctg ccacacccag ccggccacag tcgatgaatc cagaaaagcg   7140
gccattttcc accatgatat tcggcaagca ggcatcgcca tgggtcacga cgagatcctc   7200
gccgtcgggc atgctcgcct tgagcctggc gaacagttcg gctggcgcga gcccctgatg   7260
ctcttcgtcc agatcatcct gatcgacaag accggcttcc atccgagtac gtgctcgctc   7320
gatgcgatgt ttcgcttggt ggtcgaatgg gcaggtagcc ggatcaagcg tatgcagccg   7380
ccgcattgca tcagccatga tggatacttt ctcggcagga gcaaggtgag atgacaggag   7440
```

```
atcctgcccc ggcacttcgc ccaatagcag ccagtcccct cccgcttcag tgacaacgtc    7500
gagcacagct gcgcaaggaa cgcccgtcgt ggccagccac gatagccgcg ctgcctcgtc    7560
ttgcagttca ttcagggcac cggacaggtc ggtcttgaca aaaagaaccg gcgcccctg     7620
cgctgacagc cggaacacgg cggcatcaga gcagccgatt gtctgttgtg cccagtcata    7680
gccgaatagc ctctccaccc aagcggccgg agaacctgcg tgcaatccat cttgttcaat    7740
catgcgaaac gatcctcatc ctgtctcttg atcagatctt gatccctgc gccatcagat     7800
ccttggcggc aagaaagcca tccagtttac tttgcagggc ttcccaacct taccagaggg    7860
cgccccagct ggcaattccg gttcgcttgc tgtccataaa accgcccagt ctagctatcg    7920
ccatgtaagc ccactgcaag ctacctgctt tctctttgcg cttgcgtttt cccttgtcca    7980
gatagcccag tagctgacat tcatccgggg tcagcaccgt ttctgcggac tggctttcta    8040
cgtgaaaagg atctaggtga agatcctttt tgataatctc atgaccaaaa tcccttaacg    8100
tgagttttcg ttccactgag cgtcagaccc cgtagaaaag atcaaggat cttcttgaga     8160
tccttttttt ctgcgcgtaa tctgctgctt gcaaacaaaa aaaccaccgc taccagcggt    8220
ggtttgtttg ccggatcaag agctaccaac tctttttccg aaggtaactg gcttcagcag    8280
agcgcagata ccaaatactg ttcttctagt gtagccgtag ttaggccacc acttcaagaa    8340
ctctgtagca ccgcctacat acctcgctct gctaatcctg ttaccagtgg ctgctgccag    8400
tggcgataag tcgtgtctta ccgggttgga ctcaagacga tagttaccgg ataaggcgca    8460
gcggtcgggc tgaacggggg gttcgtgcac acagcccagc ttggagcgaa cgacctacac    8520
cgaactgaga tacctacagc gtgagctatg agaaagcgcc acgcttcccg aagggagaaa    8580
ggcggacagg tatccggtaa gcggcagggt cggaacagga gagcgcacga gggagcttcc    8640
agggggaaac gcctggtatc tttatagtcc tgtcgggttt cgccacctct gacttgagcg    8700
tcgatttttg tgatgctcgt caggggggcg gagcctatgg aaaaacgcca gcaacgcggc    8760
cttttacgg ttcctggcct tttgctggcc ttttgctcac atgttgtcga caatattggc      8820
tattggccat tgcatacgtt gtatctatat cataatatgt acatttatat ggctcatgt      8880
ccaatatgac cgccatgttg acattgatta ttgactagtt attaatagta atcaattacg    8940
ggttcattag ttcatagccc atatatggag ttccgcgtta cataacttac ggtaaatggc    9000
ccgcctggct gaccgcccaa cgacccccgc ccattgacgt caataatgac gtatgttccc    9060
atagtaacgc caatagggac tttccattga cgtcaatggg tggagtattt acggtaaact    9120
gcccacttgg cagtacatca agtgtatcat atgccaagtc cgccccctat tgacgtcaat    9180
gacggtaaat ggcccgcctg gcattatgcc cagtacatga ccttacggga ctttcctact    9240
tggcagtaca tctacgtatt agtcatcgct attaccatgg tgatgcggtt ttggcagtac    9300
accaatgggc gtggatagcg gtttgactca cggggatttc caagtctcca ccccattgac    9360
gtcaatggga gtttgttttg gcaccaaaat caacgggact ttccaaaatg tcgtaataac    9420
cccgccccgt tgacgcaaat gggcggtagg cgtgtacggt gggaggtcta tataagcaga    9480
gctcgtttag tgaaccgtca gatcgc                                         9506
```

<210> SEQ ID NO 9
<211> LENGTH: 9505
<212> TYPE: DNA
<213> ORGANISM: Artificial Sequence
<220> FEATURE:
<223> OTHER INFORMATION: Synthetically generated vector sequence-pGA
      2/JS7.1

<400> SEQUENCE: 9

```
atcgatgcag gactcggctt gctgaagcgc gcacggcaag aggcgagggg cggcgactgg      60
tgagtacgcc aaaaattttg actagcggag gctagaagga gagagatggg tgcgagagcg     120
tcagtattaa gcgggggaga attagatcga tgggaaaaaa ttcggttaag gccaggggga     180
aagaaaaaat ataaattaaa acatatagta tgggcaagca gggagctaga acgattcgca     240
gttaatcctg gcctgttaga aacatcagaa ggctgtagac aaatactggg acagctacaa     300
ccatcccttc agacaggatc agaagaactt agatcattat ataatacagt agcaaccctc     360
tattgtgtgc atcaaaggat agagataaaa gacaccaagg aagctttaga caagatagag     420
gaagagcaaa acaaaagtaa gaaaaaagca cagcaagcag cagctgacac aggacacagc     480
aatcaggtca gccaaaatta ccctatagtg cagaacatcc aggggcaaat ggtacatcag     540
gccatatcac ctagaacttt aaatgcatgg gtaaaagtag tagaagagaa ggctttcagc     600
ccagaagtga tacccatgtt ttcagcatta tcagaaggag ccaccccaca agatttaaac     660
accatgctaa acacagtggg gggacatcaa gcagccatgc aaatgttaaa agagaccatc     720
aatgaggaag ctgcagaatg ggatagagtg catccagtgc atgcagggcc tattgcacca     780
ggccagatga gagaaccaag gggaagtgac atagcaggaa ctactagtac ccttcaggaa     840
caaataggat ggatgacaaa taatccacct atcccagtag gagaaattta taaaagatgg     900
ataatcctgg gattaaataa aatagtaaga atgtatagcc ctaccagcat tctggacata     960
agacaaggac caaagaacc ctttagagac tatgtagacc ggttctataa aactctaaga    1020
gccgagcaag cttcacagga ggtaaaaaat tggatgacag aaaccttgtt ggtccaaaat    1080
gcgaacccag attgtaagac tattttaaaa gcattgggac cagcggctac actagaagaa    1140
atgatgacag catgtcaggg agtaggagga cccggccata aggcaagagt tttggctgaa    1200
gcaatgagcc aagtaacaaa ttcagctacc ataatgatgc agagaggcaa ttttaggaac    1260
caaagaaaga ttgttaagag cttcaatagc ggcaaagaag ggcacacagc cagaaattgc    1320
agggccccta ggaaaaaggg cagctggaaa agcggaaagg aaggacacca atgaaaagat    1380
tgtactgaga gacaggctaa ttttttaggg aagatctggc cttcctacaa gggaaggcca    1440
gggaattttc ttcagagcag accagagcca acagccccac cagaagagag cttcaggtct    1500
ggggtagaga caacaactcc ccctcagaag caggagccga tagacaagga actgtatcct    1560
ttaacttccc tcagatcact ctttggcaac gaccctcgt cacaataaag atagggggc      1620
aactaaagga agctctatta gccacaggag cagatgatac agtattagaa gaaatgagtt    1680
tgccaggaag atggaaacca aaaatgatag ggggaattgg aggttttatc aaagtaagac    1740
agtatgatca gatactcata gaaatctgtg gacataaagc tataggtaca gtattagtag    1800
gacctacacc tgtcaacata attggaagaa atctgttgac tcagattggt tgcactttaa    1860
attttcccat tagccctatt gagactgtac cagtaaaatt aaagccagga atggatggcc    1920
caaaagttaa acaatggcca ttgacagaag aaaagataaa agcattagta gaaatttgta    1980
cagagatgga aaaggaaggg aaaatttcaa aaattgggcc tgaaaatcca tacaatactc    2040
cagtatttgc cataaagaaa aaagacagta ctaaatggag aaaattagta gatttcagag    2100
aacttaataa gagaactcaa gacttctggg aagttcaatt aggaatacca catcccgcag    2160
ggttaaaaaa gaaaaaatca gtaacagtac tggatgtggg tgatgcatat ttttcagttc    2220
ccttagatga agacttcagg aaatatactg catttaccat acctagtata aacaatgaga    2280
caccagggat tagatatcag tacaatgtgc ttccacaggg atggaaagga tcaccagcaa    2340
```

-continued

```
tattccaaag tagcatgaca aaaatcttag agccttttag aaaacaaaat ccagacatag    2400
ttatctatca atacatgaac gatttgtatg taggatctga cttagaaata gggcagcata    2460
gaacaaaaat agaggagctg agacaacatc tgttgaggtg gggacttacc acaccagaca    2520
aaaaacatca gaaagaacct ccattccttt ggatgggtta tgaactccat cctgataaat    2580
ggacagtaca gcctatagtg ctgccagaaa aagacagctg gactgtcaat gacatacaga    2640
agttagtggg gaaattgaat accgcaagtc agatttaccc agggattaaa gtaaggcaat    2700
tatgtaaact ccttagagga accaaagcac taacagaagt aataccacta acagaagaag    2760
cagagctaga actggcagaa aacagagaga ttctaaaaga accagtacat ggagtgtatt    2820
atgacccatc aaaagactta atagcagaaa tacagaagca ggggcaaggc caatggacat    2880
atcaaattta tcaagagcca tttaaaaatc tgaaaacagg aaaatatgca agaatgaggg    2940
gtgcccacac taatgatgta aaacaattaa cagaggcagt gcaaaaaata accacagaaa    3000
gcatagtaat atggggaaag actcctaaat ttaaactgcc catacaaaag gaaacatggg    3060
aaacatggtg gacagagtat tggcaagcca cctggattcc tgagtgggag tttgttaata    3120
cccctccttt agtgaaatta tggtaccagt tagagaaaga acccatagta ggagcagaaa    3180
ccttctatgt agatggggca gctaacaggg agactaaatt aggaaaagca ggatatgtta    3240
ctaatagagg aagacaaaaa gttgtcaccc taactaacac aacaaatcag aaaactcagt    3300
tacaagcaat ttatctagct ttgcaggatt cgggattaga agtaaacata gtaacagact    3360
cacaatatgc attaggaatc attcaagcac aaccagatca aagtgaatca gagttagtca    3420
atcaaataat agagcagtta ataaaaaagg aaaaggtcta tctggcatgg gtaccagcac    3480
acaaaggaat tggaggaaat gaacaagtag ataaattagt cagtgctgga atcaggaaag    3540
tactattttt agatggaata gataaggccc aagatgaaca ttagaattct gcaacaactg    3600
ctgtttatcc atttcagaat tgggtgtcga catagcagaa taggcgttac tcgacagagg    3660
agagcaagaa atggagccag tagatcctag actagagccc tggaagcatc caggaagtca    3720
gcctaaaact gcttgtacca attgctattg taaaaagtgt tgctttcatt gccaagtttg    3780
tttcataaca aaagccttag gcatctccta tggcaggaag aagcggagac agcgacgaag    3840
agctcctcaa gacagtcaga ctcatcaagt ttctctatca aagcagtaag tagtaaatct    3900
aatccaacct ttacaaatat tagcaatagt agcattagta gtagcagcaa taatagcaat    3960
agttgtgtgg accatagtat tcatagaata taggaaaata ttaagacaaa gaaaaataga    4020
caggttaatt gataggataa cagaaagagc agaagacagt ggcaatgaaa gtgaagggga    4080
tcaggaagaa ttatcagcac ttgtggaaat ggggcatcat gctccttggg atgttgatga    4140
tctgtagtgc tgtagaaaat ttgtgggtca cagtttatta tggggtacct gtgtggaaag    4200
aagcaaccac cactctattt tgtgcatcag atgctaaagc atatgataca gaggtacata    4260
atgtttgggc cacacatgcc tgtgtaccca cagaccccaa cccacaagaa gtagtattgg    4320
aaaatgtgac agaaaatttt aacatgtgga aaaataacat ggtagaacag atgcatgagg    4380
atataatcag tttatgggat caaagcctaa agccatgtgt aaaattaacc ccactctgtg    4440
ttactttaaa ttgcactgat ttgaggaatg ttactaatat caataatagt agtgagggaa    4500
tgagaggaga aataaaaaac tgctctttca atatcaccac aagcataaga gataaggtga    4560
agaaagacta tgcacttttt tatagacttg atgtagtacc aatagataat gataatacta    4620
gctataggtt gataaattgt aatacctcaa ccattacaca ggcctgtcca aaggtatcct    4680
ttgagccaat tcccatacat tattgtaccc cggctggttt tgcgattcta aagtgtaaag    4740
```

```
acaagaagtt caatggaaca gggccatgta aaaatgtcag cacagtacaa tgtacacatg   4800
gaattaggcc agtagtgtca actcaactgc tgttaaatgg cagtctagca gaagaagagg   4860
tagtaattag atctagtaat ttcacagaca atgcaaaaaa cataatagta cagttgaaag   4920
aatctgtaga aattaattgt acaagaccca acaacaatac aaggaaaagt atacatatag   4980
gaccaggaag agcattttat acaacaggag aaataatagg agatataaga caagcacatt   5040
gcaacattag tagaacaaaa tggaataaca ctttaaatca aatagctaca aaattaaaag   5100
aacaatttgg gaataataaa acaatagtct ttaatcaatc ctcaggaggg gacccagaaa   5160
ttgtaatgca cagttttaat tgtggagggg aatttttcta ctgtaattca acacaactgt   5220
ttaatagtac ttggaatttt aatggtactt ggaatttaac acaatcgaat ggtactgaag   5280
gaaatgacac tatcacactc ccatgtagaa taaaacaaat tataaatatg tggcaggaag   5340
taggaaaagc aatgtatgcc cctcccatca gaggacaaat tagatgctca tcaaatatta   5400
cagggctaat attaacaaga gatggtgaaa ctaacagtag tgggtccgag atcttcagac   5460
ctgggggagg agatatgagg gacaattgga gaagtgaatt atataaatat aaagtagtaa   5520
aaattgaacc attaggagta gcacccacca aggcaaaaag aagagtggtg cagagagaaa   5580
aaagagcagt gggaacgata ggagctatgt tccttgggtt cttgggagca gcaggaagca   5640
ctatgggcgc agcgtcaata acgctgacgg tacaggccag actattattg tctggtatag   5700
tgcaacagca gaacaatttg ctgagggcta ttgaggcgca acagcatctg ttgcaactca   5760
cagtctgggg catcaagcag ctccaggcaa gagtcctggc tgtggaaaga tacctaaggg   5820
atcaacagct cctagggatt tggggttgct ctggaaaact catctgcacc actgctgtgc   5880
cttggaatgc tagttggagt aataaaactc tggatatgat ttgggataac atgacctgga   5940
tggagtggga aagagaaatc gaaaattaca caggcttaat atacacctta attgaagaat   6000
cgcagaacca acaagaaaag aatgaacaag acttattagc attagataag tgggcaagtt   6060
tgtggaattg gtttgacata tcaaattggc tgtggtatgt aaaaatcttc ataatgatag   6120
taggaggctt gataggttta agaatagttt ttactgtact ttctatagta aatagagtta   6180
ggcagggata ctcaccattg tcatttcaga cccacctccc agcccgagg ggacccgaca   6240 ggcccgaagg aatcgaagaa gaaggtggag acagagacag agacagatcc gtgcgattag   6300
tggatggatc cttagcactt atctgggacg atctgcggag cctgtgcctc ttcagctacc   6360
accgcttgag agacttactc ttgattgtaa cgaggattgt ggaacttctg gacgcaggg   6420 ggtgggaagc cctcaaatat tggtggaatc tcctacagta ttggagtcag gagctaaaga   6480
atagtgctgt tagcttgctc aatgccacag ctatagcagt agctgagggg acagatagg   6540 ttatagaagt agtacaagga gcttatagag ctattcgcca catacctaga agaataagac   6600
agggcttgga aaggattttg ctataagatg ggtggctagc cccgggtgat aaacggaccg   6660
cgcaatccct aggctgtgcc ttctagttgc cagccatctg ttgtttgccc ctccccgtg    6720 ccttccttga ccctggaagg tgccactccc actgtccttt cctaataaaa tgaggaaatt   6780
gcatcgcatt gtctgagtag gtgtcattct attctggggg gtgggtggg gcaggacagc   6840 aaggggagg attgggaaga caatagcagg catgctgggg atgcggtggg ctctatataa   6900
aaaacgcccg cgcaaccg agcgttctga acgctagagt cgacaaattc agaagaactc    6960
gtcaagaagg cgatagaagg cgatgcgctg cgaatcggga gcggcgatac cgtaaagcac   7020
gaggaagcgg tcagcccatt cgccgccaag ctcttcagca atatcacggg tagccaacgc   7080
tatgtcctga tagcggtctg ccacacccag ccggccacag tcgatgaatc cagaaaagcg   7140
```

```
gccattttcc accatgatat tcggcaagca ggcatcgcca tgggtcacga cgagatcctc      7200
gccgtcgggc atgctcgcct tgagcctggc gaacagttcg gctggcgcga ccccctgatg      7260
ctcttcgtcc agatcatcct gatcgacaag accggcttcc atccgagtac gtgctcgctc      7320
gatgcgatgt ttcgcttggt ggtcgaatgg gcaggtagcc ggatcaagcg tatgcagccg      7380
ccgcattgca tcagccatga tggatacttt ctcggcagga gcaaggtgag atgacaggag      7440
atcctgcccc ggcacttcgc ccaatagcag ccagtccctt cccgcttcag tgacaacgtc      7500
gagcacagct gcgcaaggaa cgcccgtcgt ggccagccac gatagccgcg ctgcctcgtc      7560
ttgcagttca ttcagggcac cggacaggtc ggtcttgaca aaagaaccg ggcgcccctg       7620
cgctgacagc cggaacacgg cggcatcaga gcagccgatt gtctgttgtg cccagtcata      7680
gccgaatagc ctctccaccc aagcggccgg agaacctgcg tgcaatccat cttgttcaat      7740
catgcgaaac gatcctcatc ctgtctcttg atcagatctt gatccctgc gccatcagat       7800
ccttggcgga ragaaagcca tccagtttac tttgcagggc ttcccaacct taccagaggg     7860
cgccccagct ggcaattccg gttcgcttgc tgtccataaa accgcccagt ctagctatcg      7920
ccatgtaagc ccactgcaag ctacctgctt tctctttgcg cttgcgtttt ccctttgtcca     7980
gatagcccag tagctgacat tcatccgggg tcagcaccgt ttctgcggac tggctttcta     8040
cgtgaaaagg atctaggtga agatcctttt tgataatctc atgaccaaaa tcccttaacg      8100
tgagttttcg ttccactgag cgtcagaccc cgtagaaaag atcaaaggat cttcttgaga      8160
tccttttttt ctgcgcgtaa tctgctgctt gcaaacaaaa aaaccaccgc taccagcggt      8220
ggtttgtttg ccggatcaag agctaccaac tcttttccg aaggtaactg gcttcagcag       8280
agcgcagata ccaaatactg ttcttctagt gtagccgtag ttaggccacc acttcaagaa     8340
ctctgtagca ccgcctacat acctcgctct gctaatcctg ttaccagtgg ctgctgccag     8400
tggcgataag tcgtgtctta ccgggttgga ctcaagacga tagttaccgg ataaggcgca     8460
gcggtcgggc tgaacggggg gttcgtgcac acagcccagc ttggagcgaa cgacctacac      8520
cgaactgaga tacctacagc gtgagctatg agaaagcgcc acgcttcccg aagggagaaa      8580
ggcggacagg tatccggtaa gcggcagggt cggaacagga gagcgcacga gggagcttcc      8640
agggggaaac gcctggtatc tttatagtcc tgtcgggttt cgccacctct gacttgagcg     8700
tcgatttttg tgatgctcgt caggggggcg gagcctatgg aaaaacgcca gcaacgcggc      8760
ccttttacgg ttcctggcct tttgctggcc ttttgctcac atgttgtcga caatattggc      8820
tattggccat tgcatacgtt gtatctatat cataatatgt acatttatat ggctcatgt      8880
ccaatatgac cgccatgttg acattgatta ttgactagtt attaatagta atcaattacg      8940
ggktcattag ttcatagccc atatatggag ttccgcgtta cataacttac ggtaaatggc     9000
ccgcctggct gaccgcccaa cgaccccgc ccattgacgt caataatgac gtatgttccc       9060
atagtaacgc caatagggac tttccattga cgtcaatggg tggagtattt acggtaaact      9120
gcccacttgg cagtacatca agtgtatcat atgccaagtc cgccctatt gacgtcaatg       9180
acggtaaatg gcccgcctgg cattatgccc agtacatgac cttacgggac tttcctactt      9240
ggcagtacat ctacgtatta gtcatcgcta ttaccatggt gatgcggttt tggcagtaca     9300
ccaatgggcg tggatagcgg tttgactcac ggggatttcc aagtctccac cccattgacg      9360
tcaatgggag tttgttttkgs caccaaaatc aacgggactt tccaaaatgt cgtaataacc     9420
ccgcccgtt gacgcaaatg ggcggtaggc gtgtacggtg ggaggtctat ataagcagag       9480
ctcgtttagt gaaccgtcag atcgc                                            9505
```

-continued

<210> SEQ ID NO 10
<211> LENGTH: 10447
<212> TYPE: DNA
<213> ORGANISM: Artificial Sequence
<220> FEATURE:
<223> OTHER INFORMATION: Synthetically generated vector sequence-pGA1/
      IC25

<400> SEQUENCE: 10

| | | | | | |
|---|---|---|---|---|---|
| atcgatgcaa | ggactcggct | tgctgaggtg | cacacagcaa | gaggcgagag | cgacgactgg | 60 |
| tgagtacgcc | aattttttgac | tagcggaggc | tagaaggaga | gagatgggtg | cgagagcgtc | 120 |
| agtgttaacg | gggggaaaat | tagattcatg | ggagaaaatt | aggttaaggc | caggggggaaa | 180 |
| gaaaagatat | agactaaaac | acctagtatg | ggcaagcagg | gagctggaga | gattcgcact | 240 |
| taaccctggc | ctattagaaa | cagcagaagg | atgtcaacaa | ctaatgggac | agttacaacc | 300 |
| agctctcagg | acaggatcag | aagagtttaa | atcattatat | aatatagtag | caacccttg | 360 |
| gtgcgtacat | caaagaatag | acataaaaga | cacccaggag | gccttagata | agtagagga | 420 |
| aaaacaaaat | aagagcaagc | aaaaggcaca | gcaggcagca | gctgcaacag | ccgccacagg | 480 |
| aagcagcagc | caaaattacc | ctatagtgca | aaatgcacaa | gggcaaatgg | tacatcagtc | 540 |
| catgtcacct | aggactttaa | atgcatgggt | gaaggtaata | gaagaaaagg | cttttagccc | 600 |
| agaggtaata | cccatgtttt | cagcattatc | agagggagcc | accccacaag | atttaaatat | 660 |
| gatgctaaac | atagtggggg | gacaccaggc | agcaatgcag | atgttaaaag | ataccatcaa | 720 |
| tgatgaagct | gcagaatggg | acagagtaca | tccagtacat | gcagggccta | ttccaccagg | 780 |
| ccaaatgagg | gaaccaaggg | gaagtgacat | agcaggaact | actagtaccc | ttcaagaaca | 840 |
| aataggatgg | atgacaagta | atccacctat | cccagtggga | gaaatctata | aaagatggat | 900 |
| agtcctggga | ttaaataaaa | tagtaagaat | gtatagccct | accagcattt | tggacataag | 960 |
| acaagggcca | aaagaaccct | ttagagatta | tgtagacagg | ttctttaaaa | ctttgagagc | 1020 |
| tgaacaagct | acgcaggagg | taaaaaactg | gatgacagaa | accttgttgg | tccaaaatgc | 1080 |
| gaatccagac | tgcaagtcca | ttttaagagc | attaggacca | ggggctacat | tagaagaaat | 1140 |
| gatgacatca | tgtcagggag | tgggaggacc | tggccataaa | gcaagggttt | tggctgaggc | 1200 |
| aatgagtcaa | gtacaacaga | ccaatgtaat | gatgcagaga | ggcaattta | gaggccagag | 1260 |
| aataataaag | agcttcaaca | gcggcaaaga | aggacaccta | gccagaaatt | gcaaggctcc | 1320 |
| tagaaagaga | ggcagctgga | aaagcggaaa | ggaaggacac | caaatgaaag | actgtactga | 1380 |
| aagacaggct | aattttttag | ggaaaatttg | gccttcccac | aaggggaggc | caggaaattt | 1440 |
| tcctcagagc | agaccagaac | caacagcccc | gccagcagag | agctttggag | tgggggaaga | 1500 |
| gataccctcc | tctccgaagc | aggagccgag | ggacaaggga | ctatatcctc | ccttaacttc | 1560 |
| cctcaaatca | ctctttggca | acgaccagta | gtcacagtaa | gataggggg | acagccaata | 1620 |
| gaagccctat | taaacacagg | agcagatgat | acagtattag | aagaaataag | tttaccagga | 1680 |
| aaatggaaac | caaaaatgat | agggggaatt | ggaggtttta | tcaaagtaag | acagtatgat | 1740 |
| cagatatcta | tagaaatttg | tggaaaaagg | gccataggta | cagtattagt | aggacctaca | 1800 |
| cctgtcaaca | taattggacg | aaatatgttg | actcagattg | gttgtacttt | aaattttcca | 1860 |
| attagtccta | ttgaaactgt | gccagtaaaa | ttaaagtcag | gaatggatgg | cccaaaggtt | 1920 |
| aaacaatggc | cattgacaga | agaaaaaata | aaagcattaa | agaaatttg | tgcagagatg | 1980 |
| gaaaaggaag | gaaaaattc | aaaaattggg | cctgaaaacc | catacaatac | tccaatattt | 2040 |
| gccataaaga | aaaaagatag | tactaaatgg | agaaaattag | tagatttcag | agaactcaat | 2100 |

```
aagagaactc aagacttctg ggaggtccaa ttaggaatac ctcatcctgc gggattaaaa    2160
aagaaaaaat cagtaacagt actagatgtg ggggatgcat atttttcagt tcccttagat    2220 gaagactttta gaaatatac tgcattcacc atacctagtt taaataatga dacaccaggg    2280
attagatatc agtacaatgt actcccacag ggatggaaag gatcaccagc aatatttcag    2340
gcaagcatga caaaaatctt agagcccttt agagcaaaaa atccagagat agtgatctac    2400
caatatatga acgatttata tgtaggatct gacttagaaa tagggcagca tagagcaaaa    2460
atagaggagt tgagagaaca tctattgaaa tgggggattta ccacaccaga caaaaaacat    2520
cagaaagaac ctccatttct ttggatggga tatgaactcc atcctgacaa atggacagtc    2580
cagcctatac agctgccaga aaaagacagc tggactgtca atgatataca aaaattagtg    2640
ggaaaactaa ataccgcaag tcagatttat gcaggaatta aagtaaagca attgtgtaga    2700
ctcctcaggg gagccaaagc gctaacagat gtagtaacac tgactgagga agcagaatta    2760
gaattggcag agaacaggga aattctaaaa gaacctgtac atggagtata ttatgaccca    2820
acaaaagact tagtggcaga aatacagaaa caagggcaag atcaatggac atatcaaatt    2880
tatcaagagc catttaaaaa tctaaagaca ggaaaatatg caaaaaagag gtcggcccac    2940
actaatgatg taaaacaatt aacagaggta gtgcagaaaa tagccataga aagcatagta    3000
atatggggaa agacccctaa atttagacta cccatacaaa gagaaacatg ggaagcatgg    3060
tggatggagt attggcaggc tacctggatt cctgaatggg agtttgtcaa tacccctcct    3120
ctagtaaaat tatggtacca gttagagaag gaccccataa tgggagcaga aactttctat    3180
gtagatgggg cagctaatag ggagactaag ctaggaaaag cagggtatgt cactgacaga    3240
ggaagacaaa aggttgtttc cctaattcag acaacaaatc aaaagactca gttacatgca    3300
attcatctag ccttgcagga ttcaggatca gaagtaaata tagtaacaga ctcacagtat    3360
gcattaggaa tcattcaggc acaaccagac aggagtgaat cagagttagt caatcaaata    3420
atagagaaac taatagaaaa ggacaaagtc tacctgtcat gggtaccagc acacaaaggg    3480
attggaggaa atgaacaagt agataaatta gtcagtagtg gaatcagaaa ggtactattt    3540
ttagatggaa tagataaagc ccaagatgaa cattagaatt ctgcaacagc tactgtttgt    3600
tcatttcaga attgggtgtc aacatagcag aataggcatt attccaggga gaagaggcag    3660
gaatggagct ggtagatcct agcctagagc cctggaacca cccgggaagt cagcctacaa    3720
ctgcttgtag caagtgttac tgtaaaaaat gctgctggca ttgccaattg tgctttctga    3780
acaagggctt aggcatctcc tatggcagga agaagcggag acgccgacga ggaactcctc    3840
aggaccgtca ggttcatcaa aatcctgtac caaaacagta agtagtagta attagtatat    3900
gtgatgcaat ctttacaaat agctgcaata gtaggactag tagtagcatc catagtagcc    3960
atagttgtgt ggtccatagt atttatagaa tatagaaaaa taaggaaaca gaagaaaata    4020
gacaggttac ttgagagaat aagagaaaga gcagaagata gtggcaatga gagtgatggg    4080
gatacagaag aattatccac tcttatggag agggggtatg acaatatttt ggttaatgat    4140
gatttgtaat gctgaaaagt tgtgggtcac agtctactat ggggtacctg tgtggagaga    4200
cgcagagacc accctattct gtgcatcaga tgctaaagca tatgacaaag aagcacacaa    4260
tgtctgggct acgcatgcct gcgtacccac agaccctgac ccacaagaat tacctttggt    4320
aaatgtaaca gaagagttta acatgtggaa aaataatatg gtagaacaga tgcatgaaga    4380
tataattagt ctatgggacc aaagcttaaa gccatgtgta cagctaaccc ctctctgcgt    4440
tactttaggg tgtgctgacg ctcaaaacgt caccgacacc aacaccacca tatctaatga    4500
```

```
aatgcaaggg gaaataaaaa actgctcttt caatatgacc acagaattaa gagataagaa    4560
gcagaaagtg tatgcacttt tttatagacc tgatgtaata gaaattaata aaactaagat    4620
taacaatagt aatagtagtc agtatatgtt aataaattgt aatacctcaa ccattacaca    4680
gacttgtcca aaggtatcct ttgagccaat tcccatacat tattgtgccc cagctggttt    4740
tgcaattcta aagtgtaatg atacggagtt cagtggaaaa gggacatgca agagtgtcag    4800
cacagtacaa tgcacacatg gaatcaagcc agtagtatca actcaactgc tgttaaatgg    4860
cagtctagca gaaggaaaga tagcgattag atctgagaat atctcaaaca atgccaaaac    4920
tataatagta caattgactg agcctgtaga aattaattgt atcagacctg gcaacaatac    4980
aagaaaaagt gtacgcatag gaccaggaca acattctat gcaacaggtg acataatagg    5040
agatataaga caagcacact gtaatgttag taaaatagca tgggaagaaa ctttacaaaa    5100
ggtagctgca caattaagga agcactttca gaatgccaca ataaaattta ctaaacactc    5160
aggagggat ttagaaatta caacaaatag ttttaattgt ggaggagaat ttttctattg    5220
caatacaaca aagctgttta atagcacttg gaataatgat aactcaaacc tcacagagga    5280
aaagagaaag gaaaacataa ctctccactg cagaataaag caaattgtaa atatgtggcc    5340
aagagtagga caagcaatat atgcccctcc catcccagga aacataactt gtggatcaaa    5400
cattactggg ctactattaa caagagatgg agggaataat ggtacaaatg atactgagac    5460
cttcaggcct ggaggaggag atatgaggga caattggaga agtgaattat ataaatataa    5520
agtagtaaaa attgaaccac taggtgtagc accaaccct gcaaaaagaa gagtggtgga    5580
aagagaaaaa agagcagttg gaatgggagc tttgatcttt gagttcttag gagcagcagg    5640
aagcactatg ggcgcggcgt caatggcgct gacggtacag gccagacaat tattgtctgg    5700
tatagtgcaa cagcagagca atctgctgaa ggctatagag gctcaacaac atctgttgag    5760
actcacggtc tggggcatta aacagctcca ggcaagagtc ctggctctgg aaagatacct    5820
aaaggatcaa cagctcctag gaatttgggg ctgctctgga aaactcattt gcaccactgc    5880
tgtaccttgg aactctagct ggagtaataa aagttataat gacatatggg ataacatgac    5940
ctggctgcaa tgggataaag aaattaacaa ttacacatac ataatatata atctacttga    6000
aaaatcgcag aaccagcagg aaattaatga acaagactta ttggcattag acaagtgggc    6060
aagtctgtgg aattggtttg acataacaag ctggctatgg tatataagat taggtataat    6120
gatagtagga ggcgtaatag gcttaagaat aatttttgct gtgcttacta tagtgaatag    6180
agttaggcag ggatactcac ctttgtcatt ccagacccct gcccaccacc agagggaacc    6240
cgacaggccc gaaagaatcg aagaaggagg tggcgagcaa gacagagaga gatccgtgcg    6300
cttagtgagc ggattcttag cacttgcctg gaagatctg cggagcctgt gcctcttcag    6360
ctaccgccga ttgagagact tagtcttgat tgcagcaagg actgtggaac tcctgggaca    6420
cagcagtctc aagggactga gactggggtg gaagccctc aaatatctgt ggaaccttct    6480
atcatactgg ggtcaggaac taaagaatag tgctattaat ttgcttgata caatagcaat    6540
agcagtagct aactggacag atagagttat aaaaatagta caaagaactg gtagagctat    6600
tcttaacata cctagaagga tcagataggg ctagccccgg gtgataaacg gaccgcgcaa    6660
tccctaggct gtgccttcta gttgccagcc atctgttgtt tgcccctccc ccgtgccttc    6720
cttgaccctg gaaggtgcca ctcccactgt cctttcctaa taaaatgagg aaattgcatc    6780
gcattgtctg agtaggtgtc attctattct ggggggtggg gtgggcagg acagcaaggg    6840
ggaggattgg gaagacaata gcaggcatgc tggggatgcg gtgggctcta tataaaaaac    6900
```

```
gcccggcggc aaccgagcgt tctgaacgct agagtcgaca aattcagaag aactcgtcaa   6960
gaaggcgata gaaggcgatg cgctgcgaat cgggagcggc gataccgtaa agcacgagga   7020
agcggtcagc ccattcgccg ccaagctctt cagcaatatc acgggtagcc aacgctatgt   7080
cctgatagcg gtctgccaca cccagccggc cacagtcgat gaatccagaa aagcggccat   7140
tttccaccat gatattcggc aagcaggcat cgccatgggt cacgacgaga tcctcgccgt   7200
cgggcatgct cgccttgagc ctggcgaaca gttcggctgg cgcgagcccc tgatgctctt   7260
cgtccagatc atcctgatcg acaagaccgg cttccatccg agtacgtgct cgctcgatgc   7320
gatgtttcgc ttggtggtcg aatgggcagg tagccggatc aagcgtatgc agccgccgca   7380
ttgcatcagc catgatggat actttctcgg caggagcaag gtgagatgac aggagatcct   7440
gccccggcac ttcgcccaat agcagccagt cccttcccgc ttcagtgaca acgtcgagca   7500
cagctgcgca aggaacgccc gtcgtggcca gccacgatag ccgcgctgcc tcgtcttgca   7560
gttcattcag ggcaccggac aggtcggtct tgacaaaaag aaccgggcgc ccctgcgctg   7620
acagccggaa cacggcggca tcagagcagc cgattgtctg ttgtgcccag tcatagccga   7680
atagcctctc cacccaagcg gccggagaac ctgcgtgcaa tccatcttgt tcaatcatgc   7740
gaaacgatcc tcatcctgtc tcttgatcag atcttgatcc cctgcgccat cagatccttg   7800
gcggcaagaa agccatccag tttactttgc agggcttccc aaccttacca gagggcgccc   7860
cagctggcaa ttccggttcg cttgctgtcc ataaaaccgc ccagtctagc tatcgccatg   7920
taagcccact gcaagctacc tgctttctct ttgcgcttgc gttttccctt gtccagatag   7980
cccagtagct gacattcatc cggggtcagc accgtttctg cggactggct ttctacgtga   8040
aaaggatcta ggtgaagatc ctttttgata atctcatgac caaatccctt aacgtgagt    8100
tttcgttcca ctgagcgtca ccccgtag aaaagatcaa aggatcttct tgagatcctt    8160
tttttctgcg cgtaatctgc tgcttgcaaa caaaaaaacc accgctacca gcggtggttt   8220
gtttgccgga tcaagagcta ccaactcttt ttccgaaggt aactggcttc agcagagcgc   8280
agataccaaa tactgttctt ctagtgtagc cgtagttagg ccaccacttc aagaactctg   8340
tagcaccgcc tacatacctc gctctgctaa tcctgttacc agtggctgct gccagtggcg   8400
ataagtcgtg tcttaccggg ttggactcaa gacgatagtt accggataag gcgcagcggt   8460
cgggctgaac ggggggttcg tgcacacagc ccagcttgga gcgaacgacc tacaccgaac   8520
tgagatacct acagcgtgag ctatgagaaa gcgccacgct tcccgaaggg agaaaggcgg   8580
acaggtatcc ggtaagcggc agggtcggaa caggagagcg cacgagggag cttccagggg   8640
gaaacgcctg gtatctttat agtcctgtcg ggtttcgcca cctctgactt gagcgtcgat   8700
ttttgtgatg ctcgtcaggg gggcggagcc tatggaaaaa cgccagcaac gcggcctttt   8760
tacggttcct ggccttttgc tggccttttg ctcacatgtt gtcgacaata ttggctattg   8820
gccattgcat acgttgtatc tatatcataa tatgtacatt tatattggct catgtccaat   8880
atgaccgcca tgttgacatt gattattgac tagttattaa tagtaatcaa ttacgggttc   8940
attagttcat agcccatata tggagttccg cgttacataa cttacggtaa atggcccgcc   9000
tggctgaccg cccaacgacc cccgcccatt gacgtcaata atgacgtatg ttcccatagt   9060
aacgccaata gggactttcc attgacgtca atgggtggag tatttacggt aaactgccca   9120
cttggcagta catcaagtgt atcatatgcc aagtccgccc cctattgacg tcaatgacgg   9180
taaatggccc gcctggcatt atgcccagta catgacctta cggactttc ctacttggca    9240
gtacatctac ggtattagtc atcggctatt accatggtga tgcggttttg gcagtacacc   9300
```

```
aatgggcgtg atagcggtt tgactcacgg ggatttccaa gtctccaccc cattgacgtc    9360
aatgggagtt tgttttggca ccaaaatcaa cgggactttc caaaatgtcg taataacccc    9420
gccccgttga cgcaaatggg cggtaggcgt gtacggtggg aggtctatat aagcagagct    9480
cgtttagtga accgtcagat cgcctggaga cgccatccac gctgttttga cctccataga    9540
agacaccggg accgatccag cctccgcggc cgggaacggt gcattggaac gcggattccc    9600
cgtgccaaga gtgacgtaag taccgcctat agactctata ggcacacccc tttggctctt    9660
atgcatgcta tactgttttt ggcttggggc ctatacaccc ccgcttcctt atgctatagg    9720
tgatggtata gcttagccta taggtgtggg ttattgacca ttattgacca ctcccctatt    9780
ggtgacgata cttccatta ctaatccata acatggctct tgccacaac tatctctatt    9840 ggctatatgc caatactctg tccttcagag actgacacgg actctgtatt tttacaggat    9900
ggggtcccat ttattattta caattcaca tatacaacaa cgccgtcccc cgtgcccgca    9960
gtttttatta aacatagcgt gggatctcca cgcgaatctc gggtaccgtg ttccggacat   10020
gggytcttct ccggtagcgg cggagcttcc acatccgagc cctggtccca tgcctccagc   10080
ggctcatggt cgctcggcag ctccttgctc ctaacagtgg aggccagact taggcacagc   10140
acaatgccca ccaccaccag tgtgccgcac aaggccgtgg cggtagggta tgtgtctgaa   10200
aatgagctcg gagattgggc tcgcaccgct gacgcagatg gaagacttaa ggcagcggca   10260
gaagaagatg caggcagctg agttgttgta ttctgataag agtcagaggt aactcccgtt   10320
gcggtgctgt taacggtgga gggcagtgta gtctgagcag tactcgttgc tgccgcgcgc   10380
gccaccagac ataatagctg acagactaac agactgttcc tttccatggg tcttttctgc   10440
agtcacc                                                              10447

<210> SEQ ID NO 11
<211> LENGTH: 10447
<212> TYPE: DNA
<213> ORGANISM: Artificial Sequence
<220> FEATURE:
<223> OTHER INFORMATION: Synthetically generated vector sequence-pGA1/
      IC2

<400> SEQUENCE: 11
atcgatgcaa ggactcggct tgctgaggtg cacacagcaa gaggcgagag cgacgactgg      60
tgagtacgcc aattttttgac tagcggaggc tagaaggaga gagatgggtg cgagagcgtc    120
agtgttaacg gggggaaaat tagattcatg ggagaaaatt aggttaaggc caggggggaaa   180 gaaaagatat agactaaaac acctagtatg ggcaagcagg gagctggaga gattcgcact    240
taaccctggc ctattagaaa cagcagaagg atgtcaacaa ctaatgggac agttacaacc    300
agctctcagg acaggatcag aagagtttaa atcattatat aatatagtag caacccttg    360 gtgcgtacat caaagaatag acataaaaga cacccaggag gccttagata agtagagga    420 aaaacaaaat aagagcaagc aaaaggcaca gcaggcagca gctgcaacag ccgccacagg    480
aagcagcagc caaaattacc ctatagtgca aaatgcacaa gggcaaatgg tacatcagtc    540
catgtcacct aggactttaa atgcatgggt gaaggtaata aagaaaagg cttttagccc    600 agaggtaata cccatgtttt cagcattatc agagggagcc accccacaag atttaaatat    660
gatgctaaac atagtggggg gacaccaggc agcaatgcag atgttaaaag ataccatcaa    720
tgatgaagct gcagaatggg acagagtaca tccagtacat gcagggccta ttccaccagg    780
ccaaatgagg gaaccaaggg gaagtgacat agcaggaact actagtaccc ttcaagaaca    840
```

```
aataggatgg atgacaagta atccacctat cccagtggga gaaatctata aaagatggat   900
agtcctggga ttaaataaaa tagtaagaat gtatagccct accagcattt tggacataag   960
acaagggcca aaagaaccct ttagagatta tgtagacagg ttctttaaaa ctttgagagc  1020
tgaacaagct acgcaggagg taaaaaactg gatgacagaa accttgttgg tccaaaatgc  1080
gaatccagac tgcaagtcca ttttaagagc attaggacca ggggctacat tagaagaaat  1140
gatgacatca tgtcagggag tgggaggacc tggccataaa gcaagggttt tggctgaggc  1200
aatgagtcaa gtacaacaga ccaatgtaat gatgcagaga ggcaatttta gaggccagag  1260
aataataaag agcttcaaca gcggcaaaga aggacaccta gccagaaatt gcaaggctcc  1320
tagaaagaga ggcagctgga aaagcggaaa ggaaggacac caaatgaaag actgtactga  1380
aagacaggct aatttttag ggaaaatttg gccttccac aaggggaggc caggaaattt   1440
tcctcagagc agaccagaac caacagcccc gccagcagag agctttggag tgggggaaga  1500
gataccctcc tctccgaagc aggagccgag ggacaaggga ctatatcctc ccttaacttc  1560
cctcaaatca ctctttggca acgaccagta gtcacagtaa gaatagggggg acagccaata  1620
gaagccctat tagacacagg agcagatgat acagtattag aagaaataag tttaccagga  1680
aaatggaaac caaaatgat aggggggaatt ggaggttta tcaaagtaag acagtatgat   1740
cagatatcta tagaaatttg tggaaaaagg gccataggta cagtattagt aggacctaca  1800
cctgtcaaca taattggacg aaatatgttg actcagattg gttgtacttt aaattttcca  1860
attagtccta ttgaaactgt gccagtaaaa ttaaagtcag gaatggatgg cccaaaggtt  1920
aaacaatggc cattgacaga agaaaaaata aaagcattaa agaaatttg tgcagagatg  1980
gaaaaggaag gaaaaattc aaaattggg cctgaaaacc catacaatac tccaatattt   2040
gccataaaga aaaagatag tactaaatgg agaaaattag tagatttcag agaactcaat  2100
aagagaactc aagacttctg ggaggtccaa ttaggaatac ctcatcctgc gggattaaaa  2160
aagaaaaaat cagtaacagt actagatgtg ggggatgcat attttcagt tcccttagat  2220
gaagactta gaaaatatac tgcattcacc atacctagtt taaataatga gacaccaggg  2280
attagatatc agtacaatgt actcccacag ggatggaaag gatcaccagc aatatttcag  2340
gcaagcatga caaaaatctt agagcccttt agagcaaaaa atccagagat agtgatctac  2400
caatatatga cgatttata tgtaggatct gacttagaaa tagggcagca tagagcaaaa  2460
atagaggagt tgagagaaca tctattgaaa tgggdattta ccacaccaga caaaaaacat  2520
cagaaagaac ctccatttct ttggatggga tatgaactcc atcctgacaa atggacagtc  2580
cagcctatac agctgccaga aaaagacagc tggactgtca atgatataca aaaattagtg  2640
ggaaaactaa ataccgcaag tcagatttat gcaggaatta agtaaagca attgtgtaga  2700
ctcctcaggg gagccaaagc gctaacagat gtagtaacac tgactgagga agcagaatta  2760
gaattggcag agaacaggga aattctaaaa gaacctgtac atggagtata ttatgaccca  2820
acaaaagact tagtggcaga atacagaaaa caagggcaag atcaatggac atatcaaatt  2880
tatcaagagc catttaaaaa tctaaagaca ggaaaatatg caaaaagag gtcggcccac  2940
actaatgatg taaaacaatt aacagaggta gtgcagaaaa tagccataga aagcatagta  3000
atatggggaa agaccctaa atttagacta cccatacaaa gagaaacatg gaagcatgg   3060
tggatggagt attggcaggc tacctggatt cctgaatggg agtttgtcaa tacccctcct  3120
ctagtaaaat tatggtacca gttagagaag gaccccataa tgggagcaga aactttctat  3180
gtagatgggg cagctaatag ggagactaag ctaggaaaag cagggtatgt cactgacaga  3240
```

```
ggaagacaaa aggttgtttc cctaattcag acaacaaatc aaaagactca gttacatgca   3300
attcatctag ccttgcagga ttcaggatca gaagtaaata tagtaacaga ctcacagtat   3360
gcattaggaa tcattcaggc acaaccagac aggagtgaat cagagttagt caatcaaata   3420
atagagaaac taatagaaaa ggacaaagtc tacctgtcat gggtaccagc acacaaaggg   3480
attggaggaa atgaacaagt agataaatta gtcagtagtg aatcagaaaa ggtactattt   3540
ttagatggaa tagataaagc ccaagatgaa cattagaatt ctgcaacagc tactgtttgt   3600
tcatttcaga attgggtgtc aacatagcag aataggcatt attccaggga gaagaggcag   3660
gaatggagct ggtagatcct agcctagagc cctggaacca cccgggaagt cagcctacaa   3720
ctgcttgtag caagtgttac tgtaaaaaat gctgctggca ttgccaattg tgctttctga   3780
acaagggctt aggcatctcc tatggcagga agaagcggag acgccgacga ggaactcctc   3840
aggaccgtca ggttcatcaa atcctgtac caaaacagta agtagtagta attagtatat   3900
gtgatgcaat ctttacaaat agctgcaata gtaggactag tagtagcatc catagtagcc   3960
atagttgtgt ggtccatagt atttatagaa tatagaaaaa taaggaaaca gaagaaaata   4020
gacaggttac ttgagagaat aagagaaaga gcagaagata gtggcaatga gagtgatggg   4080
gatacagaag aattatccac tcttatggag agggggtatg acaatatttt ggttaatgat   4140
gatttgtaat gctgaaaagt tgtgggtcac agtctactat ggggtacctg tgtggagaga   4200
cgcagagacc acccctattct gtgcatcaga tgctaaagca tatgacaaag aagcacacaa   4260
tgtctgggct acgcatgcct gcgtacccac agaccctgac ccacaagaat tacctttggt   4320
aaatgtaaca gaagagttta acatgtggaa aaataatatg gtagaacaga tgcatgaaga   4380
tataattagt ctatgggacc aaagcttaaa gccatgtgta cagctaaccc ctctctgcgt   4440
tactttaggg tgtgctgacg ctcaaaacgt caccgacacc aacaccacca tatctaatga   4500
aatgcaaggg gaaataaaaa actgctcttt caatatgacc acagaattaa gagataagaa   4560
gcagaaagtg tatgcacttt tttatagacc tgatgtaata gaaattaata aaactaagat   4620
taacaatagt aatagtagtc agtatatgtt aataaattgt aatacctcaa ccattacaca   4680
gacttgtcca aaggtatcct ttgagccaat tcccatacat tattgtgccc cagctggttt   4740
tgcaattcta aagtgtaatg atacggagtt cagtggaaaa gggacatgca agagtgtcag   4800
cacagtacaa tgcacacatg gaatcaagcc agtagtatca actcaactgc tgttaaatgg   4860
cagtctagca gaaggaaaga tagcgattag atctgagaat atctcaaaca atgccaaaac   4920
tataatagta caattgactg agcctgtaga aattaattgt atcagacctg gcaacaatac   4980
aagaaaaagt gtacgcatag gaccaggaca acattctat gcaacaggtg acataatagg   5040
agatataaga caagcacact gtaatgttag taaaatagca tgggaagaaa ctttacaaaa   5100
ggtagctgca caattaagga agcactttca gaatgccaca ataaaattta ctaaacactc   5160 aggagggggat ttagaaatta caacaaatag ttttaattgt ggaggagaat ttttctattg   5220
caatacaaca agctgtttta atagcacttg gaataatgat aactcaaacc tcacagagga   5280
aaagagaaag gaaacataa ctctccactg cagaataaag caaattgtaa atatgtggcc   5340
aagagtagga caagcaatat atgcccctcc catcccagga aacataactt gtggatcaaa   5400
cattactggg ctactattaa caagagatgg agggaataat ggtacaaatg atactgagac   5460
cttcaggcct ggaggaggag atatgaggga caattggaga agtgaattat ataaatataa   5520
agtagtaaaa attgaaccac taggtgtagc accaaccccct gcaaaagaa gagtggtgga   5580 aagagaaaaa agagcagttg gaatgggagc tttgatcttt gagttcttag gagcagcagg   5640
```

```
aagcactatg ggcgcggcgt caatggcgct gacggtacag gccagacaat tattgtctgg    5700
tatagtgcaa cagcagagca atctgctgaa ggctatagag gctcaacaac atctgttgag    5760
actcacggtc tggggcatta acagctcca ggcaagagtc ctggctctgg aaagatacct    5820
aaaggatcaa cagctcctag gaatttgggg ctgctctgga aaactcattt gcaccactgc    5880
tgtaccttgg aactctagct ggagtaataa aagttataat gacatatggg ataacatgac    5940
ctggctgcaa tgggataaag aaattaacaa ttacacatac ataatatata atctacttga    6000
aaaatcgcag aaccagcagg aaattaatga acaagactta ttggcattag acaagtgggc    6060
aagtctgtgg aattggtttg acataacaag ctggctatgg tatataagat taggtataat    6120
gatagtagga ggcgtaatag gcttaagaat aatttttgct gtgcttacta tagtgaatag    6180
agttaggcag ggatactcac ctttgtcatt ccagacccctt gcccaccacc agagggaacc    6240
cgacaggccc gaaagaatcg aagaaggagg tggcgagcaa gacagagaga gatccgtgcg    6300
cttagtgagc ggattcttag cacttgcctg ggaagatctg cggagcctgt gcctcttcag    6360
ctaccgccga ttgagagact tagtcttgat tgcagcaagg actgtggaac tcctgggaca    6420
cagcagtctc aagggactga gactggggtg ggaagccctc aaatatctgt ggaaccttct    6480
atcatactgg ggtcaggaac taaagaatag tgctattaat ttgcttgata caatagcaat    6540
agcagtagct aactggacag atagagttat aaaaatagta caaagaactg gtagagctat    6600
tcttaacata cctagaagga tcagataggg ctagccccgg gtgataaacg gaccgcgcaa    6660
tccctaggct gtgccttcta gttgccagcc atctgttgtt tgcccctccc ccgtgccttc    6720
cttgaccctg gaaggtgcca ctcccactgt cctttcctaa taaaatgagg aaattgcatc    6780
gcattgtctg agtaggtgtc attctattct gggggtggg gtgggcagg acagcaaggg    6840
ggaggattgg gaagacaata gcaggcatgc tggggatgcg gtgggctcta tataaaaaac    6900
gcccggcggc aaccgagcgt tctgaacgct agagtcgaca aattcagaag aactcgtcaa    6960
gaaggcgata aaggcgatg cgctgcgaat cgggagcggc gataccgtaa agcacgagga    7020
agcggtcagc ccattcgccg ccaagctctt cagcaatatc acgggtagcc aacgctatgt    7080
cctgatagcg gtctgccaca cccagccggc cacagtcgat gaatccagaa aagcggccat    7140
tttccaccat gatattcggc aagcaggcat cgccatgggt cacgacgaga tcctcgccgt    7200
cgggcatgct cgccttgagc ctggcgaaca gttcggctgg cgcgagcccc tgatgctctt    7260
cgtccagatc atcctgatcg acaagaccgg cttccatccg agtacgtgct cgctcgatgc    7320
gatgtttcgc ttggtggtcg aatgggcagg tagccggatc aagcgtatgc agccgccgca    7380
ttgcatcagc catgatggat actttctcgg caggagcaag gtgagatgac aggagatcct    7440
gccccggcac ttcgcccaat agcagccagt cccttcccgc ttcagtgaca acgtcgagca    7500
cagctgcgca aggaacgccc gtcgtggcca gccacgatag ccgcgctgcc tcgtcttgca    7560
gttcattcag ggcaccggac aggtcggtct tgacaaaaag aaccgggcgc ccctgcgctg    7620
acagccggaa cacggcggca tcagagcagc cgattgtctg ttgtgcccag tcatagccga    7680
atagcctctc cacccaagcg gccggagaac ctgcgtgcaa tccatcttgt tcaatcatgc    7740
gaaacgatcc tcatcctgtc tcttgatcag atcttgatcc cctgcgccat cagatccttg    7800
gcggcaagaa agccatccag tttactttgc agggcttccc aaccttacca gagggcgccc    7860
cagctggcaa ttccggttcg cttgctgtcc ataaaaccgc ccagtctagc tatcgccatg    7920
taagcccact gcaagctacc tgctttctct ttgcgcttgc gttttccctt gtccagatag    7980
cccagtagct gacattcatc cggggtcagc accgtttctg cggactggct ttctacgtga    8040
```

```
aaaggatcta ggtgaagatc cttttttgata atctcatgac caaaatccct taacgtgagt   8100
tttcgttcca ctgagcgtca gacccccgtag aaaagatcaa aggatcttct tgagatcctt   8160
tttttctgcg cgtaatctgc tgcttgcaaa caaaaaaacc accgctacca gcggtggttt   8220
gtttgccgga tcaagagcta ccaactcttt ttccgaaggt aactggcttc agcagagcgc   8280
agataccaaa tactgttctt ctagtgtagc cgtagttagg ccaccacttc aagaactctg   8340
tagcaccgcc tacatacctc gctctgctaa tcctgttacc agtggctgct gccagtggcg   8400
ataagtcgtg tcttaccggg ttggactcaa gacgatagtt accggataag gcgcagcggt   8460
cgggctgaac ggggggttcg tgcacacagc ccagcttgga gcgaacgacc tacaccgaac   8520
tgagatacct acagcgtgag ctatgagaaa gcgccacgct tcccgaaggg agaaaggcgg   8580
acaggtatcc ggtaagcggc agggtcggaa caggagagcg cacgagggag cttccagggg   8640
gaaacgcctg gtatctttat agtcctgtcg ggtttcgcca cctctgactt gagcgtcgat   8700
ttttgtgatg ctcgtcaggg gggcggagcc tatggaaaaa cgccagcaac gcggcccttt   8760
tacggttcct ggccttttgc tggccttttg ctcacatgtt gtcgacaata ttggctattg   8820
gccattgcat acgttgtatc tatatcataa tatgtacatt tatattggct catgtccaat   8880
atgaccgcca tgttgacatt gattattgac tagttattaa tagtaatcaa ttacgggttc   8940
attagttcat agcccatata tggagttccg cgttacataa cttacggtaa atggcccgcc   9000
tggctgaccg cccaacgacc cccgcccatt gacgtcaata atgacgtatg ttcccatagt   9060
aacgccaata gggactttcc attgacgtca atgggtggag tatttacggt aaactgccca   9120
cttggcagta catcaagtgt atcatatgcc aagtccgccc cctattgacg tcaatgacgg   9180
taaatggccc gcctggcatt atgcccagta catgacctta cgggactttc ctacttggca   9240
gtacatctac ggtattagtc atcggctatt accatggtga tgcggttttg gcagtacacc   9300
aatgggcgtg gatagcggtt tgactcacgg ggatttccaa gtctccaccc cattgacgtc   9360
aatgggagtt tgttttggca ccaaaatcaa cgggactttc caaaatgtcg taataacccc   9420
gccccgttga cgcaaatggg cggtaggcgt gtacggtggg aggtctatat aagcagagct   9480
cgtttagtga accgtcagat cgcctggaga cgccatccac gctgttttga cctccataga   9540
agacaccggg accgatccag cctccgcggc cgggaacggt gcattggaac gcggattccc   9600
cgtgccaaga gtgacgtaag taccgcctat agactctata ggcacacccc tttggctctt   9660
atgcatgcta tactgttttt ggcttggggc ctatacaccc ccgcttcctt atgctatagg   9720
tgatggtata gcttagccta taggtgtggg ttattgacca ttattgacca ctcccctatt   9780
ggtgacgata cttttccatta ctaatccata acatggctct ttgccacaac tatctctatt   9840
ggctatatgc caatactctg tccttcagag actgacacgg actctgtatt tttacaggat   9900
ggggtcccat ttattatttta caaattcaca tatacaacaa cgccgtcccc cgtgcccgca   9960
gtttttatta aacatagcgt gggatctcca cgcgaatctc gggtaccgtg ttccggacat  10020
gggytcttct ccggtagcgg cggagcttcc acatccgagc cctggtccca tgcctccagc  10080
ggctcatggt cgctcggcag ctccttgctc ctaacagtgg aggccagact taggcacagc  10140
acaatgccca ccaccaccag tgtgccgcac aaggccgtgg cggtagggta tgtgtctgaa  10200
aatgagctcg gagattgggc tcgcaccgct gacgcagatg gaagacttaa ggcagcggca  10260
gaagaagatg caggcagctg agttgttgta ttctgataag agtcagaggt aactcccgtt  10320
gcggtgctgt taacggtgga gggcagtgta gtctgagcag tactcgttgc tgccgcgcgc  10380
gccaccagac ataatagctg acagactaac agactgttcc tttccatggg tcttttctgc  10440
``` agtcacc 10447

<210> SEQ ID NO 12
<211> LENGTH: 10447
<212> TYPE: DNA
<213> ORGANISM: Artificial Sequence
<220> FEATURE:
<223> OTHER INFORMATION: Synthetically generated vector sequence-pGA1/
     IC48

<400> SEQUENCE: 12

| | | | | | |
|---|---|---|---|---|---|
| atcgatgcaa | ggactcggct | tgctgaggtg | cacacagcaa | gaggcgagag | cgacgactgg | 60 |
| tgagtacgcc | aattttttgac | tagcggaggc | tagaaggaga | gagatgggtg | cgagagcgtc | 120 |
| agtgttaacg | gggggaaaat | tagattcatg | ggagaaaatt | aggttaaggc | caggggggaaa | 180 |
| gaaaagatat | agactaaaac | acctagtatg | ggcaagcagg | gagctggaga | gattcgcact | 240 |
| taaccctggc | ctattagaaa | cagcagaagg | atgtcaacaa | ctaatgggac | agttacaacc | 300 |
| agctctcagg | acaggatcag | aagagtttaa | atcattatat | aatatagtag | caaccctttg | 360 |
| gtgcgtacat | caaagaatag | acataaaaga | cacccaggag | gccttagata | aagtagagga | 420 |
| aaaacaaaat | aagagcaagc | aaaaggcaca | gcaggcagca | gctgcaacag | ccgccacagg | 480 |
| aagcagcagc | caaaattacc | ctatagtgca | aaatgcacaa | gggcaaatgg | tacatcagtc | 540 |
| catgtcacct | aggactttaa | atgcatgggt | gaaggtaata | gaagaaaagg | cttttagccc | 600 |
| agaggtaata | cccatgtttt | cagcattatc | agagggagcc | accccacaag | atttaaatat | 660 |
| gatgctaaac | atagtggggg | gacaccaggc | agcaatgcag | atgttaaaag | ataccatcaa | 720 |
| tgatgaagct | gcagaatggg | acagagtaca | tccagtacat | gcagggccta | ttccaccagg | 780 |
| ccaaatgagg | gaaccaaggg | gaagtgacat | agcaggaact | actagtaccc | ttcaagaaca | 840 |
| aataggatgg | atgacaagta | atccacctat | cccagtggga | gaaatctata | aaagatggat | 900 |
| agtcctggga | ttaaataaaa | tagtaagaat | gtatagccct | accagcattt | tggacataag | 960 |
| acaagggcca | aaagaacctt | ttagagatta | tgtagacagg | ttctttaaaa | ctttgagagc | 1020 |
| tgaacaagct | acgcaggagg | taaaaaactg | gatgacagaa | accttgttgg | tccaaaatgc | 1080 |
| gaatccagac | tgcaagtcca | tttttaagagc | attaggacca | ggggctacat | tagaagaaat | 1140 |
| gatgacatca | tgtcagggag | tgggaggacc | tggccataaa | gcaagggttt | tggctgaggc | 1200 |
| aatgagtcaa | gtacaacaga | ccaatgtaat | gatgcagaga | ggcaatttta | gaggccagag | 1260 |
| aataataaag | agcttcaaca | gcggcaaaga | aggacaccta | gccagaaatt | gcaaggctcc | 1320 |
| tagaaagaga | ggcagctgga | aaagcggaaa | ggaaggacac | caaatgaaag | actgtactga | 1380 |
| aagacaggct | aatttttttag | ggaaaatttg | gccttcccac | aagggggaggc | caggaaattt | 1440 |
| tcctcagagc | agaccagaac | caacagcccc | gccagcagag | agctttggag | tgggggaaga | 1500 |
| gatacccctcc | tctccgaagc | aggagccgag | ggacaaggga | ctatatcctc | ccttaacttc | 1560 |
| cctcaaatca | ctctttggca | acgaccagta | gtcacagtaa | gaataggggg | acagccaata | 1620 |
| gaagccctat | tagacacagg | agcagatgat | acagtattag | aagaaataag | tttaccagga | 1680 |
| aaatggaaac | caaaaatgat | aggtggaatt | ggaggtttta | tcaaagtaag | acagtatgat | 1740 |
| cagatatcta | tagaaatttg | tggaaaaagg | gccataggta | cagtattagt | aggacctaca | 1800 |
| cctgtcaaca | taattggacg | aaatatgttg | actcagattg | gttgtacttt | aaatttttcca | 1860 |
| attagtccta | ttgaaactgt | gccagtaaaa | ttaaagtcag | gaatggatgg | cccaaaggtt | 1920 |
| aaacaatggc | cattgacaga | agaaaaaata | aaagcattaa | aagaaatttg | tgcagagatg | 1980 |
| gaaaaggaag | gaaaaatttc | aaaaattggg | cctgaaaacc | catacaatac | tccaatattt | 2040 |

```
gccataaaga aaaagatag  tactaaatgg agaaaattag tagatttcag agaactcaat   2100
aagagaactc aagacttctg ggaggtccaa ttaggaatac ctcatcctgc gggattaaaa   2160
aagaaaaaat cagtaacagt actagatgtg ggggatgcat atttttcagt tcccttagat   2220
gaagacttta gaaatatac  tgcattcacc atacctagtt taaataatga gacaccaggg   2280
attagatatc agtacaatgt actcccacag ggatggaaag gatcaccagc aatatttcag   2340
gcaagcatga caaaaatctt agagcccttt agagcaaaaa atccagagat agtgatctac   2400
caatatatga acgatttata tgtaggatct gacttagaaa tagggcagca tagagcaaaa   2460
atagaggagt tgagagaaca tctattgaaa tggggattta ccacaccaga caaaaaacat   2520
cagaaagaac ctccatttct ttggatggga tatgaactcc atcctgacaa atggacagtc   2580
cagcctatac agctgccaga aaaagacagc tggactgtca atgatataca aaaattagtg   2640
ggaaaactaa ataccgcaag tcagatttat gcaggaatta agtaaagca  attgtgtaga   2700 ctcctcaggg gagccaaagc gctaacagat gtagtaacac tgactgagga agcagaatta   2760
gaattggcag agaacaggga aattctaaaa gaacctgtac atggagtata ttatgaccca   2820
acaaaagact tagtggcaga aatacagaaa caagggcaag atcaatggac atatcaaatt   2880
tatcaagagc catttaaaaa tctaaagaca ggaaaatatg caaaaaagag gtcggcccac   2940
actaatgatg taaaacaatt aacagaggta gtgcagaaaa tagccataga aagcatagta   3000
atatggggaa agacccctaa atttagacta cccatacaaa gagaaacatg ggaagcatgg   3060
tggatggagt attggcaggc tacctggatt cctgaatggg agtttgtcaa tacccctcct   3120
ctagtaaaat tatggtacca gttagagaag acccccataa tgggagcaga aactttctat   3180
gtagatgggg cagctaatag ggagactaag ctaggaaaag cagggtatgt cactgacaga   3240
ggaagacaaa aggttgtttc cctaattcag acaacaaatc aaaagactca gttacatgca   3300
attcatctag ccttgcagga ttcaggatca gaagtaaata tagtaacaga ctcacagtat   3360
gcattaggaa tcattcaggc acaaccagac aggagtgaat cagagttagt caatcaaata   3420
atagagaaac taatagaaaa ggacaaagtc tacctgtcat gggtaccagc acacaaaggg   3480
attggaggaa atgaacaagt agataaatta gtcagtagtg aatcagaaaa ggtactattt   3540
ttagatggaa tagataaagc ccaagatgaa cattagaatt ctgcaacagc tactgtttgt   3600
tcatttcaga attgggtgtc aacatagcag aataggcatt attccaggga gaagaggcag   3660
gaatggagct ggtagatcct agcctagagc cctggaacca cccgggaagt cagcctacaa   3720
ctgcttgtag caagtgttac tgtaaaaaat gctgctggca ttgccaattg tgctttctga   3780
acaagggctt aggcatctcc tatggcagga agaagcggag acgccgacga ggaactcctc   3840
aggaccgtca ggttcatcaa atcctgtac  caaaacagta agtagtagta attagtatat   3900
gtgatgcaat ctttacaaat agctgcaata gtaggactag tagtagcatc catagtagcc   3960
atagttgtgt ggtccatagt atttatagaa tatagaaaaa taaggaaaca gaagaaaata   4020
gacaggttac ttgagagaat aagagaaaga gcagaagata gtggcaatga gagtgatggg   4080
gatacagaag aattatccac tcttatggag aggggtatg  acaatatttt ggttaatgat   4140
gatttgtaat gctgaaaagt tgtgggtcac agtctactat ggggtacctg tgtggagaga   4200
cgcagagacc accctattct gtgcatcaga tgctaaagca tatgacaaag aagcacacaa   4260
tgtctgggct acgcatgcct gcgtacccac agaccctgac ccacaagaat tacctttggt   4320
aaatgtaaca gaagagttta acatgtggaa aaataatatg gtagaacaga tgcatgaaga   4380
tataattagt ctatgggacc aaagcttaaa gccatgtgta cagctaaccc ctctctgcgt   4440
```

```
tactttaggg tgtgctgacg ctcaaaacgt caccgacacc aacaccacca tatctaatga   4500
aatgcaaggg gaaataaaaa actgctcttt caatatgacc acagaattaa gagataagaa   4560
gcagaaagtg tatgcacttt tttatagacc tgatgtaata gaaattaata aaactaagat   4620
taacaatagt aatagtagtc agtatatgtt aataaattgt aatacctcaa ccattacaca   4680
gacttgtcca aaggtatcct ttgagccaat tcccatacat tattgtgccc cagctggttt   4740
tgcaattcta aagtgtaatg atacggagtt cagtggaaaa gggacatgca agagtgtcag   4800
cacagtacaa tgcacacatg gaatcaagcc agtagtatca actcaactgc tgttaaatgg   4860
cagtctagca gaaggaaaga tagcgattag atctgagaat atctcaaaca atgccaaaac   4920
tataatagta caattgactg agcctgtaga aattaattgt atcagacctg gcaacaatac   4980
aagaaaaagt gtacgcatag gaccaggaca acattctat gcaacaggtg acataatagg   5040
agatataaga caagcacact gtaatgttag taaaatagca tgggaagaaa ctttacaaaa   5100
ggtagctgca caattaagga agcactttca gaatgccaca ataaaattta ctaaacactc   5160 aggagggat ttagaaatta caacaaatag ttttaattgt ggaggagaat ttttctattg   5220
caatacaaca aagctgttta atagcacttg gaataatgat aactcaaacc tcacagagga   5280
aaagagaaag gaaacataa ctctccactg cagaataaag caaattgtaa atatgtggcc   5340
aagagtagga caagcaatat atgcccctcc catcccagga aacataactt gtggatcaaa   5400
cattactggg ctactattaa caagagatgg agggaataat ggtacaaatg atactgagac   5460
cttcaggcct ggaggaggag atatgaggga caattggaga agtgaattat ataaatataa   5520
agtagtaaaa attgaaccac taggtgtagc accaacccct gcaaaagaa gagtggtgga   5580 aagagaaaaa agagcagttg gaatgggagc tttgatcttt gagttcttag gagcagcagg   5640
aagcactatg ggcgcggcgt caatggcgct gacggtacag gccagacaat tattgtctgg   5700
tatagtgcaa cagcagagca atctgctgaa ggctatagag gctcaacaac atctgttgag   5760
actcacggtc tggggcatta aacagctcca ggcaagagtc ctggctctgg aaagatacct   5820
aaaggatcaa cagctcctag gaatttgggg ctgctctgga aaactcattt gcaccactgc   5880
tgtaccttgg aactctagct ggagtaataa aagttataat gacatatggg ataacatgac   5940
ctggctgcaa tgggataaag aaattaacaa ttcacatac ataatatata atctacttga   6000
aaaatcgcag aaccagcagg aaattaatga acaagactta ttggcattag acaagtgggc   6060
aagtctgtgg aattggtttg acataacaag ctggctatgg tatataagat taggtataat   6120
gatagtagga ggcgtaatag gcttaagaat aattttttgct gtgcttacta tagtgaatag   6180
agttaggcag ggatactcac ctttgtcatt ccagaccctt gcccaccacc agagggaacc   6240
cgacaggccc gaaagaatcg aagaaggagg tggcgagcaa gacagagaga gatccgtgcg   6300
cttagtgagc ggattcttag cacttgcctg gaagatctg cggagcctgt gcctcttcag   6360
ctaccgccga ttgagagact tagtcttgat tgcagcaagg actgtggaac tcctgggaca   6420
cagcagtctc aagggactga gactggggtg ggaagccctc aaatatctgt ggaaccttct   6480
atcatactgg ggtcaggaac taagaatag tgctattaat ttgcttgata caatagcaat   6540
agcagtagct aactgggacag atagagttat aaaaatagta caagaactg gtagagctat   6600 tcttaacata cctagaagga tcagataggg ctagccccgg gtgataaacg gaccgcgcaa   6660
tccctaggct gtgccttcta gttgccagcc atctgttgtt tgcccctccc ccgtgccttc   6720
cttgaccctg gaaggtgcca ctcccactgt cctttcctaa taaaatgagg aaattgcatc   6780
gcattgtctg agtaggtgtc attctattct ggggggtggg gtggggcagg acagcaaggg   6840
```

```
ggaggattgg gaagacaata gcaggcatgc tggggatgcg gtgggctcta tataaaaaac    6900
gcccggcggc aaccgagcgt tctgaacgct agagtcgaca aattcagaag aactcgtcaa    6960
gaaggcgata aaggcgatg cgctgcgaat cgggagcggc gataccgtaa agcacgagga    7020
agcggtcagc ccattcgccg ccaagctctt cagcaatatc acgggtagcc aacgctatgt    7080
cctgatagcg gtctgccaca cccagccggc cacagtcgat gaatccagaa aagcggccat    7140
tttccaccat gatattcggc aagcaggcat cgccatgggt cacgacgaga tcctcgccgt    7200
cgggcatgct cgccttgagc ctggcgaaca gttcggctgg cgcgagcccc tgatgctctt    7260
cgtccagatc atcctgatcg acaagaccgg cttccatccg agtacgtgct cgctcgatgc    7320
gatgtttcgc ttggtggtcg aatgggcagg tagccggatc aagcgtatgc agccgccgca    7380
ttgcatcagc catgatggat actttctcgg caggagcaag gtgagatgac aggagatcct    7440
gccccggcac ttcgcccaat agcagccagt cccttcccgc ttcagtgaca acgtcgagca    7500
cagctgcgca aggaacgccc gtcgtggcca gccacgatag ccgcgctgcc tcgtcttgca    7560
gttcattcag gcaccggac aggtcggtct tgacaaaaag aaccgggcgc ccctgcgctg    7620
acagccggaa cacggcggca tcagagcagc cgattgtctg ttgtgcccag tcatagccga    7680
atagcctctc cacccaagcg gccggagaac ctgcgtgcaa tccatcttgt tcaatcatgc    7740
gaaacgatcc tcatcctgtc tcttgatcag atcttgatcc cctgcgccat cagatccttg    7800
gcggcaagaa agccatccag tttactttgc agggcttccc aaccttacca gagggcgccc    7860
cagctggcaa ttccggttcg cttgctgtcc ataaaaccgc ccagtctagc tatcgccatg    7920
taagcccact gcaagctacc tgctttctct ttgcgcttgc gttttccctt gtccagatag    7980
cccagtagct gacattcatc cggggtcagc accgtttctg cggactggct ttctacgtga    8040
aaaggatcta ggtgaagatc cttttgata atctcatgac caaaatccct aacgtgagt    8100 tttcgttcca ctgagcgtca gaccccgtag aaaagatcaa aggatcttct tgagatcctt    8160 ttttctgcg cgtaatctgc tgcttgcaaa caaaaaaacc accgctacca gcggtggttt    8220
gtttgccgga tcaagagcta ccaactcttt ttccgaaggt aactggcttc agcagagcgc    8280
agataccaaa tactgttctt ctagtgtagc cgtagttagg ccaccacttc aagaactctg    8340
tagcaccgcc tacatacctc gctctgctaa tcctgttacc agtggctgct gccagtggcg    8400
ataagtcgtg tcttaccggg ttggactcaa gacgatagtt accggataag gcgcagcggt    8460
cgggctgaac ggggggttcg tgcacacagc ccagcttgga gcgaacgacc tacaccgaac    8520
tgagatacct acagcgtgag ctatgagaaa gcgccacgct tcccgaaggg agaaaggcgg    8580
acaggtatcc ggtaagcggc agggtcgaa caggagagcg cacgagggag cttccagggg    8640
gaaacgcctg gtatctttat agtcctgtcg ggtttcgcca cctctgactt gagcgtcgat    8700
ttttgtgatg ctcgtcaggg gggcggagcc tatggaaaaa cgccagcaac gcggcccttt    8760
tacggttcct ggccttttgc tggccttttg ctcacatgtt gtcgacaata ttggctattg    8820
gccattgcat acgttgtatc tatatcataa tatgtacatt tatattggct catgtccaat    8880
atgaccgcca tgttgacatt gattattgac tagttattaa tagtaatcaa ttacgggttc    8940
attagttcat agcccatata tggagttccg cgttacataa cttacggtaa atggcccgcc    9000
tggctgaccg cccaacgacc cccgcccatt gacgtcaata atgacgtatg ttcccatagt    9060
aacgccaata gggactttcc attgacgtca atgggtggag tatttacggt aaactgccca    9120
cttggcagta catcaagtgt atcatatgcc aagtccgccc cctattgacg tcaatgacgg    9180
taaatggccc gcctggcatt atgcccagta catgacctta cgggactttc ctacttggca    9240
```

-continued

```
gtacatctac ggtattagtc atcggctatt accatggtga tgcggttttg gcagtacacc    9300
aatgggcgtg gatagcggtt tgactcacgg ggatttccaa gtctccaccc cattgacgtc    9360
aatgggagtt tgttttggca ccaaaatcaa cgggactttc caaaatgtcg taataacccc    9420
gccccgttga cgcaaatggg cggtaggcgt gtacggtggg aggtctatat aagcagagct    9480
cgtttagtga accgtcagat cgcctggaga cgccatccac gctgttttga cctccataga    9540
agacaccggg accgatccag cctccgcggc cgggaacggt gcattggaac gcggattccc    9600
cgtgccaaga gtgacgtaag taccgcctat agactctata ggcacacccc tttggctctt    9660
atgcatgcta tactgttttt ggcttggggc ctatacaccc ccgcttcctt atgctatagg    9720
tgatggtata gcttagccta taggtgtggg ttattgacca ttattgacca ctcccctatt    9780
ggtgacgata ctttccatta ctaatccata acatggctct tgccacaac tatctctatt     9840 ggctatatgc caatactctg tccttcagag actgacacgg actctgtatt tttacaggat    9900
ggggtcccat ttattattta caaattcaca tatacaacaa cgccgtcccc cgtgcccgca    9960
gttttattta aacatagcgt gggatctcca cgcgaatctc gggtaccgtg ttccggacat    10020
gggytcttct ccggtagcgg cggagcttcc acatccgagc cctggtccca tgcctccagc    10080
ggctcatggt cgctcggcag ctccttgctc ctaacagtgg aggccagact taggcacagc    10140
acaatgccca ccaccaccag tgtgccgcac aaggccgtgg cggtaggta tgtgtctgaa     10200 aatgagctcg gagattgggc tcgcaccgct gacgcagatg gaagacttaa ggcagcggca    10260
gaagaagatg caggcagctg agttgttgta ttctgataag agtcagaggt aactcccgtt    10320
gcggtgctgt taacggtgga gggcagtgta gtctgagcag tactcgttgc tgccgcgcgc    10380
gccaccagac ataatagctg acagactaac agactgttcc tttccatggg tcttttctgc    10440
agtcacc                                                              10447
```

<210> SEQ ID NO 13
<211> LENGTH: 10447
<212> TYPE: DNA
<213> ORGANISM: Artificial Sequence
<220> FEATURE:
<223> OTHER INFORMATION: Synthetically generated vector sequence-pGA1/
    IC90

<400> SEQUENCE: 13

```
atcgatgcaa ggactcggct tgctgaggtg cacacagcaa gaggcgagag cgacgactgg      60
tgagtacgcc aattttttgac tagcggaggc tagaaggaga gagatgggtg cgagagcgtc    120
agtgttaacg gggggaaaat tagattcatg ggagaaaatt aggttaaggc caggggaaa     180 gaaaagatat agactaaaac acctagtatg gcaagcagg gagctggaga gattcgcact     240
taaccctggc ctattagaaa cagcagaagg atgtcaacaa ctaatgggac agttacaacc    300
agctctcagg acaggatcag aagagtttaa atcattatat aatatagtag caacccttg     360 gtgcgtacat caaagaatag acataaaaga cacccaggag gccttagata agtagagga    420 aaaacaaat aagagcaagc aaaaggcaca gcaggcagca gctgcaacag ccgccacagg     480
aagcagcagc caaaattacc ctatagtgca aaatgcacaa gggcaaatgg tacatcagtc     540
catgtcacct aggactttaa atgcatgggt gaaggtaata gaagaaaagg cttttagccc     600
agaggtaata cccatgtttt cagcattatc agagggagcc accccacaag atttaaatat     660
gatgctaaac atagtggggg gacaccaggc agcaatgcag atgttaaaag ataccatcaa     720
tgatgaagct gcagaatggg acagagtaca tccagtacat gcagggccta ttccaccagg    780
```

```
ccaaatgagg gaaccaaggg gaagtgacat agcaggaact actagtaccc ttcaagaaca    840
aataggatgg atgacaagta atccacctat cccagtggga gaaatctata aaagatggat    900
agtcctggga ttaaataaaa tagtaagaat gtatagccct accagcattt tggacataag    960
acaagggcca aaagaaccct ttagagatta tgtagacagg ttctttaaaa ctttgagagc    1020
tgaacaagct acgcaggagg taaaaaactg gatgacagaa accttgttgg tccaaaatgc    1080
gaatccagac tgcaagtcca ttttaagagc attaggacca ggggctacat agaagaaat     1140
gatgacatca tgtcagggag tgggaggacc tggccataaa gcaagggttt tggctgaggc    1200
aatgagtcaa gtacaacaga ccaatgtaat gatgcagaga ggcaatttta gaggccagag    1260
aataataaag agcttcaaca gcggcaaaga aggacaccta gccagaaatt gcaaggctcc    1320
tagaaagaga ggcagctgga aaagcggaaa ggaaggacac caaatgaaag actgtactga    1380
aagacaggct aattttttag ggaaaatttg gccttcccac aaggggaggc caggaaattt    1440
tcctcagagc agaccagaac caacagcccc gccagcagag agctttggag tgggggaaga    1500
gatacccctcc tctccgaagc aggagccgag ggacaaggga ctatatcctc ccttaacttc    1560
cctcaaatca ctctttggca acgaccagta gtcacagtaa aatagggggg acagccaata    1620
gaagccctat tagacacagg agcagatgat acagtattag aagaaataag tttaccagga    1680
aaatggaaac caaaaatgat aggggggaatt ggaggtttta tcaaagtaag acagtatgat    1740
cagatatcta tagaaatttg tggaaaaagg gccataggta cagtattagt aggacctaca    1800
cctgtcaaca taattggacg aaatatgatg actcagattg gttgtacttt aaattttcca    1860
attagtccta ttgaaactgt gccagtaaaa ttaaagtcag gaatggatgg cccaaaggtt    1920
aaacaatggc cattgacaga agaaaaaata aaagcattaa agaaatttg tgcagagatg    1980
gaaaaggaag gaaaaatttc aaaaattggg cctgaaaacc catacaatac tccaatattt    2040
gccataaaga aaaagatag tactaaatgg agaaaattag tagatttcag agaactcaat    2100
aagagaactc aagacttctg ggaggtccaa ttaggaatac ctcatcctgc gggattaaaa    2160
aagaaaaaat cagtaacagt actagatgtg ggggatgcat attttcagt tcccttagat    2220
gaagacttta gaaaatatac tgcattcacc atacctagtt taaataatga gacaccaggg    2280
attagatatc agtacaatgt actcccacag ggatggaaag gatcaccagc aatatttcag    2340
gcaagcatga caaaaatctt agagcccttt agagcaaaaa atccagagat agtgatctac    2400
caatatatga acgatttata tgtaggatct gacttagaaa tagggcagca tagagcaaaa    2460
atagaggagt tgagagaaca tctattgaaa tggggattta ccacaccaga caaaaaacat    2520
cagaaagaac ctccatttct ttggatggga tatgaactcc atcctgacaa atggacagtc    2580
cagcctatac agctgccaga aaaagacagc tggactgtca atgatataca aaaattagtg    2640
ggaaaactaa ataccgcaag tcagatttat gcaggaatta agtaaagca attgtgtaga    2700
ctcctcaggg gagccaaagc gctaacagat gtagtaacac tgactgagga agcagaatta    2760
gaattggcag agaacaggga aattctaaaa gaacctgtac atggagtata ttatgaccca    2820
acaaagact tagtggcaga aatacagaaa caagggcaag atcaatggac atatcaaatt    2880
tatcaagagc catttaaaaa tctaaagaca ggaaaatatg caaaaagag gtcggcccac    2940
actaatgatg taaaacaatt aacagaggta gtgcagaaaa tagccataga aagcatagta    3000
atatggggaa agacccctaa atttagacta cccatacaaa gagaaacatg gaagcatgg    3060
tggatggagt attggcaggc tacctggatt cctgaatggg agtttgtcaa taccctcct    3120
ctagtaaaat tatggtacca gttagagaag gaccccataa tgggagcaga aactttctat    3180
```

```
gtagatgggg cagctaatag ggagactaag ctaggaaaag cagggtatgt cactgacaga   3240
ggaagacaaa aggttgtttc cctaattcag acaacaaatc aaaagactca gttacatgca   3300
attcatctag ccttgcagga ttcaggatca gaagtaaata tagtaacaga ctcacagtat   3360
gcattaggaa tcattcaggc acaaccagac aggagtgaat cagagttagt caatcaaata   3420
atagagaaac taatagaaaa ggacaaagtc tacctgtcat gggtaccagc acacaaaggg   3480
attggaggaa atgaacaagt agataaatta gtcagtagtg gaatcagaaa ggtactattt   3540
ttagatggaa tagataaagc ccaagatgaa cattagaatt ctgcaacagc tactgtttgt   3600
tcatttcaga attgggtgtc aacatagcag aataggcatt attccaggga gaagaggcag   3660
gaatggagct ggtagatcct agcctagagc cctggaacca cccgggaagt cagcctacaa   3720
ctgcttgtag caagtgttac tgtaaaaaat gctgctggca ttgccaattg tgctttctga   3780
acaagggctt aggcatctcc tatggcagga agaagcggag acgccgacga ggaactcctc   3840
aggaccgtca ggttcatcaa atcctgtac caaaacagta agtagtagta attagtatat   3900
gtgatgcaat ctttacaaat agctgcaata gtaggactag tagtagcatc catagtagcc   3960
atagttgtgt ggtccatagt atttatagaa tatagaaaaa taaggaaaca gaagaaaata   4020
gacaggttac ttgagagaat aagagaaaga gcagaagata gtggcaatga gagtgatggg   4080
gatacagaag aattatccac tcttatggag agggggtatg acaatatttt ggttaatgat   4140
gatttgtaat gctgaaaagt tgtgggtcac agtctactat ggggtacctg tgtggagaga   4200
cgcagagacc accctattct gtgcatcaga tgctaaagca tatgacaaag aagcacacaa   4260
tgtctgggct acgcatgcct gcgtacccac agaccctgac ccacaagaat tacctttggt   4320
aaatgtaaca gaaagtttta acatgtggaa aaataatatg gtagaacaga tgcatgaaga   4380
tataattagt ctatgggacc aaagcttaaa gccatgtgta cagctaaccc ctctctgcgt   4440
tactttaggg tgtgctgacg ctcaaaacgt caccgacacc aacaccacca tatctaatga   4500
aatgcaaggg gaaataaaaa actgctcttt caatatgacc acagaattaa gagataagaa   4560
gcagaaagtg tatgcacttt tttatagacc tgatgtaata gaaattaata aaactaagat   4620
taacaatagt aatagtagtc agtatatgtt aataaattgt aatacctcaa ccattacaca   4680
gacttgtcca aaggtatcct ttgagccaat tcccatacat tattgtgccc cagctggttt   4740
tgcaattcta aagtgtaatg atacggagtt cagtggaaaa gggacatgca agagtgtcag   4800
cacagtacaa tgcacacatg gaatcaagcc agtagtatca actcaactgc tgttaaatgg   4860
cagtctagca gaaggaaaga tagcgattag atctgagaat atctcaaaca atgccaaaac   4920
tataatagta caattgactg agcctgtaga aattaattgt atcagacctg gcaacaatac   4980
aagaaaaagt gtacgcatag gaccaggaca acattctat gcaacaggtg acataatagg   5040
agatataaga caagcacact gtaatgttag taaaatagca tgggaagaaa ctttacaaaa   5100
ggtagctgca caattaagga agcactttca gaatgccaca ataaaattta ctaaacactc   5160
aggaggggat ttagaaatta caacaaatag ttttaattgt ggaggagaat ttttctattg   5220
caatacaaca aagctgttta atagcacttg gaataatgat aactcaaacc tcacagagga   5280
aaagagaaag gaaaacataa ctctccactg cagaataaag caaattgtaa atatgtggcc   5340
aagagtagga caagcaatat atgccctcc catcccagga acataacctt gtggatcaaa   5400
cattactggg ctactattaa caagagatgg agggaataat ggtacaaatg atactgagac   5460
cttcaggcct ggaggaggag atatgaggga caattggaga agtgaattat ataaatataa   5520
agtagtaaaa attgaaccac taggtgtagc accaaccccct gcaaaaagaa gagtggtgga   5580
```

-continued

```
aagagaaaaa agagcagttg gaatgggagc tttgatcttt gagttcttag gagcagcagg    5640
aagcactatg ggcgcggcgt caatggcgct gacggtacag gccagacaat tattgtctgg    5700
tatagtgcaa cagcagagca atctgctgaa ggctatagag gctcaacaac atctgttgag    5760
actcacggtc tggggcatta aacagctcca ggcaagagtc ctggctctgg aaagatacct    5820
aaaggatcaa cagctcctag gaatttgggg ctgctctgga aaactcattt gcaccactgc    5880
tgtaccttgg aactctagct ggagtaataa aagttataat gacatatggg ataacatgac    5940
ctggctgcaa tgggataaag aaattaacaa ttacacatac ataatatata atctacttga    6000
aaaatcgcag aaccagcagg aaattaatga acaagactta ttggcattag acaagtgggc    6060
aagtctgtgg aattggtttg acataacaag ctggctatgg tatataagat taggtataat    6120
gatagtagga ggcgtaatag gcttaagaat aattttttgct gtgcttacta tagtgaatag    6180
agttaggcag ggatactcac ctttgtcatt ccagacccct gcccaccacc agagggaacc    6240
cgacaggccc gaaagaatcg aagaaggagg tggcgagcaa gacagagaga gatccgtgcg    6300
cttagtgagc ggattcttag cacttgcctg gaagatctg cggagcctgt gcctcttcag    6360
ctaccgccga ttgagagact tagtcttgat tgcagcaagg actgtggaac tcctgggaca    6420
cagcagtctc aagggactga gactggggtg ggaagccctc aaatatctgt ggaaccttct    6480
atcatactgg ggtcaggaac taaagaatag tgctattaat ttgcttgata caatagcaat    6540
agcagtagct aactggacag atagagttat aaaaatagta caaagaactg gtagagctat    6600
tcttaacata cctagaagga tcagatag ggctagccccgg gtgataaacg gaccgcgcaa    6660
tccctaggct gtgccttcta gttgccagcc atctgttgtt tgcccctccc ccgtgccttc    6720
cttgaccctg gaaggtgcca ctcccactgt cctttcctaa taaaatgagg aaattgcatc    6780
gcattgtctg agtaggtgtc attctattct ggggggtggg gtgggggcagg acagcaaggg    6840 ggaggattgg gaagacaata gcaggcatgc tggggatgcg gtgggctcta tataaaaaac    6900 gccccggcggc aaccgagcgt tctgaacgct agagtcgaca aattcagaag aactcgtcaa    6960
gaaggcgata aaggcgatg cgctgcgaat cgggagcggc gataccgtaa agcacgagga    7020
agcggtcagc ccattcgccg ccaagctctt cagcaatatc acgggtagcc aacgctatgt    7080
cctgatagcg gtctgccaca cccagccggc cacagtcgat gaatccagaa aagcggccat    7140
tttccaccat gatattcggc aagcaggcat cgccatgggt cacgacgaga tcctcgccgt    7200
cgggcatgct cgccttgagc ctggcgaaca gttcggctgg cgcgagcccc tgatgctctt    7260
cgtccagatc atcctgatcg acaagaccgg cttccatccg agtacgtgct cgctcgatgc    7320
gatgtttcgc ttggtggtcg aatgggcagg tagccggatc aagcgtatgc agccgccgca    7380
ttgcatcagc catgatggat actttctcgg caggagcaag gtgagatgac aggagatcct    7440
gccccggcac ttcgcccaat agcagccagt cccttcccgc ttcagtgaca acgtcgagca    7500
cagctgcgca aggaacgccc gtcgtggcca gccacgatag ccgcgctgcc tcgtcttgca    7560
gttcattcag ggcaccggac aggtcggtct tgacaaaaag aaccgggcgc ccctgcgctg    7620
acagccggaa cacggcggca tcagagcagc cgattgtctg ttgtgcccag tcatagccga    7680
atagcctctc cacccaagcg gccggagaac ctgcgtgcaa tccatcttgt tcaatcatgc    7740
gaaacgatcc tcatcctgtc tcttgatcag atcttgatcc cctgcgccat cagatccttg    7800
gcggcaagaa agccatccag tttactttgc agggcttccc aaccttacca gagggcgccc    7860
cagctggcaa ttccggttcg cttgctgtcc ataaaaccgc ccagtctagc tatcgccatg    7920
taagcccact gcaagctacc tgctttctct ttgcgcttgc gttttccctt gtccagatag    7980
```

```
cccagtagct gacattcatc cggggtcagc accgtttctg cggactggct ttctacgtga    8040
aaaggatcta ggtgaagatc ctttttgata atctcatgac caaaatccct taacgtgagt    8100
tttcgttcca ctgagcgtca gaccccgtag aaaagatcaa aggatcttct tgagatcctt    8160
ttttctgcg cgtaatctgc tgcttgcaaa caaaaaaacc accgctacca gcggtggttt    8220
gtttgccgga tcaagagcta ccaactcttt ttccgaaggt aactggcttc agcagagcgc    8280
agataccaaa tactgttctt ctagtgtagc cgtagttagg ccaccacttc aagaactctg    8340
tagcaccgcc tacatacctc gctctgctaa tcctgttacc agtggctgct gccagtggcg    8400
ataagtcgtg tcttaccggg ttggactcaa gacgatagtt accggataag gcgcagcggt    8460
cgggctgaac ggggggttcg tgcacacagc ccagcttgga gcgaacgacc tacaccgaac    8520
tgagatacct acagcgtgag ctatgagaaa gcgccacgct tcccgaaggg agaaaggcgg    8580
acaggtatcc ggtaagcggc agggtcggaa caggagagcg cacgagggag cttccagggg    8640
gaaacgcctg gtatctttat agtcctgtcg ggtttcgcca cctctgactt gagcgtcgat    8700
ttttgtgatg ctcgtcaggg gggcggagcc tatggaaaaa cgccagcaac gcggcccttt    8760
tacggttcct ggccttttgc tggccttttg ctcacatgtt gtcgacaata ttggctattg    8820
gccattgcat acgttgtatc tatatcataa tatgtacatt tatattggct catgtccaat    8880
atgaccgcca tgttgacatt gattattgac tagttattaa tagtaatcaa ttacgggttc    8940
attagttcat agcccatata tggagttccg cgttacataa cttacggtaa atggcccgcc    9000
tggctgaccg cccaacgacc cccgcccatt gacgtcaata atgacgtatg ttcccatagt    9060
aacgccaata gggactttcc attgacgtca atgggtggag tatttacggt aaactgccca    9120
cttggcagta catcaagtgt atcatatgcc aagtccgccc cctattgacg tcaatgacgg    9180
taaatggccc gcctggcatt atgcccagta catgacctta cgggactttc ctacttggca    9240
gtacatctac ggtattagtc atcggctatt accatggtga tgcggttttg gcagtacacc    9300
aatgggcgtg gatagcggtt tgactcacgg ggatttccaa gtctccaccc cattgacgtc    9360
aatgggagtt tgttttggca ccaaaatcaa cgggactttc caaaatgtcg taataacccc    9420
gccccgttga cgcaaatggg cggtaggcgt gtacggtggg aggtctatat aagcagagct    9480
cgtttagtga accgtcagat cgcctggaga cgccatccac gctgttttga cctccataga    9540
agacaccggg accgatccag cctccgcggc cgggaacggt gcattggaac gcggattccc    9600
cgtgccaaga gtgacgtaag taccgcctat agactctata ggcacacccc tttggctctt    9660
atgcatgcta tactgttttt ggcttggggc ctatacaccc ccgcttcctt atgctatagg    9720
tgatggtata gcttagccta taggtgtggg ttattgacca ttattgacca ctcccctatt    9780
ggtgacgata ctttccatta ctaatccata acatggctct ttgccacaac tatctctatt    9840
ggctatatgc caatactctg tccttcagag actgacacgg actctgtatt tttacaggat    9900
ggggtcccat ttattattta caaattcaca tatacaacaa cgccgtcccc cgtgcccgca    9960
gtttttatta aacatagcgt gggatctcca cgcgaatctc gggtaccgtg ttccggacat    10020
gggytcttct ccggtagcgg cggagcttcc acatccgagc cctggtccca tgcctccagc    10080
ggctcatggt cgctcggcag ctccttgctc ctaacagtgg aggccagact taggcacagc    10140
acaatgccca ccaccaccag tgtgccgcac aaggccgtgg cggtagggta tgtgtctgaa    10200
aatgagctcg gagattgggc tcgcaccgct gacgcagatg gaagacttaa ggcagcggca    10260
gaagaagatg caggcagctg agttgttgta ttctgataag agtcagaggt aactcccgtt    10320
gcggtgctgt taacggtgga gggcagtgta gtctgagcag tactcgttgc tgccgcgcgc    10380
```

```
gccaccagac ataatagctg acagactaac agactgttcc tttccatggg tctttctgc   10440 agtcacc                                                             10447

<210> SEQ ID NO 14
<211> LENGTH: 10466
<212> TYPE: DNA
<213> ORGANISM: Artificial Sequence
<220> FEATURE:
<223> OTHER INFORMATION: Synthetically generated vector sequence-pGA1/
      IN3

<400> SEQUENCE: 14
ggatccggct tgctgaagtg cactcggcaa gaggcgaggg gtggcggctg gtgagtacgc     60
caaattttat ttgactagcg gaggctagaa ggagagagat gggtgcgaga gcgtcaatat    120 taagagggg aaaattagat aaatgggaaa agattaggtt aaggccaggg ggaaagaaac    180
actatatgct aaaacaccta gtatgggcaa gcagggagct ggaaagattt gcacttaacc    240
ctggcctttt agagacatca gaaggctgta acaaataat aaaacagcta caaccagctc    300
ttcagacagg aacagaggaa cttaggtcat tattcaatgc agtagcaact ctctattgtg    360
tacatgcaga catagaggta cgagacacca agaagcatt agacaagata gaggaagaac    420
aaaacaaaag tcagcaaaaa acgcagcagg caaagaggc tgacaaaaag gtcgtcagtc    480
aaaattatcc tatagtgcag aatcttcaag gcaaatggt acaccaggca ctatcaccta    540
gaactttgaa tgcatgggta aaagtaatag aagaaaagc ctttagcccg gaggtaatac    600
ccatgttcac agcattatca gaaggagcca ccccacaaga tttaaacacc atgttaaata    660
ccgtgggggg acatcaagca gccatgcaaa tgttaaaaga taccatcaat gaggaggctg    720
cagaatggga tagattacat ccagtacatg cagggcctgt tgcaccaggc caaatgagag    780
aaccaagggg aagtgacata gcaggaacta ctagtaaacct tcaggaacaa atagcatgga    840
tgacaagtaa cccacctatt ccagtgggag atatctataa agatggata attctggggt    900 taaataaaat agtaagaatg tatagccctg tcagcatttt agacataaga caagggccaa    960 aggaacccttt agagattat gtagaccggt tcttaaaaac tttaagagct gaacaagctt   1020
cacaagatgt aaaaaattgg atggcagaca ccttgttggt ccaaaatgcg aacccagatt   1080
gtaagaccat tttaagagca ttaggaccag gagctacatt agaagaaatg atgacagcat   1140
gtcaaggagt gggaggacct agccacaaag caagagtgtt ggctgaggca atgagccaaa   1200
caggcagtac cataatgatg cagagaagca ttttaaagg ctctaaaaga actgttaaat   1260
ccttcaactc tggcaaggaa gggcacatag ctagaaattg cagggcccct aggaaaaaag   1320
gctcttggaa atctgaaaag gaaggacacc aaatgaaaga ctgtgctgag aggcaggcta   1380
atttttaagg gaaaatttgg ccttcccaca aggggaggcc aggaatttc cttcagaaca   1440 ggccagagcc aacagcccca ccagcagaga gcttcaggtt cgaggagaca ccccctgctc   1500
cgaagcagga gctgaaagac aggaaccct taacctccct caaatcactc tttggcagcg   1560
accccttgtc tcaataaaaa taggggccca gataaaggag ctctcttag ccacaggagc   1620 agatgataca gtattagaag aaatgaattt gccaggaaaa tggaaaccaa aaatgatagg   1680
aggaattgga ggttttatca agtaagaca gtatgatcaa atacttatag aaatttgtgg   1740
aaaaaaggct ataggtacag tattagtagg acccacacct gtcaacataa ttggaagaaa   1800
tatgctgact cagattggat gcacgctaaa ttttccaatt agtcccattg aaactgtacc   1860
agtaaaatta aagccaggaa tggatggccc aaaggttaaa caatggccat tgacagagga   1920
gaaaataaaa gcattaacag caatttgtga tgaaatggag aaggaaggaa aaattacaaa   1980
```

```
aattgggcct gaaaatccat ataacactcc aatattcgcc ataaaaaaga aggacagtac   2040
taagtggaga aaattagtag atttcagaga acttaataaa agaactcaag acttctggga   2100
agttcaatta ggaataccac acccagcagg gttaaaaaag aaaaaatcag tgacagtact   2160
agatgtgggg gatgcatatt tttcagttcc tttagatgaa agctttagga ggtatactgc   2220
attcaccata cctagtagaa acaatgaaac accagggatt agatatcaat ataatgtgct   2280
tccacaagga tggaaaggat caccagcaat attccagagt agcatgacaa aaatcttaga   2340 gcccttaga gcacaaaatc cagaaatagt catctatcaa tatatgaatg acttgtatgt   2400
aggatctgac ttagaaatag gcaacatag agcaaagata gaggaattaa gagaacatct   2460
attaaggtgg ggatttacca caccagacaa gaaacatcag aaagaacccc catttctttg   2520 gatgggtat gaactccatc ctgacaaatg gacagtacag cctatacagc tgccagaaaa   2580
ggagagctgg actgtcaatg atatacagaa gttagtggga aaattaaaca cggcaagcca   2640
gatttaccca gggattaaag taagacaact ttgtagactc cttagagggg ccaaagcact   2700
aacagacata gtaccactaa ctgaagaagc agaattagaa ttggcagaga cagggaaat   2760 tctaaaagaa ccagtacatg gagtatatta tgacccttca aaagacttga tagctgaaat   2820
acagaaacag ggacatgacc aatggacata tcaaatttac caagaaccat tcaaaaatct   2880
gaaaacaggg aagtatgcaa aaatgaggac tgcccacact aatgatgtaa aacggttaac   2940
agaggcagtg caaaaaatag ccttagaaag catagtaata tggggaaaga ttcctaaact   3000
taggttaccc atccaaaaag aaacatggga gacatggtgg actgactatt ggcaagccac   3060
ctggattcct gagtgggaat ttgttaatac tcctccccta gtaaaattat ggtaccagct   3120
agagaaggaa cccataatag gagtagaaac tttctatgta gatggagcag ctaatagga   3180 aaccaaaata ggaaaagcag ggtatgttac tgacagagga aggcagaaaa ttgtttctct   3240
aactgaaaca acaaatcaga agactcaatt acaagcaatt tatctagctt tgcaagattc   3300
aggatcagaa gtaaacatag taacagactc acagtatgca ttaggaatta ttcaagcaca   3360
accagataag agtgaatcag ggttagtcaa ccaaataata gaacaattaa taaaaaagga   3420
aagggtctac ctgtcatggg taccagcaca taaaggtatt ggaggaaatg aacaagtaga   3480
caaattagta agtagtggaa tcaggagagt gctataataa gctcgagata cttggacagg   3540
agttgaaact atcataagaa tgctgcaaca actactgttt attcatttca gaattgggtg   3600
ccagcatagc agaataggca ttatgagaca gagaagagca agaaatggag ccagtagatc   3660
ctaacctaga gccctggaac catccaggaa gtcagcctga aactgcttgc ataactgtt   3720 attgtaaacg ctatagctac cattgtctag tttgctttca gagaaaaggc ttaggcattt   3780
cctatggcag gaagaagcgg agacagcgac gaagcgctcc tcagagcagt gaggatcatc   3840
agaattttgt atcaaagcag taagtatctg taatgttaga tttagattat aaattagcag   3900
taggagcatt tatagtagca ctactcatag caatagttgt gtggaccata gtatttatag   3960
aatataggaa attgttaaga caagaaaaa tagactggtt aattaaaaga attgggaaa   4020 gagcagaaga cagtggcaat gagagtgaag gggatactga ggaattatcg acaatggtgg   4080
atatggggca tcttaggctt ttggatgtta atgatttgta atggaaactt gtgggtcaca   4140
gtctattatg gggtacctgt gtggaaagaa gcaaaaacta ctctattctg tgcatcaaat   4200
gctaaagcat atgagaaaga agtacataat gtctgggcta cacatgcctg tgtacccaca   4260
gaccccaacc cacaagaaat ggttttggaa acgtaacag aaaattttaa catgtggaaa   4320
aatgacatgg tgaatcagat gcatgaggat gtaatcagct tatgggatca aagcctaaag   4380
```

```
ccatgtgtaa agttgacccc actctgtgtc actttagaat gtagaaaggt taatgctacc    4440
cataatgcta ccaataatgg ggatgctacc cataatgtta ccaataatgg gcaagaaata    4500
caaaattgct ctttcaatgc aaccacagaa ataagagata ggaagcagag agtgtatgca    4560
cttttttata gacttgatat agtaccactt gataagaaca actctagtaa gaacaactct    4620
agtgagtatt atagattaat aaattgtaat acctcagcca taacacaagc atgtccaaag    4680
gtcagttttg atccaattcc tatacactat tgtgctccag ctggttatgc gattctaaag    4740
tgtaacaata agacattcaa tgggacagga ccatgcaata atgtcagcac agtacaatgt    4800
acacatggaa ttaagccagt ggtatcaact cagctattgt taaacggtag cctagcagaa    4860
ggagagataa taattagatc tgaaaatctg acagacaatg tcaaaacaat aatagtacat    4920
cttgatcaat ctgtagaaat tgtgtgtaca agacccaaca ataatacaag aaaaagtata    4980
aggatagggc caggacaaac attctatgca acaggaggca taatagggaa catacgacaa    5040
gcacattgta acattagtga agacaaatgg aatgaaactt tacaaagggt gggtaaaaaa    5100
ttagtagaac acttccctaa taagacaata aaatttgcac catcctcagg aggggaccta    5160
gaaattacaa cacatagctt taattgtaga ggagaatttt tctattgcag cacatcaaga    5220
ctgtttaata gtacatacat gcctaatgat acaaaaagta agtcaaacaa aaccatcaca    5280
atcccatgca gcataaaaca aattgtaaac atgtggcagg aggtaggacg agcaatgtat    5340
gcccctccca ttgaaggaaa cataacctgt agatcaaata tcacaggaat actattggta    5400
cgtgatggag gagtagattc agaagatcca gaaaataata agacagagac attccgacct    5460
ggaggaggag atatgaggaa caattgggaga agtgaattat ataaatataa agcggcagaa    5520
attaagccat tgggagtagc acccactcca gcaaaaagga gagtggtgga gagagaaaaa    5580
agagcagtag gattaggagc tgtgttcctt ggattcttgg gagcagcagg aagcactatg    5640
ggcgcagcgt caataacgct gacggtacag gccagacaat tgttgtctgg tatagtgcaa    5700
cagcaaagca atttgctgag ggctatcgag gcgcaacagc atctgttgca actcacggtc    5760
tggggcatta agcagctcca gacaagagtc ctggctatcg aaagatacct aaaggatcaa    5820
cagctcctag ggctttgggg ctgctctgga aaactcatct gcaccactaa tgtaccttgg    5880
aactccagtt ggagtaacaa atctcaaaca gatatttggg aaaacatgac ctggatgcag    5940
tgggataaag aagttagtaa ttacacagac acaatataca ggttgcttga agactcgcaa    6000
acccagcagg aaagaaatga aaaggattta ttagcattgg acaattggaa aaatctgtgg    6060
aattggttta gtataacaaa ctggctgtgg tatataaaaa tattcataat gatagtagga    6120
ggcttgatag gcttaagaat aattttttgct gtgctttcta tagtgaatag agttaggcag    6180
ggatactcac ctttgtcgtt tcagacccct accccaaacc caaggggacc cgacaggctc    6240
ggaagaatcg aagaagaagg tggagggcaa gacagagaca gatcgattcg attagtgaac    6300
ggattcttag cacttgcctg gacgacctg tggagcctgt gcctcttcag ctaccaccga    6360
ttgagagact taatatttggt gacagcgaga gcggtggaac ttctgggaca cagcagtctc    6420
aggggactac agagggggtg ggaagccctt aagtatctgg gaggtattgt gcagtattgg    6480
ggtctggaac taaaaaagag ggctattagt ctgcttgata ctgtagcaat agcagtagct    6540
gaaggcacag ataggattat agaattcctc caaagaattt gtagagctat ccgcaacata    6600
cctagaagga taagacaggg cttttgaagca gctttgcagt aaaatggcta gccccgggtg    6660
ataaacggac cgcgcaatcc ctaggctgtg ccttctagtt gccagccatc tgttgtttgc    6720
ccctcccccg tgccttcctt gaccctggaa ggtgccactc ccactgtcct ttcctaataa    6780
```

```
aatgaggaaa ttgcatcgca ttgtctgagt aggtgtcatt ctattctggg gggtggggtg      6840
gggcaggaca gcaaggggga ggattgggaa gacaatagca ggcatgctgg ggatgcggtg      6900
ggctctatat aaaaaacgcc cggcggcaac cgagcgttct gaacgctaga gtcgacaaat      6960
tcagaagaac tcgtcaagaa ggcgatagaa ggcgatgcgc tgcgaatcgg gagcggcgat      7020
accgtaaagc acgaggaagc ggtcagccca ttcgccgcca agctcttcag caatatcacg      7080
ggtagccaac gctatgtcct gatagcggtc tgccacaccc agccggccac agtcgatgaa      7140
tccagaaaag cggccatttt ccaccatgat attcggcaag caggcatcgc catgggtcac      7200
gacgagatcc tcgccgtcgg gcatgctcgc cttgagcctg gcgaacagtt cggctggcgc      7260
gagcccctga tgctcttcgt ccagatcatc ctgatcgaca gaccggcttc catccgagt       7320 acgtgctcgc tcgatgcgat gtttcgcttg gtggtcgaat gggcaggtag ccggatcaag      7380
cgtatgcagc cgccgcattg catcagccat gatggatact ttctcggcag gagcaaggtg      7440
agatgacagg agatcctgcc ccggcacttc gcccaatagc agccagtccc ttcccgcttc      7500
agtgacaacg tcgagcacag ctgcgcaagg aacgcccgtc gtggccagcc acgatagccg      7560
cgctgcctcg tcttgcagtt cattcagggc accgacagg tcggtcttga caaaaagaac       7620
cgggcgcccc tgcgctgaca gccggaacac ggcggcatca gagcagccga ttgtctgttg      7680
tgcccagtca tagccgaata gcctctccac ccaagcggcc ggagaacctg cgtgcaatcc      7740
atcttgttca atcatgcgaa acgatcctca tcctgtctct tgatcagatc ttgatcccct      7800
gcgccatcag atccttggcg gcaagaaagc catccagttt actttgcagg gcttcccaac      7860
cttaccagag ggcgcccag ctggcaattc cggttcgctt gctgtccata aaaccgccca       7920
gtctagctat cgccatgtaa gcccactgca agctacctgc tttctctttg cgcttgcgtt      7980
ttcccttgtc cagatagccc agtagctgac attcatccgg ggtcagcacc gtttctgcgg      8040
actggctttc tacgtgaaaa ggatctaggt gaagatcctt tttgataatc tcatgaccaa      8100
aatcccttaa cgtgagtttt cgttccactg agcgtcagac cccgtagaaa agatcaaagg      8160
atcttcttga tccttttttt ttctgcgcgt aatctgctgc ttgcaaacaa aaaaaccacc      8220
gctaccagcg gtggtttgtt tgccggatca agagctacca actctttttc cgaaggtaac      8280
tggcttcagc agagcgcaga taccaaatac tgttcttcta gtgtagccgt agttaggcca      8340
ccacttcaag aactctgtag caccgcctac atacctcgct ctgctaatcc tgttaccagt      8400
ggctgctgcc agtggcgata gtcgtgtct taccggggttg gactcaagac gatagttacc      8460
ggataaggcg cagcggtcgg gctgaacggg gggttcgtgc acacagccca gcttggagcg      8520
aacgacctac accgaactga gatacctaca gcgtgagcta tgagaaagcg ccacgcttcc      8580
cgaagggaga aaggcggaca ggtatccggt aagcggcagg gtcggaacag gagagcgcac      8640
gagggagctt ccaggggaa acgcctggta tctttatagt cctgtcgggt ttcgccacct       8700
ctgacttgag cgtcgatttt tgtgatgctc gtcagggggg cggagcctat ggaaaaacgc      8760
cagcaacgcg gcccttttac ggttcctggc cttttgctgg ccttttgctc acatgttgtc      8820
gacaatattg gctattggcc attgcatacg ttgtatctat atcataatat gtacatttat      8880
attggctcat gtccaatatg accgccatgt tgacattgat tattgactag ttattaatag      8940
taatcaatta cgggttcatt agttcatagc ccatatatgg agttccgcgt tacataactt      9000
acggtaaatg gcccgcctgg ctgaccgccc aacgaccccc gcccattgac gtcaataatg      9060
acgtatgttc ccatagtaac gccaataggg actttccatt gacgtcaatg ggtggagtat      9120
ttacggtaaa ctgcccactt ggcagtacat caagtgtatc atatgccaag tccgcccct       9180
```

```
attgacgtca atgacggtaa atggcccgcc tggcattatg cccagtacat gaccttacgg    9240
gactttccta cttggcagta catctacggt attagtcatc ggctattacc atggtgatgc    9300
ggttttggca gtacaccaat gggcgtggat agcggtttga ctcacgggga tttccaagtc    9360
tccaccccat tgacgtcaat gggagtttgt tttggcacca aaatcaacgg gactttccaa    9420
aatgtcgtaa taaccccgcc ccgttgacgc aaatgggcgg taggcgtgta cggtgggagg    9480
tctatataag cagagctcgt ttagtgaacc gtcagatcgc ctggagacgc catccacgct    9540
gttttgacct ccatagaaga caccgggacc gatccagcct ccgcggccgg gaacggtgca    9600
ttggaacgcg gattcccgt gccaagagtg acgtaagtac cgcctataga ctctataggc    9660
acaccccttt ggctcttatg catgctatac tgttttggc ttggggccta tacaccccg    9720
cttccttatg ctataggtga tggtatagct tagcctatag gtgtgggtta ttgaccatta    9780
ttgaccactc ccctattggt gacgatactt ccattacta atccataaca tggctctttg    9840
ccacaactat ctctattggc tatatgccaa tactctgtcc ttcagagact gacacggact    9900
ctgtattttt acaggatggg gtcccattta ttatttacaa attcacatat acaacaacgc    9960
cgtcccccgt gcccgcagtt tttattaaac atagcgtggg atctccacgc gaatctcggg   10020
taccgtgttc cggacatggg ytcttctccg gtagcggcgg agcttccaca tccgagccct   10080
ggtcccatgc ctccagcggc tcatggtcgc tcggcagctc cttgctccta acagtggagg   10140
ccagacttag gcacagcaca atgcccacca ccaccagtgt gccgcacaag gccgtggcgg   10200
tagggtatgt gtctgaaaat gagctcgag attgggctcg caccgctgac gcagatggaa   10260
gacttaaggc agcggcagaa gaagatgcag gcagctgagt tgttgtattc tgataagagt   10320
cagaggtaac tcccgttgcg gtgctgttaa cggtggaggg cagtgtagtc tgagcagtac   10380
tcgttgctgc cgcgcgcgcc accagacata atagctgaca gactaacaga ctgttccttt   10440
ccatgggtct tttctgcagt caccat                                        10466
```

```
<210> SEQ ID NO 15
<211> LENGTH: 10466
<212> TYPE: DNA
<213> ORGANISM: Artificial Sequence
<220> FEATURE:
<223> OTHER INFORMATION: Synthetically generated vector sequence-pGA1/
      IN2

<400> SEQUENCE: 15
```

```
ggatccggct tgctgaagtg cactcggcaa gaggcgaggg gtggcggctg gtgagtacgc      60
caaattttat ttgactagcg gaggctagaa ggagagagat gggtgcgaga gcgtcaatat     120
taagagggggg aaaattagat aaatgggaaa agattaggtt aaggccaggg ggaaagaaac    180
actatatgct aaaacaccta gtatgggcaa gcagggagct ggaaagattt gcacttaacc     240
ctggccttt agagacatca gaaggctgta acaaataat aaaacagcta caaccagctc      300
ttcagacagg aacagaggaa cttaggtcat tattcaatgc agtagcaact ctctattgtg    360
tacatgcaga catagaggta cgagacacca agaagcatt agacaagata gaggaagaac    420
aaaacaaaag tcagcaaaaa acgcagcagg caaagaggc tgacaaaaag gtcgtcagtc    480
aaaattatcc tatagtgcag aatcttcaag ggcaaatggt acaccaggca ctatcaccta    540
gaactttgaa tgcatgggta aaagtaatag aagaaaaagc ctttagcccg gaggtaatac    600
ccatgttcac agcattatca gaaggagcca cccacaaga tttaaacacc atgttaaata    660
ccgtgggggg acatcaagca gccatgcaaa tgttaaaaga taccatcaat gaggaggctg    720
```

```
cagaatggga tagattacat ccagtacatg cagggcctgt tgcaccaggc caaatgagag    780
aaccaagggg aagtgacata gcaggaacta ctagtaacct tcaggaacaa atagcatgga    840
tgacaagtaa cccacctatt ccagtgggag atatctataa aagatggata attctggggt    900
taaataaaat agtaagaatg tatagccctg tcagcatttt agacataaga caagggccaa    960
aggaacccct tagagattat gtagaccggt tctttaaaac tttaagagct gaacaagctt   1020
cacaagatgt aaaaaattgg atggcagaca ccttgttggt ccaaaatgcg aacccagatt   1080
gtaagaccat tttaagagca ttaggaccag gagctacatt agaagaaatg atgacagcat   1140
gtcaaggagt ggggaggacct agccacaaag caagagtgtt ggctgaggca atgagccaaa   1200
caggcagtac cataatgatg cagagaagca attttaaagg ctctaaaaga actgttaaat   1260
gcttcaactg tggcaaggaa gggcacatag ctagaaattg cagggcccct aggaaaaaag   1320
gctgttggaa atgtggaaag gaaggacacc aaatgaaaga ctgtgctgag aggcaggcta   1380
attttttagg gaaaatttgg ccttcccaca aggggaggcc agggaatttc cttcagaaca   1440
ggccagagcc aacagcccca ccagcagaga gcttcaggtt cgaggagaca acccctgctc   1500
cgaagcagga gctgaaagac agggaaccct taacctcccct caaatcactc tttggcagcg   1560
accccttgtc tcaataaaaa taggggggcca gataaaggag gctctcttag acacaggagc   1620
agatgataca gtattagaag aaatgaattt gccaggaaaa tggaaaccaa aaatgatagg   1680
aggaattgga ggttttatca agtaagaca gtatgatcaa atacttatag aaatttgtgg   1740
aaaaaaggct ataggtacag tattagtagg acccacacct gtcaacataa ttggaagaaa   1800
tatgctgact cagattggat gcacgctaaa ttttccaatt agtcccattg aaactgtacc   1860
agtaaaatta aagccaggaa tggatggccc aaaggttaaa caatggccat tgacagagga   1920
gaaaataaaa gcattaacag caatttgtga tgaaatggag aaggaaggaa aaattacaaa   1980
aattgggcct gaaaatccat ataacactcc aatattcgcc ataaaaaaga aggacagtac   2040
taagtggaga aaattagtag atttcagaga acttaataaa agaactcaag acttctggga   2100
agttcaatta ggaataccac acccagcagg gttaaaaaag aaaaaatcag tgacagtact   2160
agatgtgggg gatgcatatt tttcagttcc tttagatgaa agctttagga ggtatactgc   2220
attcaccata cctagtagaa acaatgaaac accagggatt agatatcaat ataatgtgct   2280
tccacaagga tggaaaggat caccagcaat attccagagt agcatgacaa aaatcttaga   2340 gcccttaga gcacaaaatc cagaaatagt catctatcaa tatatgaatg acttgtatgt   2400
aggatctgac ttagaaatag ggcaacatag agcaaagata gaggaattaa gagaacatct   2460
attaaggtgg ggatttacca caccagacaa gaaacatcag aaagaacccc catttctttg   2520
gatggggtat gaactccatc ctgacaaatg gacagtacag cctatacagc tgccagaaaa   2580
ggagagctgg actgtcaatg atatacagaa gttagtggga aaattaaaca cggcaagcca   2640
gatttaccca gggattaaag taagacaact ttgtagactc cttagagggg ccaaagcact   2700
aacagacata gtaccactaa ctgaagaagc agaattagaa ttggcagaga cagggaaat   2760 tctaaaagaa ccagtacatg gagtatatta tgacccttca aaagacttga tagctgaaat   2820
acagaaacag ggacatgacc aatggacata tcaaatttac caagaaccat tcaaaaatct   2880
gaaaacaggg aagtatgcaa aaatgaggac tgcccacact aatgatgtaa aacggttaac   2940
agaggcagtg caaaaaatag ccttagaaag catagtaata tggggaaaga ttcctaaact   3000
taggttaccc atccaaaaag aaacatggga gacatggtgg actgactatt ggcaagccac   3060
ctggattcct gagtgggaat ttgttaatac tcctcccta gtaaaattat ggtaccagct   3120
```

```
agagaaggaa cccataatag gagtagaaac tttctatgta gatggagcag ctaataggga    3180
aaccaaaata ggaaaagcag ggtatgttac tgacagagga aggcagaaaa ttgtttctct    3240
aactgaaaca acaaatcaga agactcaatt acaagcaatt tatctagctt tgcaagattc    3300
aggatcagaa gtaaacatag taacagactc acagtatgca ttaggaatta ttcaagcaca    3360
accagataag agtgaatcag ggttagtcaa ccaaataata gaacaattaa taaaaaagga    3420
aagggtctac ctgtcatggg taccagcaca taaaggtatt ggaggaaatg aacaagtaga    3480
caaattagta agtagtggaa tcaggagagt gctataataa gctcgagata cttggacagg    3540
agttgaaact atcataagaa tgctgcaaca actactgttt attcatttca gaattgggtg    3600
ccagcatagc agaataggca ttatgagaca gagaagagca agaaatggag ccagtagatc    3660
ctaacctaga gccctggaac catccaggaa gtcagcctga aactgcttgc ataactgtt    3720
attgtaaacg ctatagctac cattgtctag tttgctttca gagaaaaggc ttaggcattt    3780
cctatggcag gaagaagcgg agacagcgac gaagcgctcc tcagagcagt gaggatcatc    3840
agaattttgt atcaaagcag taagtatctg taatgttaga tttagattat aaattagcag    3900
taggagcatt tatagtagca ctactcatag caatagttgt gtggaccata gtatttatag    3960
aatataggaa attgttaaga caaagaaaaa tagactggtt aattaaaaga attagggaaa    4020
gagcagaaga cagtggcaat gagagtgaag gggatactga ggaattatcg acaatggtgg    4080
atatggggca tcttaggctt ttggatgtta atgatttgta atggaaactt gtgggtcaca    4140
gtctattatg gggtacctgt gtggaaagaa gcaaaaacta ctctattctg tgcatcaaat    4200
gctaaagcat atgagaaaga agtacataat gtctgggcta cacatgcctg tgtacccaca    4260
gaccccaacc cacaagaaat ggttttggaa aacgtaacag aaaattttaa catgtggaaa    4320
aatgacatgg tgaatcagat gcatgaggat gtaatcagct tatgggatca aagcctaaag    4380
ccatgtgtaa agttgacccc actctgtgtc actttagaat gtagaaaggt taatgctacc    4440
cataatgcta ccaataatgg ggatgctacc cataatgtta ccaataatgg gcaagaaata    4500
caaaattgct ctttcaatgc aaccacagaa ataagagata ggaagcagag agtgtatgca    4560
ctttttata gacttgatat agtaccactt gataagaaca actctagtaa gaacaactct    4620
agtgagtatt atagattaat aaattgtaat acctcagcca taacacaagc atgtccaaag    4680
gtcagttttg atccaattcc tatacactat tgtgctccag ctggttatgc gattctaaag    4740
tgtaacaata agacattcaa tgggacagga ccatgcaata atgtcagcac agtacaatgt    4800
acacatggaa ttaagccagt ggtatcaact cagctattgt taaacggtag cctagcagaa    4860
ggagagataa taattagatc tgaaaatctg acagacaatg tcaaaacaat aatagtacat    4920
cttgatcaat ctgtagaaat tgtgtgtaca agacccaaca ataatacaag aaaaagtata    4980
aggatagggc caggacaaac attctatgca acaggaggca ataagggaa catacgacaa    5040
gcacattgta acattagtga agacaaatgg aatgaaactt tacaaagggt gggtaaaaaa    5100
ttagtagaac acttccctaa taagacaata aaatttgcac catcctcagg aggggaccta    5160
gaaattacaa cacatagctt taattgtaga ggagaatttt tctattgcag cacatcaaga    5220
ctgtttaata gtacatacat gcctaatgat acaaaaagta agtcaaacaa aaccatcaca    5280
atcccatgca gcataaaaca aattgtaaac atgtggcagg aggtaggacg agcaatgtat    5340
gcccctccca ttgaaggaaa cataacctgt agatcaaata tcacaggaat actattggta    5400
cgtgatggag gagtagattc agaagatcca gaaaataata agacagagac attccgacct    5460
ggaggaggag atatgaggaa caattggaga agtgaattat ataaatataa agcggcagaa    5520
```

```
attaagccat tgggagtagc acccactcca gcaaaaagga gagtggtgga gagagaaaaa    5580
agagcagtag gattaggagc tgtgttcctt ggattcttgg gagcagcagg aagcactatg    5640
ggcgcagcgt caataacgct gacggtacag gccagacaat tgttgtctgg tatagtgcaa    5700
cagcaaagca atttgctgag ggctatcgag gcgcaacagc atctgttgca actcacggtc    5760
tggggcatta agcagctcca gacaagagtc ctggctatcg aaagatacct aaaggatcaa    5820
cagctcctag ggctttgggg ctgctctgga aaactcatct gcaccactaa tgtaccttgg    5880
aactccagtt ggagtaacaa atctcaaaca gatatttggg aaaacatgac ctggatgcag    5940
tgggataaag aagttagtaa ttacacagac acaatataca ggttgcttga agactcgcaa    6000
acccagcagg aaagaaatga aaaggattta ttagcattgg acaattggaa aaatctgtgg    6060
aattggttta gtataacaaa ctggctgtgg tatataaaaa tattcataat gatagtagga    6120
ggcttgatag gcttaagaat aattttttgct gtgctttcta tagtgaatag agttaggcag    6180
ggatactcac ctttgtcgtt tcagacccct accccaaacc caaggggacc cgacaggctc    6240
ggaagaatcg aagaagaagg tggagggcaa gacagagaca gatcgattcg attagtgaac    6300
ggattcttag cacttgcctg ggacgacctg tggagcctgt gcctcttcag ctaccaccga    6360
ttgagagact taatattggt gacagcgaga gcggtggaac ttctgggaca cagcagtctc    6420
aggggactac agagggggtg ggaagccctt aagtatctgg gaggtattgt gcagtattgg    6480
ggtctggaac taaaaaagag ggctattagt ctgcttgata ctgtagcaat agcagtagct    6540
gaaggcacag ataggattat agaattcctc caaagaattt gtagagctat ccgcaacata    6600
cctagaagga taagacaggg ctttgaagca gctttgcagt aaaatggcta gccccgggtg    6660
ataaacggac cgcgcaatcc ctaggctgtg ccttctagtt gccagccatc tgttgtttgc    6720
ccctcccccg tgccttcctt gaccctggaa ggtgccactc ccactgtcct ttcctaataa    6780
aatgaggaaa ttgcatcgca ttgtctgagt aggtgtcatt ctattctggg gggtggggtg    6840
gggcaggaca gcaaggggga ggattgggaa gacaatagca ggcatgctgg ggatgcggtg    6900
ggctctatat aaaaaacgcc ggcggcaac cgagcgttct gaacgctaga gtcgacaaat    6960
tcagaagaac tcgtcaagaa ggcgatagaa ggcgatgcgc tgcgaatcgg gagcggcgat    7020
accgtaaagc acgaggaagc ggtcagccca ttcgccgcca agctcttcag caatatcacg    7080
ggtagccaac gctatgtcct gatagcggtc tgccacaccc agccggccac agtcgatgaa    7140
tccagaaaag cggccatttt ccaccatgat attcggcaag caggcatcgc catgggtcac    7200
gacgagatcc tcgccgtcgg gcatgctcgc cttgagcctg gcgaacagtt cggctggcgc    7260
gagcccctga tgctcttcgt ccagatcatc ctgatcgaca agaccggctt ccatccgagt    7320
acgtgctcgc tcgatgcgat gtttcgcttg gtggtcgaat gggcaggtag ccggatcaag    7380
cgtatgcagc cgccgcattg catcagccat gatggatact ttctcggcag gagcaaggtg    7440
agatgacagg agatcctgcc ccggcacttc gcccaatagc agccagtccc ttcccgcttc    7500
agtgacaacg tcgagcacag ctgcgcaagg aacgcccgtc gtggccagcc acgatagccg    7560
cgctgcctcg tcttgcagtt cattcagggc accggacagg tcggtcttga caaaaagaac    7620
cgggcgcccc tgcgctgaca gccggaacac ggcggcatca gagcagccga ttgtctgttg    7680
tgcccagtca tagccgaata gcctctccac ccaagcggcc ggagaacctg cgtgcaatcc    7740
atcttgttca atcatgcgaa acgatcctca tcctgtctct tgatcagatc ttgatcccct    7800
gcgccatcag atccttggcg gcaagaaagc catccagttt actttgcagg gcttcccaac    7860
cttaccagag ggcgccccag ctggcaattc cggttcgctt gctgtccata aaaccgccca    7920
```

```
gtctagctat cgccatgtaa gcccactgca agctacctgc tttctctttg cgcttgcgtt    7980
ttcccttgtc cagatagccc agtagctgac attcatccgg ggtcagcacc gtttctgcgg    8040
actggctttc tacgtgaaaa ggatctaggt gaagatcctt tttgataatc tcatgaccaa    8100
aatcccttaa cgtgagtttt cgttccactg agcgtcagac cccgtagaaa agatcaaagg    8160
atcttcttga gatcctttt ttctgcgcgt aatctgctgc ttgcaaacaa aaaaaccacc    8220
gctaccagcg gtggtttgtt tgccggatca agagctacca actcttttc cgaaggtaac    8280 tggcttcagc agagcgcaga taccaaatac tgttcttcta gtgtagccgt agttaggcca    8340
ccacttcaag aactctgtag caccgcctac atacctcgct ctgctaatcc tgttaccagt    8400
ggctgctgcc agtggcgata agtcgtgtct taccgggttg gactcaagac gatagttacc    8460
ggataaggcg cagcggtcgg gctgaacggg gggttcgtgc acacagccca gcttggagcg    8520
aacgacctac accgaactga gatacctaca gcgtgagcta tgagaaagcg ccacgcttcc    8580
cgaagggaga aaggcggaca ggtatccggt aagcggcagg gtcggaacag gagagcgcac    8640
gagggagctt ccagggggaa acgcctggta tctttatagt cctgtcgggt ttcgccacct    8700
ctgacttgag cgtcgatttt tgtgatgctc gtcaggggg cggagcctat ggaaaaacgc    8760
cagcaacgcg gcccttttac ggttcctggc cttttgctgg ccttttgctc acatgttgtc    8820
gacaatattg gctattggcc attgcatacg ttgtatctat atcataatat gtacatttat    8880
attggctcat gtccaatatg accgccatgt tgacattgat tattgactag ttattaatag    8940
taatcaatta cggggtcatt agttcatagc ccatatatgg agttccgcgt tacataactt    9000
acggtaaatg gcccgcctgg ctgaccgccc aacgaccccc gcccattgac gtcaataatg    9060
acgtatgttc ccatagtaac gccaataggg actttccatt gacgtcaatg ggtggagtat    9120
ttacggtaaa ctgcccactt ggcagtacat caagtgtatc atatgccaag tccgccccct    9180
attgacgtca atgacggtaa atggcccgcc tggcattatg cccagtacat gaccttacgg    9240
gactttccta cttggcagta catctacggt attagtcatc ggctattacc atggtgatgc    9300
ggttttggca gtacaccaat gggcgtggat agcggtttga ctcacgggga tttccaagtc    9360
tccaccccat tgacgtcaat gggagtttgt tttggcacca aaatcaacgg gactttccaa    9420
aatgtcgtaa taaccccgcc ccgttgacgc aaatgggcgg taggcgtgta cggtgggagg    9480
tctatataag cagagctcgt ttagtgaacc gtcagatcgc ctggagacgc catccacgct    9540
gttttgacct ccatagaaga caccgggacc gatccagcct ccgcggccgg aacggtgca    9600 ttggaacgcg gattccccgt gccaagagtg acgtaagtac cgcctataga ctctataggc    9660
acaccccttt ggctcttatg catgctatac tgttttggc ttggggccta tacaccccg    9720 cttccttatg ctataggtga tggtatagct tagcctatag gtgtgggtta ttgaccatta    9780
ttgaccactc ccctattggt gacgatactt tccattacta atccataaca tggctctttg    9840
ccacaactat ctctattggc tatatgccaa tactctgtcc ttcagagact gacacggact    9900
ctgtattttt acaggatggg gtcccattta ttatttacaa attcacatat acaacaacgc    9960
cgtcccccgt gcccgcagtt tttattaaac atagcgtggg atctccacgc gaatctcggg   10020
taccgtgttc cggacatggg ytcttctccg gtagcggcgg agcttccaca tccgagccct   10080
ggtcccatgc ctccagcggc tcatggtcgc tcggcagctc cttgctccta acagtggagg   10140
ccagacttag gcacagcaca atgcccacca ccaccagtgt gccgcacaag gccgtggcgg   10200
tagggtatgt gtctgaaaat gagctcggag attgggctcg caccgctgac gcagatggaa   10260
gacttaaggc agcggcagaa gaagatgcag gcagctgagt tgttgtattc tgataagagt   10320
```

-continued

```
cagaggtaac tcccgttgcg gtgctgttaa cggtggaggg cagtgtagtc tgagcagtac    10380
tcgttgctgc cgcgcgcgcc accagacata atagctgaca gactaacaga ctgttccttt    10440
ccatgggtct tttctgcagt caccat                                         10466
```

<210> SEQ ID NO 16
<211> LENGTH: 35
<212> TYPE: DNA
<213> ORGANISM: Artificial Sequence
<220> FEATURE:
<223> OTHER INFORMATION: Synthetically generated oligonucleotide

<400> SEQUENCE: 16

```
ataaaaaacg cccggcggca accgagcgtt ctgaa                               35
```

<210> SEQ ID NO 17
<211> LENGTH: 33
<212> TYPE: DNA
<213> ORGANISM: Artificial Sequence
<220> FEATURE:
<223> OTHER INFORMATION: Primer

<400> SEQUENCE: 17

```
gctgctgctg tgtggagaat tcttcgtttc ggc                                 33
```

<210> SEQ ID NO 18
<211> LENGTH: 33
<212> TYPE: DNA
<213> ORGANISM: Artificial Sequence
<220> FEATURE:
<223> OTHER INFORMATION: Primer

<400> SEQUENCE: 18

```
gccgaaacga agaattctcc acacagcagc agc                                 33
```

<210> SEQ ID NO 19
<211> LENGTH: 44
<212> TYPE: DNA
<213> ORGANISM: Artificial Sequence
<220> FEATURE:
<223> OTHER INFORMATION: Primer

<400> SEQUENCE: 19

```
ctgcagtcac catggatcct tgcactcgag gatgcaatga agag                     44
```

<210> SEQ ID NO 20
<211> LENGTH: 44
<212> TYPE: DNA
<213> ORGANISM: Artificial Sequence
<220> FEATURE:
<223> OTHER INFORMATION: Primer

<400> SEQUENCE: 20

```
ctcttcattg catcctcgag tgcaaggatc catggtgact gcag                     44
```

<210> SEQ ID NO 21
<211> LENGTH: 30
<212> TYPE: DNA
<213> ORGANISM: Artificial Sequence
<220> FEATURE:
<223> OTHER INFORMATION: Primer

<400> SEQUENCE: 21

```
ccgtcagatc gcatcgatac gccatccacg                                     30
```

<210> SEQ ID NO 22

```
<211> LENGTH: 30
<212> TYPE: DNA
<213> ORGANISM: Artificial Sequence
<220> FEATURE:
<223> OTHER INFORMATION: Primer

<400> SEQUENCE: 22
cgtggatggc gtatcgatgc gatctgacgg                                        30

<210> SEQ ID NO 23
<211> LENGTH: 44
<212> TYPE: DNA
<213> ORGANISM: Artificial Sequence
<220> FEATURE:
<223> OTHER INFORMATION: Primer

<400> SEQUENCE: 23
gaactcattc tatggatcct tgctcgagtg gatgcaatga agag                        44

<210> SEQ ID NO 24
<211> LENGTH: 44
<212> TYPE: DNA
<213> ORGANISM: Artificial Sequence
<220> FEATURE:
<223> OTHER INFORMATION: Primer

<400> SEQUENCE: 24
ctcttcattg catccactcg agcaaggatc catagaatga gttc                        44

<210> SEQ ID NO 25
<211> LENGTH: 29
<212> TYPE: DNA
<213> ORGANISM: Artificial Sequence
<220> FEATURE:
<223> OTHER INFORMATION: Primer

<400> SEQUENCE: 25
gagctctatc gatgcaggac tcggcttgc                                         29

<210> SEQ ID NO 26
<211> LENGTH: 31
<212> TYPE: DNA
<213> ORGANISM: Artificial Sequence
<220> FEATURE:
<223> OTHER INFORMATION: Primer

<400> SEQUENCE: 26
ggcaggtttt aatcgctagc ctatgctctc c                                      31

<210> SEQ ID NO 27
<211> LENGTH: 17
<212> TYPE: DNA
<213> ORGANISM: Artificial Sequence
<220> FEATURE:
<223> OTHER INFORMATION: Primer

<400> SEQUENCE: 27
gggcaggagt gctagcc                                                      17

<210> SEQ ID NO 28
<211> LENGTH: 29
<212> TYPE: DNA
<213> ORGANISM: Artificial Sequence
<220> FEATURE:
<223> OTHER INFORMATION: Primer

<400> SEQUENCE: 28
```

```
ccacactact ttcggaccgc tagccaccc                                          29
```

<210> SEQ ID NO 29
<211> LENGTH: 32
<212> TYPE: DNA
<213> ORGANISM: Artificial Sequence
<220> FEATURE:
<223> OTHER INFORMATION: Primer

<400> SEQUENCE: 29

```
ggttaagagc ttcaatagcg gcaaagaagg gc                                      32
```

<210> SEQ ID NO 30
<211> LENGTH: 32
<212> TYPE: DNA
<213> ORGANISM: Artificial Sequence
<220> FEATURE:
<223> OTHER INFORMATION: Primer

<400> SEQUENCE: 30

```
gcccttcttt gccgctattg aagctcttaa cc                                      32
```

<210> SEQ ID NO 31
<211> LENGTH: 27
<212> TYPE: DNA
<213> ORGANISM: Artificial Sequence
<220> FEATURE:
<223> OTHER INFORMATION: Primer

<400> SEQUENCE: 31

```
gggcagctgg aaaagcggaa aggaagg                                            27
```

<210> SEQ ID NO 32
<211> LENGTH: 27
<212> TYPE: DNA
<213> ORGANISM: Artificial Sequence
<220> FEATURE:
<223> OTHER INFORMATION: Primer

<400> SEQUENCE: 32

```
ccttcctttc cgcttttcca gctgccc                                            27
```

<210> SEQ ID NO 33
<211> LENGTH: 44
<212> TYPE: DNA
<213> ORGANISM: Artificial Sequence
<220> FEATURE:
<223> OTHER INFORMATION: Primer

<400> SEQUENCE: 33

```
ccagacatag ttatctatca atacatgaac gatttgtatg tagg                         44
```

<210> SEQ ID NO 34
<211> LENGTH: 44
<212> TYPE: DNA
<213> ORGANISM: Artificial Sequence
<220> FEATURE:
<223> OTHER INFORMATION: Primer

<400> SEQUENCE: 34

```
cctacataca aatcgttcat gtattgatag ataactatgt ctgg                         44
```

<210> SEQ ID NO 35
<211> LENGTH: 33
<212> TYPE: DNA
<213> ORGANISM: Artificial Sequence
<220> FEATURE:

<223> OTHER INFORMATION: Primer

<400> SEQUENCE: 35
ggggaaattg aataccgcaa gtcagattta ccc                33

<210> SEQ ID NO 36
<211> LENGTH: 33
<212> TYPE: DNA
<213> ORGANISM: Artificial Sequence
<220> FEATURE:
<223> OTHER INFORMATION: Primer

<400> SEQUENCE: 36
gggtaaatct gacttgcggt attcaatttc ccc                33

<210> SEQ ID NO 37
<211> LENGTH: 40
<212> TYPE: DNA
<213> ORGANISM: Artificial Sequence
<220> FEATURE:
<223> OTHER INFORMATION: Primer

<400> SEQUENCE: 37
ccctaactaa cacaacaaat cagaaaactc agttacaagc         40

<210> SEQ ID NO 38
<211> LENGTH: 40
<212> TYPE: DNA
<213> ORGANISM: Artificial Sequence
<220> FEATURE:
<223> OTHER INFORMATION: Primer

<400> SEQUENCE: 38
gcttgtaact gagttttctg atttgttgtg ttagttaggg         40

<210> SEQ ID NO 39
<211> LENGTH: 29
<212> TYPE: DNA
<213> ORGANISM: Artificial Sequence
<220> FEATURE:
<223> OTHER INFORMATION: Primer

<400> SEQUENCE: 39
gagctctatc gatgcaggac tcggcttgc                     29

<210> SEQ ID NO 40
<211> LENGTH: 37
<212> TYPE: DNA
<213> ORGANISM: Artificial Sequence
<220> FEATURE:
<223> OTHER INFORMATION: Primer

<400> SEQUENCE: 40
ctccaattac tgtgagaatt ctaatgttca tcttggg            37

<210> SEQ ID NO 41
<211> LENGTH: 34
<212> TYPE: DNA
<213> ORGANISM: Artificial Sequence
<220> FEATURE:
<223> OTHER INFORMATION: Primer

<400> SEQUENCE: 41
ggcaactaaa ggaagctcta ttagccacag gagc               34

<210> SEQ ID NO 42

```
<211> LENGTH: 34
<212> TYPE: DNA
<213> ORGANISM: Artificial Sequence
<220> FEATURE:
<223> OTHER INFORMATION: Primer

<400> SEQUENCE: 42
gctcctgtgg ctaatagagc ttcctttagt tgcc                                  34

<210> SEQ ID NO 43
<211> LENGTH: 32
<212> TYPE: DNA
<213> ORGANISM: Artificial Sequence
<220> FEATURE:
<223> OTHER INFORMATION: Synthetically generated oligonucleotide

<400> SEQUENCE: 43
gcagtaagta gtaaatctaa tccaaccttt ac                                    32

<210> SEQ ID NO 44
<211> LENGTH: 32
<212> TYPE: DNA
<213> ORGANISM: Artificial Sequence
<220> FEATURE:
<223> OTHER INFORMATION: Synthetically generated oligonucleotide

<400> SEQUENCE: 44
gtaaaggttg gattagattt actacttact gc                                    32

<210> SEQ ID NO 45
<211> LENGTH: 30
<212> TYPE: DNA
<213> ORGANISM: Artificial Sequence
<220> FEATURE:
<223> OTHER INFORMATION: Primer

<400> SEQUENCE: 45
aagatctatc gatgcaagga ctcggcttgc                                       30

<210> SEQ ID NO 46
<211> LENGTH: 37
<212> TYPE: DNA
<213> ORGANISM: Artificial Sequence
<220> FEATURE:
<223> OTHER INFORMATION: Primer

<400> SEQUENCE: 46
ttccaattgc tgtgagaatt ctcatgctct tcttggg                               37

<210> SEQ ID NO 47
<211> LENGTH: 31
<212> TYPE: DNA
<213> ORGANISM: Artificial Sequence
<220> FEATURE:
<223> OTHER INFORMATION: Primer

<400> SEQUENCE: 47
aaggggttaa agctataata agaattctgc a                                     31

<210> SEQ ID NO 48
<211> LENGTH: 29
<212> TYPE: DNA
<213> ORGANISM: Artificial Sequence
<220> FEATURE:
<223> OTHER INFORMATION: Primer

<400> SEQUENCE: 48
```

```
cctttgctgc cctatctgat tcttctagg                                         29
```

<210> SEQ ID NO 49
<211> LENGTH: 40
<212> TYPE: DNA
<213> ORGANISM: Artificial Sequence
<220> FEATURE:
<223> OTHER INFORMATION: Primer

<400> SEQUENCE: 49

```
gccagagaat aataaagagc ttcaacagcg gcaaagaagg                             40
```

<210> SEQ ID NO 50
<211> LENGTH: 40
<212> TYPE: DNA
<213> ORGANISM: Artificial Sequence
<220> FEATURE:
<223> OTHER INFORMATION: Primer

<400> SEQUENCE: 50

```
ccttctttgc cgctgttgaa gctctttatt attctctggc                             40
```

<210> SEQ ID NO 51
<211> LENGTH: 38
<212> TYPE: DNA
<213> ORGANISM: Artificial Sequence
<220> FEATURE:
<223> OTHER INFORMATION: Primer

<400> SEQUENCE: 51

```
cctagaaaga gaggcagctg gaaaagcgga aaggaagg                               38
```

<210> SEQ ID NO 52
<211> LENGTH: 38
<212> TYPE: DNA
<213> ORGANISM: Artificial Sequence
<220> FEATURE:
<223> OTHER INFORMATION: Primer

<400> SEQUENCE: 52

```
ccttcctttc cgcttttcca gctgcctctc tttctagg                               38
```

<210> SEQ ID NO 53
<211> LENGTH: 34
<212> TYPE: DNA
<213> ORGANISM: Artificial Sequence
<220> FEATURE:
<223> OTHER INFORMATION: Primer

<400> SEQUENCE: 53

```
ccaatatatg aacgatttat atgtaggatc tgac                                   34
```

<210> SEQ ID NO 54
<211> LENGTH: 34
<212> TYPE: DNA
<213> ORGANISM: Artificial Sequence
<220> FEATURE:
<223> OTHER INFORMATION: Primer

<400> SEQUENCE: 54

```
gtcagatcct acatataaat cgttcatata ttgg                                   34
```

<210> SEQ ID NO 55
<211> LENGTH: 36
<212> TYPE: DNA
<213> ORGANISM: Artificial Sequence
<220> FEATURE:

<223> OTHER INFORMATION: Primer

<400> SEQUENCE: 55
gggaaaacta ataccgcaa gtcagattta tgcagg      36

<210> SEQ ID NO 56
<211> LENGTH: 36
<212> TYPE: DNA
<213> ORGANISM: Artificial Sequence
<220> FEATURE:
<223> OTHER INFORMATION: Primer

<400> SEQUENCE: 56
cctgcataaa tctgacttgc ggtatttagt tttccc      36

<210> SEQ ID NO 57
<211> LENGTH: 40
<212> TYPE: DNA
<213> ORGANISM: Artificial Sequence
<220> FEATURE:
<223> OTHER INFORMATION: Primer

<400> SEQUENCE: 57
ccctaattga gacaacaaat caaaagactc agttacatgc      40

<210> SEQ ID NO 58
<211> LENGTH: 40
<212> TYPE: DNA
<213> ORGANISM: Artificial Sequence
<220> FEATURE:
<223> OTHER INFORMATION: Primer

<400> SEQUENCE: 58
gcatgtaact gagtcttttg atttgttgtc tcaattaggg      40

<210> SEQ ID NO 59
<211> LENGTH: 30
<212> TYPE: DNA
<213> ORGANISM: Artificial Sequence
<220> FEATURE:
<223> OTHER INFORMATION: Primer

<400> SEQUENCE: 59
gccaatagaa gccctattaa acacaggagc      30

<210> SEQ ID NO 60
<211> LENGTH: 30
<212> TYPE: DNA
<213> ORGANISM: Artificial Sequence
<220> FEATURE:
<223> OTHER INFORMATION: Primer

<400> SEQUENCE: 60
gctcctgtgt ttaatagggc ttctattggc      30

<210> SEQ ID NO 61
<211> LENGTH: 26
<212> TYPE: DNA
<213> ORGANISM: Artificial Sequence
<220> FEATURE:
<223> OTHER INFORMATION: Synthetically generated oligonucleotide

<400> SEQUENCE: 61
cctccaattc ccactatcat ttttgg      26

<210> SEQ ID NO 62

```
<211> LENGTH: 26
<212> TYPE: DNA
<213> ORGANISM: Artificial Sequence
<220> FEATURE:
<223> OTHER INFORMATION: Synthetically generated oligonucleotide

<400> SEQUENCE: 62
cctccaattc ccactatcat ttttgg                                          26

<210> SEQ ID NO 63
<211> LENGTH: 27
<212> TYPE: DNA
<213> ORGANISM: Artificial Sequence
<220> FEATURE:
<223> OTHER INFORMATION: Synthetically generated oligonucleotide

<400> SEQUENCE: 63
ggacgaaata tgatgactca gattggt                                         27

<210> SEQ ID NO 64
<211> LENGTH: 27
<212> TYPE: DNA
<213> ORGANISM: Artificial Sequence
<220> FEATURE:
<223> OTHER INFORMATION: Synthetically generated oligonucleotide

<400> SEQUENCE: 64
accaatctga gtcatcatat ttcgtcc                                         27

<210> SEQ ID NO 65
<211> LENGTH: 22
<212> TYPE: DNA
<213> ORGANISM: Artificial Sequence
<220> FEATURE:
<223> OTHER INFORMATION: Primer

<400> SEQUENCE: 65
cgcaggatcc ggcttgctga ag                                              22

<210> SEQ ID NO 66
<211> LENGTH: 30
<212> TYPE: DNA
<213> ORGANISM: Artificial Sequence
<220> FEATURE:
<223> OTHER INFORMATION: Primer

<400> SEQUENCE: 66
tctactcgag cttattatag cactctcctg                                      30

<210> SEQ ID NO 67
<211> LENGTH: 24
<212> TYPE: DNA
<213> ORGANISM: Artificial Sequence
<220> FEATURE:
<223> OTHER INFORMATION: Primer

<400> SEQUENCE: 67
cctctcgaga tacttggaca ggag                                            24

<210> SEQ ID NO 68
<211> LENGTH: 27
<212> TYPE: DNA
<213> ORGANISM: Artificial Sequence
<220> FEATURE:
<223> OTHER INFORMATION: Primer

<400> SEQUENCE: 68
```
cacttgctag ccattttact gcaaagc                                              27

<210> SEQ ID NO 69
<211> LENGTH: 420
<212> TYPE: DNA
<213> ORGANISM: Artificial Sequence
<220> FEATURE:
<223> OTHER INFORMATION: Synthetically generated vector sequence-Plasmid
      p:W-48

<400> SEQUENCE: 69
gaattcgttg gtggtcgcca tggatggtgt tattgtatac tgtctaaacg cgttagtaaa    60
acatggcgag gaaataaatc atataaaaaa tgatttcatg attaaaccat gttgtgaaaa   120
agtcaagaac gttcacattg gcggacaatc taaaaacaat acagtgattg cagatttgcc   180
atatatggat aatgcggtat ccgatgtatg caattcactg tataaaaga atgtatcaag    240 aatatccaga tttgctaatt tgataaagat agatgacgat gacaagactc ctactggtgt   300
atataattat tttaaaccta agatgccat tcctgttatt atatccatag gaaggatag    360 agatgtttgt gaactattaa tctcatctga taaagcgtgt gcgtgtatag agttaaattc   420

<210> SEQ ID NO 70
<211> LENGTH: 44
<212> TYPE: DNA
<213> ORGANISM: Artificial Sequence
<220> FEATURE:
<223> OTHER INFORMATION: Primer

<400> SEQUENCE: 70
ctaaaagaac tgttaaatcc ttcaactctg gcaaggaagg gcac                            44

<210> SEQ ID NO 71
<211> LENGTH: 44
<212> TYPE: DNA
<213> ORGANISM: Artificial Sequence
<220> FEATURE:
<223> OTHER INFORMATION: Primer

<400> SEQUENCE: 71
gtgcccttcc ttgccagagt tgaaggattt aacagttctt ttag                            44

<210> SEQ ID NO 72
<211> LENGTH: 41
<212> TYPE: DNA
<213> ORGANISM: Artificial Sequence
<220> FEATURE:
<223> OTHER INFORMATION: Primer

<400> SEQUENCE: 72
ctaggaaaaa aggctcttgg aaatctggaa aggaaggaca c                               41

<210> SEQ ID NO 73
<211> LENGTH: 41
<212> TYPE: DNA
<213> ORGANISM: Artificial Sequence
<220> FEATURE:
<223> OTHER INFORMATION: Primer

<400> SEQUENCE: 73
gtgtccttcc tttccagatt tccaagagcc ttttttccta g                               41

<210> SEQ ID NO 74
<211> LENGTH: 34
<212> TYPE: DNA
<213> ORGANISM: Artificial Sequence

```
<220> FEATURE:
<223> OTHER INFORMATION: Primer

<400> SEQUENCE: 74
gtcatctatc aatatatgaa tgacttgtat gtag                              34

<210> SEQ ID NO 75
<211> LENGTH: 34
<212> TYPE: DNA
<213> ORGANISM: Artificial Sequence
<220> FEATURE:
<223> OTHER INFORMATION: Primer

<400> SEQUENCE: 75
ctacatacaa gtcattcata tattgataga tgac                              34

<210> SEQ ID NO 76
<211> LENGTH: 33
<212> TYPE: DNA
<213> ORGANISM: Artificial Sequence
<220> FEATURE:
<223> OTHER INFORMATION: Primer

<400> SEQUENCE: 76
gtgggaaaat taaacacggc aagccagatt tac                               33

<210> SEQ ID NO 77
<211> LENGTH: 33
<212> TYPE: DNA
<213> ORGANISM: Artificial Sequence
<220> FEATURE:
<223> OTHER INFORMATION: Primer

<400> SEQUENCE: 77
gtaaatctgg cttgccgtgt ttaattttcc cac                               33

<210> SEQ ID NO 78
<211> LENGTH: 33
<212> TYPE: DNA
<213> ORGANISM: Artificial Sequence
<220> FEATURE:
<223> OTHER INFORMATION: Primer

<400> SEQUENCE: 78
caaatcagaa gactcaatta caagcaattt atc                               33

<210> SEQ ID NO 79
<211> LENGTH: 33
<212> TYPE: DNA
<213> ORGANISM: Artificial Sequence
<220> FEATURE:
<223> OTHER INFORMATION: Primer

<400> SEQUENCE: 79
gataaattgc ttgtaattga gtcttctgat ttg                               33

<210> SEQ ID NO 80
<211> LENGTH: 29
<212> TYPE: DNA
<213> ORGANISM: Artificial Sequence
<220> FEATURE:
<223> OTHER INFORMATION: Primer

<400> SEQUENCE: 80
ggaggctctc ttagccacag gagcagatg                                    29
```

```
<210> SEQ ID NO 81
<211> LENGTH: 29
<212> TYPE: DNA
<213> ORGANISM: Artificial Sequence
<220> FEATURE:
<223> OTHER INFORMATION: Primer

<400> SEQUENCE: 81
catctgctcc tgtggctaag agagcctcc                                         29

<210> SEQ ID NO 82
<211> LENGTH: 420
<212> TYPE: DNA
<213> ORGANISM: Artificial Sequence
<220> FEATURE:
<223> OTHER INFORMATION: Synthetically generated vector sequence-plasmid
      pLW-48

<400> SEQUENCE: 82
gaatttaact ctatacacgc acacgcttta tcagatgaga ttaatagttc acaaacatct       60
ctatcctttc ctatggatat aataacagga atggcatctt taggtttaaa ataattatat      120
acaccagtag gagtcttgtc atcgtcatct atctttatca aattagcaaa tctggatatt      180
cttgatacat tcttttttata cagtgaattg catacatcgg ataccgcatt atccatatat     240
ggcaaatctg caatcactgt attgtttta gattgtccgc caatgtgaac gttcttgact       300
ttttcacaac atggtttaat catgaaatca ttttttatat gatttatttc ctcgccatgt      360
tttactaacg cgtttagaca gtatacaata acaccatcca tggcgaccac caacgaattc      420

<210> SEQ ID NO 83
<211> LENGTH: 12224
<212> TYPE: DNA
<213> ORGANISM: Artificial Sequence
<220> FEATURE:
<223> OTHER INFORMATION: Synthetically generated plasmid sequence-pLW-48

<400> SEQUENCE: 83
gaattcgttg gtggtcgcca tggatggtgt tattgtatac tgtctaaacg cgttagtaaa       60
acatggcgag gaaataaatc atataaaaaa tgatttcatg attaaccat gttgtgaaaa      120 agtcaagaac gttcacattg gcggacaatc taaaaacaat acagtgattg cagatttgcc      180
atatatggat aatgcggtat ccgatgtatg caattcactg tataaaaga atgtatcaag      240 aatatccaga tttgctaatt tgataaagat agatgacgat gacaagactc ctactggtgt      300
atataattat tttaaaccta agatgccat tcctgttatt atatccatag aaaggatag       360 agatgtttgt gaactattaa tctcatctga taaagcgtgt gcgtgtatag agttaaattc      420
atataaagta gccattcttc ccatggatgt ttccttttt accaaaggaa atgcatcatt      480
gattattctc ctgtttgatt tctctatcga tgcggcacct ctcttaagaa gtgtaaccga      540
taataatgtt attatatcta gacaccagcg tctacatgac gagcttccga gttccaattg      600
gttcaagttt tacataagta taaagtccga ctattgttct atattatata tggttgttga      660
tggatctgtg atgcatgcaa tagctgataa tagaacttac gcaaatatta gcaaaaatat      720
attagacaat actacaatta acgatgagtg tagatgctgt tatttttgaac cacagattag      780 gattcttgat agagatgaga tgctcaatgg atcatcgtgt gatatgaaca gacattgtat      840
tatgatgaat ttacctgatg taggcgaatt tggatctagt atgttgggga aatatgaacc      900
tgacatgatt aagattgctc tttcggtggc tgggtaccag gcgcgccttt catttttgttt     960 ttttctatgc tataaatggt acgtcctgta gaaaccccaa cccgtgaaat caaaaaactc     1020
```

-continued

```
gacggcctgt gggcattcag tctggatcgc gaaaactgtg gaattgatca gcgttggtgg    1080
gaaagcgcgt tacaagaaag ccgggcaatt gctgtgccag gcagttttaa cgatcagttc    1140
gccgatgcag atattcgtaa ttatgcgggc aacgtctggt atcagcgcga agtctttata    1200
ccgaaaggtt gggcaggcca gcgtatcgtg ctgcgtttcg atgcggtcac tcattacggc    1260
aaagtgtggg tcaataatca ggaagtgatg gagcatcagg gcggctatac gccatttgaa    1320
gccgatgtca cgccgtatgt tattgccggg aaaagtgtac gtatcaccgt ttgtgtgaac    1380
aacgaactga actggcagac tatcccgccg ggaatggtga ttaccgacga aaacggcaag    1440
aaaaagcagt cttacttcca tgatttcttt aactatgccg gaatccatcg cagcgtaatg    1500
ctctacacca cgccgaacac ctgggtggac gatatcaccg tggtgacgca tgtcgcgcaa    1560
gactgtaacc acgcgtctgt tgactggcag gtggtggcca atggtgatgt cagcgttgaa    1620
ctgcgtgatg cggatcaaca ggtggttgca actggacaag gcactagcgg gactttgcaa    1680
gtggtgaatc cgcaccctg gcaaccgggt gaaggttatc tctatgaact gtgcgtcaca    1740
gccaaaagcc agacagagtg tgatatctac ccgcttcgcg tcggcatccg gtcagtggca    1800
gtgaagggcg aacagttcct gattaaccac aaaccgttct actttactgg ctttggtcgt    1860
catgaagatg cggacttgcg tggcaaagga ttcgataacg tgctgatggt gcacgaccac    1920
gcattaatgg actggattgg ggccaactcc taccgtacct cgcattaccc ttacgctgaa    1980
gagatgctcg actgggcaga tgaacatggc atcgtggtga ttgatgaaac tgctgctgtc    2040
ggctttaacc tctctttagg cattggtttc gaagcgggca acaagccgaa agaactgtac    2100
agcgaagagg cagtcaacgg ggaaactcag caagcgcact acaggcgat taaagagctg    2160 atagcgcgtg acaaaaacca cccaagcgtg gtgatgtgga gtattgccaa cgaaccggat    2220
acccgtccgc aaggtgcacg ggaatatttc gcgccactgg cggaagcaac gcgtaaactc    2280
gacccgacgc gtccgatcac ctgcgtcaat gtaatgttct gcgacgctca caccgatacc    2340
atcagcgatc tctttgatgt gctgtgcctg aaccgttatt acggatggta tgtccaaagc    2400
ggcgatttgg aaacggcaga gaaggtactg gaaaaagaac ttctggcctg gcaggagaaa    2460
ctgcatcagc cgattatcat caccgaatac ggcgtggata cgttagccgg gctgcactca    2520
atgtacaccg acatgtggag tgaagagtat cagtgtgcat ggctggatat gtatcaccgc    2580
gtctttgatc gcgtcagcgc cgtcgtcggt gaacaggtat ggaatttcgc cgattttgcg    2640
acctcgcaag gcatattgcg cgttggcggt aacaagaaag ggatcttcac tcgcgaccgc    2700
aaaccgaagt cggcggcttt tctgctgcaa aaacgctgga ctggcatgaa cttcggtgaa    2760
aaaccgcagc agggaggcaa acaatgagag ctcggttgtt gatggatctg tgatgcatgc    2820
aatagctgat aatagaactt acgcaaatat tagcaaaaat atattagaca atactacaat    2880
taacgatgag tgtagatgct gttattttga accacagatt aggattcttg atagagatga    2940
gatgctcaat ggatcatcgt gtgatatgaa cagacattgt tattatgatga atttacctga    3000 tgtaggcgaa tttggatcta gtatgttggg gaaatatgaa cctgacatga ttaagattgc    3060
tctttcggtg gctggcggcc cgctcgagta aaaaatgaaa aaatattcta atttatagga    3120
cggttttgat tttctttttt tctatgctat aaataataaa tagcggccgc accatgaaag    3180 tgaagggat caggaagaat tatcagcact tgtggaaatg gggcatcatg ctccttggga    3240
tgttgatgat ctgtagtgct gtagaaaatt tgtgggtcac agtttattat ggggtacctg    3300
tgtggaaaga agcaaccacc actctatttt gtgcatcaga tgctaaagca tatgatacag    3360
aggtacataa tgtttgggcc acacatgcct gtgtacccac agaccccaac ccacaagaag    3420
```

```
tagtattgga aaatgtgaca gaaaatttta acatgtggaa aaataacatg gtagaacaga      3480
tgcatgagga tataatcagt ttatgggatc aaagcctaaa gccatgtgta aaattaaccc      3540
cactctgtgt tactttaaat tgcactgatt tgaggaatgt tactaatatc aataatagta      3600
gtgagggaat gagaggagaa ataaaaaact gctctttcaa tatcaccaca agcataagag      3660
ataaggtgaa gaaagactat gcacttttct atagacttga tgtagtacca atagataatg      3720
ataatactag ctataggttg ataaattgta atacctcaac cattacacag gcctgtccaa      3780
aggtatcctt tgagccaatt cccatacatt attgtacccc ggctggtttt gcgattctaa      3840
agtgtaaaga caagaagttc aatggaacag ggccatgtaa aaatgtcagc acagtacaat      3900
gtacacatgg aattaggcca gtagtgtcaa ctcaactgct gttaaatggc agtctagcag      3960
aagaagaggt agtaattaga tctagtaatt tcacagacaa tgcaaaaaac ataatagtac      4020
agttgaaaga atctgtagaa attaattgta caagacccaa caacaataca aggaaaagta      4080
tacatatagg accaggaaga gcattttata caacaggaga ataatagga gatataagac      4140 aagcacattg caacattagt agaacaaaat ggaataacac tttaaatcaa atagctacaa      4200
aattaaaaga acaatttggg aataataaaa caatagtctt taatcaatcc tcaggagggg      4260
acccagaaat tgtaatgcac agttttaatt gtggagggga attcttctac tgtaattcaa      4320
cacaactgtt taatagtact tggaattttta atggtacttg gaatttaaca caatcgaatg      4380
gtactgaagg aaatgacact atcacactcc catgtagaat aaaacaaatt ataaatatgt      4440
ggcaggaagt aggaaaagca atgtatgccc ctcccatcag aggacaaatt agatgctcat      4500
caaatattac agggctaata ttaacaagag atggtggaac taacagtagt gggtccgaga      4560
tcttcagacc tgggggagga gatatgaggg acaattggag aagtgaatta tataaatata      4620
aagtagtaaa aattgaacca ttaggagtag caccccaccaa ggcaaaaaga agagtggtgc      4680
agagagaaaa aagagcagtg ggaacgatag gagctatgtt ccttgggttc ttgggagcag      4740
caggaagcac tatgggcgca gcgtcaataa cgctgacggt acaggccaga ctattattgt      4800
ctggtatagt gcaacagcag aacaatttgc tgagggctat tgaggcgcaa cagcatctgt      4860
tgcaactcac agtctgggc atcaagcagc tccaggcaag agtcctggct gtggaaagat      4920
acctaaggga tcaacagctc ctagggattt ggggttgctc tggaaaactc atctgcacca      4980
ctgctgtgcc ttggaatgct agttggagta ataaaactct ggatatgatt tgggataaca      5040
tgacctggat ggagtgggaa agagaaatcg aaaattacac aggcttaata tacaccttaa      5100
ttgaggaatc gcagaaccaa caagaaaaga atgaacaaga cttattagca ttagataagt      5160
gggcaagttt gtggaattgg tttgacatat caaattggct gtggtatgta aaaatcttca      5220
taatgatagt aggaggcttg ataggtttaa gaatagtttt tactgtactt tctatagtaa      5280
atagagttag gcagggatac tcaccattgt catttcagac ccacctccca gccccgaggg      5340
gacccgacag gcccgaagga atcgaagaag aaggtggaga cagagactaa ttttttatgcg      5400 gccgctggta cccaacctaa aaattgaaaa taaatacaaa ggttcttgag ggttgtgtta      5460
aattgaaagc gagaaataat cataaataag cccgggggatc ctctagagtc gacaccatgg      5520
gtgcgagagc gtcagtatta agcggggggag aattagatcg atgggaaaaa attcggttaa      5580 ggccagggggа aaagaaaaaa tataaattaa aacatatagt atgggcaagc agggagctag      5640
aacgattcgc agttaatcct ggcctgttag aaacatcaga aggctgtaga caaatactgg      5700
gacagctaca accatcccctt cagacaggat cagaagaact tagatcatta tataatacag      5760
tagcaaccct ctattgtgtg catcaaagga tagagataaa agacaccaag gaagctttag      5820
```

```
acaagataga ggaagagcaa aacaaaagta agaaaaaagc acagcaagca gcagctgaca    5880
caggacacag caatcaggtc agccaaaatt accctatagt gcagaacatc caggggcaaa    5940
tggtacatca ggccatatca cctagaactt aaatgcatg ggtaaaagta gtagaagaga     6000
aggctttcag cccagaagtg atacccatgt tttcagcatt atcagaagga gccaccccac    6060
aagatttaaa caccatgcta aacacagtgg ggggacatca agcagccatg caaatgttaa    6120
aagagaccat caatgaggaa gctgcagaat gggatagagt gcatccagtg catgcagggc    6180
ctattgcacc aggccagatg agagaaccaa ggggaagtga catagcagga actactagta    6240
cccttcagga acaaatagga tggatgacaa ataatccacc tatcccagta ggagaaattt    6300
ataaaagatg gataatcctg ggattaaata aaatagtaag aatgtatagc cctaccagca    6360
ttctggacat aagacaagga ccaaaagaac cctttagaga ctatgtagac cggttctata    6420
aaactctaag agccgagcaa gcttcacagg aggtaaaaaa ttggatgaca gaaaccttgt    6480
tggtccaaaa tgcgaaccca gattgtaaga ctattttaaa agcattggga ccagcggcta    6540
cactagaaga aatgatgaca gcatgtcagg gagtaggagg acccggccat aaggcaagag    6600
ttttggctga agcaatgagc caagtaacaa attcagctac cataatgatg cagagaggca    6660
attttaggaa ccaaagaaag attgttaagt gtttcaattg tggcaaagaa gggcacacag    6720
ccagaaattg cagggcccct aggaaaaagg gctgttggaa atgtggaaag gaaggacacc    6780
aaatgaaaga ttgtactgag agacaggcta attttttagg gaagatctgg ccttcctaca    6840
agggaaggcc agggaatttt cttcagagca gaccagagcc aacagcccca ccagaagaga    6900
gcttcaggtc tggggtagag acaacaactc cccctcagaa gcaggagccg atagacaagg    6960
aactgtatcc tttaacttcc ctcagatcac tctttggcaa cgaccctctg tcacaataaa    7020
gatagggggg caactaaagg aagctctatt agatacagga gcagatgata cagtattaga    7080
agaaatgagt ttgccaggaa gatggaaacc aaaaatgata gggggaattg gaggttttat    7140
caaagtaaga cagtatgatc agatactcat agaaatctgt ggacataaag ctataggtac    7200
agtattagta ggacctacac ctgtcaacat aattggaaga aatctgttga ctcagattgg    7260
ttgcacttta aattttccca ttagccctat tgagactgta ccagtaaaat taaagccagg    7320
aatggatggc ccaaaagtta aacaatggcc attgacagaa gaaaaaataa aagcattagt    7380
agaaatttgt acagaaatgg aaaaggaagg gaaaatttca aaaattgggc ctgagaatcc    7440
atacaatact ccagtatttg ccataaagaa aaaagacagt actaaatgga gaaaattagt    7500
agatttcaga gaacttaata agagaactca agacttctgg gaagttcaat taggaatacc    7560
acatcccgca gggttaaaaa agaaaaaatc agtaacagta ctggatgtgg gtgatgcata    7620
tttttcagtt cccttagatg aagacttcag gaagtatact gcatttacca tacctagtat    7680
aaacaatgag acaccaggga ttagatatca gtacaatgtg cttccacagg gatggaaagg    7740
atcaccagca atattccaaa gtagcatgac aaaaatctta gagcctttta aaaaacaaaa    7800
tccagacata gttatctatc aatacatgaa cgatttgtat gtaggatctg acttagaaat    7860
agggcagcat agaacaaaaa tagaggagct gagacaacat ctgttgaggt ggggacttac    7920
cacaccagac aaaaaacatc agaaagaacc tccattcctt tggatgggtt atgaactcca    7980
tcctgataaa tggacagtac agcctatagt gctgccagaa aaagacagct ggactgtcaa    8040
tgacatacag aagttagtgg ggaaattgaa taccgcaagt cagatttacc cagggattaa    8100
agtaaggcaa ttatgtaaac tccttagagg aaccaaagca ctaacagaag taataccact    8160
aacagaagaa gcagagctag aactggcaga aaacagagag attctaaaag aaccagtaca    8220
```

-continued

```
tggagtgtat tatgacccat caaaagactt aatagcagaa atacagaagc aggggcaagg    8280
ccaatggaca tatcaaattt atcaagagcc atttaaaaat ctgaaaacag gaaaatatgc    8340
aagaatgagg ggtgcccaca ctaatgatgt aaaacaatta acagaggcag tgcaaaaaat    8400
aaccacagaa agcatagtaa tatggggaaa gactcctaaa tttaaactac ccatacaaaa    8460
ggaaacatgg gaaacatggt ggacagagta ttggcaagcc acctggattc ctgagtggga    8520
gtttgttaat acccctcctt tagtgaaatt atggtaccag ttagagaaag aacccatagt    8580
aggagcagaa accttctatg tagatggggc agctaacagg gagactaaat taggaaaagc    8640
aggatatgtt actaacaaag gaagacaaaa ggttgtcccc ctaactaaca caacaaatca    8700
gaaaactcag ttacaagcaa tttatctagc tttgcaggat tcaggattag aagtaaacat    8760
agtaacagac tcacaatatg cattaggaat cattcaagca caaccagata aaagtgaatc    8820
agagttagtc aatcaaataa tagagcagtt aataaaaaag gaaaaggtct atctggcatg    8880
ggtaccagca cacaaaggaa ttggaggaaa tgaacaagta gataaattag tcagtgctgg    8940
aatcaggaaa atactatttt tagatggaat agataaggcc caagatgaac attagttttt    9000
atgtcgacct gcagggaaag ttttataggt agttgataga acaaaataca taattttgta    9060
aaaataaatc acttttata ctaatatgac acgattacca atactttgt tactaatatc    9120 attagtatac gctacacctt ttcctcagac atctaaaaaa ataggtgatg atgcaacttt    9180
atcatgtaat cgaaataata caaatgacta cgttgttatg agtgcttggt ataaggagcc    9240
caattccatt attcttttag ctgctaaaag cgacgtcttg tattttgata attataccaa    9300
ggataaaata tcttacgact ctccatacga tgatctagtt acaactatca caattaaatc    9360
attgactgct agagatgccg gtacttatgt atgtgcattc tttatgacat cgcctacaaa    9420
tgacactgat aaagtagatt atgaagaata ctccacagag ttgattgtaa atacagatag    9480
tgaatcgact atagacataa tactatctgg atctacacat tcaccagaaa ctagttaagc    9540
ttgtctccct atagtgagtc gtattagagc ttggcgtaat catggtcata gctgtttcct    9600
gtgtgaaatt gttatccgct cacaattcca cacaacatac gagccggaag cataaagtgt    9660
aaagcctggg gtgcctaatg agtgagctaa ctcacattaa ttgcgttgcg ctcactgccc    9720
gctttcgagt cgggaaacct gtcgtgccag ctgcattaat gaatcggcca acgcgcgggg    9780
agaggcggtt tgcgtattgg gcgctcttcc gcttcctcgc tcactgactc gctgcgctcg    9840
gtcgttcggc tgcggcgagc ggtatcagct cactcaaagg cggtaatacg gttatccaca    9900
gaatcagggg ataacgcagg aaagaacatg tgagcaaaag gccagcaaaa ggccaggaac    9960
cgtaaaaagg ccgcgttgct ggcgtttttc cataggctcc gcccccctga cgagcatcac    10020
aaaaatcgac gctcaagtca gaggtggcga aacccgacag gactataaag ataccaggcg    10080
tttccccctg gaagctccct cgtgcgctct cctgttccga ccctgccgct taccggatac    10140
ctgtccgcct ttctcccttc gggaagcgtg gcgctttctc atagctcacg ctgtaggtat    10200
ctcagttcgg tgtaggtcgt tcgctccaag ctgggctgtg tgcacgaacc ccccgttcag    10260
cccgaccgct gcgccttatc cggtaactat cgtcttgagt ccaacccggt aagacacgac    10320
ttatcgccac tggcagcagc cactggtaac aggattagca gagcgaggta tgtaggcggt    10380
gctacagagt tcttgaagtg gtggcctaac tacggctaca ctagaaggac agtatttggt    10440
atctgcgctc tgctgaagcc agttaccttc ggaaaaagag ttggtagctc ttgatccggc    10500
aaacaaacca ccgctggtag cggtggtttt tttgtttgca agcagcagat tacgcgcaga    10560
aaaaaaggat ctcaagaaga tccttgatc ttttctacgg ggtctgacgc tcagtggaac    10620
```

-continued

```
gaaaactcac gttaagggat tttggtcatg agattatcaa aaaggatctt cacctagatc    10680
cttttaaatt aaaaatgaag ttttaaatca atctaaagta tatatgagta aacttggtct    10740
gacagttacc aatgcttaat cagtgaggca cctatctcag cgatctgtct atttcgttca    10800
tccatagttg cctgactccc cgtcgtgtag ataactacga tacggagggc ttaccatct    10860 ggccccagtg ctgcaatgat accgcgagac ccacgctcac cggctccaga tttatcagca    10920
ataaaccagc cagccggaag ggccgagcgc agaagtggtc ctgcaacttt atccgcctcc    10980
atccagtcta ttaattgttg ccgggaagct agagtaagta gttcgccagt taatagtttg    11040
cgcaacgttg ttggcattgc tacaggcatc gtggtgtcac gctcgtcgtt tggtatggct    11100
tcattcagct ccggttccca acgatcaagg cgagttacat gatcccccat gttgtgcaaa    11160
aaagcggtta gctccttcgg tcctccgatc gttgtcagaa gtaagttggc cgcagtgtta    11220
tcactcatgg ttatggcagc actgcataat tctcttactg tcatgccatc cgtaagatgc    11280
ttttctgtga ctggtgagta ctcaaccaag tcattctgag aatagtgtat gcggcgaccg    11340
agttgctctt gcccggcgtc aatacgggat aataccgcgc cacatagcag aactttaaaa    11400
gtgctcatca ttggaaaacg ttcttcgggg cgaaaactct caaggatctt accgctgttg    11460
agatccagtt cgatgtaacc cactcgtgca cccaactgat cttcagcatc ttttactttc    11520
accagcgttt ctgggtgagc aaaaacagga aggcaaaatg ccgcaaaaaa gggaataagg    11580
gcgacacgga aatgttgaat actcatactc ttccttttc aatattattg aagcatttat    11640
cagggttatt gtctcatgag cggatacata tttgaatgta tttagaaaaa taaacaaata    11700
ggggttccgc gcacattccc cgaaaagtgc cacctgacgt ctaagaaacc attattatca    11760
tgacattaac ctataaaaat aggcgtatca cgaggccctt tcgtctcgcg cgtttcggtg    11820
atgacggtga aaacctctga cacatgcagc tcccggagac ggtcacagct tgtctgtaag    11880
cggatgccgg gagcagacaa gcccgtcagg gcgcgtcagc gggtgttggc gggtgtcggg    11940
gctggcttaa ctatgcggca tcagagcaga ttgtactgag agtgcaccat atgcggtgtg    12000
aaataccgca cagatgcgta aggagaaaat accgcatcag gcgccattcg ccattcaggc    12060
tgcgcaactg ttgggaaggg cgatcggtgc gggcctcttc gctattacgc cagctggcga    12120
aagggggatg tgctgcaagg cgattaagtt gggtaacgcc agggttttcc cagtcacgac    12180
gttgtaaaac gacggccagt gaattggatt taggtgacac tata                    12224
```

```
<210> SEQ ID NO 84
<211> LENGTH: 74
<212> TYPE: DNA
<213> ORGANISM: Artificial Sequence
<220> FEATURE:
<223> OTHER INFORMATION: Synthetically generated promoter sequence

<400> SEQUENCE: 84
taaaaaatga aaaatattc taatttatag gacggttttg attttctttt tttctatgct    60
ataaataata aata                                                     74

<210> SEQ ID NO 85
<211> LENGTH: 2214
<212> TYPE: DNA
<213> ORGANISM: Artificial Sequence
<220> FEATURE:
<223> OTHER INFORMATION: Synthetically generated HIV env gene

<400> SEQUENCE: 85
atgaaagtga aggggatcag gaagaattat cagcacttgt ggaaatgggg catcatgctc    60
```

```
cttgggatgt tgatgatctg tagtgctgta gaaaatttgt gggtcacagt ttattatggg      120
gtacctgtgt ggaaagaagc aaccaccact ctattttgtg catcagatgc taaagcatat      180
gatacagagg tacataatgt ttgggccaca catgcctgtg tacccacaga ccccaaccca      240
caagaagtag tattggaaaa tgtgacagaa aattttaaca tgtggaaaaa taacatggta      300
gaacagatgc atgaggatat aatcagttta tgggatcaaa gcctaaagcc atgtgtaaaa      360
ttaaccccac tctgtgttac tttaaattgc actgatttga ggaatgttac taatatcaat      420
aatagtagtg agggaatgag aggagaaata aaaaactgct ctttcaatat caccacaagc      480
ataagagata aggtgaagaa agactatgca cttttctata gacttgatgt agtaccaata      540
gataatgata atactagcta taggttgata aattgtaata cctcaaccat tacacaggcc      600
tgtccaaagg tatcctttga gccaattccc atacattatt gtaccccggc tggttttgcg      660
attctaaagt gtaaagacaa gaagttcaat ggaacagggc catgtaaaaa tgtcagcaca      720
gtacaatgta cacatggaat taggccagta gtgtcaactc aactgctgtt aaatggcagt      780
ctagcagaag aagaggtagt aattagatct agtaatttca cagacaatgc aaaaaacata      840
atagtacagt tgaaagaatc tgtagaaatt aattgtacaa gacccaacaa caatacaagg      900
aaaagtatac atataggacc aggaagagca ttttatacaa caggagaaat aataggagat      960
ataagacaag cacattgcaa cattagtaga acaaaatgga ataacacttt aaatcaaata     1020
gctacaaaat taaagaaca atttgggaat aataaaacaa tagtctttaa tcaatcctca     1080
ggaggggacc cagaaattgt aatgcacagt tttaattgtg gaggggaatt cttctactgt     1140
aattcaacac aactgtttaa tagtacttgg aattttaatg gtacttggaa tttaacacaa     1200
tcgaatggta ctgaaggaaa tgacactatc acactcccat gtagaataaa acaaattata     1260
aatatgtggc aggaagtagg aaaagcaatg tatgcccctc ccatcagagg acaaattaga     1320
tgctcatcaa atattacagg gctaatatta acaagagatg gtggaactaa cagtagtggg     1380
tccgagatct tcagacctgg gggaggagat atgagggaca attggagaag tgaattatat     1440
aaatataaag tagtaaaaat tgaaccatta ggagtagcac ccaccaaggc aaaaagaaga     1500
gtggtgcaga gagaaaaaag agcagtggga acgataggag ctatgttcct tgggttcttg     1560
ggagcagcag gaagcactat gggcgcagcg tcaataacgc tgacggtaca ggccagacta     1620
ttattgtctg gtatagtgca acagcagaac aatttgctga gggctattga ggcgcaacag     1680
catctgttgc aactcacagt ctggggcatc aagcagctcc aggcaagagt cctggctgtg     1740
gaaagatacc taagggatca acagctccta gggatttggg gttgctctgg aaaactcatc     1800
tgcaccactg ctgtgccttg gaatgctagt tggagtaata aaactctgga tatgatttgg     1860
gataacatga cctggatgga gtgggaaaga gaaatcgaaa attacacagg cttaatatac     1920
accttaattg aggaatcgca gaaccaacaa gaaaagaatg aacaagactt attagcatta     1980
gataagtggg caagtttgtg gaattggttt gacatatcaa attggctgtg gtatgtaaaa     2040
atcttcataa tgatagtagg aggcttgata ggtttaagaa tagttttttac tgtactttct     2100
atagtaaata gagttaggca gggatactca ccattgtcat ttcagaccca cctcccagcc     2160
ccgaggggac ccgacaggcc cgaaggaatc gaagaagaag gtggagacag agac           2214
```

<210> SEQ ID NO 86
<211> LENGTH: 70
<212> TYPE: DNA
<213> ORGANISM: Artificial Sequence
<220> FEATURE:
<223> OTHER INFORMATION: Synthetically generated promoter sequence

<400> SEQUENCE: 86

```
aaaaattgaa ataaataca aaggttcttg agggttgtgt taaattgaaa gcgagaaata        60
atcataaata                                                              70
```

<210> SEQ ID NO 87
<211> LENGTH: 3477
<212> TYPE: DNA
<213> ORGANISM: Artificial Sequence
<220> FEATURE:
<223> OTHER INFORMATION: Synthetically generated HIV genes

<400> SEQUENCE: 87

```
atgggtgcga gagcgtcagt attaagcggg ggagaattag atcgatggga aaaaattcgg        60
ttaaggccag ggggaaagaa aaatataaa ttaaaacata tagtatgggc aagcagggag       120
ctagaacgat tcgcagttaa tcctggcctg ttagaaacat cagaaggctg tagacaaata       180
ctgggacagc tacaaccatc ccttcagaca ggatcagaag aacttagatc attatataat       240
acagtagcaa ccctctattg tgtgcatcaa aggatagaga taaaagacac caaggaagct       300
ttagacaaga tagaggaaga gcaaaacaaa agtaagaaaa agcacagca agcagcagct       360
gacacaggac acagcaatca ggtcagccaa aattacccta tagtgcagaa catccagggg       420
caaatggtac atcaggccat atcacctaga actttaaatg catgggtaaa agtagtagaa       480
gagaaggctt tcagcccaga agtgataccc atgttttcag cattatcaga aggagccacc       540
ccacaagatt taaacaccat gctaaacaca gtggggggac atcaagcagc catgcaaatg       600
ttaaaagaga ccatcaatga ggaagctgca gaatgggata gagtgcatcc agtgcatgca       660
gggcctattg caccaggcca gatgagagaa ccaaggggaa gtgacatagc aggaactact       720
agtacccttc aggaacaaat aggatggatg acaaataatc cacctatccc agtaggagaa       780
atttataaaa gatggataat cctgggatta aataaaatag taagaatgta tagccctacc       840
agcattctgg acataagaca aggaccaaaa gaacccttta gagactatgt agaccggttc       900
tataaaactc taagagccga gcaagcttca caggaggtaa aaaattggat gacagaaacc       960
ttgttggtcc aaaatgcgaa cccagattgt aagactattt taaaagcatt gggaccagcg      1020
gctacactag aagaaatgat gacagcatgt cagggagtag gaggacccgg ccataaggca      1080
agagttttgg ctgaagcaat gagccaagta acaaattcag ctaccataat gatgcagaga      1140
ggcaatttta ggaaccaaag aaagattgtt aagtgtttca attgtggcaa agaagggcac      1200
acagccagaa attgcagggc ccctaggaaa aagggctgtt ggaaatgtgg aaaggaagga      1260
caccaaatga aagattgtac tgagagacag gctaatttt tagggaagat ctggccttcc      1320
tacaagggaa ggccagggaa ttttcttcag agcagaccag agccaacagc cccaccagaa      1380
gagagcttca ggtctggggt agagacaaca actccccctc agaagcagga gccgatagac      1440
aaggaactgt atcctttaac ttccctcaga tcactctttg gcaacgaccc ctcgtcacaa      1500
taaagatagg gggcaacta aaggaagctc tattagatac aggagcagat gatacagtat      1560
tagaagaaat gagtttgcca ggaagatgga accaaaaat gatagggga attggaggtt      1620
ttatcaaagt aagacagtat gatcagatac tcatagaaat ctgtggacat aaagctatag      1680
gtacagtatt agtaggacct acacctgtca acataattgg aagaaatctg ttgactcaga      1740
ttggttgcac tttaaatttt cccattagcc ctattgagac tgtaccagta aaattaaagc      1800
caggaatgga tggcccaaaa gttaaacaat ggccattgac agaagaaaaa ataaaagcat      1860
tagtagaaat ttgtacagaa atggaaaagg aagggaaaat ttcaaaaatt gggcctgaga      1920
```

```
atccatacaa tactccagta tttgccataa agaaaaaaga cagtactaaa tggaggaaat    1980
tagtagattt cagagaactt aataagagaa ctcaagactt ctgggaagtt caattaggaa    2040
taccacatcc cgcagggtta aaaagaaaa aatcagtaac agtactggat gtgggtgatg     2100 catattttc agttccctta gatgaagact tcaggaagta tactgcattt accataccta     2160
gtataaacaa tgagacacca gggattagat atcagtacaa tgtgcttcca cagggatgga    2220
aaggatcacc agcaatattc caaagtagca tgacaaaaat cttagagcct tttaaaacaa    2280
aatccagaca tagttatcta tcaatacatg aacgatttgt atgtaggatc tgacttagaa    2340
atagggcagc atagaacaaa aatagaggag ctgagacaac atctgttgag gtggggactt    2400
accacaccag acaaaaaaca tcagaaagaa cctccattcc tttggatggg ttatgaactc    2460
catcctgata aatggacagt acagcctata gtgctgccag aaaaagacag ctggactgtc    2520
aatgacatac agaagttagt ggggaaattg aataccgcaa gtcagattta cccagggatt    2580
aaagtaaggc aattatgtaa actccttaga ggaaccaaag cactaacaga agtaatacca    2640
ctaacagaag aagcagagct agaactggca gaaaacagag agattctaaa agaaccagta    2700
catggagtgt attatgaccc atcaaaagac ttaatagcag aaatacagaa gcaggggcaa    2760
ggccaatgga catatcaaat ttatcaagag ccatttaaaa atctgaaaac aggaaaatat    2820
gcaagaatga ggggtgccca cactaatgat gtaaaacaat taacagaggc agtgcaaaaa    2880
ataaccacag aaagcatagt aatatgggga aagactccta aatttaaact acccatacaa    2940
aaggaaacat gggaaacatg gtggacagag tattggcaag ccacctggat tcctgagtgg    3000
gagtttgtta atacccctcc tttagtgaaa ttatggtacc agttagagaa agaacccata    3060
gtaggagcag aaaccttcta tgtagatggg gcagctaaca gggagactaa attaggaaaa    3120
gcaggatatg ttactaacaa aggaagacaa aaggttgtcc ccctaactaa cacaacaaat    3180
cagaaaactc agttacaagc aatttatcta gctttgcagg attcaggatt agaagtaaac    3240
atagtaacag actcacaata tgcattagga atcattcaag cacaaccaga taaaagtgaa    3300
tcagagttag tcaatcaaat aatagagcag ttaataaaaa aggaaaaggt ctatctggca    3360
tgggtaccag cacacaaagg aattggagga aatgaacaag tagataaatt agtcagtgct    3420
ggaatcagga aaatactatt tttagatgga atagataagg cccaagatga acattag      3477
```